(12) United States Patent
Søe et al.

(10) Patent No.: US 9,228,211 B2
(45) Date of Patent: Jan. 5, 2016

(54) PROCESS OF WATER DEGUMMING AN EDIBLE OIL

(75) Inventors: Jørn Borch Søe, Tilst (DK); Anne Victoria Brown, Kansas City, MO (US)

(73) Assignee: DUPONT NUTRITION BIOSCIENCES APS, Copenhagen (DK)

(*) Notice: Subject to any disclaimer, the term of this patent is extended or adjusted under 35 U.S.C. 154(b) by 687 days.

(21) Appl. No.: 12/809,901

(22) PCT Filed: Dec. 11, 2008

(86) PCT No.: PCT/GB2008/004064
§ 371 (c)(1),
(2), (4) Date: Jan. 11, 2011

(87) PCT Pub. No.: WO2009/081094
PCT Pub. Date: Jul. 2, 2009

(65) Prior Publication Data
US 2011/0136187 A1    Jun. 9, 2011

Related U.S. Application Data

(60) Provisional application No. 61/058,378, filed on Jun. 3, 2008.

(30) Foreign Application Priority Data

Dec. 21, 2007 (GB) .................................. 0725035.0
May 20, 2008 (GB) .................................. 0809177.9

(51) Int. Cl.
| | |
|---|---|
| C12P 7/64 | (2006.01) |
| C12N 9/10 | (2006.01) |
| C12N 9/20 | (2006.01) |
| A23D 7/00 | (2006.01) |
| C07H 21/04 | (2006.01) |
| C11B 3/00 | (2006.01) |

(52) U.S. Cl.
CPC .............. *C12P 7/6445* (2013.01); *C11B 3/003* (2013.01); *C12Y 203/01043* (2013.01); *C12Y 301/04003* (2013.01)

(58) Field of Classification Search
CPC ........... C11B 3/003; C12Y 301/04003; C12Y 203/01043; C12P 7/6445
USPC ........... 435/134, 193, 198; 426/601; 536/23.2
See application file for complete search history.

(56) References Cited

U.S. PATENT DOCUMENTS

| | | | |
|---|---|---|---|
| 4,683,202 A | 7/1987 | Mullis | |
| 5,674,707 A | 10/1997 | Hintz et al. | |
| 5,856,196 A * | 1/1999 | Alvarez et al. ................. | 436/71 |
| 6,180,406 B1 | 1/2001 | Stemmer | |
| 6,344,328 B1 | 2/2002 | Short | |
| 6,352,851 B1 | 3/2002 | Nielsen et al. | |
| 6,361,974 B1 | 3/2002 | Short et al. | |
| 7,226,771 B2 | 6/2007 | Gramatikova et al. | |
| 7,638,293 B2 * | 12/2009 | De Kreij et al. ................. | 435/15 |
| 7,906,307 B2 * | 3/2011 | Soe et al. ....................... | 435/193 |
| 8,192,782 B2 * | 6/2012 | Soe et al. ....................... | 426/601 |
| 2002/0182734 A1 | 12/2002 | Diaz-Torres et al. | |
| 2007/0298157 A1 * | 12/2007 | Soe et al. ....................... | 426/601 |
| 2008/0070287 A1 | 3/2008 | Soe et al. | |
| 2012/0064192 A1 | 3/2012 | Soe et al. | |
| 2013/0034627 A1 | 2/2013 | Brunstedt et al. | |

FOREIGN PATENT DOCUMENTS

| | | |
|---|---|---|
| EP | 0449375 | 10/1991 |
| EP | 0752008 | 1/1997 |
| EP | 11-228986 | 8/1999 |
| EP | 1103606 | 5/2001 |
| EP | 1138763 | 10/2001 |
| EP | 01624047 A1 | 8/2006 |

(Continued)

OTHER PUBLICATIONS

Broun et al., Catalytic plasticity of fatty acid modification enzymes underlying chemical diversity of plant lipids. Science, 1998, vol. 282: 1315-1317.*

Devos et al., Practical limits of function prediction. Proteins: Structure, Function, and Genetics. 2000, vol. 41: 98-107.*

Seffernick et al., Melamine deaminase and Atrazine chlorohydrolase: 98 percent identical but functionally different. J. Bacteriol., 2001, vol. 183 (8): 2405-2410.*

(Continued)

*Primary Examiner* — Ganapathirama Raghu
(74) *Attorney, Agent, or Firm* — Steptoe & Johnson LLP

(57) ABSTRACT

A process of water degumming an edible oil (preferably a crude edible oil) comprising the steps of: a) admixing approximately 0.1-5% w/w water with an edible oil (preferably a crude edible oil) and a lipid acyltransferase, b) agitating the admixture for between about 10 minutes and 180 minutes at about 45 to about 900 C, and c) separating the oil phase and the gum phase. Preferably said lipid acyltransferase is a polypeptide having lipid acyltransferase activity which polypeptide is obtained by expression of the nucleotide sequence shown as SEQ ID No. 49 or a nucleotide sequence which as has 70% or more identity therewith; and/or is obtained by expression of a nucleic acid which hybridizes under medium stringency conditions to a nucleic probe comprising the nucleotide sequence shown as SEQ ID No. 49; and/or is a polypeptide having lipid acyltransferase activity which polypeptide comprises the amino acid sequence shown as SEQ ID No. 68 or an amino acid sequence which as has 70% or more identity therewith. In one embodiment the lipid acyltransferase is preferably used in combination with a phospholipase C enzyme. A process for modifying the gum phase of a degummed oil using a lipid acyltransferase is also taught herein.

12 Claims, 89 Drawing Sheets

(56) References Cited

FOREIGN PATENT DOCUMENTS

| EP | 01624047 B1 | 10/2006 |
|---|---|---|
| EP | 1762622 | 3/2007 |
| EP | 1788080 | 5/2007 |
| JP | 2005523019 | 8/2005 |
| JP | 2007516717 | 6/2007 |
| JP | 2007528732 | 10/2007 |
| JP | 2007531516 | 11/2007 |
| WO | 9117243 | 11/1991 |
| WO | 9818912 | 5/1998 |
| WO | 9818912 | 7/1998 |
| WO | 9845453 | 10/1998 |
| WO | 9953001 | 10/1999 |
| WO | 0058517 | 10/2000 |
| WO | 0116308 | 3/2001 |
| WO | 0134835 | 5/2001 |
| WO | 0139544 | 5/2001 |
| WO | 0206457 | 1/2002 |
| WO | 03100044 | 11/2003 |
| WO | 03102118 | 11/2003 |
| WO | 2004064537 | 5/2004 |
| WO | 2004064987 | 5/2004 |
| WO | 2005066347 | 7/2005 |
| WO | WO 2005089562 | 9/2005 |
| WO | 2005111203 | 11/2005 |
| WO | 2006008508 | 1/2006 |
| WO | 2006031699 | 3/2006 |
| WO | 2008036863 | 3/2008 |
| WO | 2008090395 | 7/2008 |
| WO | 2008094847 | 8/2008 |
| WO | 2009024736 | 2/2009 |

OTHER PUBLICATIONS

Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Oil Mill Gazetteer Jul. 2005 vol. 111, p. 2-4.
Clausen K, "Enzymatic oil-degumming by a movel microbial phospholipase," Eur. J. Lipid Sci. Technol. 2001, vol. 103, p. 333-340.
Hui, Bailey's Industrial Oil and Fat Products, 5th edition vol. 2 Edible Oil and Fat Products: Oils and Oilseeds, Wiley Interscience11995 ISBN 0471594261 p. 513-516.
AOCS Introduction to the Processing of Fats and Oils p. III-16-III-19. Four modules on CD-ROM, American Oil Chemists Society, 2003.
Verenium Corporation leaflet Purifine® Enzyme Jan. 2008.
Altschul S.F. et al., Basic Local Alighnment Search Tool, J. Mol. Biol., 1990, vol. 215, p. 403-410.
AOAC Official method 999.10(Lead, Cadmium, Zinc, Copper, and Iron in Foods Atomic absorption Spectrophotometry after Microwave Digestion, First Action 1999 NMKL-AOAC Method.
AOCS Method 2c-25 1997 Moisture and Volatile Matter Air Oven Method.
AOCS Official Method Ca 20-99: Analysis of Phosphorus in oil by inductively Coupled Plasma Optical Emission Spectroscopy, 2001.
Archer D B & Peberdy J F, The Molecular Biology of Secreted Enzyme Production by Fungi, Critical Reviews in Biotechnology, 1997, 17(4), p. 273-306.
Ausubel, Frederick M., et al., "Short Protocols in Molecular Biology—A Compendium of Methods from Current Protocols in Molecular Biology", 1999, John Wiley & Sons, Inc., chapter 18.
Ausubel, Frederick M., et al., "Short Protocols in Molecular Biology—A Compendium of Methods from Current Protocols in Molecular Biology", 1999, John Wiley & Sons, Inc., p. 7-58-7-60.
Beaucage S.L. et al., Deoxynucleoside phosphoramidites—a new class of key intermediates for deoxypolynucleotide synthesis, Tetrahedron Letters, 1981, vol. 22, No. 20, p. 1859-1862.
Beggs J. D., Transformatin of yeast by a replicating hybrid plasmid, Nature (London), 1978, vol. 275, p. 104-109.
Bo Yang et al., Optimization of Enzymatic Degumming Process for Rapeseed Oil, JAOCS, 2006, vol. 83, No. 7, p. 653-658.
Brumlik MJ & Buckley JT, "Identification of the Catalytic Triad of the Lipase/Acyltransferase," Journal of Bacteriology, Apr. 1996, vol. 178, No. 7, p. 2060-2064.
Buchold H., Enzyme-catalyzed degumming of vegetable oils, Fett Wissenschaft Technologies, 1993, vol. 95, No. 8, p. 300-304, ISSN:0931-5985.
Caruthers MH et al. "New chemical methods for synthesizing polynucleotides," Nucleic Acids Research Symposium Series, 1980, p. 215-23.
Cereghino J. L. et al., Heterologous protein expression in the methylotrophic yeast *Pichia pastoris*, FEMS Microbiol. Rev. 2000, vol. 24, No. 1, p. 45-66.
Christou P, Genetic engineering of crop legumes and cereals: current status and recent advances, Agro-Food-Industry Hi-Tech Mar./Apr. 1994 p. 17-27.
Davis RH and de Serres FJ, Genetic and Microbiological Research Techniques for Neurospora crassa, Methods Enzymol. (1971), vol. 171, No. 1, p. 79-143.
Food Chemical Codex, 3rd edition, 1981, p. 492-493.
Higgins D.G. & Sharp P.M., "CLUSTAL: a package for performing multiple sequence alignment on a microcomputer," Gene, 1988, vol. 73, No. 1, p. 237-244.
Hilton S, Buckley JT, Studies on the Reaction Mechanism of a Microbial Lipase/Acyltransferase Using Chemical Modification and Site-directed Mutagenesis, J Biol Chem. Jan. 15, 1991; 266(2): 997-1000.
Hinchcliffe E, Kenny E, "Yeast as a vehicle for the expression of heterologous genes", Yeasts, vol. 5, Anthony H. Rose and J. Stuart Harrison, eds, 1993, 2nd edition, Academic Press Ltd, p. 325-356.
Hinnen A. et al., Transformation of yeast, Proceedings of the National Academy of Sciences of the USA, 1978, vol. 75, p. 1929-1933.
Hollenberg et al., Current Opinion Biotechnology, Oct. 1997, vol. 8, No. 5, p. 554-560.
Horn T et al., Synthesis of oligonucleotides on cellulose. Part II: design and synthetic strategy to the synthetic strategy to the synthesis of 22 oligodeoxynucleotides coding for Gastric Inhibitory Polypeptide (GIP), Nucleic Acids Reseaserch Symposium Ser 1980, 7, p. 225-232.
Horwell D.C., "The 'peptoid' approach to the design of non-peptide, small molecule agonists and antagonists of neuropeptides," Trends Biotechnol. (1995) 13 (4), 132-134.
Ito H. et al., Transformation of Intact Yeast Cells Treated with Alkali Cations, J. Bacteriology, 1983, vol. 153, p. 163-168.
Kimmel and Berger, Guide to Molecular Cloning Techniques, Methods in Enzymology, 1987, vol. 152, p. 307-316.
LaVallie E.R. et al., Gene fusion expression systems in *Escherichia coli*, Current Opinion Biotechnology 1995, 6(5) p. 501-506.
Matthes H.W.D. et al., Simultaneous rapid chemical synthesis of over one hundred oligonucleotides on a microscale, EMBO J., 1984, vol. 3, No. 4, p. 801-805.
Morinaga Y. et al., Improvement of Oligonucleotide-directed site-specific mutagenesis using double-stranded plasmid DNA, Biotechnology (1984) 2, p. 636-639.
NCBI protein accession code AAK84028.1 GI:15082088, Dec. 4, 2008.
NCBI protein accession code CAB39707.1 GI:4529178, Dec. 4, 2008.
NCBI protein accession code CAB62724.1 GI:6562793, Dec. 4, 2008.
NCBI protein accession code CAB88833.1 GI:7635996, Dec. 4, 2008.
NCBI protein accession code CAB89450.1 GI:7672261, Dec. 4, 2008.
NCBI protein accession code CAC01477.1 GI:9716139, Dec. 4, 2008.
Nelson R.M. and Long G.L., Analytical Biochemistry, 1989, vol. 180, p. 147-151.
Peelman F, et al., A proposed architecture for lecithin cholesterol acyl transferase (LCAT): Identification of the catalytic triad and molecular modeling, Protein Science Mar. 1998; 7(3): 587-599.
Phospholipase A1 activity E.C. 3.1.1.32 (1976).

(56) References Cited

OTHER PUBLICATIONS

Phospholipase A2 activity E.C. 3.1.1.4 (1983).
Phospholipase B activity E.C. 3.1.1.5 (1983).
Phospholipase C, E.C. 3.1.4.3 (1961).
Potrykus I., "Gren transfer to Plants: assessment of pblished approaches and results," Annual Review of Plant Physiology and Plant Molecular Biology, 1991, vol. 42 p. 205-225.
Punt P.J. et al., Filamentous fungi as cell factories for heterologous protein production, Trends Biotechnology May 2002, 20(5) p. 200-206.
Robertson D.L. et al., Influence of Active Site and Tyrosine Modification on the Secretion and Activity of the *Aeromonas hydrophila* Lipase/Acyltransferase, Journal of Biological Chemistry, 1994, vol. 269, No. 3, p. 2146-2150.
*Saccharomyces cerevisiae* Genbank accession No. Z75034, Dec. 4, 2008.
Saiki R.K. et al., "Primer-directed enzymatic amplication of DNA with a Thermostable DNA Polymerase," Science, 1988, vol. 239, p. 487-491.
Simon R.J. et al., "Peptoids: a molecular approach to drug discovery", Proc. Natl. Acad. Sci., (1992) 89(20), 9367-9371.
*Streptomyces coelicolor* A3(2), Genbank accession No. NC-003888. 1:8327480..83283667, Dec. 18, 2008.
Tatusova T.A. et al., BLAST2 sequences, a new tool for comparing protein and nucleotide sequences, FEMS Microbiol. Lett., 1999, 174(2), p. 247-250.
Tatusova T.A. et al., "Erratum to" BLAST2 sequences, a new tool for comparing protein and nucleotide sequences, FEMS Microbiol. Lett., 1999, 177(1): 187-8.
Triacylglycerol lipase activity (E.C. 3.1.1.3), 1961.
Trueman L.J., "Heterologous Expression in Yeast," Methods Mol. Biol., 1995, vol. 49, chapter 25, p. 341-354.
Turner G, Vectors for genetic manipulation, in Progress in Industrial Microbiology, Martinelli and Kinghorn (eds.), Elsevier, Amsterdam, 1994, 29:641-666.

* cited by examiner

FIGURE 1

SEQ ID No. 16

```
  1  ADTRPAFSRI VMFGDSLSDT GKMYSKMRGY LPSSPPYYEG RFSNGPVWLE QLTKQFPGLT
 61  IANEAEGGAT AVAYNKISWD PKYQVINNLD YEVTQFLQKD SFKPDDLVIL WVGANDYLAY
121  GWNTEQDAKR VRDAISDAAN RMVLNGAKQI LLFNLPDLGQ NPSARSQKVV EAVSHVSAYH
181  NELLDNLARQ LAPTGMVKLF EIDKQFAEML RDPQNFGLSD VENPCYDGGY VWKPFATRSV
241  STDRQLSAFS PQERLAIAGN PLLAQAVASP MARRSASPLN CEGKMFWDQV HPTTVVHAAL
301  SERAATFIET QYEFLAHG
```

FIGURE 2

(SEQ ID No. 1)

```
  1  MKKWFVCLLG LVALTVQAAD SRPAFSRIVM FGDSLSDTGK MYSKMRGYLP
 51  SSPPYYEGRF SNGPVWLEQL TKQFPGLTIA NEAEGGATAV AYNKISWNPK
101  YQVINNLDYE VTQFLQKDSF KPDDLVILWV GANDYLAYGW NTEQDAKRVR
151  DAISDAANRM VLNGAKQILL FNLPDLGQRP SARSQKVVEA VSHVSAYHNQ
201  LLLNLARQLA PTGMVKLFEI DKQFAEMLRD PQNFGLSDVE NPCYDGGYVW
251  KPFATRSVST DRQLSAFSPQ ERLAIAGNPL LAQAVASPMA RRSASPLNCE
301  GKMFWDQVHP TTVVHAALSE RAATFIANQY EFLAH*
```

FIGURE 3

(SEQ ID No. 2)

```
  1 ivafGDSlTd geayygdsdg ggwgagladr Ltallrlrar prgvdvfnrg isGrtsdGrl
 61 ivDalvallF laqslglpnL pPYLsgdflr GANFAsagAt Ilptsgpfli QvqFkdfksq
121 vlelrqalgl lqellrllpv ldakspdlvt imiGtNlit saffgpkste sdrnvsvpef
181 kdnlrqlikr Lrsnngarli vlitlvilnl gp1GC1Plkl alalassknv dasgclerln
241 eavadfneal relaiskled qlrkdglpdv kgadvpyvDl ysifqdldgi qnpsayvyGF
301 ettkaCCGyG gryNynrvCG naglcnvtak aCnpssylls flfwDgfps ekGykavAea
361 l
```

FIGURE 4

(SEQ ID No. 3)

```
  1 mkkwfvcllg lvaltvqaad srpafsrivm fgdslsdtgk myskmrgylp ssppyyegrf
 61 sngpvwleql tnefpgltia neaeggptav aynkiswnpk yqvinnldye vtqflqkdsf
121 kpddlvilwv gandylaygw nteqdakrvr daisdaanrm vlngakeill fnlpdlgqnp
181 sarsqkvvea ashvsayhnq lllnlarqla ptgmvklfei dkqfaemlrd pqnfglsdqr
241 nacyggsyvw kpfasrsast dsqlsafnpq erlaiagnpl laqavaspma arsastlnce
301 gkmfwdqvhp ttvvhaalse paatfiesqy eflah
```

FIGURE 5

SEQ ID No. 4

```
  1 mkkwfvcllg lialtvqaad trpafsrivm fgdslsdtgk myskmrgylp ssppyyegrf
 61 sngpvwleql tkqfpgltia neaeggatav aynkiswnpk yqvynnldye vtqflqkdsf
121 kpddlvilwv gandylaygw nteqdakrvr daisdaanrm vlngakqill fnlpdlgqnp
181 sarsqkvvea vshvsayhnk lllnlarqla ptgmvklfei dkqfaemlrd pqnfglsdve
241 npcydggyvw kpfatrsvst drqlsafspq erlaiagnpl laqavaspma rrsasplnce
301 gkmfwdqvhp ttvvhaalse raatfietqy eflahg
```

FIGURE 6

SEQ ID No. 5

```
  1 mpkpalrrvm tatvaavgtl algltdatah aapaqatptl dyvalgdsys agsgvlpvdp
 61 anllclrsta nyphviadtt garltdvtcg aaqtadftra qypgvapqld algtgtdlvt
121 ltiggndnst finaitacgt agvlsggkgs pckdrhgtsf ddeieantyp alkeallgvr
181 arapharvaa lgypwitpat adpscflklp laagdvpylr aiqahlndav rraaeetqat
241 yvdfsgvsdg hdaceapgtr wiepllfghs lvpvhpnalg errmaehtmd vlgld
```

FIGURE 7

SEQ ID No. 6

```
  1 mpkpalrrvm tatvaavgtl algltdatah aapaqatptl dyvalgdsys agsgvlpvdp
 61 anllclrsta nyphviadtt garltdvtcg aaqtadftra qypgvapqld algtgtdlvt
121 ltiggndnst finaitacgt agvlsggkgs pckdrhgtsf ddeieantyp alkeallgvr
181 arapharvaa lgypwitpat adpscflklp laagdvpylr aiqahlndav rraaeetqat
241 yvdfsgvsdg hdaceapgtr wiepllfghs lvpvhpnalg errmaehtmd vlgld
```

FIGURE 8

SEQ ID No. 7

```
  1 mdyekfllfg dsitefafnt rpiedgkdqy algaalvney trkmdilqrg fkgytsrwal
 61 kilpeilkhe snivmatifl gandacsagp qsvplpefid nirqmvslmk syhirpiiig
121 pglvdrekwe kekseeialg yfrtnenfai ysdalaklan eekvpfvaln kafqqeggda
181 wqqlltdglh fsgkgykifh dellkvietf ypqyhpknmq yklkdwrdvl ddgsnims
```

FIGURE 9

(SEQ ID No. 8)

```
              10         20         30         40         50         60
               |          |          |          |          |          |
        MNLRQWMGAA TAALALGLAA CGGGGTDQSG NPNVAKVQRM VVFGDSLSDI GTYTPVAQAV 70         80         90        100        110        120
               |          |          |          |          |          |
        GGGKFTTNPG PIWAETVAAQ LGVTLTPAVM GYATSVQNCP KAGCFDYAQG GSRVTDPNGI 130        140        150        160        170        180
               |          |          |          |          |          |
        GHNGGAGALT YPVQQQLANF YAASNNTFNG NNDVVFVLAG SNDIFFWTTA AATSGSGVTP 190        200        210        220        230        240
               |          |          |          |          |          |
        AIATAQVQQA ATDLVGYVKD MIAKGATQVY VFNLPDSSLT PDGVASGTTG QALLHALVGT 250        260        270        280        290        300
               |          |          |          |          |          |
        FNTTLQSGLA GTSARIIDFN AQLTAAIQNG ASFGFANTSA RACDATKINA LVPSAGGSSL 310        320        330        340
               |          |          |          |
        FCSANTLVAS GADQSYLFAD GVHPTTAGHR LIASNVLARL LADNVAH
```

FIGURE 10 (SEQ ID No. 9)

```
  1 migsyvavgd sftegvgdpg pdgafvgwad rlavlladrr pegdftytnl avrgrlldqi
 61 vaeqvprvvg lapdlvsfaa ggndiirpgt dpdevaerfe lavaaltaaa gtvlvttgfd
121 trgvpvlkhl rgkiatyngh vraiadrygc pvldiwslrs vqdrrawdad rlhlspeght
181 rvalraggal glrvpadpdq pwpplpprgt ldvrrddvhw areylvpwig rrlrgessgd
241 hvtakgtlsp daiktriaav a
```

FIGURE 11

(SEQ ID No. 10)

```
  1 mqtnpaytsl vavgdsfteg msdllpdgsy rgwadllatr maarspgfry anlavrgkli
 61 gqivdeqvdv aaamgadvit lvgglndtlr pkcdmarvrd lltqaverla phceqlvlmr
121 spgrqgpvle rfrprmealf aviddlagrh gavvvdlyga qsladprmwd vdrlhltaeg
181 hrrvaeavwq slghepedpe whapipatpp pgwvtrrtad vrfarqhllp wigrrltgrs
241 sgdglpakrp dllpyedpar
```

FIGURE 12

(SEQ ID No. 11)

```
  1 mtrgrdggag apptkhrall aaivtlivai saaiyagasa ddgsrdhalq aggrlprgda
 61 apastgawvg awatapaaae pgtettglag rsvrnvvhts vggtgaritl snlygqsplt
121 vthasialaa gpdtaaaiad tmrrltfggs arviipaggq vmsdtarlai pyganvlvtt
181 yspipsgpvt yhpqarqtsy ladgdrtadv tavayttptp ywryltaldv lsheadgtvv
241 afgdsitdqa rsqsdanhrw tdvlaarlhe aagdgrdtpr ysvvnegisg nrlltsrpgr
301 padnpsglsr fqrdvlertn vkavvvvlgv ndvlnspela drdailtglr tlvdraharg
361 lrvvgatitp fggyggytea retmrqevne eirsgrvfdt vvdfdkalrd pydprrmrsd
421 ydsgdhlhpg dkgyarmgav idlaalkgaa pvka
```

FIGURE 13 (SEQ ID No. 12)

```
  1 mtsmsrarva rriaagaayg gggiglagaa avglvvaevq larrrvgvgt ptrvpnaqgl
 61 yggtlptagd pplrlmmlgd staagqgvhr agqtpgalla sglaavaerp vrlgsvaqpg
121 acsddldrqv alvlaepdrv pdicvimvga ndvthrmpat rsvrhlssav rrlrtagaev
181 vvgtcpdlgt iervrqplrw larrasrqla aaqtigaveq ggrtvslgdl lgpefaqnpr
241 elfgpdnyhp saegyataam avlpsvcaal glwpadeehp dalrregflp varaaaeaas
301 eagtevaaam ptgprgpwal lkrrrrrrvs eaepsspsgv
```

FIGURE 14 (SEQ ID No. 13)

```
  1 mgrgtdqrtr ygrrrarval aaltaavlgv gvagcdsvgg dspapsgsps krtrtapawd
 61 tspasvaavg dsitrgfdac avlsdcpevs watgssakvd slavrllgka daaehswnya
121 vtgarmadlt aqvtraaqre pelvavmaga ndacrsttsa mtpvadfraq feeamatlrk
181 klpkaqvyvs sipdlkrlws qgrtnplgkq vwklglcpsm lgdadsldsa atlrrntvrd
241 rvadynevlr evcakdrrcr sddgavhefr fgtdqlshwd wfhpsvdgqa rlaeiayrav
301 taknp
```

FIGURE 15 (SEQ ID No. 14)

```
  1 mrlsrraata sallltpala lfgasaavsa priqatdyva lgdsyssgvg agsydsssgs
 61 ckrstksypa lwaashtgtr fnftacsgar tgdvlakqlt pvnsgtdlvs itiggndagf
121 adtmttcnlq qesaclaria karayiqqtl paqldqvyda idsrapaaqv vvlgyprfyk
181 lggscavgls eksraainaa addinavtak raadhgfafg dvnttfaghe lcsgapwlhs
241 vtlpvensyh ptangqskgy lpvlnsat
```

FIGURE 16 (SEQ ID No. 15)

```
  1 MKKWFVCLLG LIALTVQAAD TRPAFSRIVM FGDSLSDTGK MYSKMRGYLP
 51 SSPFYYEGRF SNGPVWLEQL TKQFPGLTIA NEAEGGATAV AYNKISWNPK
101 YQVINNLDYE VTQFLQKDSF KPDDLVILWV GANDYLAYGW NTEQDAKRVR
151 DAISDAANRM VLNGAKQILL FNLPDLGQNP SARSQKVVEA VSHVSAYHNK
201 LLLNLARQLA PTGMVKLFEI DKQFAEMLRD PQNFGLSDVE NPCYDGGYVW
251 KPFATRSVST DRQLSAFSPQ ERLAIAGNPL LAQAVASPMA RRSASPLNCE
301 GKMFWDQVHP TTVVHAALSE RAATFIETQY EFLAHG*
```

FIGURE 17 (SEQ ID No. 19)

```
  1 migsyvavgd sftegvgdpg pdgafvgwad rlavlladrr pegdftytnl avrgrlldqi
 61 vaeqvprvvg lapdlvsfaa ggndiirpgt dpdevaerfe lavaaltaaa gtvlvttgfd
121 trgvpvlkhl rgkiatyngh vraiadrygc pvldlwslrs vqdrrawdad rlhlspeght
181 rvalragqal glrvpadpdq pwpplpprgt ldvrrddvhw areylvpwig rrlrgessgd
241 hvtakgtlsp daiktriaav a
```

FIGURE 18 (SEQ ID No. 25)

```
  1 MFKFKKNFLV GLSAALMSIS LFSATASAAS ADSRPAFSRI VMFGDSLSDT
 51 GKMYSKMRGY LPSSPPYYEG RFSNGPVWLE QLTKQFPGLT IANEAEGGAT
101 AVAYNKISWN PKYQVINNLD YEVTQFLQKD SFKPDDLVIL WVGANDYLAY
151 GWNTEQDAKR VRDAISDAAN RMVLNGAKQI LLFNLPDLGQ NPSARSQKVV
201 EAVSHVSAYH NQLLLNLARQ LAPTGMVKLF EIDKQFAEML RDPQNFGLSD
251 VENPCYDGGY VWKPFATRSV STDRQLSAFS PQERLAIAGN PLLAQAVASP
301 MARRSASPLN CEGKMFWDQV HPTTVVHAAL SERAATFIAN QYEFLAH**
```

FIGURE 19

(SEQ ID NO. 26)

MRLTRSLSAASVIVFALLLALLGISPAQAAGPAYVALGDSYSSGNGAGSYIDSSGDCHRSN
NAYPARWAAANAPSSFTFAACSGAVTTDVINNQLGALNASTGLVSITIGGNDAGFADAMTT
CVTSSDSTCLNRLATATNYINTTLLARLDAVYSQIKARAPNARVVVLGYPRMYLASNPWYC
LGLSNTKRAAINTTADTLNSVISSRATAHGFRFGDVRPTFNNHELFFGNDWLHSLTLPVWE
SYHPTSTGHQSGYLPVLNANSST

Figure 20

SEQ ID No. 27

ZP_00058717
```
  1 mlphpagerg evgaffallv gtpqdrrlrl echetrplrg rcgcgerrvp pltlpgdgvl
 61 cttsstrdae tvwrkhlqpr pdggfrphlg vgcllagqgs pgvlwcgreg crfevcrrdt
121 pglsrtrngd ssppfragws lppkcgeisq sarktpavpr ysllrtdrpd gprgrfvgsg
181 praatrrrlf lgipalvlvt altlvlavpt gretlwrmwc eatqdwclgv pvdsrgqpae
241 dgeflllspv qaatwgnyya lgdsyssgdg ardyypgtav kggcwrsana ypelvaeayd
301 faghlsflac sgqrgyamld aidevgsqld wnsphtslvt igiggndlgf stvlktcmvr
361 vplldskact dqedairkrm akfettfeel isevrtrapd arilvvgypr ifpeeptgay
421 ytltasnqrw lnetiqefnq qlaeavavhd eeiaasggvg svefvdvyha ldgheigsde
481 pwvngvqlrd latgvtvdrs tfhpnaaghr avgervieqi etgpgrplya tfavvagatv
541 dtlagevg
```

FIGURE 21

(SEQ ID No. 28)
```
  1 mgsgpraatr rrlflgipal vlvtaltlvl avptgretlw rmwceatqdw clgvpvdsrg
 61 qpaedgefll lspvqaatwg nyyalgdsys sgdgardyyp gtavkggcwr sanaypelva
121 eaydfaghls flacsgqrgy amldaidevg sqldwnspht slvtigiggn dlgfstvlkt
181 cmvrvpllds kactdqedai rkrmakfett feelisevrt rapdarilvv gyprifpeep
241 tgayytltas nqrwlnetiq efnqqlaeav avhdeeiaas ggvgsvefvd vyhaldghei
301 gsdepwvngv qlrdlatgvt vdrstfhpna aghravgerv ieqietgpgr plyatfavva
361 gatvdtlage vg
```

FIGURE 22

(SEQ ID No. 29)

```
  1 mrttviaasa llllagcadg areetagapp gessggiree gaeastsitd vylalgdsya
 61 amggrdqplr gepfclrssg nypellhaev tdltcqgavt gdlleprtlg ertlpaqvda
121 ltedttlvtl siggndlgfg evagcireri agenaddcvd llgetigeql dqlppqldrv
181 heairdragd aqvvvtgylp lvsagdcpel gdvseadrrw aveltgqine tvreaaerhd
241 alfvlpddad ehtscappqq rwadiqgqqt dayplhptsa gheamaaavr dalglepvqp
```

FIGURE 23

(SEQ ID No. 30)

ZP_00094165

```
  1 mgqvklfarr capvllalag lapaatvare aplaegaryv algssfaagp gvgpnapgsp
 61 ercgrgtlny phllaealkl dlvdatcsga tthhvlgpwn evppqidsvn gdtrlvtlti
121 ggndvsfvgn ifaaacekma spdprcgkwr eiteeewqad eermrsivrq iharaplarv
181 vvvdyitvlp psgtcaamai spdrlaqsrs aakrlarita rvareegasl lkfshisrrh
241 hpcsakpwsn glsapaddgi pvhpnrlgha eaaaalvklv klmk //
```

FIGURE 24

SEQ ID No. 31

NP_625998.

```
  1 mrrfrlvgfl sslvlaagaa ltgaataqaa qpaaadgyva lgdsyssgvg agsyisssgd
 61 ckrstkahpy lwaaahspst fdftacsgar tgdvlsgqlg plssqtglvs isiggndagf
121 adtmttcvlq sessclsria taeayvdstl pgkldgvysa isdkapnahv vvigyprfyk
181 lgttciglse tkrtainkas dhlntvlaqr aaahgftfgd vrttftghel csgspwlhsv
241 nwlnigesyh ptaagqsggy lpvlngaa
//
```

FIGURE 25

SEQ ID No. 32

NP_827753.
```
  1 mrrsritayv tslllavgca ltgaataqas paaaatgyva lgdsyssgvg agsylsssgd
 61 ckrsskaypy lwqaahspss fsfmacsgar tgdvlanqlg tlnsstglvs ltiggndagf
121 sdvmttcvlq sdsaclsrin takayvdstl pgqldsvyta istkapsahv avlgyprfyk
181 lggsclagls etkrsainda adylnsaiak raadhgftfg dvkstftghe icssstwlhs
241 ldllnigqsy hptaagqsgg ylpvmnsva
//
```

FIGURE 26

SEQ ID No. 33

MRLTRSLSAASVIVFALLLALLGISPAQAAGPAYVALGDSYSSGNGAGSYIDSSGDCHRSN
NAYPARWAAANAPSSFTFAACSGAVTTDVINNQLGALNASTGLVSITIGGNDAGFADAMTT
CVTSSDSTCLNRLATATNYINTTLLARLDAVYSQIKARAPNARVVLGYPRMYLASNPWYC
LGLSNTKRAAINTTADTLNSVISSRATAHGFRFGDVRPTFNNHELFFGNDWLHSLTLPVWE
SYHPTSTGHQSGYLPVLNANSST

FIGURE 27

(SEQ ID No. 34)

```
ADSRPAFSRIVMFGDSLSDTGKMYSKMRGYLPSSPPYYEGRFSNGPVWLEQLTNEFPGLTIANEAEGGPT
AVAYNKISWNPKYQVINNLDYEVTQFLQKDSFKPDDLVILWVGANDYLAYGWNTEQDAKRVRDAISDAAN
RMVLNGAKEILLFNLPDLGQNPSARSQKVVEAASHVSAYHNQLLLNLARQLAPTGMVKLFEIDKQFAEML
RDPQNFGLSDQRNACYGGSYVWKPFASRSASTDSQLSAFNPQERLAIAGNPLLAQAVASPMAARSASTLN
CE
GKMFWDQVHPTTVVHAALSEPAATFIESQYEFLAH
```

FIGURE 28

(SEQ ID No. 35)

```
  1   ADTRPAFSRI VMFGDSLSDT GKMYSKMRGY LPSSPPYYEG RFSNGPVWLE QLTKQFPGLT
 61   IANEAEGGAT AVAYNKISWN PKYQVINNLD YEVTQFLQKD SFKPDDLVIL WVGANDYLAY
121   GWNTEQDAKR VRDAISDAAN RMVLNGAKQI LLFNLPDLGQ NPSARSQKVV EAVSHVSAYH
181   NKLLLNLARQ LAPTGMVKLF EIDKQFAEML RDPQNFGLSD VENPCYDGGY VWKPFATRSV
241   STDRQLSAFS PQERLAIAGN PLLAQAVASP MARRSASPLN CEGKMFWDQV HPTTVVHAAL
301   SERAATFIET QYEFLAHG
```

FIGURE 29

(SEQ ID No. 36)

```
ACAGGCCGATGCACGGAACCGTACCTTTCCGCAGTGAAGCGCTCTCCCCCCATCGTTCGC
CGGGACTTCATCCGCGATTTTGGCATGAACACTTCCTTCAACGCGCGTAGCTTGCTACAA
GTGCGGCAGCAGACCCGCTCGTTGGAGGCTCAGTGAGATTGACCCGATCCCTGTCGGCCG
CATCCGTCATCGTCTTCGCCCTGCTGCTCGCGCTGCTGGGCATCAGCCCGGCCCAGGCAG
CCGGCCCGGCCTATGTGGCCCTGGGGGATTCCTATTCCTCGGGCAACGGCGCCGGAAGTT
ACATCGATTCGAGCGGTGACTGTCACCGCAGCAACAACGCGTACCCCGCCCGCTGGGCGG
CGGCCAACGCACCGTCCTCCTTCACCTTCGCGGCCTGCTCGGGAGCGGTGACCACGGATG
TGATCAACAATCAGCTGGGCGCCCTCAACGCGTCCACCGGCCTGGTGAGCATCACCATCG
GCGGCAATGACGCGGGCTTCGCGGACGCGATGACCACCTGCGTCACCAGCTCGGACAGCA
CCTGCCTCAACCGGCTGGCCACCGCCACCAACTACATCAACACCACCCTGCTCGCCCGGC
TCGACGCGGTCTACAGCCAGATCAAGGCCCGTGCCCCAACGCCCGCGTGGTCGTCCTCG
GCTACCCGCGCATGTACCTGGCCTCGAACCCCTGGTACTGCCTGGGCCTGAGCAACACCA
AGCGCGCGGCCATCAACACCACCGCCGACACCCTCAACTCGGTGATCTCCTCCCGGGCCA
CCGCCCACGGATTCCGATTCGGCGATGTCCGCCCGACCTTCAACAACCACGAACTGTTCT
TCGGCAACGACTGGCTGCACTCACTCACCCTGCCGGTGTGGGAGTCGTACCACCCCACCA
GCACGGGCCATCAGAGCGGCTATCTGCCGGTCCTCAACGCCAACAGCTCGACCTGATCAA
CGCACGGCCGTGCCCGCCCCGCGCGTCACGCTCGGCGCGGGCGCCGCAGCGCGTTGATCA
GCCCACAGTGCCGGTGACGGTCCCACCGTCACGGTCGAGGGTGTACGTCACGGTGGCGCC
GCTCCAGAAGTGGAACGTCAGCAGGACCGTGGAGCCGTCCCTGACCTCGTCGAAGAACTC
CGGGGTCAGCGTGATCACCCCTCCCCCGTAGCCGGGGGCGAAGGCGGCGCCGAACTCCTT
GTAGGACGTCCAGTCGTGCGGCCCGGCGTTGCCACCGTCCGCGTAGACCGCTTCCATGGT
CGCCAGCCGGTCCCCGCGGAACTCGGTGGGGATGTCCGTGCCCAAGGTGGTCCCGGTGGT
GTCCGAGAGCACCGGGGGCTCGTACCGGATGATGTGCAGATCCAAAGAATT
```

FIGURE 30

(SEQ ID NO. 37):

```
MRLTRSLSAASVIVFALLLALLGISPAQAAGPAYVALGDSYSSGNGAGSYIDSSGDCHRSN
NAYPARWAAANAPSSFTFAACSGAVTTDVINNQLGALNASTGLVSITIGGNDAGFADAMTT
CVTSSDSTCLNRLATATNYINTTLLARLDAVYSQIKARAPNARVVVLGYPRMYLASNPWYC
LGLSNTKRAAINTTADTLNSVISSRATAHGFRFGDVRPTFNNHELFFGNDWLHSLTLPVWE
SYHPTSTGHQSGYLPVLNANSST
```

FIGURE 31

SEQ ID No. 38

```
  1 mlphpagerg evgaffallv gtpqdrrlrl echetrplrg rcgcgerrvp pltlpgdgvl
 61 cttsstrdae tvwrkhlqpr pdggfrphlg vgcllagqgs pgvlwcgreg crfevcrrdt
121 pglsrtrngd ssppfragws lppkcgeisq sarktpavpr ysllrtdrpd gprgrfvgsg
181 praatrrrlf lgipalvlvt altlvlavpt gretlwrmwc eatqdwclgv pvdsrgqpae
241 dgeflllspv qaatwgnyya lgdsyssgdg ardyypgtav kggcwrsana ypelvaeayd
301 faghlsflac sgqrgyamld aidevgsqld wnsphtslvt igiggndlgf stvlktcmvr
361 vplldskact dqedairkrm akfettfeel isevrtrapd arilvvgypr ifpeeptgay
421 ytltasnqrw lnetiqefnq qlaeavavhd eeiaasggvg svefvdvyha ldgheigsde
481 pwvngvqlrd latgvtvdrs tfhpnaaghr avgervieqi etgpgrplya tfavvagatv
541 dtlagevg
```

FIGURE 32

(SEQ ID No. 39)

```
   1 ggtggtgaac cagaacaccc ggtcgtcggc gtgggcgtcc aggtgcaggt gcaggttctt
  61 caactgctcc agcaggatgc cgccgtggcc gtgcacgatg gccttgggca ggcctgtggt
 121 cccgacgag tacagcaccc atagcggatg gtcgaacggc agcggggtga actccagttc
 181 cgcgccttcg cccgcggctt cgaactccgc ccaggacagg gtgtcggcga cagggccgca
 241 gcccaggtac ggcaggacga cggtgtgctg caggctgggc atgccgtcgc gcagggcttt
 301 gagcacgtca cggcggtcga agtccttacc gccgtagcgg tagccgtcca cggccagcag
 361 cactttcggt tcgatctgcg cgaaccggtc gaggacgctg cgcaccccga agtcggggga
 421 acaggacgac caggtcgcac cgatcgcggc gcaggcgagg aatgcggccg tcgcctcggc
 481 gatgttcggc aggtaggcca cgacccggtc gccggggccc accccgaggc tgcggagggc
 541 cgcagcgatc gcggcggtgc gggtccgcag ttctccccag gtccactcgg tcaacggccg
 601 gagttcggac gcgtgccgga tcgccacggc tgatgggtca cggtcgcgga agatgtgctc
 661 ggcgtagttg agggtggcgc cggggaacca gacggcgccg gcatggcgt cggaggcgag
 721 cactgtggtg tacggggtgg cggcgcgcac ccggtagtac tcccagatcg cggaccagaa
 781 tccttcgagg tcggttaccg accagcgcca cagtgcctcg tagtccggtg cgtccacacc
 841 gcggtgctcc cgcacccagc gggtgaacgc ggtgaggttg gcgcgttctt tgcgctcctc
 901 gtcgggactc cacaggatcg gcggctgcgg cttgagtgtc atgaaacgcg accccttcgt
 961 ggacggtgcg gatgcggtga gcgtcgggtg cctccctaa cgctccccgg tgacggagtg
1021 ttgtgcacca catctagcac gcgggacgcg gaaaccgtat ggagaaaaca cctacaaccc
1081 cggccggacg gtgvgtttcg gccacactta ggggtcgggt gcctgcttgc cgggcagggc
1141 agtcccgggg tgctgtggtg cggcggggag ggctgtcgct tcgaggtgtg ccggcgggac
1201 actccgggcc tcagccgtac ccgcaacggg gacagttctc ctcccttccg ggctggatgg
1261 tccttcccc cgaaatgcgg cgagatctcc cagtcagccc ggaaaacacc cgctgtgccc
1321 aggtactctt tgcttcgaac agacaggccg gacggtccac gggggaggtt tgtgggcagc
1381 ggaccacgtg cggcgaccag acgacggttg ttcctcggta tccccgctct tgtacttgtg
1441 acagcgctca cgctggtctt ggctgtcccg acggggcgcg agatgctgtg gcgcatgtgg
1501 tgtgaggcca cccaggactg gtgcctgggg gtgccggtcg actcccgcgg acagcctgcg
1561 gaggacggcg agtttctgct gctttctccg gtccaggcag cgacctgggg gaactattac
1621 gcgctcgggg attcgtactc ttcgggggac ggggcccgcg actactatcc cggcaccgcg
1681 gtgaagggcg gttgctggcg gtccgctaac gcctatccgg agctggtcgc cgaagcctac
1741 gacttcgccg gacacttgtc gttcctggcc tgcagcggcc agcgcggcta cgccatgctt
1801 gacgctatcg acgaggtcgg ctcgcagctg gactggaact ccctcacac gtcgctggtg
1861 acgatcggga tcggcggcaa cgatctgggg ttctccacgg ttttgaagac ctgcatggtg
1921 cgggtgccgc tgctggacag caaggcgtgc acggaccagg aggacgctat ccgcaagcgg
1981 atggcgaaat tcgagacgac gtttgaagag ctcatcagcg aagtgcgcac ccgcgcgccg
2041 gacgcccgga tccttgtcgt gggctacccc cggattttc cggaggaacc gaccggcgcc
2101 tactacacgc tgaccgcgag caaccagcgg tggctcaacg aaaccattca ggagttcaac
2161 cagcagctcg ccgaggctgt cgcggtccac gacgaggaga ttgccgcgtc gggcggggtg
2221 ggcagcgtgg agttcgtgga cgtctaccac gcgttggacg gccacgagat cggctcggac
2281 gagccgtggg tgaacggggt gcagttgcgg gacctcgcca ccggggtgac tgtggaccgc
2341 agtaccttcc accccaacgc cgctgggcac cgggcggtcg gtgagcgggt catcgagcag
2401 atcgaaaccg gccgggccg tccgctctat gccactttcg cggtggtggc ggggcgacc
2461 gtggacactc tcgccggcga ggtggggtga cccggcttac cgtccggccc gcaggtctgc
2521 gagcactgcg gcgatctggt ccactgccca gtgcagttcg tcttcggtga tgaccagcgg
2581 cggggagagc cggatcgttg agccgtgcgt gtctttgacg agcacacccc gctgcaggag
2641 ccgttcgcac agttctcttc cggtggccag agtcgggtcg acgtcgatcc cagcccacag
2701 gccgatgctg cgggccgcga ccacgccgtt gccgaccagt tggtcgaggc gggcgcgcag
2761 cacgggggcg agggcgcgga catggtccag gtaagggccg tcgcggacga ggctcaccac
2821 ggcagtgccg accgcgcagg cgagggcgtt gccgccgaag tgctgccgt gctggccggg
2881 gcggatcacg tcgaagactt ccgcgtcgcc taccgccgcc gccacgggca ggatgccgcc
2941 gcccagcgct tgccgaaca ggtagatatc ggcgtcgact ccgctgtggt cgcaggcccg
```

FIGURE 33

(SEQ ID No. 40)

```
  1 vgsgpraatr rrlflgipal vlvtaltlvl avptgretlw mmwceatqdw clgvpvdsrg
 61 qpaedgefll lspvqaatwg nyyalgdsys sgdgardyyp gtavkggcwr sanaypelva
121 eaydfaghls flacsgqrgy amldaidevg sqldwnspht slvtigiggn dlgfstvlkt
181 cmvrvpllds kactdqedai rkrmakfett feelisevrt rapdarilvv gyprifpeep
241 tgayytltas nqrwlnetiq efnqqlaeav avhdeeiaas ggvgsvefvd vyhaldghei
301 gsdepwvngv qlrdlatgvt vdrstfhpna aghravgerv ieqietgpgr plyatfavva
361 gatvdtlage vg
```

FIGURE 34

(SEQ ID No. 41)

```
  1 mrttviaasa lllagcadg areetagapp gessggiree gaeastsitd vyialgdsya
 61 amggrdqplr gepfclrssg nypellhaev tdltcqgavt gdlleprtlg ertlpaqvda
121 ltedttlvtl siggndlgfg evagcireri agenaddcvd llgetigeql dqlppqldrv
181 heairdragd aqvvvtgylp lvsagdcpel gdvseadrrw aveltgqine tvreaaerhd
241 alfvlpddad ehtscappqq rwadiqgqqt dayplhptsa gheamaaavr dalglepvqp
```

FIGURE 35

(SEQ ID No. 42)

```
   1 ttctggggtg ttatggggtt gttatcggct cgtcctgggt ggatcccgcc aggtggggta
  61 ttcacggggg actttttgtgt ccaacagccg agaatgagtg ccctgagcgg tgggaatgag
 121 gtgggcgggg ctgtgtcgcc atgaggggc ggcgggctct gtggtgcccc gcgaccccg
 181 gccccggtga gcggtgaatg aaatccggct gtaatcagca tcccgtgccc acccccgtcgg
 241 ggaggtcagc gcccggagtg tctacgcagt cggatcctct cggactcggc catgctgtcg
 301 gcagcatcgc gctccggggt cttggcgtcc ctcggctgtt ctgcctgctg tccctggaag
 361 gcgaaatgat caccggggag tgatacaccg gtggtctcat cccggatgcc cacttcggcg
 421 ccatccggca attcgggcag ctccgggtgg aagtaggtgg catccgatgc gtcggtgacg
 481 ccatagtggg cgaagatctc atcctgctcg agggtgctca ggccactctc cggatcgata
 541 tggggcgt ccttgatggc gtccttgctg aaaccgaggt gcagcttgtg ggcttccaat
 601 ttcgcaccac ggagcgggac gaggctggaa tgacggccga agagcccgtg gtggacctca
 661 acgaaggtgg gtagtcccgt gtcatcattg aggaacacgc cctccaccgc acccagcttg
 721 tggccggagt tgtcgtaggc gctggcatcc agaagggaaa cgatctcata tttgtcggtg
 781 tgctcagaca tgatcttcct ttgctgtcgg tgtctggtac taccacggta gggctgaatg
 841 caactgttat ttttctgtta ttttaggaat tggtccatat cccacaggct ggctgtggtc
 901 aaatcgtcat caagtaatcc ctgtcacaca aaatgggtgg tgggagccct ggtcgcggtt
 961 ccgtggggagg cgccgtgccc cgcaggatcg tcggcatcgg cggatctggc cggtaccccg
1021 cggtgaataa aatcattctg taaccttcat cacggttggt tttaggtatc cgcccttttc
1081 gtcctgaccc cgtccccggc gcgcgggagc ccgcggttg cggtagacag gggagacgtg
1141 gacaccagga ggacaaccggt catccagca agcgcattac tccttctcgc cggatgcgcg
1201 gatggggccc gggaggagac cgccggtgca gccgggtg agtcctccgg gggcatccgg
1261 gaggagggg cggaggcgtc gacaagcatc accgacgtct acatcgccct cggggattcc
1321 tatgcggcga tgggcgggcg ggatcagccg ttacgggtg agccgttctg cctgcgctcg
1381 tccggtaatt acccggaact cctccacgca gaggtcaccg atctcacctg ccagggggcg
1441 gtgaccgggg atctgctcga acccaggacg ctggggggagc gcacgctgcc ggcgcaggtg
1501 gatgcgctga cggaggacac caccctggtc accctctcca tggggggcaa tgacctcgga
1561 ttcggggagg tggcgggatg catccgggca cggatcgccg gggagaacgc tgatgattgc
1621 gtggacctgc tgggggaaac catcgggggag cagctcgatc agcttcccc gcagctggac
1681 cgcgtgcacg aggctatccg ggaccgcgcc ggggacgcgc aggttgtggt caccggttac
1741 ctgccgctcg tgtctgccgg ggactgcccc gaactggggg atgtctccga ggcggatcgt
1801 cgttgggcgg ttgagctgac cgggcagatc aacgagaccg tgcgcgaggc ggccgaacga
1861 cacgatgccc tctttgtcct gccgacgact gccgatgagc acaccagttg tgcacccccca
1921 cagccgcgct gggcggatat ccaggccaa cgaccgatg cctatccgct gcacccgacc
1981 tccccggcc atgaggcgat ggcgccgcc gtccgggacg cgctgggcct ggaaccggtc
2041 cagccgtagc gccggcgcg cgcttgtcga cgaccaaccc atgccaggct gcagtcacat
2101 ccgcacatag cgcgcgcggg cgatggagta cgcaccatag aggatgagcc cgatgccgac
2161 gatgatgagc agcacactgc cgaagggttg ttccccgagg gtgcgcagag ccgagtccag
2221 acctgcggcc tgctccggat catggcccca acggcgcatg acgatcaaca ccccaggat
2281 cccgaaggcg ataccacggg cgacataacc ggctgttccg gtgatgatga tcgcggtccc
2341 gacctgccct gacccgcac ccgcctccag atcctcccgg aaatcccggg tggccccctt
2401 ccagaggttg tagacacccg ccccagtac caccagcccg gcgaccacaa ccagcaccac
2461 accccagggt tgggatagga cggtggcggt gacatcggtg gcggtctccc catcggaggt
2521 gctgccgcc cgggcgaagg tggaggtggt caccgccagg gagaagtaga ccatggccat
2581 gaccgccccc ttggcccttt ccttgaggtc ctcgcccgcc agcagctggc tcaattgcca
2641 gagtcccagg gccgccagg cgatgccgg aacccacagg aggaactgca caccggagc
2701 ctccgcgatg gtggccaggg cacctgaatt cgaggcctca tcacccgaac cgccggatcc
2761 agtggcgatg cgcaccgcga tccaccccgat gaggatgtgc agtatgccca ggacaatgaa
2821 accacctctg gccagggtgg tcagcgcggg gtggtcctcg gcctggtcgg cagcccgttc
2881 gatcgtccgt ttcgcggatc tggtgtcgcc cttatccata gctcccattg aaccgccttg
2941 aggggtgggc ggccactgtc agggcggatt gtgatctgaa ctgtgatgtt ccatcaaccc
```

FIGURE 36

(SEQ ID No. 43)

```
  1 mrrfrlvgfl sslvlaagaa ltgaataqaa qpaaadgyva lgdsyssgvg agsyisssgd
 61 ckrstkahpy lwaaahspst fdftacsgar tgdvlsgqlg plssgtglvs isiggndagf
121 adtmttcvlq sessclsria taeayvdstl pgkldgvysa isdkapnahv vvigyprfyk
181 lgttciglse tkrtainkas dhlntvlaqr aaahgftfgd vrttftqhel csgspwlhsv
241 nwlnigesyh ptaagqsggy lpvlngaa
```

Figure 37

(SEQ ID No. 44)

```
   1 cccggcggcc cgtgcaggag cagcagccgg ccgcgatgt cctcgggcgt cgtcttcatc
  61 aggccgtcca tcgcgtcggc gaccggcgcc gtgtagttgg cccggaccctc gtcccaggtg
 121 cccgcggcga tctggcgggt ggtgcggtgc gggccgcgcc gagggagac gtaccagaag
 181 cccatcgtca cgttctccgg ctgcggttcg ggctcgtccg ccgctccgtc cgtcgcctcg
 241 ccgagcacct tctcggcgag gtcggcgctg gtcgccgtca ccgtgacgtc ggcgcccgg
 301 ctccagcgcg agatcagcag cgtccagccg tcgccctccg ccagcgtcgc gctgcggtcg
 361 tcgtcgcggg cgatccgcag cacgcgcgcg cgggcggca gcagcgtggc gcggaccgt
 421 acgcggtcga tgttcgccgc gtgcgagtac ggctgctcac ccgtggcgaa acggccgagg
 481 aacagcgcgt cgacgacgtc ggacggggag tcgctgtcgt ccacgttgag ccggatcggc
 541 agggcttcgt gcgggttcac ggacatgtcg ccatgatcgg gcaccggcc gccgcgtgca
 601 cccgctttcc cgggcacgca cagcaggggc tttctcgccg tcttccgtcc gaacttgaac
 661 gagtgtcagc catttcttgg catgacact tccagtcaac gcgcgtagct gctaccacgg
 721 ttgtggcagc aatcctgcta agggaggttc catgagacgt ttccgacttg tggcttcct
 781 gagttcgctc gtcctcgccg ccggcgccgc cctcaccggg gcagcgaccg cccaggcggc
 841 ccaaccgcc gccgccgacg gctatgtggc cctcggcgac tcctactcct ccgggtcgg
 901 agcgggcagc tacatcagct cgagcggcga ctgcaagcgc agcacgaagg cccatcccta
 961 cctgtgggcg gccgcccact cgccctccag gttcgacttc accgcctgtt ccggcgccg
1021 tacggttgat gttctccgg gacagtcgg ccgctcagc tccggcaccg gcctcgtctc
1081 gatcagcatc ggcggcaacg acgccggttt cgccgacacc atgacgacct gtgtgctcca
1141 gtccgagagc tcctgcctgt cgcggatcgc cacgcgcgag gcgtacgtcg actcgacgct
1201 gcccggcaag ctcgacggcg tctactcggc aatcagcgac aaggcgccga acgccacgt
1261 cgtcgtcatc ggctaccgc gcttctacaa gctcggcacc acctgcatcg gcctgtccga
1321 gaccaagcgg acggcgatca acaaggcctc cgaccacctc aacaccgtcc tcgcccagcg
1381 cgccgccgcc cacggcttca ccttcggcga cgtacgcacc accttcaccg gcacgagct
1441 gtgctccggc agcccctggc tgcacagcgt caactggctg aacatcggcg agtcgtacca
1501 cccacgcg gcggccagt ccggtggcta cctgccggtc ctcaacggcg ccgcctgacc
1561 tcaggcggaa ggagaagaag aaggagcgga gggagacgag gagtgggagg cccgccga
1621 cggggtcccc gtcccgtct ccgtctccgt cccggtcccg caagtcaccg agaacgccac
1681 cgcgtcggac gtgcccgca ccggactccg caacctccacg cgcacggcac tctcgaacgc
1741 gccggtgtcg tcgtcgtcg tcaccaccac gccgtcctgg cgcgagcgct cgccgccga
1801 cgggaaggac agcgtccgcc accccggatc ggagaccgac ccgtccgcgg tcacccaccg
1861 gtagccgacc tcgcgggca gcgcccgac cgtgaacgtc gccgtgaacg cgggtgccg
1921 gtcgtcgcgg gcggacagg cccccgagta gtgggtgcgc gagcccacca cggtcacctc
1981 caccgactgc gctgcggggc
```

FIGURE 38

(SEQ ID No. 45)

```
  1 mrrsritayv tslllavgca ltgaataqas paaaatgyva lgdsyssgvg agsylsssgd
 61 ckrsskaypy lwqaahspss fsfmacsgar tgdvlanqlg tlnsstglvs ltiggndagf
121 sdvmttcvlq sdsaclsrin takayvdstl pgqldsvyta istkapsahv avlgyprfyk
181 lggsclagls etkrsainda adylnsaiak raadhgftfg dvkstftghe icssstwlhs
241 ldllnigqsy hptaagqsgg ylpvmnsva
```

FIGURE 39

SEQ ID No. 46

```
    1 ccaccgcgg gtcggcggcg agtctcctgg cctcggtcgc ggagaggttg gccgtgtagc
   61 cgttcagcgc ggcgccgaac gtcttcttca ccgtgccgcc gtactcgttg atcaggccct
  121 tgcccttgct cgacgcggcc ttgaagccgg tgcccttctt gagcgtgacg atgtagctgc
  181 ccttgatcgc ggtgggggag cggcggcga gcaccgtgcc ctcggccggg gtggcctggg
  241 cgggcagtgc ggtgaatccg cccacgaggg cgccggtcgc cacggcggtt atcgcggcga
  301 tccggatctt cttgctacgc agctgtgcctca tcctcctctg ggcagcgcg
  361 cgcctgggtg gggcgcacgg ctgtgggggg tgcgcgcgtc atcacgcaca cggccctgga
  421 gcgtcgtgtt ccgccctggg ttgagtaaag cctcggccat ctacggggt ggctcaaggg
  481 agttgagacc ctgtcatgag tctgacatga gcacgcaatc aacggggccg tgagcaccc
  541 ggggcgaccc cggaaagtgc cgagaagtct tggcatggac acttcctgtc aacacgcgta
  601 gctggtacga cggttacggc agagatcctg ctaaagggag gttccatgag acgttcccga
  661 attacggcat acgtgacctc actcctcctc gccgtcggct gcgccctcac cggggcagcg
  721 acggcgcagg cgtccccagc cgccgcggcc acgggctatg tggccctcgg cgactcgtac
  781 tcgtccggtc tcggcgcgg cagctacctc agctccagcg gcgactgcaa gcgcagttcg
  841 aaggcctatc cgtacctctg gcaggccgcg cattcaccct cgtcgttcag tttcatggct
  901 tgctcggccg ctcgtacggg tgatgtcctg gccaatcage tcggcaccct gaactcgtcc
  961 accggcctgg tctccctcac catcggaggc aacgacgcgg gcttctcacga cgtcatgacg
 1021 acctgtgtgc tccagtccga cagcgcctgc ctctcccgca tcaacacggc gaaggcgtac
 1081 gtcgactcca ccctgccgg ccaactcgac agcgtgtaca cggcgatcag cacgaaggcc
 1141 ccgtcggccc atgtggccgt gctgggctac acaaactggg cggctcctgc
 1201 ctcgcgggcc tctcggagac caagcggtcc gccatcaacg acgcggcga ctatctgaac
 1261 agcgccatcg ccaagcgcgc cgccgaccac ggcttcacct tcggcgacgt caagagcacc
 1321 ttcacggcc atgagatctg ctccagcagc acctggctgc acagtctcga cctgctgaac
 1381 atcggccagt cctaccacc gaccgcggcc ggccagtcgg gcggctatct gccggtcatg
 1441 aacagcgtgg cctgagctcc cacgcctga attttaagg cctgaattt taaggcgaag
 1501 gtgaaccgga agcggaggcc ccgtccgtcg gggtctccgt cgcacaggtc accgagaacg
 1561 gcacggagtt ggacgtcgtg cgcaccgggt cgcgcaccct gacggcgatc tcgttcgaga
 1621 tcgttccgct cgtgtcgtac gtggtgacga cacctgctt ctgctgggtc tttccgccgc
 1681 tcgccggaa ggacagcgtc ttccagcccg gatccggac ctcgccttc ttggtcaccc
 1741 agccggtactc cacctcgacc ggcacccggc ccacgtgaa ggtcgccgtg aacgtgggcg
 1801 cctggcggt gggcggcggg caggcaccgg agtagtcggt gtgcacgccg gtgaccgtca
 1861 ccttcacgga ctggccggc ggggtcgtcg taccgccgcc gccaccgccg cctcccggag
 1921 tggagcccga gctgtggtcg ccccgccgt cggcgttgtc gtcctcgggg gttttcgaac
```

FIGURE 40

SEQ ID No. 47

```
  1 mgsgpraatr rrlflgipal vlvtaltlvl avptgretlw rmwceatqdw clgvpvdsrg
 61 qpaedgefll lspvqaatwg nyyalgdsys sgdgardyyp gtavkggcwr sanaypelva
121 eaydfaghls flacsgqrgy amldaidevg sqldwnspht slvtigiggn dlgfstvlkt
181 cmvrvpllds kactdqedai rkmakfett fseelisevrt rapdarilvv gyprifpeep
241 tgayytltas nqrwlnetiq efnqqlasav avhdeeisas ggvgsvefvd vyhaldghei
301 gsdepwvngv qlrdlatgvt vdrstfhpna aghravgerv ieqietgpgr plyatfavva
361 gatvdtlage vg
```

FIGURE 41

SEQ ID No. 48

```
  1   ctgcagacac ccgcccgcc ttctcccgga tcgtcatgtt cggcgactcc ctcagcgaca
 61   ccggcaagat gtactccaag atgcgcggct acctgccgtc ctccccgccg tactacgagg
121   gccgcttctc gaacggcccg gtctggctgg agcagctgac gaagcagttc cccggcctga
181   cgatcgccaa cgaggccgag gggggcgcga ccgcagtcgc ctacaacaag atctcctgga
241   acccgaagta ccaggtcatt aacaacctcg actacgaggt cacccagttc ttgcagaagg
301   actcgttcaa gccggacgac ctggtcatcc tgtgggtggg cgccaacgac tacctggcct
361   acggttggaa cacggagcag gacgccaagc gggtgcgcga cgccatctcg gacgcggcaa
421   acgcatggt cctgaacggc gcgaagcaga tcctgctgtt caacctgccc gacctggccc
481   agaaccgtc cgcccgctcc cagaaggtcg tcgaggccgt ctcgcacgtg tccgcctacc
541   acaacaagct gctcctcaac ctcgcccggc agctcgcccc gacgggcatg gtcaagctgt
601   tcgagatcga caagcagttc gcggagatgc tgcgcgaccc ccagaacttc ggcctgagcg
661   acgtggagaa cccgtgctac gacggcggct acgtgtggaa gccgttcgcc acccggtccg
721   tctcgaccga ccggcagctg tcggccttct cgcccagga gcgcctggcg atcgctggca
781   acccgctcct ggcacaggcg gtagcttcgc cgatggcccg ccgctcggcc tcgccctca
841   actgcgaggg caagatgttc tgggaccagg tccaccccac caccgtggtc cacgcgccc
901   tctcggagcg cgccgccacc ttcatcgaga cccagtacga gttcctcgcc cactagtcta
961   gaggatcc
```

Figure 42

1. L131
    2. S.avermitilis
    3. T.fusca
    4. Consensus

```
                   1                                                50
1    (1)  ---------MRLTRSLSAASVIVFALLLALLGISPAQAAG---------------
2    (1)  ---------MRRSRITAYVTSLLLAVGCALTGAATAQASPA--------------
3    (1)  VGSGPRAATRRRLFLGIPALVLVTALTLVLAVPTGRETLWRMWCEATQDW
4    (1)           MRRSRFLA  ALILLTLA AL GAA ARAAP 51                                              100
1   (32)  ------------------------------P-AYVALGDSYSSGNGAGSYID
2   (33)  -----------------------------AAATGYVALGDSYSSGVGAGSYLS
3   (51)  CLGVPVDSRGQPAEDGEFLLLSPVQAATWGNYYALGDSYSSGDGARDYYP
4   (51)                          A  A  YVALGDSYSSG GAGSY 101                                             150
1   (53)  SSGD----CHRSNNAYPARWAAANAP---SSFTFAACSGAVTTDVIN-----
2   (57)  SSGD----CKRSSKAYPYLWQAAHSP---SSFSFMACSGARTGDVLA-----
3  (101)  GTAVKGGCWRSANAYPELVAEAYDFA--GHLSFLACSGQRGYAMLDAIDE
4  (101)  SSGD    C RSTKAYPALWAAAHA   SSFSF ACSGARTYDVLA 151                                             200
1   (93)  --NQLGALNAST--GLVSITIGGNDAGFADAMTTCVTS-------SDSTCL
2   (97)  ---NQLGTLNSST--GLVSLTIGGNDAGFSDVMTTCVLQ------SDSACL
3  (149)  VGSQLDWNSPHT--SLVTIGIGGNDLGFSTVLKTCMVR-------VPLLDS
4  (151)       QL LNS T    LVSITIGGNDAGFAD MTTCVL       SDSACL 201                                             250
1  (133)  NRLATATNYINTTLLA--------RLDAVYSQIKARAPNARVVVLGYPRMY
2  (137)  SRINTAKAYVDSTLPG--------QLDSVYTAISTKAPSAHVAVLGYPRFY
3  (191)  KACTDQEDAIRKRMAKF-----ETTFEELISEVRTRAPDARILVVGYPRIF
4  (201)       RIA AK YI  TLPA        RLDSVYSAI  TRAP ARVVVLGYPRIY 251                                             300
1  (176)  LASNPWYCLGLSNTKRAAINTTADTLNSVISSRATAH---------GF
2  (180)  KLGG-SCLAGLSETKRSAINDAADYLNSAIAKRAADH---------GF
3  (237)  PEEPTGAYYTLTASNQRWLNETIQEFNQQLAEAVAHDEEIAASGGVGSV
4  (251)       SG    LGLS TKRAAINDAAD LNSVIAKRAADH          GF 301                                             350
1  (215)  RFGDVRPTFNNHELFFGNDWLHSLTLP---------------VWESYH
2  (218)  TFGDVKSTFTGHEICSSSTWLHSLDLLN--------------IGQSYH
3  (287)  EFVDVYHALDGHEIGSDEPWVNGVQLRDLATG----------VTVDRSTFH
4  (301)  TFGDV   TF GHELCSA PWLHSLTLP                V  SYH 351                             395
1  (248)  PTSTGHQSGYLPVLNANSST--------------------
2  (252)  PTAAGQSGGYLPVMNSVA------------------
3  (328)  PNAAGHRAVGERVIEQIETGPGRPLYATFAVVAGATVDTLAGEVG
4  (351)  PTA  GHAAGYLPVLNST T
```

FIGURE 43

SEQ ID No 17 which is the amino acid sequence of a lipid acyltransferase from *Candida parapsilosis*;

```
MRYFAIAFLL INTISAFVLA PKKPSQDDFY TPPQGYEAQP LGSILKTRNV PNPLTNVFTP VKVQNAWQLL
VRSEDTFGNP NAIVTTIIQP FNAKKDKLVS YQTFEDSGKL DCAPSYAIQY GSDISTLTTQ GEMYYISALL
DQGYYVVTPD YEGPKSTFTV GLQSGRATLN SLRATLKSGN LTGVSSDAET LLWGYSGGSL ASGWAAAIQK
EYAPELSKNL LGAALGGFVT NITATAEAVD SGPFAGIISN ALAGIGNEYP DFKNYLLKKV SPLLSITYRL
GNTHCLLDGG IAYFGKSFFS
RIIRYFPDGW DLVNQEPIKT ILQDNGLVYQ PKDLTPQIPL FIYHGTLDAI VPIVNSRKTF QQWCDWGLKS
GEYNEDLTNG HITESIVGAP AALTWIINRF NGQPPVDGCQ HNVRASNLEY PGTPQSIKNY FEAALHAILG
FDLGPDVKRD KVTLGGLLKL ERFAF
```

FIGURE 44

SEQ ID No 18 which is the amino acid sequence of a lipid acyltransferase from *Candida parapsilosis*;

```
MRYFAIAFLL INTISAFVLA PKKPSQDDFY TPPQGYEAQP LGSILKTRNV PNPLTNVFTP VKVQNAWQLL
VRSEDTFGNP NAIVTTIIQP FNAKKDKLVS YQTFEDSGKL DCAPSYAIQY GSDISTLTTQ GEMYYISALL
DQGYYVVTPD YEGPKSTFTV GLQSGRATLN SLRATLKSGN LTGVSSDAET LLWGYSGGSL ASGWAAAIQK
EYAPELSKNL LGAALGGFVT NITATAEAVD SGPFAGIISN ALAGIGNEYP DFKNYLLKKV SPLLSITYRL
GNTHCLLDGG IAYFGKSFFS RIIRYFPDGW DLVNQEPIKT ILQDNGLVYQ PKDLTPQIPL FIYHGTLDAI
VPIVNSRKTF QQWCDWGLKS GEYNEDLTNG HITESIVGAP AALTWIINRF NGQPPVDGCQ HNVRASNLEY
PGTPQSIKNY FEAALHAILG FDLGPDVKRD KVTLGGLLKL ERFAFHHHHH H
```

```
1DEOm     T T V Y   L   A G D S T M A K n -                - G G G S G T N G W G E Y L
          slslsl   sl   slslh7h7h7                           h1h1h1h1h1h1
1IVNn     A D T L L   I   L G D S L S A G -                  - Y R M S A S A A W P A L L
          slslsl   sl   slslh h h                            h1h1h1h1h1
P10480m   I V M   F G D S L S D T g k m y s k m r g y l p   P P y y e   G R F S M G F V W L E Q L 1DEOm     A S Y L S   A   T V -                              - - V N D A V     A R S Y T R E G R F E N I A
          h1h1h1   s2 s2   s2                                s2s2s2s2s2         h3h3h3h3h3h3h3h3h3h3h3h3
1IVNn     N D K W   q   s     k - -                          - t s v V N A S   - - S Q Q G L A   R L P A L L
          h1h1h1   s2?s2?                                    s2?s2s2s2s2s2s2     h3h3h3 h3h3h3h3h3
P10480m   T N E F P   G   L T i a n e   e   g g p   t a v a Y N K K i               y g v I N N L D Y E V T Q F L Q 1DEOm     D   V V T   A   G D Y V I V E   E   G H N   D G g s l s t d         d     a a E V C I Y S V L D G V N E T I
          h3h3         s4   s4s4s4s4         ? ? ? ?           ? ?             s?s?s?s?s?s?s?s?s?s?s?s?
1IVNm     K Q H Q P       R W V L V E   L   G G N   D G - -                  - -   - L R G F Q P
          h3h3h3           s4s4s4s4       - -                                       h4
P10480m   K D S F K   P   D D L V I L W V G A N       D Y - -                 - -   - L A Y G W N T E Q D A 1DEOm     L T F P A   Y   L E N A A K L F T A K       G A K V I L S S     Q       T P   N P W E T G T F V N S P T R
          h4h4h4h4       h4h4h4h4h4h4h4h4h4h4         s5s5s5s5s5s5
1IVNn     Q Q T E Q   T   L R Q I L Q D V K R a A   N A E P I l m g i     R L P     A N Y G R       - - R I Y N E A
          h4h4h4h4       h4h4h4h4h4h4h4h4h4h4         s5s5s5s5s5s5s?s5?s5?s5?         h5h5h5h5h5h5
P10480m   K R K V R D   A   I S D A A N R M V L       G A K E I L L F     M   L F d   l g g n P S A R S Q K V V E A A S H V S A 1DEOm     F V E Y   A   E L A A A E V A -                    - - G     - V E Y   V   D H W S Y V D S I Y E T L G N A t v n - -
          h5h5h5   h5   h5h5h5h5h5h5h5                            s6 s6   s6?h6h6h6h6h6h6h6h6h6h6h6     h h h
1IVNm     F S A I Y   P K K L A k e -                        - - F D V   P L L   L   P F F M E E V Y           L K P Q W   - - -
          h5h5h5h5h5   h5h5h5h5                                          h6 h6 h6   h6h6           s
P10480m   Y H N Q L   L N L A r g l e p t                    g   m v k   l f e i D K   Q F A E M L R D P O N F G L S D Q R N a c y g g 1DEOm     - -                                                               - - - - -                                 - - - - -
1IVNn     - -                                                               - - - - -                                 - - - - -
P10480m s y v k p     f a s r s a s t d s g   l s a f n p g e   r     l   a d   l a g n p i l l a g a v a s p m a a r s a a s t 1DEOm     -     y       F P I D H T T S P A   G A E V V A E A     F L K A   V V C T G T S L K S V L T T T S F E G T C
                        s?s?s?h7h7             h7h7h7h7h7h7h7     h7 h7     h7 h7?h7?h7?     h2h2?
1IVNm     -     h       M Q D D G I K P N R D   A Q P F I A D W M A K Q   L Q P L V N H D S L E
                                                 h7h7h7h7h7h7h7   h7 h7     h7
P10480m l n c e g k     M F W D Q V H P T T V   V H A A L S E P A T F I E S Q Y E F L A H -
```

```
                       10        20        30        40        50
60
         ....*....|....*....|....*....|....*....|....*....|....*....|
1IVN_A        4 LLILGDSLSAG------------------YRMSASAAWPALLNDKWqsk---
------ 34
P10480       28 IVMFGDSLSDTgkmyskmrgylpssppyyeGRFSNGPVWLEQLTNEFPGLTianeaeggp 87

70        80        90       100       110
120
         ....*....|....*....|....*....|....*....|....*....|....*....|
1IVN_A       35 -tsvVNASISGDT------------------------
SQQGLARLPALLKQHQPRW 65
P10480       88 tavaYNKISWNPKyq-----------------------
vINNLDYEVTQFLQKDSFKPDDL 125

130       140       150       160       170
180
         ....*....|....*....|....*....|....*....|....*....|....*....|
1IVN_A       66 VLVELGGNDG---------------------------
LRGFQPQQTEQT 87
P10480      126 VILWVGANDY--------------------------LA--
YGWNTEQDAKRVRDA 152

190       200       210       220       230
240
         ....*....|....*....|....*....|....*....|....*....|....*....|
1IVN_A       88 LRQILQDVKaANAEPllmqiRLPANYGR-----------
-------- 115
P10480      153 ISDAANRMV-LNGAK-----EILLFNLPdlg---------
----qnP 180

250       260       270       280       290
300
         ....*....|....*....|....*....|....*....|....*....|....*....|
1IVN_A      116 -------------RYNEAFSAIYPKLAke------------
fDVPLLPFFME 142
P10480      181 SARSQKVVEAASHVSAYHNQLLLNLArqlaptg---------
mvklfeiDKQFAEMLRD 230

310       320       330       340       350
360
         ....*....|....*....|....*....|....*....|....*....|....*....|
1IVN_A      143 EVYLKPQW--------------------------------
-------- 150
P10480      231
PQNFGLSDQRNacyggsyvwkpfasrsastdsqlsafnpqerlaiagnpllaqavaspma 290

370       380       390       400
         ....*....|....*....|....*....|....*....|
1IVN_A      151 ------------MQDDGI--------HPNRDAQPFIADWM 170
P10480      291 arsastlncegkMFWDQV--------HPTTVVHAALSEPA 322
```

FIGURE 52

```
                    1                                                50
P10480      (1)     MKKWFVCLLGLVALTVQAADSRPAFSRIVMFGDSLSDTGKMYSKMRGYLP
A. sal      (1)     ------------------ADTRPAFSRIVMFGDSLSDTGKMYSKMRGYLP
A. hyd      (1)     ------------------ADSRPAFSRIVMFGDSLSDTGKMYSKMRGYLP
Consensus   (1)                       AD*RPAFSRIVMFGDSLSDTGKMYSKMRGYLP
                    51                                              100
P10480      (51)    SSPPYYEGRFSNGPVWLEQLTNEFPGLTIANEAEGGPTAVAYNKISWNPK
A. sal      (33)    SSPPYYEGRFSNGPVWLEQLTKQFPGLTIANEAEGGATAVAYNKISWNPK
A. hyd      (33)    SSPPYYEGRFSNGPVWLEQLTKQFPGLTIANEAEGGATAVAYNKISWNPK
Consensus   (51)    SSPPYYEGRFSNGPVWLEQLT**FPGLTIANEAEGG*TAVAYNKISWNPK
                    101                                             150
P10480      (101)   YQVINNLDYEVTQFLQKDSFKPDDLVILWVGANDYLAYGWNTEQDAKRVR
A. sal      (83)    YQVINNLDYEVTQFLQKDSFKPDDLVILWVGANDYLAYGWNTEQDAKRVR
A. hyd      (83)    YQVINNLDYEVTQFLQKDSFKPDDLVILWVGANDYLAYGWNTEQDAKRVR
Consensus   (101)   YQVINNLDYEVTQFLQKDSFKPDDLVILWVGANDYLAYGWNTEQDAKRVR
                    151                                             200
P10480      (151)   DAISDAANRMVLNGAKEILLFNLPDLGQNPSARSQKVVEAASHVSAYHNQ
A. sal      (133)   DAISDAANRMVLNGAKQILLFNLPDLGQNPSARSQKVVEAVSHVSAYHNK
A. hyd      (133)   DAISDAANRMVLNGAKQILLFNLPDLGQNPSARSQKVVEAVSHVSAYHNQ
Consensus   (151)   DAISDAANRMVLNGAK*ILLFNLPDLGQNPSARSQKVVEA*SHVSAYHN*
                    201                                             250
P10480      (201)   LLLNLARQLAPTGMVKLFEIDKQFAEMLRDPQNFGLSDQRNACYGGSYVW
A. sal      (183)   LLLNLARQLAPTGMVKLFEIDKQFAEMLRDPQNFGLSDVENPCYDGGYVW
A. hyd      (183)   LLLNLARQLAPTGMVKLFEIDKQFAEMLRDPQNFGLSDVENPCYDGGYVW
Consensus   (201)   LLLNLARQLAPTGMVKLFEIDKQFAEMLRDPQNFGLSD**N*CY*G*YVW
                    251                                             300
P10480      (251)   KPFASRSASTDSQLSAFNPQERLAIAGNPLLAQAVASPMAARSASTLNCE
A. sal      (233)   KPFATRSVSTDRQLSAFSPQERLAIAGNPLLAQAVASPMARRSASPLNCE
A. hyd      (233)   KPFATRSVSTDRQLSAFSPQERLAIAGNPLLAQAVASPMARRSASPLNCE
Consensus   (251)   KPFA*RS*STD*QLSAF*PQERLAIAGNPLLAQAVASPMA*RSAS*LNCE
                    301                     336
P10480      (301)   GKMFWDQVHPTTVVHAALSEPAATFIESQYEFLAH--
A. sal      (283)   GKMFWDQVHPTTVVHAALSERAATFIETQYEFLAHG
A. hyd      (283)   GKMFWDQVHPTTVVHAALSERAATFIANQYEFLAH--
Consensus   (301)   GKMFWDQVHPTTVVHAALSE*AATFI**QYEFLAH*
```

FIGURE 53

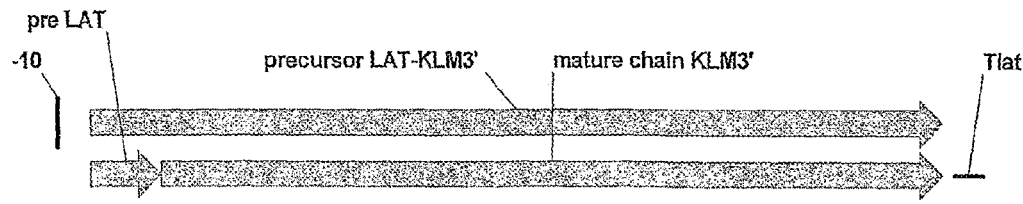

Gene construct for KLM3' expression 1182 bp

FIGURE 55

```
                                                           -35
  1  GCTTTTCTTT TGGAAGAAAA TATAGGGAAA ATGGTACTTG TTAAAAATTC GGAATATTTA
     CGAAAAGAAA ACCTTCTTTT ATATCCCTTT TACCATGAAC AATTTTTAAG CCTTATAAAT
     -10                                          M  K  Q  Q  K  R  L·
 61  TACAATATCA TATGTTTCAC ATTGAAAGGG GAGGAGAATC ATGAAACAAC AAAAACGGCT
     ATGTTATAGT ATACAAAGTG TAACTTTCCC CTCCTCTTAG TACTTTGTTG TTTTTGCCGA
     · Y  A  R  L  L  T  L  L  F  A  L  I  F  L  L  P  H  S  A  A ·
121  TTACGCCCGA TTGCTGACGC TGTTATTTGC GCTCATCTTC TTGCTGCCTC ATTCTGCAGC
     AATGCGGGCT AACGACTGCG ACAATAAACG CGAGTAGAAG AACGACGGAG TAAGACGTCG
     · S  A  A  D  T  R  P  A  F  S  R  I  V  M  F  G  D  S  L  S ·
181  TTCAGCAGCA GATACAAGAC CGGCGTTTAG CCGGATCGTC ATGTTTGGAG ATAGCCTGAG
     AAGTCGTCGT CTATGTTCTG GCCGCAAATC GGCCTAGCAG TACAAACCTC TATCGGACTC
     · D  T  G  K  M  Y  S  K  M  R  G  Y  L  P  S  S  P  Y  Y ·
241  CGATACGGGC AAAATGTATA GCAAAATGAG AGGCTATCTT CCGTCAAGCC CGCCGTATTA
     GCTATGCCCG TTTTACATAT CGTTTTACTC TCCGATAGAA GGCAGTTCGG GCGGCATAAT
     · E  G  R  F  S  N  G  P  V  W  L  E  Q  L  T  K  Q  F  P  G ·
301  TGAAGGCCGC TTTAGCAATG GACCGGTCTG GCTGGAACAA CTGACGAAAC AATTTCCGGG
     ACTTCCGGCG AAATCGTTAC CTGGCCAGAC CGACCTTGTT GACTGCTTTG TTAAAGGCCC
     · L  T  I  A  N  E  A  E  G  G  A  T  A  V  A  Y  N  K  I  S ·
361  ACTGACGATC GCTAATGAAG CAGAAGGAGG AGCAACAGCG GTCGCCTATA ACAAAATCAG
     TGACTGCTAG CGATTACTTC GTCTTCCTCC TCGTTGTCGC CAGCGGATAT TGTTTTAGTC
     · W  D  P  K  Y  Q  V  I  N  N  L  D  Y  E  V  T  Q  F  L  Q ·
421  CTGGGACCCG AAATATCAGG TCATCAACAA CCTGGACTAT GAAGTCACAC AGTTTCTTCA
     GACCCTGGGC TTTATAGTCC AGTAGTTGTT GGACCTGATA CTTCAGTGTG TCAAAGAAGT
     · K  D  S  F  K  P  D  D  L  V  I  L  W  V  G  A  N  D  Y  L ·
481  GAAAGACAGC TTTAAACCGG ATGATCTGGT CATCCTTTGG GTCGGCGCCA ATGATTATCT
     CTTTCTGTCG AAATTTGGCC TACTAGACCA GTAGGAAACC CAGCCGCGGT TACTAATAGA
     · A  Y  G  W  N  T  E  Q  D  A  K  R  V  R  D  A  I  S  D  A ·
541  GGCGTATGGC TGGAACACAG AACAAGATGC CAAAAGAGTC AGAGATGCCA TCAGCGATGC
     CCGCATACCG ACCTTGTGTC TTGTTCTACG GTTTTCTCAG TCTCTACGGT AGTCGCTACG
     · A  N  R  M  V  L  N  G  A  K  Q  I  L  L  F  N  L  P  D  L ·
601  CGCTAATAGA ATGGTCCTGA ACGGCGCCAA ACAAATCCTG CTGTTTAACC TGCCGGATCT
     GCGATTATCT TACCAGGACT TGCCGCGGTT TGTTTAGGAC GACAAATTGG ACGGCCTAGA
     · G  Q  N  P  S  A  R  S  Q  K  V  V  E  A  V  S  H  V  S  A ·
661  GGGACAAAAT CCGAGCGCCA GAAGCCAAAA GTCGTCGAA GCAGTCAGCC ATGTCAGCGC
     CCCTGTTTTA GGCTCGCGGT CTTCGGTTTT CAGCAGCTT CGTCAGTCGG TACAGTCGCG
     · Y  H  N  K  L  L  N  L  A  R  Q  L  A  P  T  G  M  V  K ·
721  CTATCATAAC AAACTGCTGC TGAACCTGGC AAGACAATTG GCACCGACGG GAATGGTTAA
     GATAGTATTG TTTGACGACG ACTTGGACCG TTCTGTTAAC CGTGGCTGCC CTTACCAATT
     · L  F  E  I  D  K  Q  F  A  E  M  L  R  D  P  Q  N  F  G  L ·
781  ATTGTTTGAA ATTGACAAAC AGTTTGCCGA AATGCTGAGA GATCCGCAAA ATTTTGGCCT
     TAACAAACTT TAACTGTTTG TCAAACGGCT TTACGACTCT CTAGGCGTTT TAAAACCGGA
     · S  D  V  E  N  P  C  Y  D  G  G  Y  V  W  K  P  F  A  T  R ·
841  GAGCGATGTC GAAAACCCGT GCTATGATGG CGGATATGTC TGGAAACCGT TTGCCACAAG
     CTCGCTACAG CTTTTGGGCA CGATACTACC GCCTATACAG ACCTTTGGCA AACGGTGTTC
     · S  V  S  T  D  R  Q  L  S  A  F  S  P  Q  E  R  L  A  I  A ·
901  AAGCGTCAGC ACGGATAGAC AAACTGTCAG CGTTTAGCCCG CAAGAAAGAC TGGCAATCGC
     TTCGCAGTCG TGCCTATCTG TTTGACAGTC GCAAATCGGGC GTTCTTTCTG ACCGTTAGCG
     · G  N  P  L  L  A  Q  A  V  A  S  P  M  A  R  R  S  A  S  P ·
961  CGGAAATCCG CTTTTGGCAC AAGCAGTTGC TTCACCGATG GCAAGAAGAT CAGCAAGCCC
     GCCTTTAGGC GAAACCGTG TTCGTCAACG AAGTGGCTAC CGTTCTTCTA GTCGTTCGGG
     · L  N  C  E  G  K  M  F  W  D  Q  V  H  P  T  T  V  V  H  A ·
1021 GCTGAATTGC GAAGGCAAAA TGTTTTGGGA TCAGGTCCAT CCGACAACAG TTGTCCATGC
     CGACTTAACG CTTCCGTTTT ACAAAACCCT AGTCCAGGTA GGCTGTTGTC AACAGGTACG
     · A  L  S  E  R  A  A  T  F  I  E  T  Q  Y  E  F  L  A  H  G ·
1081 TGCCCTTTCA GAAAGAGCGG CGACGTTTAT CGAAACACAG TATGAATTTC TGGCCCATGG
     ACGGGAAAGT CTTTCTCGCC GCTGCAAATA GCTTTGTGTC ATACTTAAAG ACCGGGTACC
     ·stop
1141 CTGAGTTAAC AGAGGACGGA TTTCCTGAAG GAAATCCGTT TTTTTATTTT AAGCTTGGAG
     GACTCAATTG TCTCCTGCCT AAAGGACTTC CTTTAGGCAA AAAAATAAAA TTCGAACCTC
1201 ACAAGGTAAA GGATAAAACC TCGAG
     TGTTCCATTT CCTATTTTGG AGCTC
```

FIGURE 57 (SEQ ID No 49)

```
   1   ATGAAACAAC AAAAACGGCT TTACGCCCGA TTGCTGACGC TGTTATTTGC
       TACTTTGTTG TTTTTGCCGA AATGCGGGCT AACGACTGCG ACAATAAACG

51   GCTCATCTTC TTGCTGCCTC ATTCTGCAGC TTCAGCAGCA GATACAAGAC
       CGAGTAGAAG AACGACGGAG TAAGACGTCG AAGTCGTCGT CTATGTTCTG

101   CGGCGTTTAG CCGGATCGTC ATGTTTGGAG ATAGCCTGAG CGATACGGGC
       GCCGCAAATC GGCCTAGCAG TACAAACCTC TATCGGACTC GCTATGCCCG

151   AAAATGTATA GCAAAATGAG AGGCTATCTT CCGTCAAGCC CGCCGTATTA
       TTTTACATAT CGTTTTACTC TCCGATAGAA GGCAGTTCGG GCGGCATAAT

201   TGAAGGCCGC TTTAGCAATG GACCGGTCTG GCTGGAACAA CTGACGAAAC
       ACTTCCGGCG AAATCGTTAC CTGGCCAGAC CGACCTTGTT GACTGCTTTG

251   AATTTCCGGG ACTGACGATC GCTAATGAAG CAGAAGGAGG AGCAACAGCG
       TTAAAGGCCC TGACTGCTAG CGATTACTTC GTCTTCCTCC TCGTTGTCGC

301   GTCGCCTATA ACAAAATCAG CTGGGACCCG AAATATCAGG TCATCAACAA
       CAGCGGATAT TGTTTTAGTC GACCCTGGGC TTTATAGTCC AGTAGTTGTT

351   CCTGGACTAT GAAGTCACAC AGTTTCTTCA GAAAGACAGC TTTAAACCGG
       GGACCTGATA CTTCAGTGTG TCAAAGAAGT CTTTCTGTCG AAATTTGGCC

401   ATGATCTGGT CATCCTTTGG GTCGGCGCCA ATGATTATCT GGCGTATGGC
       TACTAGACCA GTAGGAAACC CAGCCGCGGT TACTAATAGA CCGCATACCG

451   TGGAACACAG AACAAGATGC CAAAAGAGTC AGAGATGCCA TCAGCGATGC
       ACCTTGTGTC TTGTTCTACG GTTTTCTCAG TCTCTACGGT AGTCGCTACG

501   CGCTAATAGA ATGGTCCTGA ACGGCGCCAA ACAAATCCTG CTGTTTAACC
       GCGATTATCT TACCAGGACT TGCCGCGGTT TGTTTAGGAC GACAAATTGG

551   TGCCGGATCT GGGACAAAAT CCGAGCGCCA GAAGCCAAAA AGTCGTCGAA
       ACGGCCTAGA CCCTGTTTTA GGCTCGCGGT CTTCGGTTTT TCAGCAGCTT

601   GCAGTCAGCC ATGTCAGCGC CTATCATAAC AAACTGCTGC TGAACCTGGC
       CGTCAGTCGG TACAGTCGCG GATAGTATTG TTTGACGACG ACTTGGACCG

651   AAGACAATTG GCACCGACGG GAATGGTTAA ATTGTTTGAA ATTGACAAAC
       TTCTGTTAAC CGTGGCTGCC CTTACCAATT TAACAAACTT TAACTGTTTG

701   AGTTTGCCGA AATGCTGAGA GATCCGCAAA ATTTTGGCCT GAGCGATGTC
       TCAAACGGCT TTACGACTCT CTAGGCGTTT TAAAACCGGA CTCGCTACAG

751   GAAAACCCGT GCTATGATGG CGGATATGTC TGGAAACCGT TTGCCACAAG
       CTTTTGGGCA CGATACTACC GCCTATACAG ACCTTTGGCA AACGGTGTTC

801   AAGCGTCAGC ACGGATAGAC AACTGTCAGC GTTTAGCCCG CAAGAAAGAC
       TTCGCAGTCG TGCCTATCTG TTGACAGTCG CAAATCGGGC GTTCTTTCTG

851   TGGCAATCGC CGGAAATCCG CTTTTGGCAC AAGCAGTTGC TTCACCGATG
       ACCGTTAGCG GCCTTTAGGC GAAAACCGTG TTCGTCAACG AAGTGGCTAC

901   GCAAGAAGAT CAGCAAGCCC GCTGAATTGC GAAGGCAAAA TGTTTGGGA
       CGTTCTTCTA GTCGTTCGGG CGACTTAACG CTTCCGTTTT ACAAACCCT

951   TCAGGTCCAT CCGACAACAG TTGTCCATGC TGCCCTTTCA GAAAGAGCGG
       AGTCCAGGTA GGCTGTTGTC AACAGGTACG ACGGGAAAGT CTTTCTCGCC

1001   CGACGTTTAT CGAAACACAG TATGAATTTC TGGCCCATGG CTGA
       GCTGCAAATA GCTTTGTGTC ATACTTAAAG ACCGGGTACC GACT
```

FIGURE 58 (SEQ ID No. 50)

```
  1  ATGAAAAAAT GGTTTGTGTG TTTATTGGGA TTGGTCGCGC TGACAGTTCA GGCAGCCGAC
 61  AGCCGTCCCG CCTTCTCCCG GATCGTGATG TTTGGCGACA GCCTCTCCGA TACCGGCAAG
121  ATGTACAGCA AGATGCGCGG TTACCTCCCC TCCAGCCCCC CCTACTATGA GGGCCGCTTC
181  TCCAACGGGC CCGTCTGGCT GGAGCAGCTG ACCAACGAGT TCCCGGGCCT GACCATAGCC
241  AACGAGGCGG AAGGCGGACC GACCGCCGTG GCTTACAACA AGATCTCCTG GAATCCCAAG
301  TATCAGGTCA TCAACAACCT GGACTACGAG GTCACCCAGT TCCTGCAAAA AGACAGCTTC
361  AAGCGGACG ATCTGGTGAT CCTCTGGGTC GGCGCCAACG ACTATCTGGC CTATGGCTGG
421  AACACAGAGC AGGATGCCAA GCGGGTGCGC GACGCCATCA GCGATGCGGC CAACCGCATG
481  GTGCTGAACG GCGCCAAGGA GATACTGCTG TTCAACCTGC CGGATCTGGG CCAGAACCCC
541  TCGGCCCGCA GCCAGAAGGT GGTCGAGGCG GCCAGCCATG TCTCCGCCTA CCACAACCAG
601  CTGCTGCTGA ACCTGGCACG CCAGCTGGCT CCCACCGGCA TGGTGAAGCT GTTCGAGATC
661  GACAAGCAGT TTGCCGAGAT GCTGCGTGAT CCGCAGAACT TCGGCCTGAG CGACCAGAGG
721  AACGCCTGCT ACGGTGGCAG CTATGTATGG AAGCCGTTTG CCTCCCGCAG CGCCAGCACC
781  GACAGCCAGC TCTCCGCCTT CAACCCGCAG GAGCGCCTCG CCATCGCCGG CAACCCGCTG
841  CTGGCCCAGG CCGTCGCCAG CCCCATGGCT GCCCGCAGCG CCAGCACCCT CAACTGTGAG
901  GGCAAGATGT TCTGGGATCA GGTCCACCCC ACCACTGTCG TGCACGCCGC CCTGAGCGAG
961  CCCGCCGCCA CCTTCATCGA GAGCCAGTAC GAGTTCCTCG CCCAC
```

FIGURE 59 (SEQ ID No. 51)

```
  1  ATGAAAAAAT GGTTTGTTTG TTTATTGGGG TTGATCGCGC TGACAGTTCA GGCAGCCGAC
 61  ACTCGCCCCG CCTTCTCCCG GATCGTGATG TTCGGCGACA GCCTCTCCGA TACCGGCAAA
121  ATGTACAGCA AGATGCGCGG TTACCTCCCC TCCAGCCCGC CCTACTATGA GGGCCGTTTC
181  TCCAACGGAC CCGTCTGGCT GGAGCAGCTG ACCAAGCAGT TCCCGGGTCT GACCATCGCC
241  AACGAAGCGG AAGGCGGTGC CACTGCCGTG GCTTACAACA AGATCTCCTG GAATCCCAAG
301  TATCAGGTCT ACAACAACCT GGACTACGAG GTCACCCAGT TCTTGCAGAA AGACAGCTTC
361  AAGCCGGACG ATCTGGTGAT CCTCTGGGTC GGTGCCAATG ACTATCTGGC ATATGGCTGG
421  AATACGGAGC AGGATGCCAA GCGAGTTCGC GATGCCATCA GCGATGCGGC CAACCGCATG
481  GTACTGAACG GTGCCAAGCA GATACTGCTG TTCAACCTGC CGGATCTGGG CCAGAACCCG
541  TCAGCCCGCA GTCAGAAGGT GGTCGAGGCG GTCAGCCATG TCTCCGCCTA TCACAACAAG
601  CTGCTGCTGA ACCTGGCACG CCAGCTGGCC CCCACCGGCA TGGTAAAGCT GTTCGAGATC
661  GACAAGCAAT TTGCCGAGAT GCTGCGTGAT CCGCAGAACT TCGGCCTGAG CGACGTCGAG
721  AACCCCTGCT ACGACGGCGG CTATGTGTGG AAGCCGTTTG CCACCCGCAG CGTCAGCACC
781  GACCGCCAGC TCTCCGCCTT CAGTCCGCAG GAACGCCTCG CCATCGCCGG CAACCCGCTG
841  CTGGCACAGG CCGTTGCCAG TCCTATGGCC CGCCGCAGCG CCAGCCCCCT CAACTGTGAG
901  GGCAAGATGT TCTGGGATCA GGTACACCCG ACCACTGTCG TGCACGCAGC CCTGAGCGAG
961  CGCGCCGCCA CCTTCATCGA GACCCAGTAC GAGTTCCTCG CCCACGGATG A
```

FIGURE 60 (SEQ ID No. 52)

```
  1  ATGCCGAAGC CTGCCCTTCG CCGTGTCATG ACCGCGACAG TCGCCGCCGT CGGCACGCTC
 61  GCCCTCGGCC TCACCGACGC CACCGCCCAC GCCGCGCCCG CCCAGGCCAC TCCGACCCTG
121  GACTACGTCG CCCTCGGCGA CAGCTACAGC GCCGGCTCCG GCGTCCTGCC CGTCGACCCC
181  GCCAACCTGC TCTGTCTGCG CTCGACGGCC AACTACCCCC ACGTCATCGC GGACACGACG
241  GGCGCCCGCC TCACGGACGT CACCTGCGGC GCCGGCGACA CCGCCGACTT CACGCGGGCC
301  CAGTACCCGG CGGTCGCACC CCAGTTGGAC GCGCTCGGCA CCGGCACGGA CCTGGTCACG
361  CTCACCATCG GCGGCAACGA CAACAGCACC TTCATCAACG CCATCACGGC CTGCGGCACG
421  GCGGGTGTCC TCAGCGGCGG CAAGGGCAGC CCCTGCAAGG ACAGGCACGG CACCTCCTTC
481  GACGACGAGA TCGAGGCCAA CACGTACCCC GCGCTCAAGG AGGCGCTGCT CGGCGTCCGC
541  GCCAGGGCTC CCCACGCCAG GGTGGCGGCT CTCGGCTACC CGTGGATCAC CCCGGCCACC
601  GCCGACCCGT CCTGCTTCCT GAAGCTCCCC CTCGCCCCGC GTGACCTGCG CTACCTGCGG
661  GCCATCCAGG CACACCTCAA CGACGCGGTC CGGCGGGCCG CCGAGGAGAC CGGAGCCACC
721  TACGTGGACT CTCCGGGGT GTCCGACGGC ACGACGCCT GCGAGGCCCC CGGCACCCGC
781  TGGATCGAAC CGCTGCTCTT CGGGCACAGC CTCGTTCCCG TCCACCCCAA CGCCCTGGGC
841  GAGCGGCGCA TGGCCGAGCA CACGATGGAC GTCCTCGGCC TGGACTGA
```

FIGURE 61 (SEQ ID No. 53)

```
  1 TCAGTCCAGG CCGAGGACGT CCATCGTGTG CTCGGCCATG CGCCGCTCGC CCAGGGCGTT
 61 GGGGTGGACG GGAACGAGGC TGTGCCCGAA GAGCAGCGGT TCGATCCAGC GGGTGCCGGG
121 GGCCTCGCAG GCGTCGTGGC CGTCGGACAC CCCGGAGAAG TCCACGTAGG TGGGCTCCGGT
181 CTCCTCGGCG GCCCGCCGGA CCGCGTCGTT GAGGTGTGCC TGGATGGCCC GCAGGTAGGG
241 CACGTCACCG GCGGCGAGGG GGAGCTTCAG GAAGCAGGAC GGGTCGGCGG TGGCCGGGGT
301 GATCCACGGG TAGCCGAGAG CCGCCACCCT GGCGTGGGGA GCCCTGGCGC GGACGCCGAG
361 CAGCGCCTCC TTGAGCGCGG GGTACGTGTT GGCCTCGATC TCGTCGTCGA AGGAGGTGCC
421 GTGCCTGTCC TTGCAGGGGC TGCCCTTGCC GCCGCTGAGG ACACCCGCCG TGCCGCAGGC
481 CGTGATGGCG TTGATGAAGG TGCTGTTGTC GTTGCCGCCG ATGGTGAGCG TGACCAGGTC
541 CGTGCCGGTG CCGAGCGCGT CCAACTGGGG TGCGACGCCC GGGTACTGGG CCCGCGTGAA
601 GTCGGCGGTC TGCGCGGCGC CGCAGGTGAC GTCCGTGAGG CGGGCGCCCG TCGTGTCCGC
661 GATGACGTGG GGGTAGTTGG CCGTCGAGCG CAGACAGAGC AGGTTGGCGG GGTCGACGGG
721 CAGGACGCCG GAGCCGGCGC TGTAGCTGTC GCCGAGGGCG ACGTAGTCCA GGGTCGGAGT
781 GGCCTGGGCG GGCGCGGCGT GGGCGGTGGC GTCGGTGAGG CCGAGGGCGA GCGTGCCGAC
841 GGCGGCGACT GTCGCGGTCA TGACACGGCG AAGGGCAGGC TTCGGCAT
```

FIGURE 62 (SEQ ID No. 54)

```
  1 ATGGATTACG AGAAGTTTCT GTTATTTGGG GATTCCATTA CTGAATTTGC TTTTAATACT
 61 AGGCCCATTG AAGATGGCAA AGATCAGTAT GCTCTTGGAG CCGCATTAGT CAACGAATAT
121 ACGAGAAAAA TGGATATTCT TCAAAGAGGG TTCAAAGGGT ACACTTCTAG ATGGGCGTTG
181 AAAATACTTC CTGAGATTTT AAAGCATGAA TCCAATATTG TCATGGCCAC AATATTTTTG
241 GGTGCCAACG ATGCATGCTC AGCAGGTCCC CAAAGTGTCC CCTCCCCGA ATTTATCGAT
301 AATATTCGTC AAATGGTATC TTTGATGAAG TCTTACCATA TCCGTCCTAT TATAATAGGA
361 CCGGGGCTAG TAGATAGAGA GAAGTGGGAA AAAGAAAAAT CTGAAGAAAT AGCTCTCGGA
421 TACTTCCGTA CCAACGAGAA CTTTGCCATT TATTCCGATG CCTTAGCAAA ACTAGCCAAT
481 GAGGAAAAAG TTCCCTTCGT GGCTTTGAAT AAGGCGTTTC AACAGGAAGG TGGTGATGCT
541 TGGCAACAAC TGCTAACAGA TGGACTGCAC TTTTCCGGAA AAGGGTACAA AATTTTTCAT
601 GACGAATTAT TGAAGGTCAT TGAGACATTC TACCCCCAAT ATCATCCCAA AAACATGCAG
661 TACAAACTGA AGATTGGAG AGATGTGCTA GATGATGGAT CTAACATAAT GTCTTGA
```

FIGURE 63 (SEQ ID No. 55)

```
  atgaacctgc gtcaatggat gggcgccgcc acggctgccc ttgccttggg cttggccgcg   60
  tgcgggggcg gtgggaccga ccagagcggc aatcccaatg tcgccaaggt gcagcgcatg  120
  gtggtgttcg gcgacagcct gagcgatatc ggcacctaca ccccgtcgc gcaggcggtg  180
  ggcggcggca agttcaccac caacccgggc ccgatctggg ccgagaccgt ggccgcgcaa  240
  ctgggcgtga cgctcacgcc ggcggtgatg ggctacgcca cctccgtgca gaattgcccc  300
  aaggccggct gcttcgacta tgcagggc ggctcgcgcg tgaccgatcc gaacggcatc  360
  ggccacaacg gcggcgcggg ggcgctgacc tacccggttc agcagcagct cgccaacttc  420
  tacgcggcca gcaacaacac attcaacggc aataacgatg tcgtcttcgt gctggcggc   480
  agcaacgaca ttttcttctg gaccactgcg gcggccacca gcggctccgg cgtgacgccc  540
  gccattgcca cggcccaggt gcagcaggcc gcgacggacc tggtcggcta tgtcaaggac  600
  atgatcgcca agggtgcgac gcaggtctac gtgttcaacc tgcccgacag cagcctgacg  660
  ccggacggcg tggcaagcgg cacgaccggc caggcgctgc tgcacgcgct ggtgggcacg  720
  ttcaacacga cgctgcaaag cgggctggcc ggcacctcgg cgcgcatcat cgacttcaac  780
  gcacaactga ccgcggcgat ccagaatggc gcctcgttcg gcttcgccaa caccagcgcc  840
  cgggcctgcg acgccaccaa gatcaatgcc ctggtgccga gcgccggcgg cagctcgctg  900
  ttctgctcgg ccaacacgct ggtggcttcc ggtgcggacc agagctacct gttcgccgac  960
  ggcgtgcacc cgaccacggc cggccatcgc ctgatcgcca gcaacgtgct ggcgcgcctg 1020
  ctggcggata acgtcgcgca ctga                                        1044
```

FIGURE 64 (SEQ ID No. 56)

```
  1 gtgatcgggt cgtacgtggc ggtgggggac agcttcaccg agggcgtcgg cgaccccggc
 61 cccgacgggg cgttcgtcgg ctgggccgac cggctcgccg tactgctcgc ggacggcgc
121 cccgagggcg acttcacgta cacgaacctc gccgtgcgcg gcaggctcct cgaccagatc
181 gtggcggaac aggtcccgcg ggtcgtcgga ctcgcgcccg acctcgtctc gttcgcggcg
241 ggcggcaacg acatcatccg gcccggcacc gatcccgacg aggtcgccga gcggttcgag
301 ctggcggtgg ccgcgctgac cgccgcggcc ggaaccgtcc tggtgaccac cgggttcgac
361 acccgggggg tgcccgtcct caagcacctg cgcggcaaga tcgccacgta caacgggcac
421 gtccgcgcca tcgccgaccg ctacggctgc ccggtgctcg acctgtggtc gctgcggagc
481 gtccaggacc gagggcgtg ggacgccgac cggctgcacc tgtcgccgga ggggcacacc
541 cgggtggcgc tgcgcgcggg gcaggccctg ggcctgcgcg tcccggccga ccctgaccag
601 ccctggccgc ccctgccgcc gcgcggcacg ctcgacgtcc ggcgcgacga cgtgcactgg
661 gcgcgcgagt acctggtgcc gtggatcggg cgccggctgc ggggcgagtc gtcgggcgac
721 cacgtgacgg ccaaggggac gctgtcgccg gacgccatca agacgcggat cgccgcggtg
781 gcctga
```

FIGURE 65 (SEQ ID No. 57)

```
  1 atgcagacga accccgcgta caccagtctc gtcgccgtcg gcgactcctt caccgagggc
 61 atgtcggacc tgctgcccga cggctcctac cgtggctggg ccgacctcct cgccacccgg
121 atggcggccc gctccccgg cttccggtac gccaacctgg cggtgcgcgg gaagctgatc
181 ggacagatcg tcgacgagca ggtggacgtg gccgccgcca tgggagccga cgtgatcacg
241 ctggtcggcg ggctcaacga cacgctgcgg cccaagtgcg acatgccccg ggtgcgggac
301 ctgctgaccc aggccgtgga acggctcgcc ccgcactgcg agcagctggt gctgatgcgc
361 agtcccggtc gccagggtcc ggtgctggag cgcttccggc ccgcatgga ggccctgttc
421 gccgtgatcg acgacctggc cgggcggcac ggcgccgtgg tcgtcgacct gtacggggcc
481 cagtcgctgg ccgaccctcg gatgtgggac gtggaccggc tgcacctgac cgccgagggc
541 caccgccggg tcgcggaggc ggtgtgcag tcgctcggcc acgagcccga ggaccccgag
601 tggcacgcgc cgatcccggc gacgccgccg ccggggtggg tgacgcgcag gaccgcggac
661 gtccggttcg cccggcagca cctgctgccc tggataggcc gcaggctgac cgggcgctcg
721 tccggggacg gcctgccggc caagcgcccg gacctgctgc cctacgagga ccccgcacgg
781 tga
```

FIGURE 66 (SEQ ID No. 58)

```
   1 atgacccggg gtcgtgacgg gggtgcgggg gcgccccca ccaagcaccg tgccctgctc
  61 gcggcgatcg tcaccctgat agtggcgatc tccgcggcca tatacgccgg agcgtccgcg
 121 gacgacggca gcagggacca cgcgctgcag gccggaggcc gtctcccacg aggagacgcc
 181 gcccccgcgt ccaccggtgc ctgggtgggc gcctgggcca ccgcaccggc cgcggccgag
 241 ccgggcaccg agacgaccgg cctggcgggc cgctccgtgc gcaacgtcgt gcacacctcg
 301 gtcggcggca ccggcgcgcg gatcaccctc tcgaacctgt acggcagtc gccgctgacc
 361 gtcacacacg cctcgatcgc cctggccgcc gggccgcgcc gccgcgcgc gatcgccgac
 421 accatgcgcc ggctcacctt cggcggcagc gcccgggtga tcatcccgcc gggcggccag
 481 gtgatgagcg acaccgcccg cctcgccatc ccctacgggg cgaacgtcct ggtcaccacg
 541 tactcccca tcccgtccgg gccggtgacc taccatccgc aggcccggca gaccagctac
 601 ctggccgacg gcgaccgcac ggcggacgtc accgccgtcg cgtacaccac ccccacgccc
 661 tactggcgct acctgaccgc cctcgacgtg ctgagccacg aggccgacgg cacggtcgtg
 721 gcgttcgcgg actccatcac cgacgccgcg cgctcggaca cgacgccaa ccaccgctgg
 781 accgacgtcc tcgccgcacg cctgcacgag gcggcgggcg acggccggga cacgcccgc
 841 tacagcgtcg tcaacgaggg catcagcggc aaccggctcc tgaccagcag gccggggcgg
 901 ccggccgaca acccgagcgg actgagccgg ttccagcggg acgtgctgga acgcaccaac
 961 gtcaaggccg tcgtcgtcgt cctcggcgtc aacgacgtcc tgaacagccc ggaactcgcc
1021 gaccgcgacg ccatcctgac cggcctcgcc accctcgtcg accgggcgca cgcccgggga
1081 ctgcgggtcg tcggcgccac gatcacgccg ttcggcgcgt acggcgcta cacgcggcc
1141 cgcgagacga tgcggcagga ggtcaacgag gagatccgct ccggccgggt cttcgacacg
1201 gtcgtcgact tcgacaaggc cctgcgcgac cgtacgacc gcgccggat gcgctccgac
1261 tacgacagcg gcgaccacct gcaccccggc gacaagggt acgcgcgcat gggcgcggtc
1321 atcgacctgg ccgcgctgaa gggcgcggcg ccggtcaagg cgtag
```

FIGURE 67 (SEQ ID No. 59)

```
   1 atgacgagca tgtcgagggc gagggtggcg cggcggatcg cggccggcgc ggcgtacggc
  61 ggcggcggca tcggcctggc gggagcggcg gcggtcggtc tggtggtggc cgaggtgcag
 121 ctggccagac gcagggtggg ggtgggcacg ccgaccgggg tgccgaacgc gcagggactg
 181 tacggcggca ccctgcccac ggccggcgac ccgccgctgc ggctgatgat gctgggcgac
 241 tccacggccg ccggcaggg cgtgcaccgg gccgggcaga cgccgggcgc gctgctggcg
 301 tccgggctcg cggcggtggc ggagcggccg gtgcggctgg ggtcggtcgc ccagccgggg
 361 gcgtgctcgg acgacctgga ccggcaggtg gcgctggtgc tcgccgagcc ggaccgggtg
 421 cccgacatct gcgtgatcat ggtcggcgcc aacgacgtca cccaccggat gccggcgacc
 481 cgctcggtgc ggcacctgtc ctcggcggta cggcggctgc gcacggccgg tgcggaggtg
 541 gtggtcggca cctgtccgga cctgagcggg tgcggcagcc gtgcgcggcc gctgcgctgg
 601 ctggcccggc gggcctcacg gcagctcgcg gcggcacaga ccatcggcgc cgtcgagcag
 661 ggcggcgca cggtgtcgct gggcgacctg ctgggtccgg agttcgcgca gaaccccgcgg
 721 gagctcttcg gccccgacaa ctaccacccc tccgccgagg gtacgccac ggccgcgatg
 781 gcggtactgc cctcggtgtg cgccgcgctc ggcctgtggc cggccgacga ggagcacccg
 841 gacgcgctgc gccgcgaggg cttcctgccg gtgcgcgcg cggccggcga ggcggcgtcc
 901 gaggcgggta cggaggtcgc cgccgccatg cctacggggc ctcggggcc ctgggcgctg
 961 ctgaagcgcc ggagacggcg tcgggtgtcg gaggcggaac cgtccagccc gtccggcgtt
1021 tga
```

FIGURE 68 (SEQ ID No. 60)

```
   1 atgggtcgag ggacggacca gcggacgcgg tacggccgtc gccggcgcg tgtcgcgctc
  61 gccgccctga ccgcgccgt cctgggcgtg ggcgtggcgg gctgcgactc cgtgggcggc
 121 gactcaccg ctccttccgg cagcccgtcg aagcggacga ggacggcgcc cgcctgggac
 181 accagcccgg cgtccgtcgc cgccgtgggc gactccatca cgcgcggctt cgacgcctgt
 241 gcggtgctgt cggactgccc ggaggtgtcg tgggcgaccg gcagcagcgc gaaggtcgac
 301 tcgctggccg tacggctgct ggggaaggcg gacgcggccg agcacagctg gaactacgcg
 361 gtcaccgggg cccggatggc ggacctgacc gctcaggtga cgcgggcggc gcagcgcgag
 421 ccggagctgg tggcggtgat ggccggggcg aacgacgcgt gccggtccac gacctcgggcg
 481 atgacgccgg tggcggactt ccgggcgcag ttcgaggagg cgatgccac cctgcgcaag
 541 aagctcccca aggcgcaggt gtacgtgtcg agcatcccgg acctcaagcg gctctggtcc
 601 cagggccgca ccaacccgct gggcaagcag gtgtggaagc tcggcctgtg cccgtcgatg
 661 ctgggcgacg cggactccct ggactcggcg gcgaccctgc ggcgcaacac ggtgcgcgac
 721 cgggtggcgc actacaacga ggtgctgcgg gaggtctgcg cgaaggaccg gcggtgccgc
 781 agcgacgacg gcgcggtgca cgagttccgg ttcggcacgg accagttgag ccactgggac
 841 tggttccacc cgagtgtgga cggccagcc cggctggcgg agatcgccta ccgcgcggtc
 901 accgcgaaga atccctga
```

FIGURE 69 (SEQ ID No. 61)

```
   1 ttcatcacaa cgatgtcaca acaccggcca tccgggtcat ccctgatcgt gggaatgggt
  61 gacaagccgt cccgtgacga aagggtcctg ctacatcaga aatgacagaa atcctgctca
 121 gggaggttcc atgagactgt cccgacggc ggccacggcg tccgcgctcc tcctcacccc
 181 ggcgctcgcg ctcttcggcg cgagcgccgc cgtgtccgcg ccgcgaatcc aggccaccga
 241 ctacgtggcc ctcggcgact cctactcctc ggggtcggc gcgggcagct acgacagcag
 301 cagtggctcc tgtaagcgca gcaccaagtc ctacccggcc ctgtggggccg cctcgcacac
 361 cggtacgcgg ttcaacttca ccgcctgttc gggcgcccgc acaggagacg tgctggccaa
 421 gcagctgacc ccggtcaact cctggtcagc attaccatcg gcggcaacga
 481 cgcgggcttc gccgacacca tgaccacctg caacctccag ggcgagagcg cgtgcctggc
 541 gcggatcgcc aaggcgcgcg cctacatcca gcagacgctg cccgcccagc tggaccaggt
 601 ctacgacgcc atcgacagcc gggcccccgc agccaggtc gtcgtcctgg gctacccgcg
 661 cttctacaag ctgggcggca gctgcgccgt cggtctctcg gagaagtccc gcgcggccat
 721 caacgccgcc gccgacgaca tcaacgccgt ccgcgccgcg accacggctt
 781 cgccttcggg gacgtcaaca cgaccttcgc cgggcacgag ctgtgctccg gcgcccctg
 841 gctgcacagc gtcacccttc ccgtggagaa ctcctaccac cccacggcca acggacagtc
 901 caaggcctac ctgcccgtcc tgaactccgc cacctgatct cgcggctact ccgccctga
 961 cgaagtcccg ccccgggcg gggcttcgcc gtaggtgcgc gtaccgccgt cgcccgtcgc
1021 gccggtggcc ccgccgtacg tgccgccgcc cccggacgcg gtcggttc
```

FIGURE 70 (SEQ ID No. 62)

```
   1  ATGAAAAAAT GGTTTGTGTG TTTATTGGGA TTGGTCGCGC TGACAGTTCA
      TACTTTTTTA CCAAACACAC AAATAACCCT AACCAGCGCG ACTGTCAAGT

51  GGCAGCCGAC AGTCGCCCCG CCTTTTCCCG GATCGTGATG TTCGGCGACA
      CCGTCGGCTG TCAGCGGGGC GGAAAAGGGC CTAGCACTAC AAGCCGCTGT

101  GCCTCTCCGA TACCGGCAAA ATGTACAGCA AGATGCGCGG TTACCTCCCC
      CGGAGAGGCT ATGGCCGTTT TACATGTCGT TCTACGCGCC AATGGAGGGG

151  TCCAGCCCGC CCTACTATGA GGGCCGTTTC TCCAACGGAC CCGTCTGGCT
      AGGTCGGGCG GGATGATACT CCCGGCAAAG AGGTTGCCTG GGCAGACCGA

201  GGAGCAGCTG ACCAAACAGT TCCCGGGTCT GACCATCGCC AACGAAGCGG
      CCTCGTCGAC TGGTTTGTCA AGGGCCCAGA CTGGTAGCGG TTGCTTCGCC

251  AAGGCGGTGC CACTGCCGTG GCTTACAACA AGATCTCCTG GAATCCCAAG
      TTCCGCCACG GTGACGGCAC CGAATGTTGT TCTAGAGGAC CTTAGGGTTC

301  TATCAGGTCA TCAACAACCT GGACTACGAG GTCACCCAGT TCTTGCAGAA
      ATAGTCCAGT AGTTGTTGGA CCTGATGCTC CAGTGGGTCA AGAACGTCTT

351  AGACAGCTTC AAGCCGGACG ATCTGGTGAT CCTCTGGGTC GGTGCCAATG
      TCTGTCGAAG TTCGGCCTGC TAGACCACTA GGAGACCCAG CCACGGTTAC

401  ACTATCTGGC CTATGGCTGG AACACGGAGC AGGATGCCAA GCGGGTTCGC
      TGATAGACCG GATACCGACC TTGTGCCTCG TCCTACGGTT CGCCCAAGCG

451  GATGCCATCA GCGATGCGGC CAACCGCATG GTACTGAACG GTGCCAAGCA
      CTACGGTAGT CGCTACGCCG GTTGGCGTAC CATGACTTGC CACGGTTCGT

501  GATACTGCTG TTCAACCTGC CGGATCTGGG CCAGAACCCG TCAGCTCGCA
      CTATGACGAC AAGTTGGACG GCCTAGACCC GGTCTTGGGC AGTCGAGCGT

551  GTCAGAAGGT GGTCGAGGCG GTCAGCCATG TCTCCGCCTA TCACAACCAG
      CAGTCTTCCA CCAGCTCCGC CAGTCGGTAC AGAGGCGGAT AGTGTTGGTC

601  CTGCTGCTGA ACCTGGCACG CCAGCTGGCC CCCACCGGCA TGGTAAAGCT
      GACGACGACT TGGACCGTGC GGTCGACCGG GGGTGGCCGT ACCATTTCGA

651  GTTCGAGATC GACAAGCAAT TTGCCGAGAT GCTGCGTGAT CCGCAGAACT
      CAAGCTCTAG CTGTTCGTTA AACGGCTCTA CGACGCACTA GGCGTCTTGA

701  TCGGCCTGAG CGACGTCGAG AACCCCTGCT ACGACGGCGG CTATGTGTGG
      AGCCGGACTC GCTGCAGCTC TTGGGGACGA TGCTGCCGCC GATACACACC

751  AAGCCGTTTG CCACCCGCAG CGTCAGCACC GACCGCCAGC TCTCCGCCTT
      TTCGGCAAAC GGTGGGCGTC GCAGTCGTGG CTGGCGGTCG AGAGGCGGAA

801  CAGTCCGCAG GAACGCCTCG CCATCGCCGG CAACCCGCTG CTGGCACAGG
      GTCAGGCGTC CTTGCGGAGC GGTAGCGGCC GTTGGGCGAC GACCGTGTCC

851  CCGTTGCCAG TCCTATGGCC CGCCGCAGCG CCAGCCCCCT CAACTGTGAG
      GGCAACGGTC AGGATACCGG GCGGCGTCGC GGTCGGGGA GTTGACACTC

901  GGCAAGATGT TCTGGGATCA GGTACACCCG ACCACTGTCG TGCACGCAGC
      CCGTTCTACA AGACCCTAGT CCATGTGGGC TGGTGACAGC ACGTGCGTCG

951  CCTGAGCGAG CGCGCCGCCA CCTTCATCGC GAACCAGTAC GAGTTCCTCG
      GGACTCGCTC GCGCGGCGGT GGAAGTAGCG CTTGGTCATG CTCAAGGAGC

1001  CCCAC TGA
      GGGTG ACT
```

FIGURE 71 (SEQ ID No. 63)

```
   1 ATGAAAAAAT GGTTTGTTTG TTTATTGGGG TTGATCGCGC TGACAGTTCA
     TACTTTTTTA CCAAACAAAC AAATAACCCC AACTAGCGCG ACTGTCAAGT

51 GGCAGCCGAC ACTCGCCCCG CCTTCTCCCG GATCGTGATG TTCGGCGACA
     CCGTCGGCTG TGAGCGGGGC GGAAGAGGGC CTAGCACTAC AAGCCGCTGT

101 GCCTCTCCGA TACCGGCAAA ATGTACAGCA AGATGCGCGG TTACCTCCCC
     CGGAGAGGCT ATGGCCGTTT TACATGTCGT TCTACGCGCC AATGGAGGGG

151 TCCAGCCCGC CCTACTATGA GGGCCGTTTC TCCAACGGAC CCGTCTGGCT
     AGGTCGGGCG GGATGATACT CCCGGCAAAG AGGTTGCCTG GGCAGACCGA

201 GGAGCAGCTG ACCAAGCAGT TCCCGGGTCT GACCATCGCC AACGAAGCGG
     CCTCGTCGAC TGGTTCGTCA AGGGCCCAGA CTGGTAGCGG TTGCTTCGCC

251 AAGGCGGTGC CACTGCCGTG GCTTACAACA AGATCTCCTG GAATCCCAAG
     TTCCGCCACG GTGACGGCAC CGAATGTTGT TCTAGAGGAC CTTAGGGTTC

301 TATCAGGTCA TCAACAACCT GGACTACGAG GTCACCCAGT TCTTGCAGAA
     ATAGTCCAGT AGTTGTTGGA CCTGATGCTC CAGTGGGTCA AGAACGTCTT

351 AGACAGCTTC AAGCCGGACG ATCTGGTGAT CCTCTGGGTC GGTGCCAATG
     TCTGTCGAAG TTCGGCCTGC TAGACCACTA GGAGACCCAG CCACGGTTAC

401 ACTATCTGGC ATATGGCTGG AATACGGAGC AGGATGCCAA GCGAGTTCGC
     TGATAGACCG TATACCGACC TTATGCCTCG TCCTACGGTT CGCTCAAGCG

451 GATGCCATCA GCGATGCGGC CAACCGCATG GTACTGAACG GTGCCAAGCA
     CTACGGTAGT CGCTACGCCG GTTGGCGTAC CATGACTTGC CACGGTTCGT

501 GATACTGCTG TTCAACCTGC CGGATCTGGG CCAGAACCCG TCAGCCCGCA
     CTATGACGAC AAGTTGGACG GCCTAGACCC GGTCTTGGGC AGTCGGGCGT

551 GTCAGAAGGT GGTCGAGGCG GTCAGCCATG TCTCCGCCTA TCACAACAAG
     CAGTCTTCCA CCAGCTCCGC CAGTCGGTAC AGAGGCGGAT AGTGTTGTTC

601 CTGCTGCTGA ACCTGGCACG CCAGCTGGCC CCCACCGGCA TGGTAAAGCT
     GACGACGACT TGGACCGTGC GGTCGACCGG GGGTGGCCGT ACCATTTCGA

651 GTTCGAGATC GACAAGCAAT TTGCCGAGAT GCTGCGTGAT CCGCAGAACT
     CAAGCTCTAG CTGTTCGTTA AACGGCTCTA CGACGCACTA GGCGTCTTGA

701 TCGGCCTGAG CGACGTCGAG AACCCCTGCT ACGACGGCGG CTATGTGTGG
     AGCCGGACTC GCTGCAGCTC TTGGGGACGA TGCTGCCGCC GATACACACC

751 AAGCCGTTTG CCACCCGCAG CGTCAGCACC GACCGCCAGC TCTCCGCCTT
     TTCGGCAAAC GGTGGGCGTC GCAGTCGTGG CTGGCGGTCG AGAGGCGGAA

801 CAGTCCGCAG GAACGCCTCG CCATCGCCGG CAACCCGCTG CTGGCACAGG
     GTCAGGCGTC CTTGCGGAGC GGTAGCGGCC GTTGGGCGAC GACCGTGTCC

851 CCGTTGCCAG TCCTATGGCC CGCCGCAGCG CCAGCCCCCT CAACTGTGAG
     GGCAACGGTC AGGATACCGG GCGGCGTCGC GGTCGGGGGA GTTGACACTC

901 GGCAAGATGT TCTGGGATCA GGTACACCCG ACCACTGTCG TGCACGCAGC
     CCGTTCTACA AGACCCTAGT CCATGTGGGC TGGTGACAGC ACGTGCGTCG

951 CCTGAGCGAG CGCGCCGCCA CCTTCATCGA GACCCAGTAC GAGTTCCTCG
     GGACTCGCTC GCGCGGCGGT GGAAGTAGCT CTGGGTCATG CTCAAGGAGC

1001 CCCACGGATG A
     GGGTGCCTAC T
```

FIGURE 72 (SEQ ID No. 24)

```
   1  ATGTTTAAGT TTAAAAAGAA TTTCTTAGTT GGATTATCGG CAGCTTTAAT
      TACAAATTCA AATTTTTCTT AAAGAATCAA CCTAATAGCC GTCGAAATTA

51  GAGTATTAGC TTGTTTTCGG CAACCGCCTC TGCAGCTAGC GCCGACAGCC
      CTCATAATCG AACAAAAGCC GTTGGCGGAG ACGTCGATCG CGGCTGTCGG

101  GTCCCGCCTT TTCCCGGATC GTGATGTTCG GCGACAGCCT CTCCGATACC
      CAGGGCGGAA AAGGGCCTAG CACTACAAGC CGCTGTCGGA GAGGCTATGG

151  GGCAAAATGT ACAGCAAGAT GCGCGGTTAC CTCCCCTCCA GCCCGCCCTA
      CCGTTTTACA TGTCGTTCTA CGCGCCAATG GAGGGGAGGT CGGGCGGGAT

201  CTATGAGGGC CGTTTCTCCA ACGGACCCGT CTGGCTGGAG CAGCTGACCA
      GATACTCCCG GCAAAGAGGT TGCCTGGGCA GACCGACCTC GTCGACTGGT

251  AACAGTTCCC GGGTCTGACC ATCGCCAACG AAGCGGAAGG CGGTGCCACT
      TTGTCAAGGG CCCAGACTGG TAGCGGTTGC TTCGCCTTCC GCCACGGTGA

301  GCCGTGGCTT ACAACAAGAT CTCCTGGAAT CCCAAGTATC AGGTCATCAA
      CGGCACCGAA TGTTGTTCTA GAGGACCTTA GGGTTCATAG TCCAGTAGTT

351  CAACCTGGAC TACGAGGTCA CCCAGTTCTT GCAGAAAGAC AGCTTCAAGC
      GTTGGACCTG ATGCTCCAGT GGGTCAAGAA CGTCTTTCTG TCGAAGTTCG

401  CGGACGATCT GGTGATCCTC TGGGTCGGTG CCAATGACTA TCTGGCCTAT
      GCCTGCTAGA CCACTAGGAG ACCCAGCCAC GGTTACTGAT AGACCGGATA

451  GGCTGGAACA CGGAGCAGGA TGCCAAGCGG GTTCGCGATG CCATCAGCGA
      CCGACCTTGT GCCTCGTCCT ACGGTTCGCC CAAGCGCTAC GGTAGTCGCT

501  TGCGGCCAAC CGCATGGTAC TGAACGGTGC CAAGCAGATA CTGCTGTTCA
      ACGCCGGTTG GCGTACCATG ACTTGCCACG GTTCGTCTAT GACGACAAGT

551  ACCTGCCGGA TCTGGGCCAG AACCCGTCAG CTCGCAGTCA GAAGGTGGTC
      TGGACGGCCT AGACCCGGTC TTGGGCAGTC GAGCGTCAGT CTTCCACCAG

601  GAGGCGGTCA GCCATGTCTC CGCCTATCAC AACCAGCTGC TGCTGAACCT
      CTCCGCCAGT CGGTACAGAG GCGGATAGTG TTGGTCGACG ACGACTTGGA

651  GGCACGCCAG CTGGCCCCCA CCGGCATGGT AAAGCTGTTC GAGATCGACA
      CCGTGCGGTC GACCGGGGGT GGCCGTACCA TTTCGACAAG CTCTAGCTGT

701  AGCAATTTGC CGAGATGCTG CGTGATCCGC AGAACTTCGG CCTGAGCGAC
      TCGTTAAACG GCTCTACGAC GCACTAGGCG TCTTGAAGCC GGACTCGCTG

751  GTCGAGAACC CCTGCTACGA CGGCGGCTAT GTGTGGAAGC CGTTTGCCAC
      CAGCTCTTGG GGACGATGCT GCCGCCGATA CACACCTTCG GCAAACGGTG

801  CCGCAGCGTC AGCACCGACC GCCAGCTCTC CGCCTTCAGT CCGCAGGAAC
      GGCGTCGCAG TCGTGGCTGG CGGTCGAGAG GCGGAAGTCA GGCGTCCTTG

851  GCCTCGCCAT CGCCGGCAAC CCGCTGCTGG CACAGGCCGT TGCCAGTCCT
      CGGAGCGGTA GCGGCCGTTG GGCGACGACC GTGTCCGGCA ACGGTCAGGA

901  ATGGCCCGCC GCAGCGCCAG CCCCCTCAAC TGTGAGGGCA AGATGTTCTG
      TACCGGGCGG CGTCGCGGTC GGGGGAGTTG ACACTCCCGT TCTACAAGAC

951  GGATCAGGTA CACCCGACCA CTGTCGTGCA CGCAGCCCTG AGCGAGCGCG
      CCTAGTCCAT GTGGGCTGGT GACAGCACGT GCGTCGGGAC TCGCTCGCGC

1001  CCGCCACCTT CATCGCGAAC CAGTACGAGT TCCTCGCCCA CTGATGA
      GGCGGTGGAA GTAGCGCTTG GTCATGCTCA AGGAGCGGGT GACTACT
```

FIGURE 73

SEQ ID No. 68

```
  1  ADTRPAFSRI VMFGDSLSDT GKMYSKMRGY LPSSPPYYEG RFSNGPVWLE QLTKQFPGLT
 61  IANEAEGGAT AVAYNKISWD PKYQVINNLD YEVTQFLQKD SFKPDDLVIL WVGANDYLAY
121  GWNTEQDAKR VRDAISDAAN RMVLNGAKQI LLFNDPDLGQ NPSARSQKVV EAVSHVSAYH
181  NKLLLNLARQ LAPTGMVKLF EIDKQFAEML RDPQNFGLSD VENPCYDGGY VWKPF

236  RSASPLNCEG KMFWDQVHPT TVVHAALSER AATFIETQYE FLAHG
```

CONVENTIONAL PROCESS (for comparison only)

PROCESS OF PRESENT INVENTION

FIG. 93
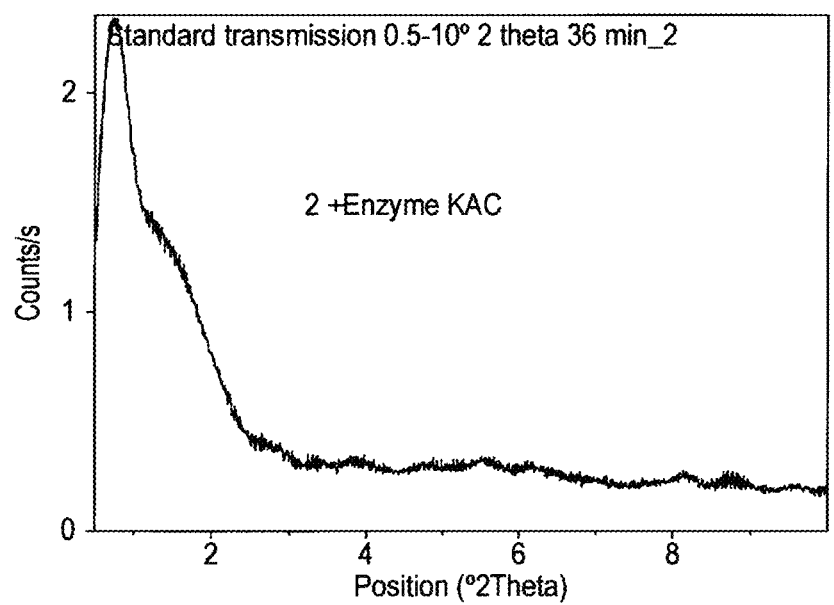
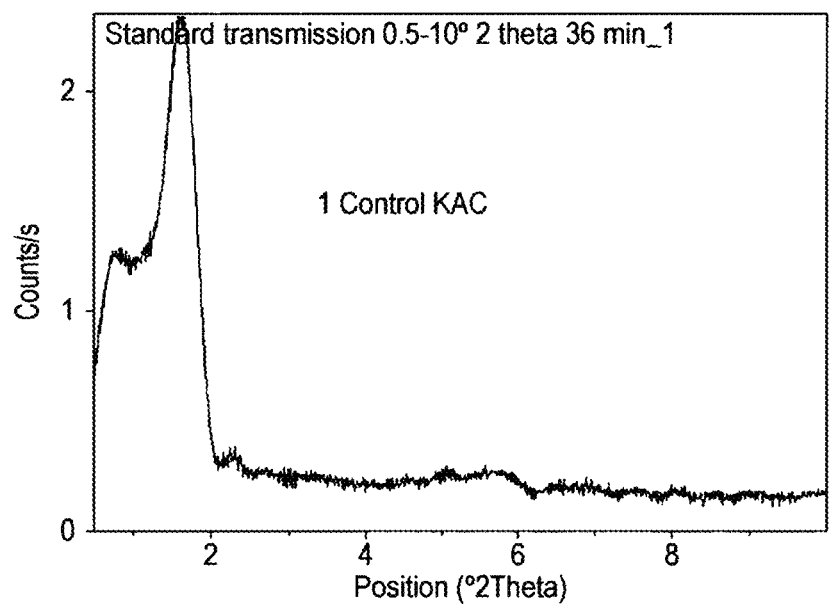

FIGURE 95
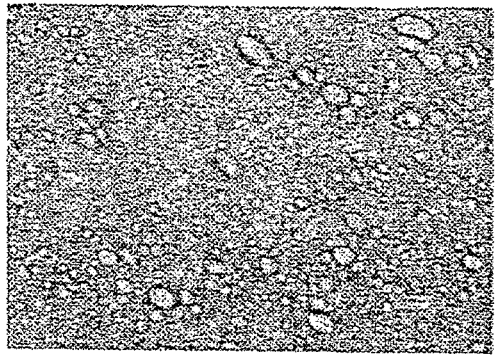 
With enzyme　　　　　　　　　No enzyme

SEQUENCE LISTING

<160> NUMBER OF SEQ ID NOS: 121

<210> SEQ ID NO 1
<211> LENGTH: 335
<212> TYPE: PRT
<213> ORGANISM: Aeromonas hydrophila

<400> SEQUENCE: 1

```
Met Lys Lys Trp Phe Val Cys Leu Leu Gly Leu Val Ala Leu Thr Val
1               5                   10                  15

Gln Ala Ala Asp Ser Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
        35                  40                  45

Leu Pro Ser Ser Pro Pro Tyr Tyr Glu Gly Arg Phe Ser Asn Gly Pro
    50                  55                  60

Val Trp Leu Glu Gln Leu Thr Lys Gln Phe Pro Gly Leu Thr Ile Ala
65                  70                  75                  80

Asn Glu Ala Glu Gly Gly Ala Thr Ala Val Ala Tyr Asn Lys Ile Ser
                85                  90                  95

Trp Asn Pro Lys Tyr Gln Val Ile Asn Asn Leu Asp Tyr Glu Val Thr
            100                 105                 110

Gln Phe Leu Gln Lys Asp Ser Phe Lys Pro Asp Leu Val Ile Leu
        115                 120                 125

Trp Val Gly Ala Asn Asp Tyr Leu Ala Tyr Gly Trp Asn Thr Glu Gln
    130                 135                 140

Asp Ala Lys Arg Val Arg Asp Ala Ile Ser Asp Ala Ala Asn Arg Met
145                 150                 155                 160

Val Leu Asn Gly Ala Lys Gln Ile Leu Leu Phe Asn Leu Pro Asp Leu
                165                 170                 175

Gly Gln Asn Pro Ser Ala Arg Ser Gln Lys Val Val Glu Ala Val Ser
            180                 185                 190

His Val Ser Ala Tyr His Asn Gln Leu Leu Leu Asn Leu Ala Arg Gln
        195                 200                 205

Leu Ala Pro Thr Gly Met Val Lys Leu Phe Glu Ile Asp Lys Gln Phe
    210                 215                 220

Ala Glu Met Leu Arg Asp Pro Gln Asn Phe Gly Leu Ser Asp Val Glu
225                 230                 235                 240

Asn Pro Cys Tyr Asp Gly Gly Tyr Val Trp Lys Pro Phe Ala Thr Arg
                245                 250                 255

Ser Val Ser Thr Asp Arg Gln Leu Ser Ala Phe Ser Pro Gln Glu Arg
            260                 265                 270

Leu Ala Ile Ala Gly Asn Pro Leu Leu Ala Gln Ala Val Ala Ser Pro
        275                 280                 285

Met Ala Arg Arg Ser Ala Ser Pro Leu Asn Cys Glu Gly Lys Met Phe
    290                 295                 300

Trp Asp Gln Val His Pro Thr Thr Val Val His Ala Ala Leu Ser Glu
305                 310                 315                 320

Arg Ala Ala Thr Phe Ile Ala Asn Gln Tyr Glu Phe Leu Ala His
                325                 330                 335
```

<210> SEQ ID NO 2
<211> LENGTH: 361
<212> TYPE: PRT
<213> ORGANISM: Artificial
<220> FEATURE:

<223> OTHER INFORMATION: Consensus sequence

<400> SEQUENCE: 2

```
Ile Val Ala Phe Gly Asp Ser Leu Thr Asp Gly Glu Ala Tyr Tyr Gly
1               5                   10                  15

Asp Ser Asp Gly Gly Gly Trp Gly Ala Gly Leu Ala Asp Arg Leu Thr
            20                  25                  30

Ala Leu Leu Arg Leu Arg Ala Arg Pro Arg Gly Val Asp Val Phe Asn
        35                  40                  45

Arg Gly Ile Ser Gly Arg Thr Ser Asp Gly Arg Leu Ile Val Asp Ala
    50                  55                  60

Leu Val Ala Leu Leu Phe Leu Ala Gln Ser Leu Gly Leu Pro Asn Leu
65                  70                  75                  80

Pro Pro Tyr Leu Ser Gly Asp Phe Leu Arg Gly Ala Asn Phe Ala Ser
            85                  90                  95

Ala Gly Ala Thr Ile Leu Pro Thr Ser Gly Pro Phe Leu Ile Gln Val
            100                 105                 110

Gln Phe Lys Asp Phe Lys Ser Gln Val Leu Glu Leu Arg Gln Ala Leu
        115                 120                 125

Gly Leu Leu Gln Glu Leu Leu Arg Leu Leu Pro Val Leu Asp Ala Lys
    130                 135                 140

Ser Pro Asp Leu Val Thr Ile Met Ile Gly Thr Asn Asp Leu Ile Thr
145                 150                 155                 160

Ser Ala Phe Phe Gly Pro Lys Ser Thr Glu Ser Asp Arg Asn Val Ser
            165                 170                 175

Val Pro Glu Phe Lys Asp Asn Leu Arg Gln Leu Ile Lys Arg Leu Arg
            180                 185                 190

Ser Asn Asn Gly Ala Arg Ile Ile Val Leu Ile Thr Leu Val Ile Leu
    195                 200                 205

Asn Leu Gly Pro Leu Gly Cys Leu Pro Leu Lys Leu Ala Leu Ala Leu
210                 215                 220

Ala Ser Ser Lys Asn Val Asp Ala Ser Gly Cys Leu Glu Arg Leu Asn
225                 230                 235                 240

Glu Ala Val Ala Asp Phe Asn Glu Ala Leu Arg Glu Leu Ala Ile Ser
            245                 250                 255

Lys Leu Glu Asp Gln Leu Arg Lys Asp Gly Leu Pro Asp Val Lys Gly
        260                 265                 270

Ala Asp Val Pro Tyr Val Asp Leu Tyr Ser Ile Phe Gln Asp Leu Asp
        275                 280                 285

Gly Ile Gln Asn Pro Ser Ala Tyr Val Tyr Gly Phe Glu Thr Thr Lys
    290                 295                 300

Ala Cys Cys Gly Tyr Gly Gly Arg Tyr Asn Tyr Asn Arg Val Cys Gly
305                 310                 315                 320

Asn Ala Gly Leu Cys Asn Val Thr Ala Lys Ala Cys Asn Pro Ser Ser
            325                 330                 335

Tyr Leu Leu Ser Phe Leu Phe Trp Asp Gly Phe His Pro Ser Glu Lys
            340                 345                 350

Gly Tyr Lys Ala Val Ala Glu Ala Leu
        355                 360
```

<210> SEQ ID NO 3
<211> LENGTH: 335
<212> TYPE: PRT
<213> ORGANISM: Aeromonas hydrophila

```
<400> SEQUENCE: 3

Met Lys Lys Trp Phe Val Cys Leu Leu Gly Leu Val Ala Leu Thr Val
1               5                   10                  15

Gln Ala Ala Asp Ser Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
            35                  40                  45

Leu Pro Ser Ser Pro Tyr Tyr Glu Gly Arg Phe Ser Asn Gly Pro
    50                  55                      60

Val Trp Leu Glu Gln Leu Thr Asn Glu Phe Pro Gly Leu Thr Ile Ala
65                  70                  75                  80

Asn Glu Ala Glu Gly Gly Pro Thr Ala Val Ala Tyr Asn Lys Ile Ser
                    85                  90                  95

Trp Asn Pro Lys Tyr Gln Val Ile Asn Asn Leu Asp Tyr Glu Val Thr
                100                 105                 110

Gln Phe Leu Gln Lys Asp Ser Phe Lys Pro Asp Asp Leu Val Ile Leu
            115                 120                 125

Trp Val Gly Ala Asn Asp Tyr Leu Ala Tyr Gly Trp Asn Thr Glu Gln
130                 135                 140

Asp Ala Lys Arg Val Arg Asp Ala Ile Ser Asp Ala Ala Asn Arg Met
145                 150                 155                 160

Val Leu Asn Gly Ala Lys Glu Ile Leu Leu Phe Asn Leu Pro Asp Leu
                165                 170                 175

Gly Gln Asn Pro Ser Ala Arg Ser Gln Lys Val Val Glu Ala Ala Ser
            180                 185                 190

His Val Ser Ala Tyr His Asn Gln Leu Leu Leu Asn Leu Ala Arg Gln
            195                 200                 205

Leu Ala Pro Thr Gly Met Val Lys Leu Phe Glu Ile Asp Lys Gln Phe
210                 215                 220

Ala Glu Met Leu Arg Asp Pro Gln Asn Phe Gly Leu Ser Asp Gln Arg
225                 230                 235                 240

Asn Ala Cys Tyr Gly Gly Ser Tyr Val Trp Lys Pro Phe Ala Ser Arg
                245                 250                 255

Ser Ala Ser Thr Asp Ser Gln Leu Ser Ala Phe Asn Pro Gln Glu Arg
            260                 265                 270

Leu Ala Ile Ala Gly Asn Pro Leu Leu Ala Gln Ala Val Ala Ser Pro
            275                 280                 285

Met Ala Ala Arg Ser Ala Ser Thr Leu Asn Cys Glu Gly Lys Met Phe
290                 295                 300

Trp Asp Gln Val His Pro Thr Thr Val Val His Ala Ala Leu Ser Glu
305                 310                 315                 320

Pro Ala Ala Thr Phe Ile Glu Ser Gln Tyr Glu Phe Leu Ala His
                325                 330                 335

<210> SEQ ID NO 4
<211> LENGTH: 336
<212> TYPE: PRT
<213> ORGANISM: Aeromonas salmonicida

<400> SEQUENCE: 4

Met Lys Lys Trp Phe Val Cys Leu Leu Gly Leu Ile Ala Leu Thr Val
1               5                   10                  15

Gln Ala Ala Asp Thr Arg Pro Ala Phe Ser Arg Ile Val Met Phe Gly
            20                  25                  30
```

```
Asp Ser Leu Ser Asp Thr Gly Lys Met Tyr Ser Lys Met Arg Gly Tyr
            35                  40                  45

Leu Pro Ser Ser Pro Tyr Tyr Glu Gly Arg Phe Ser Asn Gly Pro
 50                  55                  60

Val Trp Leu Glu Gln Leu Thr Lys Gln Phe Pro Gly Leu Thr Ile Ala
 65                  70                  75                  80

Asn Glu Ala Glu Gly Gly Ala Thr Ala Val Ala Tyr Asn Lys Ile Ser
                    85                  90                  95

Trp Asn Pro Lys Tyr Gln Val Tyr Asn Asn Leu Asp Tyr Glu Val Thr
                100                 105                 110

Gln Phe Leu Gln Lys Asp Ser Phe Lys Pro Asp Leu Val Ile Leu
            115                 120                 125

Trp Val Gly Ala Asn Asp Tyr Leu Ala Tyr Gly Trp Asn Thr Glu Gln
130                 135                 140

Asp Ala Lys Arg Val Arg Asp Ala Ile Ser Asp Ala Ala Asn Arg Met
145                 150                 155                 160

Val Leu Asn Gly Ala Lys Gln Ile Leu Leu Phe Asn Leu Pro Asp Leu
                    165                 170                 175

Gly Gln Asn Pro Ser Ala Arg Ser Gln Lys Val Val Glu Ala Val Ser
                180                 185                 190

His Val Ser Ala Tyr His Asn Lys Leu Leu Leu Asn Leu Ala Arg Gln
            195                 200                 205

Leu Ala Pro Thr Gly Met Val Lys Leu Phe Glu Ile Asp Lys Gln Phe
            210                 215                 220

Ala Glu Met Leu Arg Asp Pro Gln Asn Phe Gly Leu Ser Asp Val Glu
225                 230                 235                 240

Asn Pro Cys Tyr Asp Gly Gly Tyr Val Trp Lys Pro Phe Ala Thr Arg
                245                 250                 255

Ser Val Ser Thr Asp Arg Gln Leu Ser Ala Phe Ser Pro Gln Glu Arg
                260                 265                 270

Leu Ala Ile Ala Gly Asn Pro Leu Leu Ala Gln Ala Val Ala Ser Pro
            275                 280                 285

Met Ala Arg Arg Ser Ala Ser Pro Leu Asn Cys Glu Gly Lys Met Phe
290                 295                 300

Trp Asp Gln Val His Pro Thr Thr Val Val His Ala Ala Leu Ser Glu
305                 310                 315                 320

Arg Ala Ala Thr Phe Ile Glu Thr Gln Tyr Glu Phe Leu Ala His Gly
                325                 330                 335

<210> SEQ ID NO 5
<211> LENGTH: 295
<212> TYPE: PRT
<213> ORGANISM: Streptomyces coelicolor

<400> SEQUENCE: 5

Met Pro Lys Pro Ala Leu Arg Arg Val Met Thr Ala Thr Val Ala Ala
 1               5                  10                  15

Val Gly Thr Leu Ala Leu Gly Leu Thr Asp Ala Thr Ala His Ala Ala
                20                  25                  30

Pro Ala Gln Ala Thr Pro Thr Leu Asp Tyr Val Ala Leu Gly Asp Ser
            35                  40                  45

Tyr Ser Ala Gly Ser Gly Val Leu Pro Val Asp Pro Ala Asn Leu Leu
 50                  55                  60

Cys Leu Arg Ser Thr Ala Asn Tyr Pro His Val Ile Ala Asp Thr Thr
 65                  70                  75                  80
```

```
Gly Ala Arg Leu Thr Asp Val Thr Cys Gly Ala Ala Gln Thr Ala Asp
                85                  90                  95

Phe Thr Arg Ala Gln Tyr Pro Gly Val Ala Pro Gln Leu Asp Ala Leu
            100                 105                 110

Gly Thr Gly Thr Asp Leu Val Thr Leu Thr Ile Gly Gly Asn Asp Asn
        115                 120                 125

Ser Thr Phe Ile Asn Ala Ile Thr Ala Cys Gly Thr Ala Gly Val Leu
    130                 135                 140

Ser Gly Gly Lys Gly Ser Pro Cys Lys Asp Arg His Gly Thr Ser Phe
145                 150                 155                 160

Asp Asp Glu Ile Glu Ala Asn Thr Tyr Pro Ala Leu Lys Glu Ala Leu
                165                 170                 175

Leu Gly Val Arg Ala Arg Ala Pro His Ala Arg Val Ala Ala Leu Gly
            180                 185                 190

Tyr Pro Trp Ile Thr Pro Ala Thr Ala Asp Pro Ser Cys Phe Leu Lys
        195                 200                 205

Leu Pro Leu Ala Ala Gly Asp Val Pro Tyr Leu Arg Ala Ile Gln Ala
    210                 215                 220

His Leu Asn Asp Ala Val Arg Arg Ala Ala Glu Glu Thr Gly Ala Thr
225                 230                 235                 240

Tyr Val Asp Phe Ser Gly Val Ser Asp Gly His Asp Ala Cys Glu Ala
                245                 250                 255

Pro Gly Thr Arg Trp Ile Glu Pro Leu Leu Phe Gly His Ser Leu Val
            260                 265                 270

Pro Val His Pro Asn Ala Leu Gly Glu Arg Arg Met Ala Glu His Thr
        275                 280                 285

Met Asp Val Leu Gly Leu Asp
    290                 295

<210> SEQ ID NO 6
<211> LENGTH: 295
<212> TYPE: PRT
<213> ORGANISM: Streptomyces coelicolor

<400> SEQUENCE: 6

Met Pro Lys Pro Ala Leu Arg Arg Val Met Thr Ala Thr Val Ala Ala
1               5                   10                  15

Val Gly Thr Leu Ala Leu Gly Leu Thr Asp Ala Thr Ala His Ala Ala
            20                  25                  30

Pro Ala Gln Ala Thr Pro Thr Leu Asp Tyr Val Ala Leu Gly Asp Ser
        35                  40                  45

Tyr Ser Ala Gly Ser Gly Val Leu Pro Val Asp Pro Ala Asn Leu Leu
    50                  55                  60

Cys Leu Arg Ser Thr Ala Asn Tyr Pro His Val Ile Ala Asp Thr Thr
65                  70                  75                  80

Gly Ala Arg Leu Thr Asp Val Thr Cys Gly Ala Ala Gln Thr Ala Asp
                85                  90                  95

Phe Thr Arg Ala Gln Tyr Pro Gly Val Ala Pro Gln Leu Asp Ala Leu
            100                 105                 110

Gly Thr Gly Thr Asp Leu Val Thr Leu Thr Ile Gly Gly Asn Asp Asn
        115                 120                 125

Ser Thr Phe Ile Asn Ala Ile Thr Ala Cys Gly Thr Ala Gly Val Leu
    130                 135                 140

Ser Gly Gly Lys Gly Ser Pro Cys Lys Asp Arg His Gly Thr Ser Phe
```

```
                145                 150                 155                 160
Asp Asp Glu Ile Glu Ala Asn Thr Tyr Pro Ala Leu Lys Glu Ala Leu
                    165                 170                 175

Leu Gly Val Arg Ala Arg Ala Pro His Ala Arg Val Ala Ala Leu Gly
                180                 185                 190

Tyr Pro Trp Ile Thr Pro Ala Thr Ala Asp Pro Ser Cys Phe Leu Lys
                195                 200                 205

Leu Pro Leu Ala Ala Gly Asp Val Pro Tyr Leu Arg Ala Ile Gln Ala
210                 215                 220

His Leu Asn Asp Ala Val Arg Arg Ala Ala Glu Glu Thr Gly Ala Thr
225                 230                 235                 240

Tyr Val Asp Phe Ser Gly Val Ser Asp Gly His Asp Ala Cys Glu Ala
                245                 250                 255

Pro Gly Thr Arg Trp Ile Glu Pro Leu Leu Phe Gly His Ser Leu Val
                260                 265                 270

Pro Val His Pro Asn Ala Leu Gly Glu Arg Arg Met Ala Glu His Thr
                275                 280                 285

Met Asp Val Leu Gly Leu Asp
                290                 295

<210> SEQ ID NO 7
<211> LENGTH: 238
<212> TYPE: PRT
<213> ORGANISM: Saccharomyces cerevisiae

<400> SEQUENCE: 7

Met Asp Tyr Glu Lys Phe Leu Leu Phe Gly Asp Ser Ile Thr Glu Phe
1               5                   10                  15

Ala Phe Asn Thr Arg Pro Ile Glu Asp Gly Lys Asp Gln Tyr Ala Leu
                20                  25                  30

Gly Ala Ala Leu Val Asn Glu Tyr Thr Arg Lys Met Asp Ile Leu Gln
            35                  40                  45

Arg Gly Phe Lys Gly Tyr Thr Ser Arg Trp Ala Leu Lys Ile Leu Pro
50                  55                  60

Glu Ile Leu Lys His Glu Ser Asn Ile Val Met Ala Thr Ile Phe Leu
65                  70                  75                  80

Gly Ala Asn Asp Ala Cys Ser Ala Gly Pro Gln Ser Val Pro Leu Pro
                85                  90                  95

Glu Phe Ile Asp Asn Ile Arg Gln Met Val Ser Leu Met Lys Ser Tyr
                100                 105                 110

His Ile Arg Pro Ile Ile Ile Gly Pro Gly Leu Val Asp Arg Glu Lys
            115                 120                 125

Trp Glu Lys Glu Lys Ser Glu Gly Ile Ala Leu Gly Tyr Phe Arg Thr
130                 135                 140

Asn Glu Asn Phe Ala Ile Tyr Ser Asp Ala Leu Ala Lys Leu Ala Asn
145                 150                 155                 160

Glu Glu Lys Val Pro Phe Val Ala Leu Asn Lys Ala Phe Gln Gln Glu
                165                 170                 175

Gly Gly Asp Ala Trp Gln Gln Leu Leu Thr Asp Gly Leu His Phe Ser
            180                 185                 190

Gly Lys Gly Tyr Lys Ile Phe His Asp Glu Leu Leu Lys Val Ile Glu
        195                 200                 205

Thr Phe Tyr Pro Gln Tyr His Pro Lys Asn Met Gln Tyr Lys Leu Lys
    210                 215                 220
```

Asp Trp Arg Asp Val Leu Asp Gly Ser Asn Ile Met Ser
225                 230                 235

<210> SEQ ID NO 8
<211> LENGTH: 347
<212> TYPE: PRT
<213> ORGANISM: Ralstonia sp.

<400> SEQUENCE: 8

Met Asn Leu Arg Gln Trp Met Gly Ala Ala Thr Ala Ala Leu Ala Leu
1               5                   10                  15

Gly Leu Ala Ala Cys Gly Gly Gly Thr Asp Gln Ser Gly Asn Pro
            20                  25                  30

Asn Val Ala Lys Val Gln Arg Met Val Val Phe Gly Asp Ser Leu Ser
                35                  40                  45

Asp Ile Gly Thr Tyr Thr Pro Val Ala Gln Ala Val Gly Gly Gly Lys
    50                  55                  60

Phe Thr Thr Asn Pro Gly Pro Ile Trp Ala Glu Thr Val Ala Ala Gln
65                  70                  75                  80

Leu Gly Val Thr Leu Thr Pro Ala Val Met Gly Tyr Ala Thr Ser Val
                85                  90                  95

Gln Asn Cys Pro Lys Ala Gly Cys Phe Asp Tyr Ala Gln Gly Gly Ser
            100                 105                 110

Arg Val Thr Asp Pro Asn Gly Ile Gly His Asn Gly Ala Gly Ala
            115                 120                 125

Leu Thr Tyr Pro Val Gln Gln Gln Leu Ala Asn Phe Tyr Ala Ala Ser
    130                 135                 140

Asn Asn Thr Phe Asn Gly Asn Asn Asp Val Val Phe Val Leu Ala Gly
145                 150                 155                 160

Ser Asn Asp Ile Phe Phe Trp Thr Thr Ala Ala Ala Thr Ser Gly Ser
                165                 170                 175

Gly Val Thr Pro Ala Ile Ala Thr Ala Gln Val Gln Gln Ala Ala Thr
            180                 185                 190

Asp Leu Val Gly Tyr Val Lys Asp Met Ile Ala Lys Gly Ala Thr Gln
    195                 200                 205

Val Tyr Val Phe Asn Leu Pro Asp Ser Ser Leu Thr Pro Asp Gly Val
210                 215                 220

Ala Ser Gly Thr Thr Gly Gln Ala Leu Leu His Ala Leu Val Gly Thr
225                 230                 235                 240

Phe Asn Thr Thr Leu Gln Ser Gly Leu Ala Gly Thr Ser Ala Arg Ile
                245                 250                 255

Ile Asp Phe Asn Ala Gln Leu Thr Ala Ala Ile Gln Asn Gly Ala Ser
            260                 265                 270

Phe Gly Phe Ala Asn Thr Ser Ala Arg Ala Cys Asp Ala Thr Lys Ile
    275                 280                 285

Asn Ala Leu Val Pro Ser Ala Gly Gly Ser Ser Leu Phe Cys Ser Ala
290                 295                 300

Asn Thr Leu Val Ala Ser Gly Ala Asp Gln Ser Tyr Leu Phe Ala Asp
305                 310                 315                 320

Gly Val His Pro Thr Thr Ala Gly His Arg Leu Ile Ala Ser Asn Val
                325                 330                 335

Leu Ala Arg Leu Leu Ala Asp Asn Val Ala His
            340                 345

<210> SEQ ID NO 9

```
<211> LENGTH: 261
<212> TYPE: PRT
<213> ORGANISM: Streptomyces coelicolor

<400> SEQUENCE: 9

Met Ile Gly Ser Tyr Val Ala Val Gly Asp Ser Phe Thr Glu Gly Val
1               5                   10                  15

Gly Asp Pro Gly Pro Asp Gly Ala Phe Val Gly Trp Ala Asp Arg Leu
            20                  25                  30

Ala Val Leu Leu Ala Asp Arg Arg Pro Glu Gly Asp Phe Thr Tyr Thr
        35                  40                  45

Asn Leu Ala Val Arg Gly Arg Leu Leu Asp Gln Ile Val Ala Glu Gln
    50                  55                  60

Val Pro Arg Val Val Gly Leu Ala Pro Asp Leu Val Ser Phe Ala Ala
65                  70                  75                  80

Gly Gly Asn Asp Ile Ile Arg Pro Gly Thr Asp Pro Asp Glu Val Ala
                85                  90                  95

Glu Arg Phe Glu Leu Ala Val Ala Leu Thr Ala Ala Ala Gly Thr
            100                 105                 110

Val Leu Val Thr Thr Gly Phe Asp Thr Arg Gly Val Pro Val Leu Lys
        115                 120                 125

His Leu Arg Gly Lys Ile Ala Thr Tyr Asn Gly His Val Arg Ala Ile
    130                 135                 140

Ala Asp Arg Tyr Gly Cys Pro Val Leu Asp Leu Trp Ser Leu Arg Ser
145                 150                 155                 160

Val Gln Asp Arg Arg Ala Trp Asp Ala Asp Arg Leu His Leu Ser Pro
                165                 170                 175

Glu Gly His Thr Arg Val Ala Leu Arg Ala Gly Gln Ala Leu Gly Leu
            180                 185                 190

Arg Val Pro Ala Asp Pro Asp Gln Pro Trp Pro Leu Pro Pro Arg
        195                 200                 205

Gly Thr Leu Asp Val Arg Arg Asp Asp Val His Trp Ala Arg Glu Tyr
    210                 215                 220

Leu Val Pro Trp Ile Gly Arg Arg Leu Arg Gly Glu Ser Ser Gly Asp
225                 230                 235                 240

His Val Thr Ala Lys Gly Thr Leu Ser Pro Asp Ala Ile Lys Thr Arg
                245                 250                 255

Ile Ala Ala Val Ala
            260

<210> SEQ ID NO 10
<211> LENGTH: 260
<212> TYPE: PRT
<213> ORGANISM: Streptomyces coelicolor

<400> SEQUENCE: 10

Met Gln Thr Asn Pro Ala Tyr Thr Ser Leu Val Ala Val Gly Asp Ser
1               5                   10                  15

Phe Thr Glu Gly Met Ser Asp Leu Leu Pro Asp Gly Ser Tyr Arg Gly
            20                  25                  30

Trp Ala Asp Leu Leu Ala Thr Arg Met Ala Ala Arg Ser Pro Gly Phe
        35                  40                  45

Arg Tyr Ala Asn Leu Ala Val Arg Gly Lys Leu Ile Gly Gln Ile Val
    50                  55                  60

Asp Glu Gln Val Asp Val Ala Ala Ala Met Gly Ala Asp Val Ile Thr
65                  70                  75                  80
```

Leu Val Gly Gly Leu Asn Asp Thr Leu Arg Pro Lys Cys Asp Met Ala
                85                  90                  95

Arg Val Arg Asp Leu Leu Thr Gln Ala Val Glu Arg Leu Ala Pro His
            100                 105                 110

Cys Glu Gln Leu Val Leu Met Arg Ser Pro Gly Arg Gln Gly Pro Val
        115                 120                 125

Leu Glu Arg Phe Arg Pro Arg Met Glu Ala Leu Phe Ala Val Ile Asp
    130                 135                 140

Asp Leu Ala Gly Arg His Gly Ala Val Val Asp Leu Tyr Gly Ala
145                 150                 155                 160

Gln Ser Leu Ala Asp Pro Arg Met Trp Asp Val Asp Arg Leu His Leu
                165                 170                 175

Thr Ala Glu Gly His Arg Arg Val Ala Glu Ala Val Trp Gln Ser Leu
            180                 185                 190

Gly His Glu Pro Glu Asp Pro Glu Trp His Ala Pro Ile Pro Ala Thr
        195                 200                 205

Pro Pro Pro Gly Trp Val Thr Arg Arg Thr Ala Asp Val Arg Phe Ala
    210                 215                 220

Arg Gln His Leu Leu Pro Trp Ile Gly Arg Arg Leu Thr Gly Arg Ser
225                 230                 235                 240

Ser Gly Asp Gly Leu Pro Ala Lys Arg Pro Asp Leu Leu Pro Tyr Glu
                245                 250                 255

Asp Pro Ala Arg
            260

<210> SEQ ID NO 11
<211> LENGTH: 454
<212> TYPE: PRT
<213> ORGANISM: Streptomyces coelicolor

<400> SEQUENCE: 11

Met Thr Arg Gly Arg Asp Gly Ala Gly Ala Pro Pro Thr Lys His
1               5                   10                  15

Arg Ala Leu Leu Ala Ala Ile Val Thr Leu Ile Val Ala Ile Ser Ala
            20                  25                  30

Ala Ile Tyr Ala Gly Ala Ser Ala Asp Asp Gly Ser Arg Asp His Ala
        35                  40                  45

Leu Gln Ala Gly Gly Arg Leu Pro Arg Gly Asp Ala Ala Pro Ala Ser
    50                  55                  60

Thr Gly Ala Trp Val Gly Ala Trp Ala Thr Ala Pro Ala Ala Ala Glu
65                  70                  75                  80

Pro Gly Thr Glu Thr Thr Gly Leu Ala Gly Arg Ser Val Arg Asn Val
                85                  90                  95

Val His Thr Ser Val Gly Gly Thr Gly Ala Arg Ile Thr Leu Ser Asn
            100                 105                 110

Leu Tyr Gly Gln Ser Pro Leu Thr Val Thr His Ala Ser Ile Ala Leu
        115                 120                 125

Ala Ala Gly Pro Asp Thr Ala Ala Ile Ala Asp Thr Met Arg Arg
    130                 135                 140

Leu Thr Phe Gly Gly Ser Ala Arg Val Ile Ile Pro Ala Gly Gly Gln
145                 150                 155                 160

Val Met Ser Asp Thr Ala Arg Leu Ala Ile Pro Tyr Gly Ala Asn Val
                165                 170                 175

Leu Val Thr Thr Tyr Ser Pro Ile Pro Ser Gly Pro Val Thr Tyr His

```
              180                 185                 190
Pro Gln Ala Arg Gln Thr Ser Tyr Leu Ala Asp Gly Asp Arg Thr Ala
            195                 200                 205
Asp Val Thr Ala Val Ala Tyr Thr Pro Thr Pro Tyr Trp Arg Tyr
    210                 215                 220
Leu Thr Ala Leu Asp Val Leu Ser His Glu Ala Asp Gly Thr Val Val
225                 230                 235                 240
Ala Phe Gly Asp Ser Ile Thr Asp Gly Ala Arg Ser Gln Ser Asp Ala
            245                 250                 255
Asn His Arg Trp Thr Asp Val Leu Ala Ala Arg Leu His Glu Ala Ala
            260                 265                 270
Gly Asp Gly Arg Asp Thr Pro Arg Tyr Ser Val Val Asn Glu Gly Ile
        275                 280                 285
Ser Gly Asn Arg Leu Leu Thr Ser Arg Pro Gly Arg Pro Ala Asp Asn
    290                 295                 300
Pro Ser Gly Leu Ser Arg Phe Gln Arg Asp Val Leu Glu Arg Thr Asn
305                 310                 315                 320
Val Lys Ala Val Val Val Leu Gly Val Asn Asp Val Leu Asn Ser
            325                 330                 335
Pro Glu Leu Ala Asp Arg Asp Ala Ile Leu Thr Gly Leu Arg Thr Leu
            340                 345                 350
Val Asp Arg Ala His Ala Arg Gly Leu Arg Val Val Gly Ala Thr Ile
        355                 360                 365
Thr Pro Phe Gly Gly Tyr Gly Gly Tyr Thr Glu Ala Arg Glu Thr Met
    370                 375                 380
Arg Gln Glu Val Asn Glu Glu Ile Arg Ser Gly Arg Val Phe Asp Thr
385                 390                 395                 400
Val Val Asp Phe Asp Lys Ala Leu Arg Asp Pro Tyr Asp Pro Arg Arg
            405                 410                 415
Met Arg Ser Asp Tyr Asp Ser Gly Asp His Leu His Pro Gly Asp Lys
            420                 425                 430
Gly Tyr Ala Arg Met Gly Ala Val Ile Asp Leu Ala Ala Leu Lys Gly
        435                 440                 445
Ala Ala Pro Val Lys Ala
        450

<210> SEQ ID NO 12
<211> LENGTH: 340
<212> TYPE: PRT
<213> ORGANISM: Streptomyces coelicolor

<400> SEQUENCE: 12

Met Thr Ser Met Ser Arg Ala Arg Val Ala Arg Ile Ala Ala Gly
1               5                   10                  15
Ala Ala Tyr Gly Gly Gly Gly Ile Gly Leu Ala Gly Ala Ala Val
            20                  25                  30
Gly Leu Val Val Ala Glu Val Gln Leu Ala Arg Arg Val Gly Val
        35                  40                  45
Gly Thr Pro Thr Arg Val Pro Asn Ala Gln Gly Leu Tyr Gly Gly Thr
    50                  55                  60
Leu Pro Thr Ala Gly Asp Pro Pro Leu Arg Leu Met Met Leu Gly Asp
65                  70                  75                  80
Ser Thr Ala Ala Gly Gln Gly Val His Arg Ala Gly Gln Thr Pro Gly
            85                  90                  95
```

```
Ala Leu Leu Ala Ser Gly Leu Ala Ala Val Ala Glu Arg Pro Val Arg
                100                 105                 110

Leu Gly Ser Val Ala Gln Pro Gly Ala Cys Ser Asp Asp Leu Asp Arg
            115                 120                 125

Gln Val Ala Leu Val Leu Ala Glu Pro Asp Arg Val Pro Asp Ile Cys
        130                 135                 140

Val Ile Met Val Gly Ala Asn Asp Val Thr His Arg Met Pro Ala Thr
145                 150                 155                 160

Arg Ser Val Arg His Leu Ser Ser Ala Val Arg Arg Leu Arg Thr Ala
                165                 170                 175

Gly Ala Glu Val Val Gly Thr Cys Pro Asp Leu Gly Thr Ile Glu
            180                 185                 190

Arg Val Arg Gln Pro Leu Arg Trp Leu Ala Arg Ala Ser Arg Gln
            195                 200                 205

Leu Ala Ala Ala Gln Thr Ile Gly Ala Val Glu Gln Gly Gly Arg Thr
        210                 215                 220

Val Ser Leu Gly Asp Leu Leu Gly Pro Glu Phe Ala Gln Asn Pro Arg
225                 230                 235                 240

Glu Leu Phe Gly Pro Asp Asn Tyr His Pro Ser Ala Glu Gly Tyr Ala
                245                 250                 255

Thr Ala Ala Met Ala Val Leu Pro Ser Val Cys Ala Ala Leu Gly Leu
            260                 265                 270

Trp Pro Ala Asp Glu Glu His Pro Asp Ala Leu Arg Glu Gly Phe
            275                 280                 285

Leu Pro Val Ala Arg Ala Ala Glu Ala Ala Ser Glu Ala Gly Thr
            290                 295                 300

Glu Val Ala Ala Ala Met Pro Thr Gly Pro Arg Gly Pro Trp Ala Leu
305                 310                 315                 320

Leu Lys Arg Arg Arg Arg Arg Val Ser Glu Ala Glu Pro Ser Ser
                325                 330                 335

Pro Ser Gly Val
            340

<210> SEQ ID NO 13
<211> LENGTH: 305
<212> TYPE: PRT
<213> ORGANISM: Streptomyces coelicolor

<400> SEQUENCE: 13

Met Gly Arg Gly Thr Asp Gln Arg Thr Arg Tyr Gly Arg Arg Arg Ala
1               5                   10                  15

Arg Val Ala Leu Ala Ala Leu Thr Ala Ala Val Leu Gly Val Gly Val
            20                  25                  30

Ala Gly Cys Asp Ser Val Gly Gly Asp Ser Pro Ala Pro Ser Gly Ser
            35                  40                  45

Pro Ser Lys Arg Thr Arg Thr Ala Pro Ala Trp Asp Thr Ser Pro Ala
        50                  55                  60

Ser Val Ala Ala Val Gly Asp Ser Ile Thr Arg Gly Phe Asp Ala Cys
65                  70                  75                  80

Ala Val Leu Ser Asp Cys Pro Glu Val Ser Trp Ala Thr Gly Ser Ser
                85                  90                  95

Ala Lys Val Asp Ser Leu Ala Val Arg Leu Leu Gly Lys Ala Asp Ala
            100                 105                 110

Ala Glu His Ser Trp Asn Tyr Ala Val Thr Gly Ala Arg Met Ala Asp
            115                 120                 125
```

```
Leu Thr Ala Gln Val Thr Arg Ala Ala Gln Arg Glu Pro Glu Leu Val
        130                 135                 140

Ala Val Met Ala Gly Ala Asn Asp Ala Cys Arg Ser Thr Thr Ser Ala
145                 150                 155                 160

Met Thr Pro Val Ala Asp Phe Arg Ala Gln Phe Glu Glu Ala Met Ala
                165                 170                 175

Thr Leu Arg Lys Lys Leu Pro Lys Ala Gln Val Tyr Val Ser Ser Ile
            180                 185                 190

Pro Asp Leu Lys Arg Leu Trp Ser Gln Gly Arg Thr Asn Pro Leu Gly
        195                 200                 205

Lys Gln Val Trp Lys Leu Gly Leu Cys Pro Ser Met Leu Gly Asp Ala
    210                 215                 220

Asp Ser Leu Asp Ser Ala Ala Thr Leu Arg Arg Asn Thr Val Arg Asp
225                 230                 235                 240

Arg Val Ala Asp Tyr Asn Glu Val Leu Arg Glu Val Cys Ala Lys Asp
                245                 250                 255

Arg Arg Cys Arg Ser Asp Asp Gly Ala Val His Glu Phe Arg Phe Gly
            260                 265                 270

Thr Asp Gln Leu Ser His Trp Asp Trp Phe His Pro Ser Val Asp Gly
        275                 280                 285

Gln Ala Arg Leu Ala Glu Ile Ala Tyr Arg Ala Val Thr Ala Lys Asn
    290                 295                 300

Pro
305

<210> SEQ ID NO 14
<211> LENGTH: 268
<212> TYPE: PRT
<213> ORGANISM: Streptomyces rimosus

<400> SEQUENCE: 14

Met Arg Leu Ser Arg Arg Ala Ala Thr Ala Ser Ala Leu Leu Leu Thr
1               5                   10                  15

Pro Ala Leu Ala Leu Phe Gly Ala Ser Ala Ala Val Ser Ala Pro Arg
            20                  25                  30

Ile Gln Ala Thr Asp Tyr Val Ala Leu Gly Asp Ser Tyr Ser Ser Gly
        35                  40                  45

Val Gly Ala Gly Ser Tyr Asp Ser Ser Ser Gly Ser Cys Lys Arg Ser
    50                  55                  60

Thr Lys Ser Tyr Pro Ala Leu Trp Ala Ala Ser His Thr Gly Thr Arg
65                  70                  75                  80

Phe Asn Phe Thr Ala Cys Ser Gly Ala Arg Thr Gly Asp Val Leu Ala
                85                  90                  95

Lys Gln Leu Thr Pro Val Asn Ser Gly Thr Asp Leu Val Ser Ile Thr
            100                 105                 110

Ile Gly Gly Asn Asp Ala Gly Phe Ala Asp Thr Met Thr Thr Cys Asn
        115                 120                 125

Leu Gln Gly Glu Ser Ala Cys Leu Ala Arg Ile Ala Lys Ala Arg Ala
    130                 135                 140

Tyr Ile Gln Gln Thr Leu Pro Ala Gln Leu Asp Gln Val Tyr Asp Ala
145                 150                 155                 160

Ile Asp Ser Arg Ala Pro Ala Ala Gln Val Val Val Leu Gly Tyr Pro
                165                 170                 175

Arg Phe Tyr Lys Leu Gly Gly Ser Cys Ala Val Gly Leu Ser Glu Lys
```

```
                180                 185                 190
Ser Arg Ala Ala Ile Asn Ala Ala Asp Asp Ile Asn Ala Val Thr
            195                 200                 205
Ala Lys Arg Ala Ala Asp His Gly Phe Ala Phe Gly Asp Val Asn Thr
            210                 215                 220
Thr Phe Ala Gly His Glu Leu Cys Ser Gly Ala Pro Trp Leu His Ser
225                 230                 235                 240
Val Thr Leu Pro Val Glu Asn Ser Tyr His Pro Thr Ala Asn Gly Gln
            245                 250                 255
Ser Lys Gly Tyr Leu Pro Val Leu Asn Ser Ala Thr
            260                 265

<210> SEQ ID NO 15
<211> LENGTH: 336
<212> TYPE: PRT
<213> ORGANISM: Aeromonas salmonicida

<400> SEQUENCE: 15

Met Lys Lys Trp Phe Val Cys Leu Leu Gly Leu Ile Ala Leu Thr Val
1               5                  10                  15
Gln Ala Ala Asp Thr Arg Pro Ala Phe Ser Arg Ile Val Met Phe Gly
            20                  25                  30
Asp Ser Leu Ser Asp Thr Gly Lys Met Tyr Ser Lys Met Arg Gly Tyr
        35                  40                  45
Leu Pro Ser Ser Pro Pro Tyr Tyr Glu Gly Arg Phe Ser Asn Gly Pro
    50                  55                  60
Val Trp Leu Glu Gln Leu Thr Lys Gln Phe Pro Gly Leu Thr Ile Ala
65                  70                  75                  80
Asn Glu Ala Glu Gly Gly Ala Thr Ala Val Ala Tyr Asn Lys Ile Ser
                85                  90                  95
Trp Asn Pro Lys Tyr Gln Val Ile Asn Asn Leu Asp Tyr Glu Val Thr
            100                 105                 110
Gln Phe Leu Gln Lys Asp Ser Phe Lys Pro Asp Asp Leu Val Ile Leu
        115                 120                 125
Trp Val Gly Ala Asn Asp Tyr Leu Ala Tyr Gly Trp Asn Thr Glu Gln
    130                 135                 140
Asp Ala Lys Arg Val Arg Asp Ala Ile Ser Asp Ala Ala Asn Arg Met
145                 150                 155                 160
Val Leu Asn Gly Ala Lys Gln Ile Leu Leu Phe Asn Leu Pro Asp Leu
                165                 170                 175
Gly Gln Asn Pro Ser Ala Arg Ser Gln Lys Val Val Glu Ala Val Ser
            180                 185                 190
His Val Ser Ala Tyr His Asn Lys Leu Leu Leu Asn Leu Ala Arg Gln
        195                 200                 205
Leu Ala Pro Thr Gly Met Val Lys Leu Phe Glu Ile Asp Lys Gln Phe
    210                 215                 220
Ala Glu Met Leu Arg Asp Pro Gln Asn Phe Gly Leu Ser Asp Val Glu
225                 230                 235                 240
Asn Pro Cys Tyr Asp Gly Gly Tyr Val Trp Lys Pro Phe Ala Thr Arg
                245                 250                 255
Ser Val Ser Thr Asp Arg Gln Leu Ser Ala Phe Ser Pro Gln Glu Arg
            260                 265                 270
Leu Ala Ile Ala Gly Asn Pro Leu Leu Ala Gln Ala Val Ala Ser Pro
        275                 280                 285
```

```
Met Ala Arg Arg Ser Ala Ser Pro Leu Asn Cys Glu Gly Lys Met Phe
            290                 295                 300

Trp Asp Gln Val His Pro Thr Thr Val Val His Ala Ala Leu Ser Glu
305                 310                 315                 320

Arg Ala Ala Thr Phe Ile Glu Thr Gln Tyr Glu Phe Leu Ala His Gly
                325                 330                 335

<210> SEQ ID NO 16
<211> LENGTH: 318
<212> TYPE: PRT
<213> ORGANISM: Aeromonas salmonicida

<400> SEQUENCE: 16

Ala Asp Thr Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
            20                  25                  30

Ser Ser Pro Pro Tyr Tyr Glu Gly Arg Phe Ser Asn Gly Pro Val Trp
        35                  40                  45

Leu Glu Gln Leu Thr Lys Gln Phe Pro Gly Leu Thr Ile Ala Asn Glu
    50                  55                  60

Ala Glu Gly Gly Ala Thr Ala Val Ala Tyr Asn Lys Ile Ser Trp Asp
65                  70                  75                  80

Pro Lys Tyr Gln Val Ile Asn Asn Leu Asp Tyr Glu Val Thr Gln Phe
                85                  90                  95

Leu Gln Lys Asp Ser Phe Lys Pro Asp Asp Leu Val Ile Leu Trp Val
            100                 105                 110

Gly Ala Asn Asp Tyr Leu Ala Tyr Gly Trp Asn Thr Glu Gln Asp Ala
        115                 120                 125

Lys Arg Val Arg Asp Ala Ile Ser Asp Ala Ala Asn Arg Met Val Leu
    130                 135                 140

Asn Gly Ala Lys Gln Ile Leu Leu Phe Asn Leu Pro Asp Leu Gly Gln
145                 150                 155                 160

Asn Pro Ser Ala Arg Ser Gln Lys Val Val Glu Ala Val Ser His Val
                165                 170                 175

Ser Ala Tyr His Asn Lys Leu Leu Leu Asn Leu Ala Arg Gln Leu Ala
            180                 185                 190

Pro Thr Gly Met Val Lys Leu Phe Glu Ile Asp Lys Gln Phe Ala Glu
        195                 200                 205

Met Leu Arg Asp Pro Gln Asn Phe Gly Leu Ser Asp Val Glu Asn Pro
    210                 215                 220

Cys Tyr Asp Gly Gly Tyr Val Trp Lys Pro Phe Ala Thr Arg Ser Val
225                 230                 235                 240

Ser Thr Asp Arg Gln Leu Ser Ala Phe Ser Pro Gln Glu Arg Leu Ala
                245                 250                 255

Ile Ala Gly Asn Pro Leu Leu Ala Gln Ala Val Ala Ser Pro Met Ala
            260                 265                 270

Arg Arg Ser Ala Ser Pro Leu Asn Cys Glu Gly Lys Met Phe Trp Asp
        275                 280                 285

Gln Val His Pro Thr Thr Val Val His Ala Ala Leu Ser Glu Arg Ala
    290                 295                 300

Ala Thr Phe Ile Glu Thr Gln Tyr Glu Phe Leu Ala His Gly
305                 310                 315

<210> SEQ ID NO 17
```

<211> LENGTH: 465
<212> TYPE: PRT
<213> ORGANISM: Candida parapsilosis

<400> SEQUENCE: 17

```
Met Arg Tyr Phe Ala Ile Ala Phe Leu Leu Ile Asn Thr Ile Ser Ala
1               5                   10                  15

Phe Val Leu Ala Pro Lys Lys Pro Ser Gln Asp Asp Phe Tyr Thr Pro
            20                  25                  30

Pro Gln Gly Tyr Glu Ala Gln Pro Leu Gly Ser Ile Leu Lys Thr Arg
        35                  40                  45

Asn Val Pro Asn Pro Leu Thr Asn Val Phe Thr Pro Val Lys Val Gln
    50                  55                  60

Asn Ala Trp Gln Leu Leu Val Arg Ser Glu Asp Thr Phe Gly Asn Pro
65                  70                  75                  80

Asn Ala Ile Val Thr Thr Ile Ile Gln Pro Phe Asn Ala Lys Lys Asp
                85                  90                  95

Lys Leu Val Ser Tyr Gln Thr Phe Glu Asp Ser Gly Lys Leu Asp Cys
            100                 105                 110

Ala Pro Ser Tyr Ala Ile Gln Tyr Gly Ser Asp Ile Ser Thr Leu Thr
        115                 120                 125

Thr Gln Gly Glu Met Tyr Tyr Ile Ser Ala Leu Leu Asp Gln Gly Tyr
    130                 135                 140

Tyr Val Val Thr Pro Asp Tyr Glu Gly Pro Lys Ser Thr Phe Thr Val
145                 150                 155                 160

Gly Leu Gln Ser Gly Arg Ala Thr Leu Asn Ser Leu Arg Ala Thr Leu
                165                 170                 175

Lys Ser Gly Asn Leu Thr Gly Val Ser Ser Asp Ala Glu Thr Leu Leu
            180                 185                 190

Trp Gly Tyr Ser Gly Ser Leu Ala Ser Gly Trp Ala Ala Ala Ile
        195                 200                 205

Gln Lys Glu Tyr Ala Pro Glu Leu Ser Lys Asn Leu Leu Gly Ala Ala
    210                 215                 220

Leu Gly Gly Phe Val Thr Asn Ile Thr Ala Thr Ala Glu Ala Val Asp
225                 230                 235                 240

Ser Gly Pro Phe Ala Gly Ile Ile Ser Asn Ala Leu Ala Gly Ile Gly
                245                 250                 255

Asn Glu Tyr Pro Asp Phe Lys Asn Tyr Leu Leu Lys Lys Val Ser Pro
            260                 265                 270

Leu Leu Ser Ile Thr Tyr Arg Leu Gly Asn Thr His Cys Leu Leu Asp
        275                 280                 285

Gly Gly Ile Ala Tyr Phe Gly Lys Ser Phe Phe Ser Arg Ile Ile Arg
    290                 295                 300

Tyr Phe Pro Asp Gly Trp Asp Leu Val Asn Gln Glu Pro Ile Lys Thr
305                 310                 315                 320

Ile Leu Gln Asp Asn Gly Leu Val Tyr Gln Pro Lys Asp Leu Thr Pro
                325                 330                 335

Gln Ile Pro Leu Phe Ile Tyr His Gly Thr Leu Asp Ala Ile Val Pro
            340                 345                 350

Ile Val Asn Ser Arg Lys Thr Phe Gln Gln Trp Cys Asp Trp Gly Leu
        355                 360                 365

Lys Ser Gly Glu Tyr Asn Glu Asp Leu Thr Asn Gly His Ile Thr Glu
    370                 375                 380

Ser Ile Val Gly Ala Pro Ala Ala Leu Thr Trp Ile Ile Asn Arg Phe
```

```
                385                 390                 395                 400
Asn Gly Gln Pro Pro Val Asp Gly Cys Gln His Asn Val Arg Ala Ser
            405                 410                 415

Asn Leu Glu Tyr Pro Gly Thr Pro Gln Ser Ile Lys Asn Tyr Phe Glu
            420                 425                 430

Ala Ala Leu His Ala Ile Leu Gly Phe Asp Leu Gly Pro Asp Val Lys
            435                 440                 445

Arg Asp Lys Val Thr Leu Gly Gly Leu Leu Lys Leu Glu Arg Phe Ala
450                 455                 460

Phe
465

<210> SEQ ID NO 18
<211> LENGTH: 471
<212> TYPE: PRT
<213> ORGANISM: Candida parapsilosis

<400> SEQUENCE: 18

Met Arg Tyr Phe Ala Ile Ala Phe Leu Leu Ile Asn Thr Ile Ser Ala
1               5                   10                  15

Phe Val Leu Ala Pro Lys Lys Pro Ser Gln Asp Asp Phe Tyr Thr Pro
            20                  25                  30

Pro Gln Gly Tyr Glu Ala Gln Pro Leu Gly Ser Ile Leu Lys Thr Arg
        35                  40                  45

Asn Val Pro Asn Pro Leu Thr Asn Val Phe Thr Pro Val Lys Val Gln
50                  55                  60

Asn Ala Trp Gln Leu Leu Val Arg Ser Glu Asp Thr Phe Gly Asn Pro
65                  70                  75                  80

Asn Ala Ile Val Thr Thr Ile Ile Gln Pro Phe Asn Ala Lys Lys Asp
                85                  90                  95

Lys Leu Val Ser Tyr Gln Thr Phe Glu Asp Ser Gly Lys Leu Asp Cys
            100                 105                 110

Ala Pro Ser Tyr Ala Ile Gln Tyr Gly Ser Asp Ile Ser Thr Leu Thr
        115                 120                 125

Thr Gln Gly Glu Met Tyr Tyr Ile Ser Ala Leu Leu Asp Gln Gly Tyr
    130                 135                 140

Tyr Val Val Thr Pro Asp Tyr Glu Gly Pro Lys Ser Thr Phe Thr Val
145                 150                 155                 160

Gly Leu Gln Ser Gly Arg Ala Thr Leu Asn Ser Leu Arg Ala Thr Leu
                165                 170                 175

Lys Ser Gly Asn Leu Thr Gly Val Ser Ser Asp Ala Glu Thr Leu Leu
            180                 185                 190

Trp Gly Tyr Ser Gly Gly Ser Leu Ala Ser Gly Trp Ala Ala Ala Ile
        195                 200                 205

Gln Lys Glu Tyr Ala Pro Glu Leu Ser Lys Asn Leu Leu Gly Ala Ala
    210                 215                 220

Leu Gly Gly Phe Val Thr Asn Ile Thr Ala Thr Ala Glu Ala Val Asp
225                 230                 235                 240

Ser Gly Pro Phe Ala Gly Ile Ile Ser Asn Ala Leu Ala Gly Ile Gly
                245                 250                 255

Asn Glu Tyr Pro Asp Phe Lys Asn Tyr Leu Leu Lys Lys Val Ser Pro
            260                 265                 270

Leu Leu Ser Ile Thr Tyr Arg Leu Gly Asn Thr His Cys Leu Leu Asp
        275                 280                 285
```

```
Gly Gly Ile Ala Tyr Phe Gly Lys Ser Phe Phe Ser Arg Ile Ile Arg
            290                 295                 300

Tyr Phe Pro Asp Gly Trp Asp Leu Val Asn Gln Glu Pro Ile Lys Thr
305                 310                 315                 320

Ile Leu Gln Asp Asn Gly Leu Val Tyr Gln Pro Lys Asp Leu Thr Pro
                325                 330                 335

Gln Ile Pro Leu Phe Ile Tyr His Gly Thr Leu Asp Ala Ile Val Pro
            340                 345                 350

Ile Val Asn Ser Arg Lys Thr Phe Gln Gln Trp Cys Asp Trp Gly Leu
                355                 360                 365

Lys Ser Gly Glu Tyr Asn Glu Asp Leu Thr Asn Gly His Ile Thr Glu
370                 375                 380

Ser Ile Val Gly Ala Pro Ala Ala Leu Thr Trp Ile Ile Asn Arg Phe
385                 390                 395                 400

Asn Gly Gln Pro Pro Val Asp Gly Cys Gln His Asn Val Arg Ala Ser
                405                 410                 415

Asn Leu Glu Tyr Pro Gly Thr Pro Gln Ser Ile Lys Asn Tyr Phe Glu
            420                 425                 430

Ala Ala Leu His Ala Ile Leu Gly Phe Asp Leu Gly Pro Asp Val Lys
            435                 440                 445

Arg Asp Lys Val Thr Leu Gly Gly Leu Leu Lys Leu Glu Arg Phe Ala
450                 455                 460

Phe His His His His His His
465                 470

<210> SEQ ID NO 19
<211> LENGTH: 261
<212> TYPE: PRT
<213> ORGANISM: Streptomyces coelicolor

<400> SEQUENCE: 19

Met Ile Gly Ser Tyr Val Ala Val Gly Asp Ser Phe Thr Glu Gly Val
1               5                   10                  15

Gly Asp Pro Gly Pro Asp Gly Ala Phe Val Gly Trp Ala Asp Arg Leu
            20                  25                  30

Ala Val Leu Leu Ala Asp Arg Arg Pro Glu Gly Asp Phe Thr Tyr Thr
        35                  40                  45

Asn Leu Ala Val Arg Gly Arg Leu Leu Asp Gln Ile Val Ala Glu Gln
    50                  55                  60

Val Pro Arg Val Val Gly Leu Ala Pro Asp Leu Val Ser Phe Ala Ala
65                  70                  75                  80

Gly Gly Asn Asp Ile Ile Arg Pro Gly Thr Asp Pro Asp Glu Val Ala
                85                  90                  95

Glu Arg Phe Glu Leu Ala Val Ala Ala Leu Thr Ala Ala Gly Thr
            100                 105                 110

Val Leu Val Thr Thr Gly Phe Asp Thr Arg Gly Val Pro Val Leu Lys
        115                 120                 125

His Leu Arg Gly Lys Ile Ala Thr Tyr Asn Gly His Val Arg Ala Ile
    130                 135                 140

Ala Asp Arg Tyr Gly Cys Pro Val Leu Asp Leu Trp Ser Leu Arg Ser
145                 150                 155                 160

Val Gln Asp Arg Arg Ala Trp Asp Ala Asp Arg Leu His Leu Ser Pro
                165                 170                 175

Glu Gly His Thr Arg Val Ala Leu Arg Ala Gly Gln Ala Leu Gly Leu
            180                 185                 190
```

```
Arg Val Pro Ala Asp Pro Asp Gln Pro Trp Pro Leu Pro Pro Arg
        195                 200                 205

Gly Thr Leu Asp Val Arg Arg Asp Asp Val His Trp Ala Arg Glu Tyr
    210                 215                 220

Leu Val Pro Trp Ile Gly Arg Arg Leu Arg Gly Glu Ser Ser Gly Asp
225                 230                 235                 240

His Val Thr Ala Lys Gly Thr Leu Ser Pro Asp Ala Ile Lys Thr Arg
                245                 250                 255

Ile Ala Ala Val Ala
                260
```

<210> SEQ ID NO 20
<211> LENGTH: 230
<212> TYPE: PRT
<213> ORGANISM: Aspergillus aculeatus

<400> SEQUENCE: 20

```
Thr Thr Val Tyr Leu Ala Gly Asp Ser Thr Met Ala Lys Asn Gly Gly
1               5                   10                  15

Gly Ser Gly Thr Asn Gly Trp Gly Glu Tyr Leu Ala Ser Tyr Leu Ser
                20                  25                  30

Ala Thr Val Val Asn Asp Ala Val Gly Arg Ser Ala Arg Ser Tyr
            35                  40                  45

Thr Arg Glu Gly Arg Phe Glu Asn Ile Ala Asp Val Thr Ala Gly
    50                  55                  60

Asp Tyr Val Ile Val Glu Phe Gly His Asn Asp Gly Gly Ser Leu Ser
65                  70                  75                  80

Thr Asp Asn Gly Arg Thr Asp Cys Ser Gly Thr Gly Ala Glu Val Cys
                85                  90                  95

Tyr Ser Val Tyr Asp Gly Val Asn Glu Thr Ile Leu Thr Phe Pro Ala
                100                 105                 110

Tyr Leu Glu Asn Ala Ala Lys Leu Phe Thr Ala Lys Gly Ala Lys Val
                115                 120                 125

Ile Leu Ser Ser Gln Thr Pro Asn Asn Pro Trp Glu Thr Gly Thr Phe
130                 135                 140

Val Asn Ser Pro Thr Arg Phe Val Glu Tyr Ala Glu Leu Ala Ala Glu
145                 150                 155                 160

Val Ala Gly Val Glu Tyr Val Asp His Trp Ser Tyr Val Asp Ser Ile
                165                 170                 175

Tyr Glu Thr Leu Gly Asn Ala Thr Val Asn Ser Tyr Phe Pro Ile Asp
                180                 185                 190

His Thr His Thr Ser Pro Ala Gly Ala Glu Val Val Ala Glu Ala Phe
                195                 200                 205

Leu Lys Ala Val Val Cys Thr Gly Thr Ser Leu Lys Ser Val Leu Thr
    210                 215                 220

Thr Thr Ser Phe Glu Gly
225                 230
```

<210> SEQ ID NO 21
<211> LENGTH: 18
<212> TYPE: PRT
<213> ORGANISM: Aeromonas sp.

<400> SEQUENCE: 21

```
Met Lys Lys Trp Phe Val Cys Leu Leu Gly Leu Ile Ala Leu Thr Val
1               5                   10                  15
```

<210> SEQ ID NO 22
<211> LENGTH: 29
<212> TYPE: PRT
<213> ORGANISM: Bacillus subtilis

<400> SEQUENCE: 22

Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala
            20                  25

<210> SEQ ID NO 23
<211> LENGTH: 29
<212> TYPE: PRT
<213> ORGANISM: Bacillus licheniformis

<400> SEQUENCE: 23

Met Met Arg Lys Lys Ser Phe Trp Phe Gly Met Leu Thr Ala Phe Met
1               5                   10                  15

Leu Val Phe Thr Met Glu Phe Ser Asp Ser Ala Ser Ala
            20                  25

<210> SEQ ID NO 24
<211> LENGTH: 1047
<212> TYPE: DNA
<213> ORGANISM: Aeromonas hydrophila

<400> SEQUENCE: 24

```
atgtttaagt ttaaaaagaa tttcttagtt ggattatcgg cagctttaat gagtattagc      60
ttgttttcgg caaccgcctc tgcagctagc gccgacagcc gtcccgcctt ttcccggatc     120
gtgatgttcg gcgacagcct ctccgatacc ggcaaaatgt acagcaagat gcgcggttac     180
ctcccctcca gcccgcccta tatgagggc cgtttctcca acggaccccgt ctggctggag     240
cagctgacca aacagttccc gggtctgacc atcgccaacg aagcggaagg cggtgccact     300
gccgtggctt acaacaagat ctcctggaat cccaagtatc aggtcatcaa caacctggac     360
tacgaggtca cccagttctt gcagaaagac agcttcaagc cggacgatct ggtgatcctc     420
tgggtcggtg ccaatgacta tctggccat ggctggaaca cggagcagga tgccaagcgg     480
gttcgcgatg ccatcagcga tgcggccaac gcatggtac tgaacggtgc caagcagata     540
ctgctgttca acctgccgga tctgggccag aacccgtcag ctcgcagtca gaaggtggtc     600
gaggcggtca gccatgtctc cgcctatcac aaccagctgc tgctgaacct ggcacgccag     660
ctggccccca ccggcatggt aaagctgttc gagatcgaca gcaatttgc cgagatgctg     720
cgtgatccgc agaacttcgg cctgagcgac gtcgagaacc cctgctacga cggcggctat     780
gtgtggaagc cgtttgccac ccgcagcgtc agcaccgacc gccagctctc cgccttcagt     840
ccgcaggaac gcctcgccat cgccggcaac ccgctgctgg cacaggccgt tgccagtcct     900
atggcccgcc gcagcgccag ccccctcaac tgtgagggca agatgttctg ggatcaggta     960
cacccgacca ctgtcgtgca cgcagccctg agcgagcgcg ccgccacctt catcgcgaac    1020
cagtacgagt cctcgcccca ctgatga                                       1047
```

<210> SEQ ID NO 25
<211> LENGTH: 347
<212> TYPE: PRT

<213> ORGANISM: Artificial
<220> FEATURE:
<223> OTHER INFORMATION: Fusion construct

<400> SEQUENCE: 25

| Met | Phe | Lys | Phe | Lys | Asn | Phe | Leu | Val | Gly | Leu | Ser | Ala | Ala | Leu |
|-----|-----|-----|-----|-----|-----|-----|-----|-----|-----|-----|-----|-----|-----|-----|
| 1   |     |     |     | 5   |     |     |     |     | 10  |     |     |     |     | 15  |

Met Ser Ile Ser Leu Phe Ser Ala Thr Ala Ser Ala Ala Ser Ala Asp
            20                  25                  30

Ser Arg Pro Ala Phe Ser Arg Ile Val Met Phe Gly Asp Ser Leu Ser
                35                  40                  45

Asp Thr Gly Lys Met Tyr Ser Lys Met Arg Gly Tyr Leu Pro Ser Ser
        50                  55                  60

Pro Pro Tyr Tyr Glu Gly Arg Phe Ser Asn Gly Pro Val Trp Leu Glu
65                  70                  75                  80

Gln Leu Thr Lys Gln Phe Pro Gly Leu Thr Ile Ala Asn Glu Ala Glu
                85                  90                  95

Gly Gly Ala Thr Ala Val Ala Tyr Asn Lys Ile Ser Trp Asn Pro Lys
            100                 105                 110

Tyr Gln Val Ile Asn Asn Leu Asp Tyr Glu Val Thr Gln Phe Leu Gln
                115                 120                 125

Lys Asp Ser Phe Lys Pro Asp Asp Leu Val Ile Leu Trp Val Gly Ala
    130                 135                 140

Asn Asp Tyr Leu Ala Tyr Gly Trp Asn Thr Glu Gln Asp Ala Lys Arg
145                 150                 155                 160

Val Arg Asp Ala Ile Ser Asp Ala Ala Asn Arg Met Val Leu Asn Gly
                165                 170                 175

Ala Lys Gln Ile Leu Leu Phe Asn Leu Pro Asp Leu Gly Gln Asn Pro
            180                 185                 190

Ser Ala Arg Ser Gln Lys Val Val Glu Ala Val Ser His Val Ser Ala
        195                 200                 205

Tyr His Asn Gln Leu Leu Leu Asn Leu Ala Arg Gln Leu Ala Pro Thr
    210                 215                 220

Gly Met Val Lys Leu Phe Glu Ile Asp Lys Gln Phe Ala Glu Met Leu
225                 230                 235                 240

Arg Asp Pro Gln Asn Phe Gly Leu Ser Asp Val Glu Asn Pro Cys Tyr
                245                 250                 255

Asp Gly Gly Tyr Val Trp Lys Pro Phe Ala Thr Arg Ser Val Ser Thr
            260                 265                 270

Asp Arg Gln Leu Ser Ala Phe Ser Pro Gln Glu Arg Leu Ala Ile Ala
        275                 280                 285

Gly Asn Pro Leu Leu Ala Gln Ala Val Ala Ser Pro Met Ala Arg Arg
    290                 295                 300

Ser Ala Ser Pro Leu Asn Cys Glu Gly Lys Met Phe Trp Asp Gln Val
305                 310                 315                 320

His Pro Thr Thr Val Val His Ala Ala Leu Ser Glu Arg Ala Ala Thr
                325                 330                 335

Phe Ile Ala Asn Gln Tyr Glu Phe Leu Ala His
            340                 345

<210> SEQ ID NO 26
<211> LENGTH: 267
<212> TYPE: PRT
<213> ORGANISM: Streptomyces sp.

<400> SEQUENCE: 26

```
Met Arg Leu Thr Arg Ser Leu Ser Ala Ala Ser Val Ile Val Phe Ala
1               5                   10                  15

Leu Leu Leu Ala Leu Leu Gly Ile Ser Pro Ala Gln Ala Ala Gly Pro
            20                  25                  30

Ala Tyr Val Ala Leu Gly Asp Ser Tyr Ser Ser Gly Asn Gly Ala Gly
                35                  40                  45

Ser Tyr Ile Asp Ser Ser Gly Asp Cys His Arg Ser Asn Asn Ala Tyr
    50                  55                  60

Pro Ala Arg Trp Ala Ala Asn Ala Pro Ser Ser Phe Thr Phe Ala
65                  70                  75                  80

Ala Cys Ser Gly Ala Val Thr Thr Asp Val Ile Asn Asn Gln Leu Gly
                85                  90                  95

Ala Leu Asn Ala Ser Thr Gly Leu Val Ser Ile Thr Ile Gly Gly Asn
            100                 105                 110

Asp Ala Gly Phe Ala Asp Ala Met Thr Thr Cys Val Thr Ser Ser Asp
            115                 120                 125

Ser Thr Cys Leu Asn Arg Leu Ala Thr Ala Thr Asn Tyr Ile Asn Thr
    130                 135                 140

Thr Leu Leu Ala Arg Leu Asp Ala Val Tyr Ser Gln Ile Lys Ala Arg
145                 150                 155                 160

Ala Pro Asn Ala Arg Val Val Val Leu Gly Tyr Pro Arg Met Tyr Leu
                165                 170                 175

Ala Ser Asn Pro Trp Tyr Cys Leu Gly Leu Ser Asn Thr Lys Arg Ala
                180                 185                 190

Ala Ile Asn Thr Thr Ala Asp Thr Leu Asn Ser Val Ile Ser Ser Arg
                195                 200                 205

Ala Thr Ala His Gly Phe Arg Phe Gly Asp Val Arg Pro Thr Phe Asn
            210                 215                 220

Asn His Glu Leu Phe Phe Gly Asn Asp Trp Leu His Ser Leu Thr Leu
225                 230                 235                 240

Pro Val Trp Glu Ser Tyr His Pro Thr Ser Thr Gly His Gln Ser Gly
                245                 250                 255

Tyr Leu Pro Val Leu Asn Ala Asn Ser Ser Thr
                260                 265

<210> SEQ ID NO 27
<211> LENGTH: 548
<212> TYPE: PRT
<213> ORGANISM: Thermobifida sp.

<400> SEQUENCE: 27

Met Leu Pro His Pro Ala Gly Glu Arg Gly Glu Val Gly Ala Phe Phe
1               5                   10                  15

Ala Leu Leu Val Gly Thr Pro Gln Asp Arg Arg Leu Arg Leu Glu Cys
            20                  25                  30

His Glu Thr Arg Pro Leu Arg Gly Arg Cys Gly Cys Gly Glu Arg Arg
            35                  40                  45

Val Pro Pro Leu Thr Leu Pro Gly Asp Gly Val Leu Cys Thr Thr Ser
    50                  55                  60

Ser Thr Arg Asp Ala Glu Thr Val Trp Arg Lys His Leu Gln Pro Arg
65                  70                  75                  80

Pro Asp Gly Gly Phe Arg Pro His Leu Gly Val Gly Cys Leu Leu Ala
                85                  90                  95

Gly Gln Gly Ser Pro Gly Val Leu Trp Cys Gly Arg Glu Gly Cys Arg
```

```
              100                 105                 110
Phe Glu Val Cys Arg Arg Asp Thr Pro Gly Leu Ser Arg Thr Arg Asn
            115                 120                 125

Gly Asp Ser Ser Pro Pro Phe Arg Ala Gly Trp Ser Leu Pro Pro Lys
130                 135                 140

Cys Gly Glu Ile Ser Gln Ser Ala Arg Lys Thr Pro Ala Val Pro Arg
145                 150                 155                 160

Tyr Ser Leu Leu Arg Thr Asp Arg Pro Asp Gly Pro Arg Gly Arg Phe
                165                 170                 175

Val Gly Ser Gly Pro Arg Ala Ala Thr Arg Arg Leu Phe Leu Gly
                180                 185                 190

Ile Pro Ala Leu Val Leu Val Thr Ala Leu Thr Leu Val Leu Ala Val
                195                 200                 205

Pro Thr Gly Arg Glu Thr Leu Trp Arg Met Trp Cys Glu Ala Thr Gln
210                 215                 220

Asp Trp Cys Leu Gly Val Pro Val Asp Ser Arg Gly Gln Pro Ala Glu
225                 230                 235                 240

Asp Gly Glu Phe Leu Leu Leu Ser Pro Val Gln Ala Ala Thr Trp Gly
                245                 250                 255

Asn Tyr Tyr Ala Leu Gly Asp Ser Tyr Ser Ser Gly Asp Gly Ala Arg
                260                 265                 270

Asp Tyr Tyr Pro Gly Thr Ala Val Lys Gly Gly Cys Trp Arg Ser Ala
                275                 280                 285

Asn Ala Tyr Pro Glu Leu Val Ala Glu Ala Tyr Asp Phe Ala Gly His
            290                 295                 300

Leu Ser Phe Leu Ala Cys Ser Gly Gln Arg Gly Tyr Ala Met Leu Asp
305                 310                 315                 320

Ala Ile Asp Glu Val Gly Ser Gln Leu Asp Trp Asn Ser Pro His Thr
                325                 330                 335

Ser Leu Val Thr Ile Gly Ile Gly Gly Asn Asp Leu Gly Phe Ser Thr
                340                 345                 350

Val Leu Lys Thr Cys Met Val Arg Val Pro Leu Leu Asp Ser Lys Ala
                355                 360                 365

Cys Thr Asp Gln Glu Asp Ala Ile Arg Lys Arg Met Ala Lys Phe Glu
370                 375                 380

Thr Thr Phe Glu Glu Leu Ile Ser Glu Val Arg Thr Arg Ala Pro Asp
385                 390                 395                 400

Ala Arg Ile Leu Val Val Gly Tyr Pro Arg Ile Phe Pro Glu Glu Pro
                405                 410                 415

Thr Gly Ala Tyr Tyr Thr Leu Thr Ala Ser Asn Gln Arg Trp Leu Asn
                420                 425                 430

Glu Thr Ile Gln Glu Phe Asn Gln Gln Leu Ala Glu Ala Val Ala Val
            435                 440                 445

His Asp Glu Glu Ile Ala Ala Ser Gly Val Gly Ser Val Glu Phe
            450                 455                 460

Val Asp Val Tyr His Ala Leu Asp Gly His Glu Ile Gly Ser Asp Glu
465                 470                 475                 480

Pro Trp Val Asn Gly Val Gln Leu Arg Asp Leu Ala Thr Gly Val Thr
                485                 490                 495

Val Asp Arg Ser Thr Phe His Pro Asn Ala Ala Gly His Arg Ala Val
                500                 505                 510

Gly Glu Arg Val Ile Glu Gln Ile Glu Thr Gly Pro Gly Arg Pro Leu
            515                 520                 525
```

-continued

```
Tyr Ala Thr Phe Ala Val Val Ala Gly Ala Thr Val Asp Thr Leu Ala
        530                 535                 540
Gly Glu Val Gly
545

<210> SEQ ID NO 28
<211> LENGTH: 372
<212> TYPE: PRT
<213> ORGANISM: Thermobifida sp.

<400> SEQUENCE: 28

Met Gly Ser Gly Pro Arg Ala Ala Thr Arg Arg Leu Phe Leu Gly
1               5                   10                  15

Ile Pro Ala Leu Val Leu Val Thr Ala Leu Thr Leu Val Leu Ala Val
                20                  25                  30

Pro Thr Gly Arg Glu Thr Leu Trp Arg Met Trp Cys Glu Ala Thr Gln
            35                  40                  45

Asp Trp Cys Leu Gly Val Pro Val Asp Ser Arg Gly Gln Pro Ala Glu
    50                  55                  60

Asp Gly Glu Phe Leu Leu Leu Ser Pro Val Gln Ala Ala Thr Trp Gly
65                  70                  75                  80

Asn Tyr Tyr Ala Leu Gly Asp Ser Tyr Ser Ser Gly Asp Gly Ala Arg
                85                  90                  95

Asp Tyr Tyr Pro Gly Thr Ala Val Lys Gly Gly Cys Trp Arg Ser Ala
            100                 105                 110

Asn Ala Tyr Pro Glu Leu Val Ala Glu Ala Tyr Asp Phe Ala Gly His
        115                 120                 125

Leu Ser Phe Leu Ala Cys Ser Gly Gln Arg Gly Tyr Ala Met Leu Asp
130                 135                 140

Ala Ile Asp Glu Val Gly Ser Gln Leu Asp Trp Asn Ser Pro His Thr
145                 150                 155                 160

Ser Leu Val Thr Ile Gly Ile Gly Gly Asn Asp Leu Gly Phe Ser Thr
                165                 170                 175

Val Leu Lys Thr Cys Met Val Arg Val Pro Leu Leu Asp Ser Lys Ala
            180                 185                 190

Cys Thr Asp Gln Glu Asp Ala Ile Arg Lys Arg Met Ala Lys Phe Glu
        195                 200                 205

Thr Thr Phe Glu Glu Leu Ile Ser Glu Val Arg Thr Arg Ala Pro Asp
210                 215                 220

Ala Arg Ile Leu Val Val Gly Tyr Pro Arg Ile Phe Pro Glu Glu Pro
225                 230                 235                 240

Thr Gly Ala Tyr Tyr Thr Leu Thr Ala Ser Asn Gln Arg Trp Leu Asn
                245                 250                 255

Glu Thr Ile Gln Glu Phe Asn Gln Gln Leu Ala Glu Ala Val Ala Val
            260                 265                 270

His Asp Glu Glu Ile Ala Ala Ser Gly Val Gly Ser Val Glu Phe
        275                 280                 285

Val Asp Val Tyr His Ala Leu Asp Gly His Glu Ile Gly Ser Asp Glu
    290                 295                 300

Pro Trp Val Asn Gly Val Gln Leu Arg Asp Leu Ala Thr Gly Val Thr
305                 310                 315                 320

Val Asp Arg Ser Thr Phe His Pro Asn Ala Ala Gly His Arg Ala Val
                325                 330                 335

Gly Glu Arg Val Ile Glu Gln Ile Glu Thr Gly Pro Gly Arg Pro Leu
```

```
                   340                 345                 350
Tyr Ala Thr Phe Ala Val Val Ala Gly Ala Thr Val Asp Thr Leu Ala
                355                 360                 365
Gly Glu Val Gly
        370

<210> SEQ ID NO 29
<211> LENGTH: 300
<212> TYPE: PRT
<213> ORGANISM: Corynebacterium efficiens

<400> SEQUENCE: 29

Met Arg Thr Thr Val Ile Ala Ala Ser Ala Leu Leu Leu Leu Ala Gly
1               5                   10                  15

Cys Ala Asp Gly Ala Arg Glu Glu Thr Ala Gly Ala Pro Pro Gly Glu
                20                  25                  30

Ser Ser Gly Gly Ile Arg Glu Glu Gly Ala Glu Ala Ser Thr Ser Ile
            35                  40                  45

Thr Asp Val Tyr Ile Ala Leu Gly Asp Ser Tyr Ala Ala Met Gly Gly
        50                  55                  60

Arg Asp Gln Pro Leu Arg Gly Glu Pro Phe Cys Leu Arg Ser Ser Gly
65                  70                  75                  80

Asn Tyr Pro Glu Leu Leu His Ala Glu Val Thr Asp Leu Thr Cys Gln
                85                  90                  95

Gly Ala Val Thr Gly Asp Leu Leu Glu Pro Arg Thr Leu Gly Glu Arg
            100                 105                 110

Thr Leu Pro Ala Gln Val Asp Ala Leu Thr Glu Asp Thr Thr Leu Val
        115                 120                 125

Thr Leu Ser Ile Gly Gly Asn Asp Leu Gly Phe Gly Glu Val Ala Gly
    130                 135                 140

Cys Ile Arg Glu Arg Ile Ala Gly Glu Asn Ala Asp Asp Cys Val Asp
145                 150                 155                 160

Leu Leu Gly Glu Thr Ile Gly Glu Gln Leu Asp Gln Leu Pro Pro Gln
                165                 170                 175

Leu Asp Arg Val His Glu Ala Ile Arg Asp Arg Ala Gly Asp Ala Gln
            180                 185                 190

Val Val Val Thr Gly Tyr Leu Pro Leu Val Ser Ala Gly Asp Cys Pro
        195                 200                 205

Glu Leu Gly Asp Val Ser Glu Ala Asp Arg Arg Trp Ala Val Glu Leu
    210                 215                 220

Thr Gly Gln Ile Asn Glu Thr Val Arg Glu Ala Ala Glu Arg His Asp
225                 230                 235                 240

Ala Leu Phe Val Leu Pro Asp Asp Ala Asp Glu His Thr Ser Cys Ala
                245                 250                 255

Pro Pro Gln Gln Arg Trp Ala Asp Ile Gln Gly Gln Thr Asp Ala
            260                 265                 270

Tyr Pro Leu His Pro Thr Ser Ala Gly His Glu Ala Met Ala Ala Ala
        275                 280                 285

Val Arg Asp Ala Leu Gly Leu Glu Pro Val Gln Pro
    290                 295                 300

<210> SEQ ID NO 30
<211> LENGTH: 284
<212> TYPE: PRT
<213> ORGANISM: Novosphingobium aromaticivorans
```

```
<400> SEQUENCE: 30

Met Gly Gln Val Lys Leu Phe Ala Arg Arg Cys Ala Pro Val Leu Leu
1               5                   10                  15

Ala Leu Ala Gly Leu Ala Pro Ala Ala Thr Val Ala Arg Glu Ala Pro
            20                  25                  30

Leu Ala Glu Gly Ala Arg Tyr Val Ala Leu Gly Ser Ser Phe Ala Ala
        35                  40                  45

Gly Pro Gly Val Gly Pro Asn Ala Pro Gly Ser Pro Glu Arg Cys Gly
    50                  55                  60

Arg Gly Thr Leu Asn Tyr Pro His Leu Leu Ala Glu Ala Leu Lys Leu
65                  70                  75                  80

Asp Leu Val Asp Ala Thr Cys Ser Gly Ala Thr Thr His His Val Leu
                85                  90                  95

Gly Pro Trp Asn Glu Val Pro Pro Gln Ile Asp Ser Val Asn Gly Asp
            100                 105                 110

Thr Arg Leu Val Thr Leu Thr Ile Gly Gly Asn Asp Val Ser Phe Val
        115                 120                 125

Gly Asn Ile Phe Ala Ala Ala Cys Glu Lys Met Ala Ser Pro Asp Pro
    130                 135                 140

Arg Cys Gly Lys Trp Arg Glu Ile Thr Glu Glu Trp Gln Ala Asp
145                 150                 155                 160

Glu Glu Arg Met Arg Ser Ile Val Arg Gln Ile His Ala Arg Ala Pro
                165                 170                 175

Leu Ala Arg Val Val Val Val Asp Tyr Ile Thr Val Leu Pro Pro Ser
            180                 185                 190

Gly Thr Cys Ala Ala Met Ala Ile Ser Pro Asp Arg Leu Ala Gln Ser
        195                 200                 205

Arg Ser Ala Ala Lys Arg Leu Ala Arg Ile Thr Ala Arg Val Ala Arg
    210                 215                 220

Glu Glu Gly Ala Ser Leu Leu Lys Phe Ser His Ile Ser Arg Arg His
225                 230                 235                 240

His Pro Cys Ser Ala Lys Pro Trp Ser Asn Gly Leu Ser Ala Pro Ala
                245                 250                 255

Asp Asp Gly Ile Pro Val His Pro Asn Arg Leu Gly His Ala Glu Ala
            260                 265                 270

Ala Ala Ala Leu Val Lys Leu Val Lys Leu Met Lys
        275                 280

<210> SEQ ID NO 31
<211> LENGTH: 268
<212> TYPE: PRT
<213> ORGANISM: Streptomyces coelicolor

<400> SEQUENCE: 31

Met Arg Arg Phe Arg Leu Val Gly Phe Leu Ser Ser Leu Val Leu Ala
1               5                   10                  15

Ala Gly Ala Ala Leu Thr Gly Ala Ala Thr Ala Gln Ala Ala Gln Pro
            20                  25                  30

Ala Ala Ala Asp Gly Tyr Val Ala Leu Gly Asp Ser Tyr Ser Ser Gly
        35                  40                  45

Val Gly Ala Gly Ser Tyr Ile Ser Ser Ser Gly Asp Cys Lys Arg Ser
    50                  55                  60

Thr Lys Ala His Pro Tyr Leu Trp Ala Ala Ala His Ser Pro Ser Thr
65                  70                  75                  80
```

-continued

```
Phe Asp Phe Thr Ala Cys Ser Gly Ala Arg Thr Gly Asp Val Leu Ser
                85                  90                  95

Gly Gln Leu Gly Pro Leu Ser Ser Gly Thr Gly Leu Val Ser Ile Ser
            100                 105                 110

Ile Gly Gly Asn Asp Ala Gly Phe Ala Asp Thr Met Thr Thr Cys Val
            115                 120                 125

Leu Gln Ser Glu Ser Ser Cys Leu Ser Arg Ile Ala Thr Ala Glu Ala
        130                 135                 140

Tyr Val Asp Ser Thr Leu Pro Gly Lys Leu Asp Gly Val Tyr Ser Ala
145                 150                 155                 160

Ile Ser Asp Lys Ala Pro Asn Ala His Val Val Ile Gly Tyr Pro
                165                 170                 175

Arg Phe Tyr Lys Leu Gly Thr Thr Cys Ile Gly Leu Ser Glu Thr Lys
                180                 185                 190

Arg Thr Ala Ile Asn Lys Ala Ser Asp His Leu Asn Thr Val Leu Ala
            195                 200                 205

Gln Arg Ala Ala Ala His Gly Phe Thr Phe Gly Asp Val Arg Thr Thr
        210                 215                 220

Phe Thr Gly His Glu Leu Cys Ser Gly Ser Pro Trp Leu His Ser Val
225                 230                 235                 240

Asn Trp Leu Asn Ile Gly Glu Ser Tyr His Pro Thr Ala Ala Gly Gln
                245                 250                 255

Ser Gly Gly Tyr Leu Pro Val Leu Asn Gly Ala Ala
                260                 265

<210> SEQ ID NO 32
<211> LENGTH: 269
<212> TYPE: PRT
<213> ORGANISM: Streptomyces avermitilis

<400> SEQUENCE: 32

Met Arg Arg Ser Arg Ile Thr Ala Tyr Val Thr Ser Leu Leu Leu Ala
1               5                   10                  15

Val Gly Cys Ala Leu Thr Gly Ala Ala Thr Ala Gln Ala Ser Pro Ala
                20                  25                  30

Ala Ala Ala Thr Gly Tyr Val Ala Leu Gly Asp Ser Tyr Ser Ser Gly
            35                  40                  45

Val Gly Ala Gly Ser Tyr Leu Ser Ser Ser Gly Asp Cys Lys Arg Ser
        50                  55                  60

Ser Lys Ala Tyr Pro Tyr Leu Trp Gln Ala Ala His Ser Pro Ser Ser
65                  70                  75                  80

Phe Ser Phe Met Ala Cys Ser Gly Ala Arg Thr Gly Asp Val Leu Ala
                85                  90                  95

Asn Gln Leu Gly Thr Leu Asn Ser Ser Thr Gly Leu Val Ser Leu Thr
            100                 105                 110

Ile Gly Gly Asn Asp Ala Gly Phe Ser Asp Val Met Thr Thr Cys Val
            115                 120                 125

Leu Gln Ser Asp Ser Ala Cys Leu Ser Arg Ile Asn Thr Ala Lys Ala
        130                 135                 140

Tyr Val Asp Ser Thr Leu Pro Gly Gln Leu Asp Ser Val Tyr Thr Ala
145                 150                 155                 160

Ile Ser Thr Lys Ala Pro Ser Ala His Val Ala Val Leu Gly Tyr Pro
                165                 170                 175

Arg Phe Tyr Lys Leu Gly Gly Ser Cys Leu Ala Gly Leu Ser Glu Thr
                180                 185                 190
```

```
Lys Arg Ser Ala Ile Asn Asp Ala Asp Tyr Leu Asn Ser Ala Ile
            195                 200                 205

Ala Lys Arg Ala Ala Asp His Gly Phe Thr Phe Gly Asp Val Lys Ser
        210                 215                 220

Thr Phe Thr Gly His Glu Ile Cys Ser Ser Thr Trp Leu His Ser
225                 230                 235                 240

Leu Asp Leu Leu Asn Ile Gly Gln Ser Tyr His Pro Thr Ala Ala Gly
            245                 250                 255

Gln Ser Gly Gly Tyr Leu Pro Val Met Asn Ser Val Ala
            260                 265
```

<210> SEQ ID NO 33
<211> LENGTH: 267
<212> TYPE: PRT
<213> ORGANISM: Streptomyces sp.

<400> SEQUENCE: 33

```
Met Arg Leu Thr Arg Ser Leu Ser Ala Ala Ser Val Ile Val Phe Ala
1               5                   10                  15

Leu Leu Leu Ala Leu Leu Gly Ile Ser Pro Ala Gln Ala Ala Gly Pro
            20                  25                  30

Ala Tyr Val Ala Leu Gly Asp Ser Tyr Ser Ser Gly Asn Gly Ala Gly
        35                  40                  45

Ser Tyr Ile Asp Ser Ser Gly Asp Cys His Arg Ser Asn Asn Ala Tyr
    50                  55                  60

Pro Ala Arg Trp Ala Ala Asn Ala Pro Ser Ser Phe Thr Phe Ala
65                  70                  75                  80

Ala Cys Ser Gly Ala Val Thr Thr Asp Val Ile Asn Asn Gln Leu Gly
                85                  90                  95

Ala Leu Asn Ala Ser Thr Gly Leu Val Ser Ile Thr Ile Gly Gly Asn
            100                 105                 110

Asp Ala Gly Phe Ala Asp Ala Met Thr Thr Cys Val Thr Ser Ser Asp
        115                 120                 125

Ser Thr Cys Leu Asn Arg Leu Ala Thr Ala Thr Asn Tyr Ile Asn Thr
    130                 135                 140

Thr Leu Leu Ala Arg Leu Asp Ala Val Tyr Ser Gln Ile Lys Ala Arg
145                 150                 155                 160

Ala Pro Asn Ala Arg Val Val Val Leu Gly Tyr Pro Arg Met Tyr Leu
                165                 170                 175

Ala Ser Asn Pro Trp Tyr Cys Leu Gly Leu Ser Asn Thr Lys Arg Ala
            180                 185                 190

Ala Ile Asn Thr Thr Ala Asp Thr Leu Asn Ser Val Ile Ser Ser Arg
        195                 200                 205

Ala Thr Ala His Gly Phe Arg Phe Gly Asp Val Arg Pro Thr Phe Asn
    210                 215                 220

Asn His Glu Leu Phe Phe Gly Asn Asp Trp Leu His Ser Leu Thr Leu
225                 230                 235                 240

Pro Val Trp Glu Ser Tyr His Pro Thr Ser Thr Gly His Gln Ser Gly
                245                 250                 255

Tyr Leu Pro Val Leu Asn Ala Asn Ser Ser Thr
            260                 265
```

<210> SEQ ID NO 34
<211> LENGTH: 317
<212> TYPE: PRT

<213> ORGANISM: Aeromonas hydrophila

<400> SEQUENCE: 34

```
Ala Asp Ser Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
            20                  25                  30

Ser Ser Pro Pro Tyr Tyr Glu Gly Arg Phe Ser Asn Gly Pro Val Trp
        35                  40                  45

Leu Glu Gln Leu Thr Asn Glu Phe Pro Gly Leu Thr Ile Ala Asn Glu
    50                  55                  60

Ala Glu Gly Gly Pro Thr Ala Val Ala Tyr Asn Lys Ile Ser Trp Asn
65                  70                  75                  80

Pro Lys Tyr Gln Val Ile Asn Asn Leu Asp Tyr Glu Val Thr Gln Phe
                85                  90                  95

Leu Gln Lys Asp Ser Phe Lys Pro Asp Asp Leu Val Ile Leu Trp Val
            100                 105                 110

Gly Ala Asn Asp Tyr Leu Ala Tyr Gly Trp Asn Thr Glu Gln Asp Ala
        115                 120                 125

Lys Arg Val Arg Asp Ala Ile Ser Asp Ala Ala Asn Arg Met Val Leu
130                 135                 140

Asn Gly Ala Lys Glu Ile Leu Leu Phe Asn Leu Pro Asp Leu Gly Gln
145                 150                 155                 160

Asn Pro Ser Ala Arg Ser Gln Lys Val Val Glu Ala Ala Ser His Val
                165                 170                 175

Ser Ala Tyr His Asn Gln Leu Leu Leu Asn Leu Ala Arg Gln Leu Ala
            180                 185                 190

Pro Thr Gly Met Val Lys Leu Phe Glu Ile Asp Lys Gln Phe Ala Glu
        195                 200                 205

Met Leu Arg Asp Pro Gln Asn Phe Gly Leu Ser Asp Gln Arg Asn Ala
    210                 215                 220

Cys Tyr Gly Gly Ser Tyr Val Trp Lys Pro Phe Ala Ser Arg Ser Ala
225                 230                 235                 240

Ser Thr Asp Ser Gln Leu Ser Ala Phe Asn Pro Gln Glu Arg Leu Ala
                245                 250                 255

Ile Ala Gly Asn Pro Leu Leu Ala Gln Ala Val Ala Ser Pro Met Ala
            260                 265                 270

Ala Arg Ser Ala Ser Thr Leu Asn Cys Glu Gly Lys Met Phe Trp Asp
        275                 280                 285

Gln Val His Pro Thr Thr Val Val His Ala Ala Leu Ser Glu Pro Ala
    290                 295                 300

Ala Thr Phe Ile Glu Ser Gln Tyr Glu Phe Leu Ala His
305                 310                 315
```

<210> SEQ ID NO 35
<211> LENGTH: 318
<212> TYPE: PRT
<213> ORGANISM: Aeromonas salmonicida

<400> SEQUENCE: 35

```
Ala Asp Thr Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
            20                  25                  30

Ser Ser Pro Pro Tyr Tyr Glu Gly Arg Phe Ser Asn Gly Pro Val Trp
```

```
          35                  40                  45
Leu Glu Gln Leu Thr Lys Gln Phe Pro Gly Leu Thr Ile Ala Asn Glu
 50                  55                  60

Ala Glu Gly Gly Ala Thr Ala Val Ala Tyr Asn Lys Ile Ser Trp Asn
 65                  70                  75                  80

Pro Lys Tyr Gln Val Ile Asn Asn Leu Asp Tyr Glu Val Thr Gln Phe
                     85                  90                  95

Leu Gln Lys Asp Ser Phe Lys Pro Asp Asp Leu Val Ile Leu Trp Val
                100                 105                 110

Gly Ala Asn Asp Tyr Leu Ala Tyr Gly Trp Asn Thr Glu Gln Asp Ala
                115                 120                 125

Lys Arg Val Arg Asp Ala Ile Ser Asp Ala Ala Asn Arg Met Val Leu
            130                 135                 140

Asn Gly Ala Lys Gln Ile Leu Leu Phe Asn Leu Pro Asp Leu Gly Gln
145                 150                 155                 160

Asn Pro Ser Ala Arg Ser Gln Lys Val Val Glu Ala Val Ser His Val
                165                 170                 175

Ser Ala Tyr His Asn Lys Leu Leu Leu Asn Leu Ala Arg Gln Leu Ala
                180                 185                 190

Pro Thr Gly Met Val Lys Leu Phe Glu Ile Asp Lys Gln Phe Ala Glu
            195                 200                 205

Met Leu Arg Asp Pro Gln Asn Phe Gly Leu Ser Asp Val Glu Asn Pro
210                 215                 220

Cys Tyr Asp Gly Gly Tyr Val Trp Lys Pro Phe Ala Thr Arg Ser Val
225                 230                 235                 240

Ser Thr Asp Arg Gln Leu Ser Ala Phe Ser Pro Gln Glu Arg Leu Ala
                245                 250                 255

Ile Ala Gly Asn Pro Leu Leu Ala Gln Ala Val Ala Ser Pro Met Ala
                260                 265                 270

Arg Arg Ser Ala Ser Pro Leu Asn Cys Glu Gly Lys Met Phe Trp Asp
            275                 280                 285

Gln Val His Pro Thr Thr Val Val His Ala Ala Leu Ser Glu Arg Ala
290                 295                 300

Ala Thr Phe Ile Glu Thr Gln Tyr Glu Phe Leu Ala His Gly
305                 310                 315

<210> SEQ ID NO 36
<211> LENGTH: 1311
<212> TYPE: DNA
<213> ORGANISM: Streptomyces thermosacchari

<400> SEQUENCE: 36
cgggacttca tccgcgattt tggcatgaac acttccttca acgcgcgtag cttgctacaa     60
gtgcggcagc agacccgctc gttggaggct cagtgagatt gacccgatcc ctgtcggccg    120
catccgtcat cgtcttcgcc ctgctgctcg cgctgctggg catcagcccg gcccaggcag    180
ccggcccggc ctatgtggcc tgggggatt cctattcctc gggcaacggc gccggaagtt    240
acatcgattc gagcggtgac tgtcaccgca gcaacaacgc gtaccccgcc cgctgggcgg    300
cggccaacgc accgtcctcc ttcaccttcg cggcctgctc gggagcggtg accacggatg    360
tgatcaacaa tcagctgggc gccctcaacg cgtccaccgg cctggtgagc atcaccatcg    420
gcggcaatga cgcgggcttc gcggacgcga tgaccacctg cgtcaccagc tcggacagca    480
cctgcctcaa ccggctggcc accgccacca actacatcaa caccaccctg ctcgcccggc    540
```

|  |  |  |  |  |
|---|---|---|---|---|
| tcgacgcggt | ctacagccag | atcaaggccc | gtgcccccaa | cgcccgcgtg gtcgtcctcg | 600 |
| gctacccgcg | catgtacctg | gcctcgaacc | cctggtactg | cctgggcctg agcaacacca | 660 |
| agcgcgcggc | catcaacacc | accgccgaca | ccctcaactc | ggtgatctcc tcccgggcca | 720 |
| ccgcccacgg | attccgattc | ggcgatgtcc | gcccgacctt | caacaaccac gaactgttct | 780 |
| tcggcaacga | ctggctgcac | tcactcaccc | tgccggtgtg | ggagtcgtac caccccacca | 840 |
| gcacgggcca | tcagagcggc | tatctgccgg | tcctcaacgc | caacagctcg acctgatcaa | 900 |
| cgcacggccg | tgcccgcccc | gcgcgtcacg | ctcggcgcgg | gcgccgcagc gcgttgatca | 960 |
| gcccacagtg | ccggtgacgg | tcccaccgtc | acggtcgagg | gtgtacgtca cggtggcgcc | 1020 |
| gctccagaag | tggaacgtca | gcaggaccgt | ggagccgtcc | ctgacctcgt cgaagaactc | 1080 |
| cggggtcagc | gtgatcaccc | ctcccccgta | gccggggggcg | aaggcggcgc cgaactcctt | 1140 |
| gtaggacgtc | cagtcgtgcg | gcccggcgtt | gccaccgtcc | gcgtagaccg cttccatggt | 1200 |
| cgccagccgg | tccccgcgga | actcggtggg | gatgtccgtg | cccaaggtgg tcccggtggt | 1260 |
| gtccgagagc | accgggggct | cgtaccggat | gatgtgcaga | tccaaagaat t | 1311 |

<210> SEQ ID NO 37
<211> LENGTH: 267
<212> TYPE: PRT
<213> ORGANISM: Streptomyces thermosacchari

<400> SEQUENCE: 37

```
Met Arg Leu Thr Arg Ser Leu Ser Ala Ala Ser Val Ile Val Phe Ala
1               5                   10                  15

Leu Leu Leu Ala Leu Leu Gly Ile Ser Pro Ala Gln Ala Ala Gly Pro
            20                  25                  30

Ala Tyr Val Ala Leu Gly Asp Ser Tyr Ser Ser Gly Asn Gly Ala Gly
        35                  40                  45

Ser Tyr Ile Asp Ser Ser Gly Asp Cys His Arg Ser Asn Asn Ala Tyr
    50                  55                  60

Pro Ala Arg Trp Ala Ala Asn Ala Pro Ser Ser Phe Thr Phe Ala
65                  70                  75                  80

Ala Cys Ser Gly Ala Val Thr Thr Asp Val Ile Asn Asn Gln Leu Gly
                85                  90                  95

Ala Leu Asn Ala Ser Thr Gly Leu Val Ser Ile Thr Ile Gly Gly Asn
            100                 105                 110

Asp Ala Gly Phe Ala Asp Ala Met Thr Thr Cys Val Thr Ser Ser Asp
        115                 120                 125

Ser Thr Cys Leu Asn Arg Leu Ala Thr Ala Thr Asn Tyr Ile Asn Thr
    130                 135                 140

Thr Leu Leu Ala Arg Leu Asp Ala Val Tyr Ser Gln Ile Lys Ala Arg
145                 150                 155                 160

Ala Pro Asn Ala Arg Val Val Val Leu Gly Tyr Pro Arg Met Tyr Leu
                165                 170                 175

Ala Ser Asn Pro Trp Tyr Cys Leu Gly Leu Ser Asn Thr Lys Arg Ala
            180                 185                 190

Ala Ile Asn Thr Thr Ala Asp Thr Leu Asn Ser Val Ile Ser Ser Arg
        195                 200                 205

Ala Thr Ala His Gly Phe Arg Phe Gly Asp Val Arg Pro Thr Phe Asn
    210                 215                 220

Asn His Glu Leu Phe Phe Gly Asn Asp Trp Leu His Ser Leu Thr Leu
225                 230                 235                 240
```

Pro Val Trp Glu Ser Tyr His Pro Thr Ser Thr Gly His Gln Ser Gly
            245                 250                 255

Tyr Leu Pro Val Leu Asn Ala Asn Ser Ser Thr
            260                 265

<210> SEQ ID NO 38
<211> LENGTH: 548
<212> TYPE: PRT
<213> ORGANISM: Thermobifida fusca

<400> SEQUENCE: 38

Met Leu Pro His Pro Ala Gly Glu Arg Gly Glu Val Gly Ala Phe Phe
1               5                   10                  15

Ala Leu Leu Val Gly Thr Pro Gln Asp Arg Arg Leu Arg Leu Glu Cys
            20                  25                  30

His Glu Thr Arg Pro Leu Arg Gly Arg Cys Gly Cys Gly Glu Arg Arg
        35                  40                  45

Val Pro Pro Leu Thr Leu Pro Gly Asp Gly Val Leu Cys Thr Thr Ser
    50                  55                  60

Ser Thr Arg Asp Ala Glu Thr Val Trp Arg Lys His Leu Gln Pro Arg
65                  70                  75                  80

Pro Asp Gly Gly Phe Arg Pro His Leu Gly Val Gly Cys Leu Leu Ala
                85                  90                  95

Gly Gln Gly Ser Pro Gly Val Leu Trp Cys Gly Arg Glu Gly Cys Arg
            100                 105                 110

Phe Glu Val Cys Arg Arg Asp Thr Pro Gly Leu Ser Arg Thr Arg Asn
        115                 120                 125

Gly Asp Ser Ser Pro Pro Phe Arg Ala Gly Trp Ser Leu Pro Pro Lys
    130                 135                 140

Cys Gly Glu Ile Ser Gln Ser Ala Arg Lys Thr Pro Ala Val Pro Arg
145                 150                 155                 160

Tyr Ser Leu Leu Arg Thr Asp Arg Pro Asp Gly Pro Arg Gly Arg Phe
                165                 170                 175

Val Gly Ser Gly Pro Arg Ala Ala Thr Arg Arg Arg Leu Phe Leu Gly
            180                 185                 190

Ile Pro Ala Leu Val Leu Val Thr Ala Leu Thr Leu Val Leu Ala Val
        195                 200                 205

Pro Thr Gly Arg Glu Thr Leu Trp Arg Met Trp Cys Glu Ala Thr Gln
    210                 215                 220

Asp Trp Cys Leu Gly Val Pro Val Asp Ser Arg Gly Gln Pro Ala Glu
225                 230                 235                 240

Asp Gly Glu Phe Leu Leu Leu Ser Pro Val Gln Ala Ala Thr Trp Gly
                245                 250                 255

Asn Tyr Tyr Ala Leu Gly Asp Ser Tyr Ser Ser Gly Asp Gly Ala Arg
            260                 265                 270

Asp Tyr Tyr Pro Gly Thr Ala Val Lys Gly Gly Cys Trp Arg Ser Ala
        275                 280                 285

Asn Ala Tyr Pro Glu Leu Val Ala Glu Ala Tyr Asp Phe Ala Gly His
    290                 295                 300

Leu Ser Phe Leu Ala Cys Ser Gly Gln Arg Gly Tyr Ala Met Leu Asp
305                 310                 315                 320

Ala Ile Asp Glu Val Gly Ser Gln Leu Asp Trp Asn Ser Pro His Thr
                325                 330                 335

Ser Leu Val Thr Ile Gly Ile Gly Gly Asn Asp Leu Gly Phe Ser Thr
            340                 345                 350

```
Val Leu Lys Thr Cys Met Val Arg Val Pro Leu Leu Asp Ser Lys Ala
            355                 360                 365

Cys Thr Asp Gln Glu Asp Ala Ile Arg Lys Arg Met Ala Lys Phe Glu
    370                 375                 380

Thr Thr Phe Glu Glu Leu Ile Ser Glu Val Arg Thr Arg Ala Pro Asp
385                 390                 395                 400

Ala Arg Ile Leu Val Val Gly Tyr Pro Arg Ile Phe Pro Glu Pro
                405                 410                 415

Thr Gly Ala Tyr Tyr Thr Leu Thr Ala Ser Asn Gln Arg Trp Leu Asn
                420                 425                 430

Glu Thr Ile Gln Glu Phe Asn Gln Gln Leu Ala Glu Ala Val Ala Val
            435                 440                 445

His Asp Glu Glu Ile Ala Ala Ser Gly Gly Val Gly Ser Val Glu Phe
            450                 455                 460

Val Asp Val Tyr His Ala Leu Asp Gly His Glu Ile Gly Ser Asp Glu
465                 470                 475                 480

Pro Trp Val Asn Gly Val Gln Leu Arg Asp Leu Ala Thr Gly Val Thr
                485                 490                 495

Val Asp Arg Ser Thr Phe His Pro Asn Ala Ala Gly His Arg Ala Val
            500                 505                 510

Gly Glu Arg Val Ile Glu Gln Ile Glu Thr Gly Pro Gly Arg Pro Leu
            515                 520                 525

Tyr Ala Thr Phe Ala Val Val Ala Gly Ala Thr Val Asp Thr Leu Ala
            530                 535                 540

Gly Glu Val Gly
545

<210> SEQ ID NO 39
<211> LENGTH: 3000
<212> TYPE: DNA
<213> ORGANISM: Thermobifida fusca

<400> SEQUENCE: 39
ggtggtgaac cagaacaccc ggtcgtcggc gtgggcgtcc aggtgcaggt gcaggttctt     60
caactgctcc agcaggatgc cgccgtggcc gtgcacgatg ccttgggca  ggcctgtggt    120 ccccgacgag tacagcaccc atagcggatg gtcgaacggc agcggggtga actccagttc    180
cgcgccttcg cccgcggctt cgaactccgc ccaggacagg gtgtcggcga cagggccgca    240
gcccaggtac ggcaggacga cggtgtgctg caggctgggc atgccgtcgc gcagggcttt    300
gagcacgtca cggcggtcga agtccttacc gccgtagcgg tagccgtcca cggccagcag    360
cactttcggt tcgatctgcg cgaaccggtc gaggacgctg cgcacccga  agtcggggga    420 acaggacgac caggtcgcac cgatcgcggc gcaggcgagg aatgcggccg tcgcctcggc    480
gatgttcggc aggtaggcca cgacccggtc gccgggcccc accccgaggc tgcgagggc    540 cgcagcgatc gcggcggtgc gggtccgcag ttctccccag gtccactcgg tcaacggccg    600
gagttcggac gcgtgccgga tcgccacggc tgatgggtca cggtcgcgga agatgtgctc    660
ggcgtagttg agggtggcgc cggggaacca gacggcgccg gcatggcgt cggaggcgag    720 cactgtggtg tacggggtgg cggcgcgcac ccggtagtac tcccagatcg cggaccagaa    780
tccttcgagg tcggttaccg accagcgcca cagtgcctcg tagtccggtg cgtccacacc    840
gcggtgctcc cgcaccccagc gggtgaacgc ggtgaggttg gcgcgttctt tgcgctcctc    900
gtcgggactc cacaggatcg gcggctgcgg cttgagtgtc atgaaacgcg accccttcgt    960
```

| | | | |
|---|---|---|---|
| ggacggtgcg gatgcggtga gcgtcgggtg cctcccctaa cgctcccggt gacggagtg | 1020 |
| ttgtgcacca catctagcac gcgggacgcg gaaaccgtat ggagaaaaca cctacaaccc | 1080 |
| cggccggacg gtgggtttcg gccacactta ggggtcgggt gcctgcttgc cgggcagggc | 1140 |
| agtcccgggg tgctgtggtg cgggcggag ggctgtcgct tcgaggtgtg ccggcgggac | 1200 |
| actccgggcc tcagccgtac ccgcaacggg gacagttctc ctcccttccg ggctggatgg | 1260 |
| tcccttcccc cgaaatgcgg cgagatctcc cagtcagccc ggaaaacacc cgctgtgccc | 1320 |
| aggtactctt tgcttcgaac agacaggccg gacggtccac gggggaggtt tgtgggcagc | 1380 |
| ggaccacgtg cggcgaccag cgacggttg ttcctcggta tccccgctct tgtacttgtg | 1440 |
| acagcgctca cgctggtctt ggctgtcccg acggggcgcg agacgctgtg gcgcatgtgg | 1500 |
| tgtgaggcca cccaggactg gtgcctgggg gtgccggtcg actcccgcgg acagcctgcg | 1560 |
| gaggacggcg agtttctgct gctttctccg gtccaggcag cgacctgggg gaactattac | 1620 |
| gcgctcgggg attcgtactc ttcgggggac ggggcccgcg actactatcc cggcaccgcg | 1680 |
| gtgaagggcg gttgctggcg gtccgctaac gcctatccgg agctggtcgc cgaagcctac | 1740 |
| gacttcgccg gacacttgtc gttcctggcc tgcagcggcc agcgcggcta cgccatgctt | 1800 |
| gacgctatcg acgaggtcgg ctcgcagctg gactggaact cccctcacac gtcgctggtg | 1860 |
| acgatcggga tcgcggcaa cgatctgggg ttctccacgg ttttgaagac ctgcatggtg | 1920 |
| cgggtgccgc tgctggacag caaggcgtgc acggaccagg aggacgctat ccgcaagcgg | 1980 |
| atggcgaaat tcgagacgac gtttgaagag ctcatcagcg aagtgcgcac ccgcgcgccg | 2040 |
| gacgcccgga tccttgtcgt gggctacccc cggattttc cggaggaacc gaccggcgcc | 2100 |
| tactacacgc tgaccgcgag caaccagcgg tggctcaacg aaaccattca ggagttcaac | 2160 |
| cagcagctcg ccgaggctgt cgcggtccac gacgaggaga ttgccgcgtc gggcggggtg | 2220 |
| ggcagcgtgg agttcgtgga cgtctaccac gcgttggacg gccacgagat cggctcggac | 2280 |
| gagccgtggg tgaacggggt gcagttgcgg gacctcgcca ccggggtgac tgtggaccgc | 2340 |
| agtaccttcc accccaacgc cgctgggcac cgggcggtcg gtgagcgggt catcgagcag | 2400 |
| atcgaaaccg gcccgggccg tccgctctat gccactttcg cggtggtggc gggggcgacc | 2460 |
| gtggacactc tcgcgggcga ggtgggggtga cccggcttac cgtccggccc gcaggtctgc | 2520 |
| gagcactgcg gcgatctggt ccactgccca gtgcagttcg tcttcggtga tgaccagcgg | 2580 |
| cggggagagc cggatcgttg agccgtgcgt gtctttgacg agcacacccc gctgcaggag | 2640 |
| ccgttcgcac agttctcttc cggtggccag agtcgggtcg acgtcgatcc cagcccacag | 2700 |
| gccgatgctg cgggccgcga ccacgccgtt gccgaccagt tggtcgaggc gggcgcgcag | 2760 |
| cacggggcg agggcgcgga catggtccag gtaaggccg tcgcggacga ggctcaccac | 2820 |
| ggcagtgccg accgcgcagg cgagggcgtt gccgccgaag gtgctgccgt gctggccggg | 2880 |
| gcggatcacg tcgaagactt ccgcgtcgcc taccgccgcc gcacgggca ggatgccgcc | 2940 |
| gcccagcgct ttgccgaaca ggtagatatc ggcgtcgact ccgctgtggt cgcaggcccg | 3000 |

<210> SEQ ID NO 40
<211> LENGTH: 372
<212> TYPE: PRT
<213> ORGANISM: Thermobifida fusca

<400> SEQUENCE: 40

Val Gly Ser Gly Pro Arg Ala Ala Thr Arg Arg Arg Leu Phe Leu Gly
1               5                   10                  15

```
Ile Pro Ala Leu Val Leu Val Thr Ala Leu Thr Leu Val Leu Ala Val
            20                  25                  30

Pro Thr Gly Arg Glu Thr Leu Trp Arg Met Trp Cys Glu Ala Thr Gln
        35                  40                  45

Asp Trp Cys Leu Gly Val Pro Val Asp Ser Arg Gly Gln Pro Ala Glu
    50                  55                  60

Asp Gly Glu Phe Leu Leu Leu Ser Pro Val Gln Ala Ala Thr Trp Gly
65                  70                  75                  80

Asn Tyr Tyr Ala Leu Gly Asp Ser Tyr Ser Ser Gly Asp Gly Ala Arg
                85                  90                  95

Asp Tyr Tyr Pro Gly Thr Ala Val Lys Gly Gly Cys Trp Arg Ser Ala
            100                 105                 110

Asn Ala Tyr Pro Glu Leu Val Ala Glu Ala Tyr Asp Phe Ala Gly His
        115                 120                 125

Leu Ser Phe Leu Ala Cys Ser Gly Gln Arg Gly Tyr Ala Met Leu Asp
130                 135                 140

Ala Ile Asp Glu Val Gly Ser Gln Leu Asp Trp Asn Ser Pro His Thr
145                 150                 155                 160

Ser Leu Val Thr Ile Gly Ile Gly Gly Asn Asp Leu Gly Phe Ser Thr
                165                 170                 175

Val Leu Lys Thr Cys Met Val Arg Val Pro Leu Leu Asp Ser Lys Ala
            180                 185                 190

Cys Thr Asp Gln Glu Asp Ala Ile Arg Lys Arg Met Ala Lys Phe Glu
        195                 200                 205

Thr Thr Phe Glu Glu Leu Ile Ser Glu Val Arg Thr Arg Ala Pro Asp
210                 215                 220

Ala Arg Ile Leu Val Val Gly Tyr Pro Arg Ile Phe Pro Glu Glu Pro
225                 230                 235                 240

Thr Gly Ala Tyr Tyr Thr Leu Thr Ala Ser Asn Gln Arg Trp Leu Asn
                245                 250                 255

Glu Thr Ile Gln Glu Phe Asn Gln Gln Leu Ala Glu Ala Val Ala Val
            260                 265                 270

His Asp Glu Glu Ile Ala Ala Ser Gly Gly Val Gly Ser Val Glu Phe
        275                 280                 285

Val Asp Val Tyr His Ala Leu Asp Gly His Glu Ile Gly Ser Asp Glu
290                 295                 300

Pro Trp Val Asn Gly Val Gln Leu Arg Asp Leu Ala Thr Gly Val Thr
305                 310                 315                 320

Val Asp Arg Ser Thr Phe His Pro Asn Ala Ala Gly His Arg Ala Val
                325                 330                 335

Gly Glu Arg Val Ile Glu Gln Ile Glu Thr Gly Pro Gly Arg Pro Leu
            340                 345                 350

Tyr Ala Thr Phe Ala Val Val Ala Gly Ala Thr Val Asp Thr Leu Ala
        355                 360                 365

Gly Glu Val Gly
    370

<210> SEQ ID NO 41
<211> LENGTH: 300
<212> TYPE: PRT
<213> ORGANISM: Corynebacterium efficiens

<400> SEQUENCE: 41

Met Arg Thr Thr Val Ile Ala Ala Ser Ala Leu Leu Leu Leu Ala Gly
```

```
              1               5                  10                 15
         Cys Ala Asp Gly Ala Arg Glu Glu Thr Ala Gly Ala Pro Pro Gly Glu
                         20                 25                 30
         Ser Ser Gly Gly Ile Arg Glu Glu Gly Ala Glu Ala Ser Thr Ser Ile
                         35                 40                 45
         Thr Asp Val Tyr Ile Ala Leu Gly Asp Ser Tyr Ala Ala Met Gly Gly
                 50                 55                 60
         Arg Asp Gln Pro Leu Arg Gly Glu Pro Phe Cys Leu Arg Ser Ser Gly
         65                 70                 75                 80
         Asn Tyr Pro Glu Leu Leu His Ala Glu Val Thr Asp Leu Thr Cys Gln
                         85                 90                 95
         Gly Ala Val Thr Gly Asp Leu Leu Glu Pro Arg Thr Leu Gly Glu Arg
                         100                105                110
         Thr Leu Pro Ala Gln Val Asp Ala Leu Thr Glu Asp Thr Thr Leu Val
                         115                120                125
         Thr Leu Ser Ile Gly Gly Asn Asp Leu Gly Phe Gly Glu Val Ala Gly
                         130                135                140
         Cys Ile Arg Glu Arg Ile Ala Gly Glu Asn Ala Asp Asp Cys Val Asp
         145                150                155                160
         Leu Leu Gly Glu Thr Ile Gly Glu Gln Leu Asp Gln Leu Pro Pro Gln
                         165                170                175
         Leu Asp Arg Val His Glu Ala Ile Arg Asp Arg Ala Gly Asp Ala Gln
                         180                185                190
         Val Val Val Thr Gly Tyr Leu Pro Leu Val Ser Ala Gly Asp Cys Pro
                         195                200                205
         Glu Leu Gly Asp Val Ser Glu Ala Asp Arg Arg Trp Ala Val Glu Leu
                         210                215                220
         Thr Gly Gln Ile Asn Glu Thr Val Arg Glu Ala Ala Glu Arg His Asp
         225                230                235                240
         Ala Leu Phe Val Leu Pro Asp Asp Ala Asp Glu His Thr Ser Cys Ala
                         245                250                255
         Pro Pro Gln Gln Arg Trp Ala Asp Ile Gln Gly Gln Thr Asp Ala
                         260                265                270
         Tyr Pro Leu His Pro Thr Ser Ala Gly His Glu Ala Met Ala Ala Ala
                         275                280                285
         Val Arg Asp Ala Leu Gly Leu Glu Pro Val Gln Pro
                         290                295                300

<210> SEQ ID NO 42
<211> LENGTH: 3000
<212> TYPE: DNA
<213> ORGANISM: Corynebacterium efficiens

<400> SEQUENCE: 42
ttctggggtg ttatgggggtt gttatcggct cgtcctgggt ggatcccgcc aggtggggta      60
ttcacggggg acttttgtgt ccaacagccg agaatgagtg ccctgagcgg tgggaatgag     120
gtgggcgggg ctgtgtcgcc atgagggggc ggcgggctct gtggtgcccc gcgaccccg      180 gccccggtga gcggtgaatg aaatccggct gtaatcagca tcccgtgccc acccgtcgg     240 ggaggtcagc gcccggagtg tctacgcagt cggatcctct cggactcggc catgctgtcg     300
gcagcatcgc gctcccgggt cttggcgtcc ctcggctgtt ctgcctgctg tccctggaag     360
gcgaaatgat caccggggag tgatacaccg gtggtctcat cccggatgcc cacttcggcg     420
ccatccggca attcgggcag ctccgggtgg aagtaggtgg catccgatgc gtcggtgacg     480
```

```
ccatagtggg cgaagatctc atcctgctcg agggtgctca ggccactctc cggatcgata    540
tcggggcgt ccttgatggc gtccttgctg aaaccgaggt gcagcttgtg ggcttccaat    600
ttcgcaccac ggagcgggac gaggctggaa tgacggccga agagcccgtg gtggacctca    660
acgaaggtgg gtagtcccgt gtcatcattg aggaacacgc cctccaccgc acccagcttg    720
tggccggagt tgtcgtaggc gctggcatcc agaagggaaa cgatctcata tttgtcggtg    780
tgctcagaca tgatcttcct ttgctgtcgg tgtctggtac taccacggta gggctgaatg    840
caactgttat ttttctgtta ttttaggaat tggtccatat cccacaggct ggctgtggtc    900
aaatcgtcat caagtaatcc ctgtcacaca aatgggtgg tgggagccct ggtcgcggtt    960
ccgtgggagg cgccgtgccc cgcaggatcg tcggcatcgg cggatctggc cggtaccccg   1020
cggtgaataa aatcattctg taaccttcat cacggttggt tttaggtatc cgccccttc    1080
gtcctgaccc cgtccccggc gcgcgggagc ccgcgggttg cggtagacag gggagacgtg   1140
gacaccatga ggacaacggt catcgcagca agcgcattac tccttctcgc cggatgcgcg   1200
gatggggccc gggaggagac cgccggtgca ccgccgggtg agtcctccgg gggcatccgg   1260
gaggaggggg cggaggcgtc gacaagcatc accgacgtct acatcgccct cggggattcc   1320
tatgcggcga tgggcgggcg ggatcagccg ttacggggtg agccgttctg cctgcgctcg   1380
tccggtaatt acccggaact cctccacgca gaggtcaccg atctcacctg caggggcg    1440
gtgaccgggg atctgctcga acccaggacg ctggggagc gcacgctgcc ggcgcaggtg   1500
gatgcgctga cggaggacac caccctggtc accctctcca tcgggggcaa tgacctcgga   1560
ttcggggagg tggcgggatg catccgggaa cggatcgccg gggagaacgc tgatgattgc   1620
gtggacctgc tggggaaaac catcggggag cagctcgatc agcttccccc gcagctggac   1680
cgcgtgcacg aggctatccg ggaccgcgcc ggggacgcgc aggttgtggt caccggttac   1740
ctgccgctcg tgtctgccgg ggactgcccc gaactggggg atgtctccga ggcggatcgt   1800
cgttgggcgg ttgagctgac cgggcagatc aacgagaccg tgcgcgaggc ggccgaacga   1860
cacgatgccc tctttgtcct gcccgacgat gccgatgagc acaccagttg tgcaccccca   1920
cagcagcgct gggcggatat ccaggccaa cagaccgatg cctatccgct gcacccgacc   1980
tccgccggcc atgaggcgat ggccgccgcc gtccgggacg cgctgggcct ggaaccggtc   2040
cagccgtagc gccgggcgcg cgcttgtcga cgaccaaccc atgccaggct gcagtcacat   2100
ccgcacatag cgcgcgcggg cgatggagta cgcaccatag aggatgagcc cgatgccgac   2160
gatgatgagc agcacactgc cgaagggttg ttccccgagg gtgcgcagag ccgagtccag   2220
acctgcggcc tgctccggat catgggccca accggcgatg acgatcaaca cccccaggat   2280
cccgaaggcg ataccacggg cgacataacc ggctgttccg gtgatgatga tcgcggtccc   2340
gacctgccct gaccccgcac ccgcctccag atcctcccgg aaatcccggg tggcccctt    2400
ccagaggttg tagacacccg ccccccagtac caccagcccg cgaccacaa ccagcaccac   2460
accccagggt tgggatagga cggtggcggt gacatcggtg gcggtctccc catcggaggt   2520
gctgccgccc cgggcgaagg tggaggtggt caccgccagg gagaagtaga ccatggccat   2580
gaccgccccc ttggcccttt ccttgaggtc ctcgcccgcc agcagctggc tcaattgcca   2640
gagtcccagg gccgccaggg cgatgacggc aacccacagg aggaactgcc cacccggagc   2700
ctccgcgatg gtgccaggg cacctgaatt cgaggcctca tcacccgaac cgccggatcc   2760
agtggcgatg cgcaccgcga tccacccgat gaggatgtgc agtatgccca ggacaatgaa   2820
```

```
accacctctg gccagggtgg tcagcgcggg gtggtcctcg gcctggtcgg cagcccgttc    2880
gatcgtccgt ttcgcggatc tggtgtcgcc cttatccata gctcccattg aaccgccttg    2940
aggggtgggc ggccactgtc agggcggatt gtgatctgaa ctgtgatgtt ccatcaaccc    3000
```

<210> SEQ ID NO 43
<211> LENGTH: 268
<212> TYPE: PRT
<213> ORGANISM: Streptomyces coelicolor

<400> SEQUENCE: 43

```
Met Arg Arg Phe Arg Leu Val Gly Phe Leu Ser Ser Leu Val Leu Ala
1               5                   10                  15

Ala Gly Ala Ala Leu Thr Gly Ala Ala Thr Ala Gln Ala Ala Gln Pro
            20                  25                  30

Ala Ala Ala Asp Gly Tyr Val Ala Leu Gly Asp Ser Tyr Ser Ser Gly
        35                  40                  45

Val Gly Ala Gly Ser Tyr Ile Ser Ser Ser Gly Asp Cys Lys Arg Ser
    50                  55                  60

Thr Lys Ala His Pro Tyr Leu Trp Ala Ala His Ser Pro Ser Thr
65                  70                  75                  80

Phe Asp Phe Thr Ala Cys Ser Gly Ala Arg Thr Gly Asp Val Leu Ser
                85                  90                  95

Gly Gln Leu Gly Pro Leu Ser Ser Gly Thr Gly Leu Val Ser Ile Ser
            100                 105                 110

Ile Gly Gly Asn Asp Ala Gly Phe Ala Asp Thr Met Thr Thr Cys Val
        115                 120                 125

Leu Gln Ser Glu Ser Ser Cys Leu Ser Arg Ile Ala Thr Glu Ala
    130                 135                 140

Tyr Val Asp Ser Thr Leu Pro Gly Lys Leu Asp Gly Val Tyr Ser Ala
145                 150                 155                 160

Ile Ser Asp Lys Ala Pro Asn Ala His Val Val Ile Gly Tyr Pro
                165                 170                 175

Arg Phe Tyr Lys Leu Gly Thr Thr Cys Ile Gly Leu Ser Glu Thr Lys
            180                 185                 190

Arg Thr Ala Ile Asn Lys Ala Ser Asp His Leu Asn Thr Val Leu Ala
        195                 200                 205

Gln Arg Ala Ala Ala His Gly Phe Thr Phe Gly Asp Val Arg Thr Thr
    210                 215                 220

Phe Thr Gly His Glu Leu Cys Ser Gly Ser Pro Trp Leu His Ser Val
225                 230                 235                 240

Asn Trp Leu Asn Ile Gly Glu Ser Tyr His Pro Thr Ala Ala Gly Gln
                245                 250                 255

Ser Gly Gly Tyr Leu Pro Val Leu Asn Gly Ala Ala
            260                 265
```

<210> SEQ ID NO 44
<211> LENGTH: 2000
<212> TYPE: DNA
<213> ORGANISM: Streptomyces coelicolor

<400> SEQUENCE: 44

```
cccggcggcc cgtgcaggag cagcagccgg cccgcgatgt cctcgggcgt cgtcttcatc     60
aggccgtcca tcgcgtcggc gaccggcgcc gtgtagttgg cccggacctc gtcccaggtg    120
cccgcggcga tctggcgggt ggtgcggtgc gggccgcgcc gaggggagac gtaccagaag    180
```

| | |
|---|---|
| cccatcgtca cgttctccgg ctgcggttcg ggctcgtccg ccgctccgtc cgtcgcctcg | 240 |
| ccgagcacct tctcggcgag gtcggcgctg gtcgccgtca ccgtgacgtc ggcgccccgg | 300 |
| ctccagcgcg agatcagcag cgtccagccg tcgccctccg ccagcgtcgc gctgcggtcg | 360 |
| tcgtcgcggg cgatccgcag cacgcgcgcg ccgggcggca gcagcgtggc gccggaccgt | 420 |
| acgcggtcga tgttcgccgc gtgcgagtac ggctgctcac ccgtggcgaa acggccgagg | 480 |
| aacagcgcgt cgacgacgtc ggacggggag tcgctgtcgt ccacgttgag ccggatcggc | 540 |
| agggcttcgt gcgggttcac ggacatgtcg ccatgatcgg gcacccggcc gccgcgtgca | 600 |
| cccgcttcc cgggcacgca cgacaggggc tttctcgccg tcttccgtcc gaacttgaac | 660 |
| gagtgtcagc catttcttgg catggacact tccagtcaac gcgcgtagct gctaccacgg | 720 |
| ttgtggcagc aatcctgcta agggaggttc catgagacgt ttccgacttg tcggcttcct | 780 |
| gagttcgctc gtcctcgccg ccggcgccgc cctcaccggg gcagcgaccg cccaggcggc | 840 |
| ccaacccgcc gccgccgacg gctatgtggc cctcggcgac tcctactcct ccggggtcgg | 900 |
| agcgggcagc tacatcagct cgagcggcga ctgcaagcgc agcacgaagg cccatcccta | 960 |
| cctgtgggcg gccgcccact cgccctccac gttcgacttc accgcctgtt ccggcgcccg | 1020 |
| tacgggtgat gttctctccg gacagctcgg cccgctcagc tccggcaccg gctcgtctc | 1080 |
| gatcagcatc ggcggcaacg acgccggttt cgccgacacc atgacgacct gtgtgctcca | 1140 |
| gtccgagagc tcctgcctgt cgcggatcgc caccgccgag gcgtacgtcg actcgacgct | 1200 |
| gcccggcaag ctcgacggcg tctactcggc aatcagcgac aaggcgccga acgcccacgt | 1260 |
| cgtcgtcatc ggctacccgc gcttctacaa gctcggcacc acctgcatcg gcctgtccga | 1320 |
| gaccaagcgg acggcgatca acaaggcctc cgaccacctc aacaccgtcc tcgcccagcg | 1380 |
| cgccgccgcc cacggcttca ccttcggcga cgtacgcacc accttcaccg gccacgagct | 1440 |
| gtgctccggc agcccctggc tgcacagcgt caactggctg aacatcggcg agtcgtacca | 1500 |
| ccccaccgcg gccggccagt ccggtggcta cctgccggtc ctcaacggcg ccgcctgacc | 1560 |
| tcaggcggaa ggagaagaag aaggagcgga gggagacgag gagtgggagg ccccgcccga | 1620 |
| cggggtcccc gtccccgtct ccgtctccgt cccggtcccg caagtcaccg agaacgccac | 1680 |
| cgcgtcggac gtggcccgca ccggactccg cacctccacg cgcacggcac tctcgaacgc | 1740 |
| gccggtgtcg tcgtgcgtcg tcaccaccac gccgtcctgg cgcgagcgct cgccgcccga | 1800 |
| cgggaaggac agcgtccgcc accccggatc ggagaccgac ccgtccgcgg tcacccaccg | 1860 |
| gtagccgacc tccgcgggca gccgcccgac cgtgaacgtc gccgtgaacg cgggtgcccg | 1920 |
| gtcgtgcggc ggcggacagg cccccgagta gtgggtgcgc gagcccacca cggtcacctc | 1980 |
| caccgactgc gctgcggggc | 2000 |

<210> SEQ ID NO 45
<211> LENGTH: 269
<212> TYPE: PRT
<213> ORGANISM: Streptomyces avermitilis

<400> SEQUENCE: 45

Met Arg Arg Ser Arg Ile Thr Ala Tyr Val Thr Ser Leu Leu Leu Ala
1               5                   10                  15

Val Gly Cys Ala Leu Thr Gly Ala Ala Thr Ala Gln Ala Ser Pro Ala
                20                  25                  30

Ala Ala Ala Thr Gly Tyr Val Ala Leu Gly Asp Ser Tyr Ser Ser Gly
            35                  40                  45

Val Gly Ala Gly Ser Tyr Leu Ser Ser Ser Gly Asp Cys Lys Arg Ser
 50                  55                  60

Ser Lys Ala Tyr Pro Tyr Leu Trp Gln Ala Ala His Ser Pro Ser Ser
 65                  70                  75                  80

Phe Ser Phe Met Ala Cys Ser Gly Ala Arg Thr Gly Asp Val Leu Ala
                 85                  90                  95

Asn Gln Leu Gly Thr Leu Asn Ser Ser Thr Gly Leu Val Ser Leu Thr
            100                 105                 110

Ile Gly Gly Asn Asp Ala Gly Phe Ser Asp Val Met Thr Thr Cys Val
            115                 120                 125

Leu Gln Ser Asp Ser Ala Cys Leu Ser Arg Ile Asn Thr Ala Lys Ala
            130                 135                 140

Tyr Val Asp Ser Thr Leu Pro Gly Gln Leu Asp Ser Val Tyr Thr Ala
145                 150                 155                 160

Ile Ser Thr Lys Ala Pro Ser Ala His Val Ala Val Leu Gly Tyr Pro
                165                 170                 175

Arg Phe Tyr Lys Leu Gly Gly Ser Cys Leu Ala Gly Leu Ser Glu Thr
            180                 185                 190

Lys Arg Ser Ala Ile Asn Asp Ala Ala Asp Tyr Leu Asn Ser Ala Ile
            195                 200                 205

Ala Lys Arg Ala Ala Asp His Gly Phe Thr Phe Gly Asp Val Lys Ser
            210                 215                 220

Thr Phe Thr Gly His Glu Ile Cys Ser Ser Ser Thr Trp Leu His Ser
225                 230                 235                 240

Leu Asp Leu Leu Asn Ile Gly Gln Ser Tyr His Pro Thr Ala Ala Gly
                245                 250                 255

Gln Ser Gly Gly Tyr Leu Pro Val Met Asn Ser Val Ala
            260                 265

<210> SEQ ID NO 46
<211> LENGTH: 1980
<212> TYPE: DNA
<213> ORGANISM: Streptomyces avermitilis

<400> SEQUENCE: 46

```
ccaccgccgg gtcggcggcg agtctcctgg cctcggtcgc ggagaggttg gccgtgtagc      60
cgttcagcgc ggcgccgaac gtcttcttca ccgtgccgcc gtactcgttg atcaggccct     120
tgcccttgct cgacgcggcc ttgaagccgg tgcccttctt gagcgtgacg atgtagctgc     180
ccttgatcgc ggtgggggag ccggcggcga gcaccgtgcc ctcggccggg gtggcctggg     240
cgggcagtgc ggtgaatccg cccacgaggg cgccggtcgc cacggcggtt atcgcggcga     300
tccggatctt cttgctacgc agctgtgcca tacgagggag tcctcctctg ggcagcggcg     360
cgcctgggtg gggcgcacgg ctgtgggggg tgcgcgcgtc atcacgcaca cggccctgga     420
gcgtcgtgtt ccgccctggg ttgagtaaag cctcggccat ctacggggt ggctcaaggg     480 agttgagacc ctgtcatgag tctgacatga gcacgcaatc aacggggccg tgagcacccc     540
ggggcgaccc cggaaagtgc cgagaagtct tggcatggac acttcctgtc aacacgcgta     600
gctggtacga cggttacggc agagatcctg ctaaagggag gttccatgag acgttcccga     660
attacggcat acgtgaccct actcctcctc gccgtcggct gcgccctcac cggggcagcg     720
acggcgcagg cgtccccagc cgccgcggcc acgggctatg tggccctcgg cgactcgtac     780
tcgtccggtg tcggcgccgg cagctacctc agctccagcg gcgactgcaa gcgcagttcg     840
aaggcctatc cgtacctctg gcaggccgcg cattcaccct cgtcgttcag tttcatggct     900
```

-continued

```
tgctcgggcg ctcgtacggg tgatgtcctg gccaatcagc tcggcaccct gaactcgtcc      960
accggcctgg tctccctcac catcggaggc aacgacgcgg gcttctccga cgtcatgacg     1020
acctgtgtgc tccagtccga cagcgcctgc ctctcccgca tcaacacggc gaaggcgtac     1080
gtcgactcca ccctgcccgg ccaactcgac agcgtgtaca cggcgatcag cacgaaggcc     1140
ccgtcggccc atgtggccgt gctgggctac ccccgcttct acaaactggg cggctcctgc     1200
ctcgcgggcc tctcggagac caagcggtcc gccatcaacg acgcggccga ctatctgaac     1260
agcgccatcg ccaagcgcgc cgccgaccac ggcttcacct tcggcgacgt caagagcacc     1320
ttcaccggcc atgagatctg ctccagcagc acctggctgc acagtctcga cctgctgaac     1380
atcggccagt cctaccaccc gaccgcggcc ggccagtccg gcggctatct gccggtcatg     1440
aacagcgtgg cctgagctcc cacggcctga attttttaagg cctgaatttt taaggcgaag     1500
gtgaaccgga agcggaggcc ccgtccgtcg gggtctccgt cgcacaggtc accgagaacg     1560
gcacggagtt ggacgtcgtg cgcaccgggt cgcgcacctc gacggcgatc tcgttcgaga     1620
tcgttccgct cgtgtcgtac gtggtgacga cacctgctt ctgctgggtc tttccgccgc     1680
tcgccgggaa ggacagcgtc ttccagcccg gatccgggac ctcgcccttc ttggtcaccc     1740
agcggtactc cacctcgacc ggcacccggc ccaccgtgaa ggtcgccgtg aacgtgggcg     1800
cctgggcggt gggcggcggg caggcaccgg agtagtcggt gtgcacgccg gtgaccgtca     1860
ccttcacgga ctgggccggc ggggtcgtcg taccgccgcc gccaccgccg cctcccggag     1920
tggagcccga gctgtggtcg ccccgccgt cggcgttgtc gtcctcgggg gttttcgaac      1980
```

<210> SEQ ID NO 47
<211> LENGTH: 372
<212> TYPE: PRT
<213> ORGANISM: Thermobifida fusca

<400> SEQUENCE: 47

```
Met Gly Ser Gly Pro Arg Ala Ala Thr Arg Arg Leu Phe Leu Gly
1               5                   10                  15

Ile Pro Ala Leu Val Leu Val Thr Ala Leu Thr Leu Val Leu Ala Val
            20                  25                  30

Pro Thr Gly Arg Glu Thr Leu Trp Arg Met Trp Cys Glu Ala Thr Gln
        35                  40                  45

Asp Trp Cys Leu Gly Val Pro Val Asp Ser Arg Gly Gln Pro Ala Glu
    50                  55                  60

Asp Gly Glu Phe Leu Leu Leu Ser Pro Val Gln Ala Ala Thr Trp Gly
65                  70                  75                  80

Asn Tyr Tyr Ala Leu Gly Asp Ser Tyr Ser Ser Gly Asp Gly Ala Arg
                85                  90                  95

Asp Tyr Tyr Pro Gly Thr Ala Val Lys Gly Gly Cys Trp Arg Ser Ala
            100                 105                 110

Asn Ala Tyr Pro Glu Leu Val Ala Glu Ala Tyr Asp Phe Ala Gly His
        115                 120                 125

Leu Ser Phe Leu Ala Cys Ser Gly Gln Arg Gly Tyr Ala Met Leu Asp
    130                 135                 140

Ala Ile Asp Glu Val Gly Ser Gln Leu Asp Trp Asn Ser Pro His Thr
145                 150                 155                 160

Ser Leu Val Thr Ile Gly Ile Gly Gly Asn Asp Leu Gly Phe Ser Thr
                165                 170                 175

Val Leu Lys Thr Cys Met Val Arg Val Pro Leu Leu Asp Ser Lys Ala
```

```
                180                 185                 190
Cys Thr Asp Gln Glu Asp Ala Ile Arg Lys Arg Met Ala Lys Phe Glu
            195                 200                 205

Thr Thr Phe Glu Glu Leu Ile Ser Glu Val Arg Thr Arg Ala Pro Asp
210                 215                 220

Ala Arg Ile Leu Val Val Gly Tyr Pro Arg Ile Phe Pro Glu Glu Pro
225                 230                 235                 240

Thr Gly Ala Tyr Tyr Thr Leu Thr Ala Ser Asn Gln Arg Trp Leu Asn
                245                 250                 255

Glu Thr Ile Gln Glu Phe Asn Gln Gln Leu Ala Glu Ala Val Ala Val
            260                 265                 270

His Asp Glu Glu Ile Ala Ala Ser Gly Gly Val Gly Ser Val Glu Phe
        275                 280                 285

Val Asp Val Tyr His Ala Leu Asp Gly His Glu Ile Gly Ser Asp Glu
    290                 295                 300

Pro Trp Val Asn Gly Val Gln Leu Arg Asp Leu Ala Thr Gly Val Thr
305                 310                 315                 320

Val Asp Arg Ser Thr Phe His Pro Asn Ala Ala Gly His Arg Ala Val
                325                 330                 335

Gly Glu Arg Val Ile Glu Gln Ile Glu Thr Gly Pro Gly Arg Pro Leu
            340                 345                 350

Tyr Ala Thr Phe Ala Val Val Ala Gly Ala Thr Val Asp Thr Leu Ala
        355                 360                 365

Gly Glu Val Gly
    370

<210> SEQ ID NO 48
<211> LENGTH: 968
<212> TYPE: DNA
<213> ORGANISM: Thermobifida fusca

<400> SEQUENCE: 48
ctgcagacac ccgccccgcc ttctcccgga tcgtcatgtt cggcgactcc ctcagcgaca    60
ccggcaagat gtactccaag atgcgcggct acctgccgtc ctccccgccg tactacgagg   120
gccgcttctc gaacggcccg gtctggctgg agcagctgac gaagcagttc cccggcctga   180
cgatcgccaa cgaggccgag gggggcgcga ccgcagtcgc ctacaacaag atctcctgga   240
acccgaagta ccaggtcatt aacaacctcg actacgaggt cacccagttc ttgcagaagg   300
actcgttcaa gcccgacgac ctggtcatcc tgtgggtggg cgccaacgac tacctggcct   360
acggttggaa cacggagcag gacgccaagc gggtgcgcga cgccatctcg gacgcggcaa   420
accgcatggt cctgaacggc gcgaagcaga tcctgctgtt caacctgccc gacctgggcc   480
agaacccgtc cgcccgctcc cagaaggtcg tcgaggccgt ctcgcacgtg tccgcctacc   540
acaacaagct gctcctcaac ctcgcccggc agctcgcccc gacgggcatg gtcaagctgt   600
tcgagatcga caagcagttc gcggagatgc tgcgcgaccc ccagaacttc ggcctgagcg   660
acgtggagaa cccgtgctac gacggcggct acgtgtggaa gccgttcgcc acccggtccg   720
tctcgaccga ccggcagctg tcggccttct cgccccagga gcgcctggcg atcgctggca   780
acccgctcct ggcacaggcg gtagcttcgc cgatggcccg ccgctcggcc tcgcccctca   840
actgcgaggg caagatgttc tgggaccagg tccaccccac caccgtggtc cacgccgccc   900
tctcggagcg cgccgccacc ttcatcgaga cccagtacga gttcctcgcc cactagtcta   960
gaggatcc                                                              968
```

<210> SEQ ID NO 49
<211> LENGTH: 1044
<212> TYPE: DNA
<213> ORGANISM: Aeromonas salmonicida

<400> SEQUENCE: 49

| | | |
|---|---|---|
| atgaaacaac aaaaacggct ttacgcccga ttgctgacgc tgttatttgc gctcatcttc | 60 |
| ttgctgcctc attctgcagc ttcagcagca gatacaagac cggcgtttag ccggatcgtc | 120 |
| atgtttggag atagcctgag cgatacgggc aaaatgtata gcaaaatgag aggctatctt | 180 |
| ccgtcaagcc cgccgtatta tgaaggccgc tttagcaatg accggtctg gctggaacaa | 240 |
| ctgacgaaac aatttccggg actgacgatc gctaatgaag cagaaggagg agcaacagcg | 300 |
| gtcgcctata caaaatcag ctgggacccg aaatatcagg tcatcaacaa cctggactat | 360 |
| gaagtcacac agtttcttca gaaagacagc tttaaaccgg atgatctggt catcctttgg | 420 |
| gtcggcgcca atgattatct ggcgtatggc tggaacacag aacaagatgc caaaagagtc | 480 |
| agagatgcca tcagcgatgc cgctaataga atggtcctga acggcgccaa acaaatcctg | 540 |
| ctgtttaacc tgccggatct gggacaaaat ccgagcgcca aagccaaaa agtcgtcgaa | 600 |
| gcagtcagcc atgtcagcgc ctatcataac aaactgctgc tgaacctggc aagacaattg | 660 |
| gcaccgacgg gaatggttaa attgtttgaa attgacaaac agtttgccga atgctgaga | 720 |
| gatccgcaaa attttggcct gagcgatgtc gaaaacccgt gctatgatgg cggatatgtc | 780 |
| tggaaaccgt ttgccacaag aagcgtcagc acggatagac aactgtcagc gtttagcccg | 840 |
| caagaaagac tggcaatcgc cggaaatccg cttttggcac aagcagttgc ttcaccgatg | 900 |
| gcaagaagat cagcaagccc gctgaattgc gaaggcaaaa tgttttggga tcaggtccat | 960 |
| ccgacaacag ttgtccatgc tgcccttca gaaagagcgg cgacgtttat cgaaacacag | 1020 |
| tatgaatttc tggcccatgg ctga | 1044 |

<210> SEQ ID NO 50
<211> LENGTH: 1005
<212> TYPE: DNA
<213> ORGANISM: Aeromonas hydrophila

<400> SEQUENCE: 50

| | | |
|---|---|---|
| atgaaaaaat ggtttgtgtg tttattggga ttggtcgcgc tgacagttca ggcagccgac | 60 |
| agccgtcccg ccttctcccg gatcgtgatg tttggcgaca gcctctccga taccggcaag | 120 |
| atgtacagca gatgcgcgg ttacctcccc tccagccccc cctactatga gggccgcttc | 180 |
| tccaacgggc ccgtctggct ggagcagctg accaacgagt tcccgggcct gaccatagcc | 240 |
| aacgaggcgg aaggcggacc gaccgccgtg gcttacaaca gatctcctg gaatcccaag | 300 |
| tatcaggtca tcaacaacct ggactacgag gtcacccagt tcctgcaaaa agacagcttc | 360 |
| aagccggacg atctggtgat cctctgggtc ggcgccaacg actatctggc ctatggctgg | 420 |
| aacacagagc aggatgccaa gcgggtgcgc gacgccatca gcgatgcggc caaccgcatg | 480 |
| gtgctgaacg cgccaaggga gatactgctg ttcaacctgc cggatctggg ccagaaccccc | 540 |
| tcggcccgca gccagaaggt ggtcgaggcg ccagccatg tctccgccta ccacaaccag | 600 |
| ctgctgctga acctggcacg ccagctggct cccaccggca tggtgaagct gttcgagatc | 660 |
| gacaagcagt ttgccgagat gctgcgtgat ccgcagaact tcggcctgag cgaccagagg | 720 |
| aacgcctgct acggtggcag ctatgtatgg aagccgtttg cctcccgcag cgccagcacc | 780 |

| | |
|---|---|
| gacagccagc tctccgcctt caacccgcag gagcgcctcg ccatcgccgg caacccgctg | 840 |
| ctggcccagg ccgtcgccag ccccatggct gcccgcagcg ccagcaccct caactgtgag | 900 |
| ggcaagatgt tctgggatca ggtccacccc accactgtcg tgcacgccgc cctgagcgag | 960 |
| cccgccgcca ccttcatcga gagccagtac gagttcctcg cccac | 1005 |

<210> SEQ ID NO 51
<211> LENGTH: 1011
<212> TYPE: DNA
<213> ORGANISM: Aeromonas salmonicida

<400> SEQUENCE: 51

| | |
|---|---|
| atgaaaaaat ggtttgtttg tttattgggg ttgatcgcgc tgacagttca ggcagccgac | 60 |
| actcgccccg ccttctcccg gatcgtgatg ttcggcgaca gcctctccga taccggcaaa | 120 |
| atgtacagca agatgcgcgg ttacctcccc tccagcccgc cctactatga gggccgtttc | 180 |
| tccaacggac ccgtctggct ggagcagctg accaagcagt tcccgggtct gaccatcgcc | 240 |
| aacgaagcgg aaggcggtgc cactgccgtg gcttacaaca agatctcctg gaatcccaag | 300 |
| tatcaggtct acaacaacct ggactacgag gtcaccccagt tcttgcagaa agacagcttc | 360 |
| aagccggacg atctggtgat cctctgggtc ggtgccaatg actatctggc atatggctgg | 420 |
| aatacggagc aggatgccaa gcgagttcgc gatgccatca gcgatgcggc caaccgcatg | 480 |
| gtactgaacg tgccaagca gatactgctg ttcaacctgc cggatctggg ccagaacccg | 540 |
| tcagcccgca gtcagaaggt ggtcgaggcg gtcagccatg tctccgccta tcacaacaag | 600 |
| ctgctgctga acctggcacg ccagctgcc cccaccggca tggtaaagct gttcgagatc | 660 |
| gacaagcaat tgccgagat gctgcgtgat ccgcagaact tcggcctgag cgacgtcgag | 720 |
| aaccctgct acgacggcgg ctatgtgtgg aagccgtttg ccacccgcag cgtcagcacc | 780 |
| gaccgccagc tctccgcctt cagtccgcag gaacgcctcg ccatcgccgg caacccgctg | 840 |
| ctggcacagg ccgttgccag tcctatggcc cgccgcagcg ccagcccct caactgtgag | 900 |
| ggcaagatgt tctgggatca ggtacacccg accactgtcg tgcacgcagc cctgagcgag | 960 |
| cgcgccgcca ccttcatcga gacccagtac gagttcctcg cccacggatg a | 1011 |

<210> SEQ ID NO 52
<211> LENGTH: 888
<212> TYPE: DNA
<213> ORGANISM: Streptomyces coelicolor

<400> SEQUENCE: 52

| | |
|---|---|
| atgccgaagc ctgcccttcg ccgtgtcatg accgcgacag tcgccgccgt cggcacgctc | 60 |
| gccctcggcc tcaccgacgc caccgcccac gccgcgcccg cccaggccac tccgaccctg | 120 |
| gactacgtcg ccctcggcga cagctacagc gccggctccg gcgtcctgcc cgtcgacccc | 180 |
| gccaacctgc tctgtctgcg ctcgacggcc aactaccccc acgtcatcgc ggacacgacg | 240 |
| ggcgcccgcc tcacggacgt cacctgcggc gccgcgcaga ccgccgactt cacgcgggcc | 300 |
| cagtacccgg gcgtcgcacc ccagttggac gcgctcggca ccggcacgga cctggtcacg | 360 |
| ctcaccatcg gcggcaacga caacagcacc ttcatcaacg ccatcacggc ctgcggcacg | 420 |
| gcgggtgtcc tcagcggcgg caagggcagc ccctgcaagg acaggcacgg cacctccttc | 480 |
| gacgacgaga tcgaggccaa cacgtacccc gcgctcaagg aggcgctgct cggcgtccgc | 540 |
| gccagggctc cccacgccag ggtggcggct ctcggctacc cgtggatcac cccggccacc | 600 |
| gccgacccgt cctgcttcct gaagctcccc ctcgccgccg gtgacgtgcc ctacctgcgg | 660 |

```
gccatccagg cacacctcaa cgacgcggtc cggcgggccg ccgaggagac cggagccacc    720
tacgtggact tctccggggt gtccgacggc acgacgcct gcgaggcccc cggcacccgc    780
tggatcgaac cgctgctctt cgggcacagc ctcgttcccg tccaccccaa cgccctgggc    840
gagcggcgca tggccgagca cacgatggac gtcctcggcc tggactga                888

<210> SEQ ID NO 53
<211> LENGTH: 888
<212> TYPE: DNA
<213> ORGANISM: Streptomyces coelicolor

<400> SEQUENCE: 53
tcagtccagg ccgaggacgt ccatcgtgtg ctcggccatg cgccgctcgc ccagggcgtt     60
ggggtggacg ggaacgaggc tgtgcccgaa gagcagcggt tcgatccagc gggtgccggg    120
ggcctcgcag gcgtcgtggc cgtcggacac cccggagaag tccacgtagg tggctccggt    180
ctcctcggcg gcccgccgga ccgcgtcgtt gaggtgtgcc tggatggccc gcaggtaggg    240
cacgtcaccg gcggcgaggg ggagcttcag gaagcaggac gggtcggcgg tggccggggt    300
gatccacggg tagccgagag ccgccaccct ggcgtgggga gccctggcgc ggacgccgag    360
cagcgcctcc ttgagcgcgg ggtacgtgtt ggcctcgatc tcgtcgtcga aggaggtgcc    420
gtgcctgtcc ttgcagggg ctgcccttgcc gccgctgagg acaccgccg tgccgcaggc    480 cgtgatggcg ttgatgaagg tgctgttgtc gttgccgccg atggtgagcg tgaccaggtc    540
cgtgccggtg ccgagcgcgt ccaactgggg tgcgacgccc gggtactggg cccgcgtgaa    600
gtcggcggtc tgcgcggcgc cgcaggtgac gtccgtgagg cgggcgcccg tcgtgtccgc    660
gatgacgtgg gggtagttgg ccgtcgagcg cagacagagc aggttggcgg ggtcgacggg    720
caggacgccg gagccggcgc tgtagctgtc gccgagggcg acgtagtcca gggtcggagt    780
ggcctgggcg ggcgcggcgt gggcggtggc gtcggtgagg ccgagggcga gcgtgccgac    840
ggcggcgact gtcgcggtca tgacacggcg aagggcaggc ttcggcat                888

<210> SEQ ID NO 54
<211> LENGTH: 717
<212> TYPE: DNA
<213> ORGANISM: Saccharomyces cerevisiae

<400> SEQUENCE: 54
atggattacg agaagtttct gttatttggg gattccatta ctgaatttgc ttttaatact     60
aggcccattg aagatggcaa agatcagtat gctcttggag ccgcattagt caacgaatat    120
acgagaaaaa tggatattct tcaaagaggg ttcaaagggt acacttctag atgggcgttg    180
aaaatacttc ctgagatttt aaagcatgaa tccaatattg tcatggccac aatattttg    240 ggtgccaacg atgcatgctc agcaggtccc caaagtgtcc ccctccccga atttatcgat    300
aatattcgtc aaatggtatc tttgatgaag tcttaccata tccgtcctat tataatagga    360
ccggggctag tagatagaga gaagtgggaa aaagaaaaat ctgaagaaat agctctcgga    420
tacttccgta ccaacgagaa cttttgccatt tattccgatg ccttagcaaa actagccaat    480
gaggaaaaag ttcccttcgt ggctttgaat aaggcgtttc aacaggaagg tggtgatgct    540
tggcaacaac tgctaacaga tggactgcac ttttccggaa aagggtacaa aattttttcat    600 gacgaattat tgaaggtcat tgagacattc taccccccaa atcatcccaa aaacatgcag    660
tacaaactga agattggag agatgtgcta gatgatggat ctaacataat gtcttga       717
```

<210> SEQ ID NO 55
<211> LENGTH: 1044
<212> TYPE: DNA
<213> ORGANISM: Ralstonia sp.

<400> SEQUENCE: 55

```
atgaacctgc gtcaatggat gggcgccgcc acggctgccc ttgccttggg cttggccgcg      60
tgcgggggcg gtgggaccga ccagagcggc aatcccaatg tcgccaaggt gcagcgcatg     120
gtggtgttcg gcgacagcct gagcgatatc ggcacctaca cccccgtcgc gcaggcggtg     180
ggcggcggca agttcaccac caaccccggg ccgatctggg ccgagaccgt ggccgcgcaa     240
ctgggcgtga cgctcacgcc ggcggtgatg ggctacgcca cctccgtgca gaattgcccc     300
aaggccggct gcttcgacta tgcgcagggc ggctcgcgcg tgaccgatcc gaacggcatc     360
ggccacaacg gcgcgcgggg gcgctgacc tacccggttc agcagcagct cgccaacttc     420
tacgcggcca gcaacaacac attcaacggc aataacgatg tcgtcttcgt gctggccggc     480
agcaacgaca ttttcttctg gaccactgcg gcggccacca cgcgcctccgg cgtgacgccc     540
gccattgcca cggcccaggt gcagcaggcc gcgacggacc tggtcggcta tgtcaaggac     600
atgatcgcca agggtgcgac gcaggtctac gtgttcaacc tgcccgacag cagcctgacg     660
ccggacggcg tggcaagcgg cacgaccggc caggcgctgc tgcacgcgct ggtgggcacg     720
ttcaacacga cgctgcaaag cgggctggcc ggcacctcgg cgcgcatcat cgacttcaac     780
gcacaactga ccgcggcgat ccagaatggc gcctcgttcg gcttcgccaa caccagcgcc     840
cgggcctgcg acgccaccaa gatcaatgcc ctggtgccga cgccggcgg cagctcgctg     900
ttctgctcgg ccaacacgct ggtggcttcc ggtgcggacc agagctacct gttcgccgac     960
ggcgtgcacc cgaccacggc cggccatcgc ctgatcgcca gcaacgtgct ggcgcgcctg    1020
ctggcggata acgtcgcgca ctga                                            1044
```

<210> SEQ ID NO 56
<211> LENGTH: 786
<212> TYPE: DNA
<213> ORGANISM: Streptomyces coelicolor

<400> SEQUENCE: 56

```
gtgatcgggt cgtacgtggc ggtgggggac agcttcaccg agggcgtcgg cgaccccggc      60
cccgacgggg cgttcgtcgg ctgggccgac cggctcgccg tactgctcgc ggaccggcgc     120
cccgagggcg acttcacgta cacgaacctc gccgtgcgcg caggctcct cgaccagatc     180
gtggcggaac aggtcccgcg ggtcgtcgga ctcgcgcccg acctcgtctc gttcgcggcg     240
ggcggcaacg acatcatccg gcccggcacc gatcccgacg aggtcgccga gcggttcgag     300
ctggcggtgg ccgcgctgac cgccgcggcc ggaaccgtcc tggtgaccac cgggttcgac     360
acccgggggg tgcccgtcct caagcacctg cgcggcaaga tcgccacgta caacgggcac     420
gtccgcgcca tcgccgaccg ctacggctgc ccggtgctcg acctgtggtc gctgcggagc     480
gtccaggacc gcagggcgtg ggacgccgac cggctgcacc tgtcgccgga ggggcacacc     540
cgggtggcgc tgcgcgcggg gcaggccctg gcctgcgcg tccggccga ccctgaccag     600
ccctggccgc cctgccgcc gcgcggcacg ctcgacgtcc ggcgcgacga cgtgcactgg     660
gcgcgcgagt acctggtgcc gtggatcggg cgccggctgc ggggcgagtc gtcgggcgac     720
cacgtgacgg ccaaggggac gctgtcgccg gacgccatca gacgcggat cgccgcggtg     780
gcctga                                                                786
```

<210> SEQ ID NO 57
<211> LENGTH: 783
<212> TYPE: DNA
<213> ORGANISM: Streptomyces coelicolor

<400> SEQUENCE: 57

| | | | | | |
|---|---|---|---|---|---|
| atgcagacga | accccgcgta | caccagtctc | gtcgccgtcg | gcgactcctt | caccgagggc | 60 |
| atgtcggacc | tgctgcccga | cggctcctac | cgtggctggg | ccgacctcct | cgccacccgg | 120 |
| atggcggccc | gctccccggg | cttccggtac | gccaacctgg | cggtgcgcgg | aagctgatc | 180 |
| ggacagatcg | tcgacgagca | ggtggacgtg | ccgccgcca | tgggagccga | cgtgatcacg | 240 |
| ctggtcggcg | ggctcaacga | cacgctgcgg | cccaagtgcg | acatggcccg | ggtgcgggac | 300 |
| ctgctgaccc | aggccgtgga | acggctcgcc | ccgcactgcg | agcagctggt | gctgatgcgc | 360 |
| agtcccggtc | gccagggtcc | ggtgctggag | cgcttccggc | cccgcatgga | ggccctgttc | 420 |
| gccgtgatcg | acgacctggc | cgggcggcac | ggcgccgtgg | tcgtcgacct | gtacggggcc | 480 |
| cagtcgctgg | ccgaccctcg | gatgtgggac | gtggaccggc | tgcacctgac | cgccgagggc | 540 |
| caccgccggg | tcgcggaggc | ggtgtggcag | tcgctcggcc | acgagcccga | ggaccccgag | 600 |
| tggcacgcgc | cgatcccggc | gacgccgccg | ccggggtggg | tgacgcgcag | gaccgcggac | 660 |
| gtccggttcg | cccggcagca | cctgctgccc | tggataggcc | gcaggctgac | cgggcgctcg | 720 |
| tccggggacg | gcctgccggc | caagcgcccg | gacctgctgc | cctacgagga | ccccgcacgg | 780 |
| tga | | | | | | 783 |

<210> SEQ ID NO 58
<211> LENGTH: 1365
<212> TYPE: DNA
<213> ORGANISM: Streptomyces coelicolor

<400> SEQUENCE: 58

| | | | | | |
|---|---|---|---|---|---|
| atgacccggg | gtcgtgacgg | gggtgcgggg | gcgccccca | ccaagcaccg | tgccctgctc | 60 |
| gcggcgatcg | tcaccctgat | agtggcgatc | tccgcggcca | tatacgccgg | agcgtccgcg | 120 |
| gacgacggca | gcagggacca | cgcgctgcag | gccgaggcc | gtctcccacg | aggagacgcc | 180 |
| gcccccgcgt | ccaccggtgc | ctgggtgggc | gcctgggcca | ccgcaccggc | cgcggccgag | 240 |
| ccgggcaccg | agacgaccgg | cctggcgggc | cgctccgtgc | gcaacgtcgt | gcacacctcg | 300 |
| gtcggcggca | ccggcgcgcg | gatcaccctc | tcgaacctgt | acgggcagtc | gccgctgacc | 360 |
| gtcacacacg | cctcgatcgc | cctggccgcc | gggcccgaca | ccgccgccgc | gatcgccgac | 420 |
| accatgcgcc | ggctcacctt | cggcggcagc | gcccgggtga | tcatcccggc | gggcggccag | 480 |
| gtgatgagcg | acaccgcccg | cctcgccatc | ccctacgggg | cgaacgtcct | ggtcaccacg | 540 |
| tactcccca | tcccgtccgg | gccggtgacc | taccatccgc | aggcccggca | gaccagctac | 600 |
| ctggccgacg | cgaccgcac | ggcggacgtc | ccgccgtcg | cgtacaccac | ccccacgccc | 660 |
| tactggcgct | acctgaccgc | cctcgacgtg | ctgagccacg | aggccgacgg | cacggtcgtg | 720 |
| gcgttcggcg | actccatcac | cgacggcgcc | cgctcgcaga | gcgacgccaa | ccaccgctgg | 780 |
| accgacgtcc | tcgccgcacg | cctgcacgag | gcggcgggca | acggcgggga | cacgcccgc | 840 |
| tacagcgtcg | tcaacgaggg | catcagcggc | aaccggctcc | tgaccagcag | gccggggcgg | 900 |
| ccggccgaca | acccgagcgg | actgagccgg | ttccagcggg | acgtgctgga | acgcaccaac | 960 |
| gtcaaggccg | tcgtcgtcgt | cctcggcgtc | aacgacgtcc | tgaacagccc | ggaactcgcc | 1020 |

| | |
|---|---:|
| gaccgcgacg ccatcctgac cggcctgcgc accctcgtcg accgggcgca cgcccgggga | 1080 |
| ctgcgggtcg tcggcgccac gatcacgccg ttcggcggct acggcggcta caccgaggcc | 1140 |
| cgcgagacga tgcggcagga ggtcaacgag gagatccgct ccggccgggt cttcgacacg | 1200 |
| gtcgtcgact tcgacaaggc cctgcgcgac ccgtacgacc cgcgccggat gcgctccgac | 1260 |
| tacgacagcg gcgaccacct gcaccccggc gacaaggggt acgcgcgcat gggcgcggtc | 1320 |
| atcgacctgg ccgcgctgaa gggcgcggcg ccggtcaagg cgtag | 1365 |

<210> SEQ ID NO 59
<211> LENGTH: 1023
<212> TYPE: DNA
<213> ORGANISM: Streptomyces coelicolor

<400> SEQUENCE: 59

| | |
|---|---:|
| atgacgagca tgtcgagggc gagggtggcg cggcggatcg cggccggcgc ggcgtacggc | 60 |
| ggcggcggca tcggcctggc gggagcggcg gcggtcggtc tggtggtggc cgaggtgcag | 120 |
| ctggccagac gcagggtggg ggtgggcacg ccgacccggg tgccgaacgc gcagggactg | 180 |
| tacggcggca ccctgcccac ggccggcgac ccgccgctgc ggctgatgat gctgggcgac | 240 |
| tccacggccg ccgggcaggg cgtgcaccgg gccgggcaga cgccgggcgc gctgctggcg | 300 |
| tccgggctcg cggcggtggc ggagcggccg gtgcggctgg ggtcggtcgc ccagccgggg | 360 |
| gcgtgctcgg acgacctgga ccggcaggtg gcgctggtgc tcgccgagcc ggaccgggtg | 420 |
| cccgacatct gcgtgatcat ggtcggcgcc aacgacgtca cccaccggat gccggcgacc | 480 |
| cgctcggtgc ggcacctgtc ctcggcggta cggcggctgc gcacggccgg tgcggaggtg | 540 |
| gtggtcggca cctgtccgga cctgggcacg atcgagcggg tgcggcagcc gctgcgctgg | 600 |
| ctggcccggc gggcctcacg gcagctgcgc gcggcacaga ccatcggcgc cgtcgagcag | 660 |
| ggcgggcgca cggtgtcgct gggcgacctg ctgggtccgg agttcgcgca gaacccgcgg | 720 |
| gagctcttcg ccccgacaa ctaccacccc tccgccgagg ggtacgccac ggccgcgatg | 780 |
| gcggtactgc cctcggtgtg cgccgcgctc ggcctgtggc cggccgacga ggagcacccg | 840 |
| gacgcgctgc gccgcgaggg cttcctgccg gtggcgcgcg cggcggcgga gcggcgtcc | 900 |
| gaggcgggta cggaggtcgc cgccgccatg cctacggggc ctcgggggcc ctgggcgctg | 960 |
| ctgaagcgcc ggagacggcg tcgggtgtcg gaggcggaac cgtccagccc gtccggcgtt | 1020 |
| tga | 1023 |

<210> SEQ ID NO 60
<211> LENGTH: 918
<212> TYPE: DNA
<213> ORGANISM: Streptomyces coelicolor

<400> SEQUENCE: 60

| | |
|---|---:|
| atgggtcgag ggacggacca gcggacgcgc tacggccgtc gccgggcgcg tgtcgcgctc | 60 |
| gccgccctga ccgccgccgt cctgggcgtg ggcgtggcgg gctgcgactc cgtgggcggc | 120 |
| gactcacccg ctccttccgg cagcccgtcg aagcggacga ggacggcgcc cgcctgggac | 180 |
| accagcccgg cgtccgtcgc cgccgtggcc gactccatca cgcgcggctt cgacgccgt | 240 |
| gcggtgctgt cggactgccc ggaggtgtcg tgggcgaccg gcagcagcgc gaaggtcgac | 300 |
| tcgctggccg tacggctgct ggggaaggcg gacgcggccg agcacagctg gaactacgcg | 360 |
| gtcaccgggg cccggatggc ggacctgacc gctcaggtga cgcggcggc gcagcgcgag | 420 |
| ccggagctgg tggcggtgat ggccggggcg aacgacgcgt gccggtccac gacctcggcg | 480 |

```
atgacgccgg tggcggactt ccgggcgcag ttcgaggagg cgatggccac cctgcgcaag      540
aagctcccca aggcgcaggt gtacgtgtcg agcatcccgg acctcaagcg gctctggtcc      600
cagggccgca ccaacccgct gggcaagcag gtgtggaagc tcggcctgtg cccgtcgatg      660
ctgggcgacg cggactccct ggactcggcg gcgaccctgc ggcgcaacac ggtgcgcgac      720
cgggtggcgg actacaacga ggtgctgcgg gaggtctgcg cgaaggaccg gcggtgccgc      780
agcgacgacg cgcgggtgca cgagttccgg ttcggcacgg accagttgag ccactgggac      840
tggttccacc cgagtgtgga cggccaggcc cggctggcgg agatcgccta ccgcgcggtc      900
accgcgaaga atccctga                                                    918
```

```
<210> SEQ ID NO 61
<211> LENGTH: 1068
<212> TYPE: DNA
<213> ORGANISM: Streptomyces rimosus

<400> SEQUENCE: 61
ttcatcacaa cgatgtcaca acaccggcca tccgggtcat ccctgatcgt gggaatgggt      60
gacaagcctt cccgtgacga aagggtcctg ctacatcaga aatgacagaa atcctgctca      120
gggaggttcc atgagactgt cccgacgcgc ggccacggcg tccgcgctcc tcctcacccc      180
ggcgctcgcg ctcttcggcg cgagcgccgc cgtgtccgcg ccgcgaatcc aggccaccga      240
ctacgtggcc ctcggcgact cctactcctc gggggtcggc gcgggcagct acgacagcag      300
cagtggctcc tgtaagcgca gcaccaagtc ctacccggcc ctgtgggccg cctcgcacac      360
cggtacgcgg ttcaacttca ccgcctgttc gggcgcccgc acaggagacg tgctggccaa      420
gcagctgacc ccggtcaact ccggcaccga cctggtcagc attaccatcg gcggcaacga      480
cgcgggcttc gccgacacca tgaccacctg caacctccag ggcgagagcg cgtgcctggc      540
gcggatcgcc aaggcgcgcg cctacatcca gcagacgctg cccgcccagc tggaccaggt      600
ctacgacgcc atcgacagcc gggcccccgc agcccaggtc gtcgtcctgg gctacccgcg      660
cttctacaag ctgggcggca gctgcgccgt cggtctctcg gagaagtccc gcgcggccat      720
caacgccgcc gccgacgaca tcaacgccgt caccgccaag cgcgccgccg accacggctt      780
cgccttcggg gacgtcaaca cgaccttcgc cgggcacgag ctgtgctccg gcgcccctg      840 gctgcacagc gtcaccctct ccgtggagaa ctcctaccac cccacggcca acggacagtc      900
caagggctac ctgcccgtcc tgaactccgc cacctgatct cgcggctact ccgcccctga      960
cgaagtcccg cccccgggcg gggcttcgcc gtaggtgcgc gtaccgccgt cgcccgtcgc      1020
gccggtggcc ccgccgtacg tgccgccgcc cccggacgcg gtcggttc                  1068
```

```
<210> SEQ ID NO 62
<211> LENGTH: 1008
<212> TYPE: DNA
<213> ORGANISM: Aeromonas hydrophila

<400> SEQUENCE: 62
atgaaaaaat ggtttgtgtg tttattggga ttggtcgcgc tgacagttca ggcagccgac      60
agtcgccccg ccttttcccg gatcgtgatg ttcggcgaca gcctctccga taccggcaaa      120
atgtacagca agatgcgcgg ttacctcccc tccagcccgc cctactatga gggccgtttc      180
tccaacggac ccgtctggct ggagcagctg accaaaacagt tcccgggtct gaccatcgcc      240
aacgaagcgg aaggcggtgc cactgccgtg gcttacaaca agatctcctg gaatcccaag      300
```

| | |
|---|---|
| tatcaggtca tcaacaacct ggactacgag gtcacccagt tcttgcagaa agacagcttc | 360 |
| aagccggacg atctggtgat cctctgggtc ggtgccaatg actatctggc ctatggctgg | 420 |
| aacacggagc aggatgccaa gcgggttcgc gatgccatca gcgatgcggc caaccgcatg | 480 |
| gtactgaacg gtgccaagca gatactgctg ttcaacctgc cggatctggg ccagaacccg | 540 |
| tcagctcgca gtcagaaggt ggtcgaggcg gtcagccatg tctccgccta tcacaaccag | 600 |
| ctgctgctga acctggcacg ccagctgccc ccaccggca tggtaaagct gttcgagatc | 660 |
| gacaagcaat tgccgagat gctgcgtgat ccgcagaact tcggcctgag cgacgtcgag | 720 |
| aaccctgct acgacggcgg ctatgtgtgg aagccgtttg ccaccgcag cgtcagcacc | 780 |
| gaccgccagc tctccgcctt cagtccgcag gaacgcctcg ccatcgccgg caacccgctg | 840 |
| ctggcacagg ccgttgccag tcctatggcc cgccgcagcg ccagccccct caactgtgag | 900 |
| ggcaagatgt tctgggatca ggtacacccg accactgtcg tgcacgcagc cctgagcgag | 960 |
| cgcgccgcca ccttcatcgc gaaccagtac gagttcctcg cccactga | 1008 |

<210> SEQ ID NO 63
<211> LENGTH: 1011
<212> TYPE: DNA
<213> ORGANISM: Aeromonas salmonicida

<400> SEQUENCE: 63

| | |
|---|---|
| atgaaaaaat ggtttgtttg tttattgggg ttgatcgcgc tgacagttca ggcagccgac | 60 |
| actcgccccg ccttctcccg gatcgtgatg ttcggcgaca gcctctccga taccggcaaa | 120 |
| atgtacagca agatgcgcgg ttacctcccc tccagcccgc cctactatga gggccgtttc | 180 |
| tccaacggac ccgtctggct ggagcagctg accaagcagt tcccgggtct gaccatcgcc | 240 |
| aacgaagcg aaggcggtgc cactgccgtg gcttacaaca agatctcctg gaatcccaag | 300 |
| tatcaggtca tcaacaacct ggactacgag gtcacccagt tcttgcagaa agacagcttc | 360 |
| aagccggacg atctggtgat cctctgggtc ggtgccaatg actatctggc atatggctgg | 420 |
| aatacggagc aggatgccaa gcgagttcgc gatgccatca gcgatgcggc caaccgcatg | 480 |
| gtactgaacg gtgccaagca gatactgctg ttcaacctgc cggatctggg ccagaacccg | 540 |
| tcagcccgca gtcagaaggt ggtcgaggcg gtcagccatg tctccgccta tcacaacaag | 600 |
| ctgctgctga acctggcacg ccagctgccc ccaccggca tggtaaagct gttcgagatc | 660 |
| gacaagcaat tgccgagat gctgcgtgat ccgcagaact tcggcctgag cgacgtcgag | 720 |
| aaccctgct acgacggcgg ctatgtgtgg aagccgtttg ccaccgcag cgtcagcacc | 780 |
| gaccgccagc tctccgcctt cagtccgcag gaacgcctcg ccatcgccgg caacccgctg | 840 |
| ctggcacagg ccgttgccag tcctatggcc cgccgcagcg ccagccccct caactgtgag | 900 |
| ggcaagatgt tctgggatca ggtacacccg accactgtcg tgcacgcagc cctgagcgag | 960 |
| cgcgccgcca ccttcatcga gacccagtac gagttcctcg cccacggatg a | 1011 |

<210> SEQ ID NO 64
<211> LENGTH: 51
<212> TYPE: DNA
<213> ORGANISM: Artificial
<220> FEATURE:
<223> OTHER INFORMATION: Terminator sequence

<400> SEQUENCE: 64

| | |
|---|---|
| cgggacttac cgaaagaaac catcaatgat ggtttctttt tgttcataa a | 51 |

```
<210> SEQ ID NO 65
<211> LENGTH: 59
<212> TYPE: DNA
<213> ORGANISM: Artificial
<220> FEATURE:
<223> OTHER INFORMATION: Terminator sequence

<400> SEQUENCE: 65
caagactaaa gaccgttcgc ccgttttttgc aataagcggg cgaatcttac ataaaaata        59

<210> SEQ ID NO 66
<211> LENGTH: 61
<212> TYPE: DNA
<213> ORGANISM: Artificial
<220> FEATURE:
<223> OTHER INFORMATION: Terminator sequence

<400> SEQUENCE: 66
acggccgtta gatgtgacag cccgttccaa aaggaagcgg gctgtcttcg tgtattattg        60
t                                                                       61

<210> SEQ ID NO 67
<211> LENGTH: 54
<212> TYPE: DNA
<213> ORGANISM: Artificial
<220> FEATURE:
<223> OTHER INFORMATION: Terminator sequence

<400> SEQUENCE: 67
tcttttaaag gaaaggctgg aatgcccggc attccagcca catgatcatc gttt              54

<210> SEQ ID NO 68
<211> LENGTH: 280
<212> TYPE: PRT
<213> ORGANISM: Aeromonas salmonicida

<400> SEQUENCE: 68
```

Ala Asp Thr Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
            20                  25                  30

Ser Ser Pro Pro Tyr Tyr Glu Gly Arg Phe Ser Asn Gly Pro Val Trp
        35                  40                  45

Leu Glu Gln Leu Thr Lys Gln Phe Pro Gly Leu Thr Ile Ala Asn Glu
    50                  55                  60

Ala Glu Gly Gly Ala Thr Ala Val Ala Tyr Asn Lys Ile Ser Trp Asp
65                  70                  75                  80

Pro Lys Tyr Gln Val Ile Asn Asn Leu Asp Tyr Glu Val Thr Gln Phe
                85                  90                  95

Leu Gln Lys Asp Ser Phe Lys Pro Asp Asp Leu Val Ile Leu Trp Val
            100                 105                 110

Gly Ala Asn Asp Tyr Leu Ala Tyr Gly Trp Asn Thr Glu Gln Asp Ala
        115                 120                 125

Lys Arg Val Arg Asp Ala Ile Ser Asp Ala Ala Asn Arg Met Val Leu
    130                 135                 140

Asn Gly Ala Lys Gln Ile Leu Leu Phe Asn Leu Pro Asp Leu Gly Gln
145                 150                 155                 160

Asn Pro Ser Ala Arg Ser Gln Lys Val Val Glu Ala Val Ser His Val
                165                 170                 175

Ser Ala Tyr His Asn Lys Leu Leu Leu Asn Leu Ala Arg Gln Leu Ala

```
                    180                 185                 190
Pro Thr Gly Met Val Lys Leu Phe Glu Ile Asp Lys Gln Phe Ala Glu
            195                 200                 205
Met Leu Arg Asp Pro Gln Asn Phe Gly Leu Ser Asp Val Glu Asn Pro
        210                 215                 220
Cys Tyr Asp Gly Gly Tyr Val Trp Lys Pro Phe Arg Ser Ala Ser Pro
225                 230                 235                 240
Leu Asn Cys Glu Gly Lys Met Phe Trp Asp Gln Val His Pro Thr Thr
                245                 250                 255
Val Val His Ala Ala Leu Ser Glu Arg Ala Thr Phe Ile Glu Thr
            260                 265                 270
Gln Tyr Glu Phe Leu Ala His Gly
        275                 280

<210> SEQ ID NO 69
<211> LENGTH: 102
<212> TYPE: DNA
<213> ORGANISM: Artificial
<220> FEATURE:
<223> OTHER INFORMATION: Oligonucleotide primer

<400> SEQUENCE: 69
ccccgctcga ggcttttctt ttggaagaaa atatagggaa aatggtactt gttaaaaatt      60
cggaatattt atacaatatc atatgtttca cattgaaagg gg                        102

<210> SEQ ID NO 70
<211> LENGTH: 35
<212> TYPE: DNA
<213> ORGANISM: Artificial
<220> FEATURE:
<223> OTHER INFORMATION: Oligonucleotide primer

<400> SEQUENCE: 70
tggaatctcg aggtttttatc ctttaccttg tctcc                               35

<210> SEQ ID NO 71
<211> LENGTH: 8
<212> TYPE: PRT
<213> ORGANISM: Artificial
<220> FEATURE:
<223> OTHER INFORMATION: Consensus sequence

<400> SEQUENCE: 71

Met Arg Arg Ser Arg Phe Leu Ala
1               5

<210> SEQ ID NO 72
<211> LENGTH: 8
<212> TYPE: PRT
<213> ORGANISM: Artificial
<220> FEATURE:
<223> OTHER INFORMATION: Consensus sequence

<400> SEQUENCE: 72

Ala Leu Ile Leu Leu Thr Leu Ala
1               5

<210> SEQ ID NO 73
<211> LENGTH: 5
<212> TYPE: PRT
<213> ORGANISM: Artificial
<220> FEATURE:
<223> OTHER INFORMATION: Consensus sequence
```

```
<400> SEQUENCE: 73

Ala Arg Ala Ala Pro
1               5

<210> SEQ ID NO 74
<211> LENGTH: 11
<212> TYPE: PRT
<213> ORGANISM: Artificial
<220> FEATURE:
<223> OTHER INFORMATION: Consensus sequence

<400> SEQUENCE: 74

Tyr Val Ala Leu Gly Asp Ser Tyr Ser Ser Gly
1               5                   10

<210> SEQ ID NO 75
<211> LENGTH: 5
<212> TYPE: PRT
<213> ORGANISM: Artificial
<220> FEATURE:
<223> OTHER INFORMATION: Consensus sequence

<400> SEQUENCE: 75

Gly Ala Gly Ser Tyr
1               5

<210> SEQ ID NO 76
<211> LENGTH: 4
<212> TYPE: PRT
<213> ORGANISM: Artificial
<220> FEATURE:
<223> OTHER INFORMATION: Consensus sequence

<400> SEQUENCE: 76

Ser Ser Gly Asp
1

<210> SEQ ID NO 77
<211> LENGTH: 15
<212> TYPE: PRT
<213> ORGANISM: Artificial
<220> FEATURE:
<223> OTHER INFORMATION: Consensus sequence

<400> SEQUENCE: 77

Arg Ser Thr Lys Ala Tyr Pro Ala Leu Trp Ala Ala Ala His Ala
1               5                   10                  15

<210> SEQ ID NO 78
<211> LENGTH: 5
<212> TYPE: PRT
<213> ORGANISM: Artificial
<220> FEATURE:
<223> OTHER INFORMATION: Consensus sequence

<400> SEQUENCE: 78

Ser Ser Phe Ser Phe
1               5

<210> SEQ ID NO 79
<211> LENGTH: 12
<212> TYPE: PRT
<213> ORGANISM: Artificial
<220> FEATURE:
<223> OTHER INFORMATION: Consensus sequence
```

```
<400> SEQUENCE: 79

Ala Cys Ser Gly Ala Arg Thr Tyr Asp Val Leu Ala
1               5                   10

<210> SEQ ID NO 80
<211> LENGTH: 15
<212> TYPE: PRT
<213> ORGANISM: Artificial
<220> FEATURE:
<223> OTHER INFORMATION: Consensus sequence

<400> SEQUENCE: 80

Leu Val Ser Ile Thr Ile Gly Gly Asn Asp Ala Gly Phe Ala Asp
1               5                   10                  15

<210> SEQ ID NO 81
<211> LENGTH: 6
<212> TYPE: PRT
<213> ORGANISM: Artificial
<220> FEATURE:
<223> OTHER INFORMATION: Consensus sequence

<400> SEQUENCE: 81

Met Thr Thr Cys Val Leu
1               5

<210> SEQ ID NO 82
<211> LENGTH: 6
<212> TYPE: PRT
<213> ORGANISM: Artificial
<220> FEATURE:
<223> OTHER INFORMATION: Consensus sequence

<400> SEQUENCE: 82

Ser Asp Ser Ala Cys Leu
1               5

<210> SEQ ID NO 83
<211> LENGTH: 4
<212> TYPE: PRT
<213> ORGANISM: Artificial
<220> FEATURE:
<223> OTHER INFORMATION: Consensus sequence

<400> SEQUENCE: 83

Thr Leu Pro Ala
1

<210> SEQ ID NO 84
<211> LENGTH: 9
<212> TYPE: PRT
<213> ORGANISM: Artificial
<220> FEATURE:
<223> OTHER INFORMATION: Consensus sequence

<400> SEQUENCE: 84

Arg Leu Asp Ser Val Tyr Ser Ala Ile
1               5

<210> SEQ ID NO 85
<211> LENGTH: 4
<212> TYPE: PRT
<213> ORGANISM: Artificial
<220> FEATURE:
<223> OTHER INFORMATION: Consensus sequence

<400> SEQUENCE: 85
```

Thr Arg Ala Pro
1

<210> SEQ ID NO 86
<211> LENGTH: 12
<212> TYPE: PRT
<213> ORGANISM: Artificial
<220> FEATURE:
<223> OTHER INFORMATION: Consensus sequence

<400> SEQUENCE: 86

Ala Arg Val Val Val Leu Gly Tyr Pro Arg Ile Tyr
1               5                   10

<210> SEQ ID NO 87
<211> LENGTH: 4
<212> TYPE: PRT
<213> ORGANISM: Artificial
<220> FEATURE:
<223> OTHER INFORMATION: Consensus sequence

<400> SEQUENCE: 87

Leu Gly Leu Ser
1

<210> SEQ ID NO 88
<211> LENGTH: 11
<212> TYPE: PRT
<213> ORGANISM: Artificial
<220> FEATURE:
<223> OTHER INFORMATION: Consensus sequence

<400> SEQUENCE: 88

Thr Lys Arg Ala Ala Ile Asn Asp Ala Ala Asp
1               5                   10

<210> SEQ ID NO 89
<211> LENGTH: 12
<212> TYPE: PRT
<213> ORGANISM: Artificial
<220> FEATURE:
<223> OTHER INFORMATION: Consensus sequence

<400> SEQUENCE: 89

Leu Asn Ser Val Ile Ala Lys Arg Ala Ala Asp His
1               5                   10

<210> SEQ ID NO 90
<211> LENGTH: 7
<212> TYPE: PRT
<213> ORGANISM: Artificial
<220> FEATURE:
<223> OTHER INFORMATION: Consensus sequence

<400> SEQUENCE: 90

Gly Phe Thr Phe Gly Asp Val
1               5

<210> SEQ ID NO 91
<211> LENGTH: 7
<212> TYPE: PRT
<213> ORGANISM: Artificial
<220> FEATURE:
<223> OTHER INFORMATION: Consensus sequence

<400> SEQUENCE: 91

Gly His Glu Leu Cys Ser Ala
1               5

<210> SEQ ID NO 92
<211> LENGTH: 9
<212> TYPE: PRT
<213> ORGANISM: Artificial
<220> FEATURE:
<223> OTHER INFORMATION: Consensus sequence

<400> SEQUENCE: 92

Pro Trp Leu His Ser Leu Thr Leu Pro
1               5

<210> SEQ ID NO 93
<211> LENGTH: 6
<212> TYPE: PRT
<213> ORGANISM: Artificial
<220> FEATURE:
<223> OTHER INFORMATION: Consensus sequence

<400> SEQUENCE: 93

Ser Tyr His Pro Thr Ala
1               5

<210> SEQ ID NO 94
<211> LENGTH: 13
<212> TYPE: PRT
<213> ORGANISM: Artificial
<220> FEATURE:
<223> OTHER INFORMATION: Consensus sequence

<400> SEQUENCE: 94

Gly His Ala Ala Gly Tyr Leu Pro Val Leu Asn Ser Ile
1               5                   10

<210> SEQ ID NO 95
<211> LENGTH: 232
<212> TYPE: PRT
<213> ORGANISM: Aspergillus aculeatus

<400> SEQUENCE: 95

Thr Thr Val Tyr Leu Ala Gly Asp Ser Thr Met Ala Lys Asn Gly Gly
1               5                   10                  15

Gly Ser Gly Thr Asn Gly Trp Gly Glu Tyr Leu Ala Ser Tyr Leu Ser
            20                  25                  30

Ala Thr Val Val Asn Asp Ala Val Ala Gly Arg Ser Ala Arg Ser Tyr
        35                  40                  45

Thr Arg Glu Gly Arg Phe Glu Asn Ile Ala Asp Val Val Thr Ala Gly
    50                  55                  60

Asp Tyr Val Ile Val Glu Phe Gly His Asn Asp Gly Gly Ser Leu Ser
65                  70                  75                  80

Thr Asp Asn Gly Arg Thr Asp Cys Ser Gly Thr Gly Ala Glu Val Cys
                85                  90                  95

Tyr Ser Val Tyr Asp Gly Val Asn Glu Thr Ile Leu Thr Phe Pro Ala
            100                 105                 110

Tyr Leu Glu Asn Ala Ala Lys Leu Phe Thr Ala Lys Gly Ala Lys Val
        115                 120                 125

Ile Leu Ser Ser Gln Thr Pro Asn Asn Pro Trp Glu Thr Gly Thr Phe
    130                 135                 140

Val Asn Ser Pro Thr Arg Phe Val Glu Tyr Ala Glu Leu Ala Ala Glu
145                 150                 155                 160

```
Val Ala Gly Val Glu Tyr Val Asp His Trp Ser Tyr Val Asp Ser Ile
            165                 170                 175

Tyr Glu Thr Leu Gly Asn Ala Thr Val Asn Ser Tyr Phe Pro Ile Asp
            180                 185                 190

His Thr His Thr Ser Pro Ala Gly Ala Glu Val Val Ala Glu Ala Phe
            195                 200                 205

Leu Lys Ala Val Val Cys Thr Gly Thr Ser Leu Lys Ser Val Leu Thr
            210                 215                 220

Thr Thr Ser Phe Glu Gly Thr Cys
225                 230

<210> SEQ ID NO 96
<211> LENGTH: 184
<212> TYPE: PRT
<213> ORGANISM: Escherichia coli

<400> SEQUENCE: 96

Ala Asp Thr Leu Leu Ile Leu Gly Asp Ser Leu Ser Ala Gly Tyr Arg
1               5                   10                  15

Met Ser Ala Ser Ala Ala Trp Pro Ala Leu Leu Asn Asp Lys Trp Gln
            20                  25                  30

Ser Lys Thr Ser Val Val Asn Ala Ser Ile Ser Gly Asp Thr Ser Gln
        35                  40                  45

Gln Gly Leu Ala Arg Leu Pro Ala Leu Leu Lys Gln His Gln Pro Arg
    50                  55                  60

Trp Val Leu Val Glu Leu Gly Gly Asn Asp Gly Leu Arg Gly Phe Gln
65                  70                  75                  80

Pro Gln Gln Thr Glu Gln Thr Leu Arg Gln Ile Leu Gln Asp Val Lys
                85                  90                  95

Ala Ala Asn Ala Glu Pro Leu Leu Met Gln Ile Arg Leu Pro Ala Asn
            100                 105                 110

Tyr Gly Arg Arg Tyr Asn Glu Ala Phe Ser Ala Ile Tyr Pro Lys Leu
        115                 120                 125

Ala Lys Glu Phe Asp Val Pro Leu Leu Pro Phe Phe Met Glu Glu Val
    130                 135                 140

Tyr Leu Lys Pro Gln Trp Met Gln Asp Asp Gly Ile His Pro Asn Arg
145                 150                 155                 160

Asp Ala Gln Pro Phe Ile Ala Asp Trp Met Ala Lys Gln Leu Gln Pro
                165                 170                 175

Leu Val Asn His Asp Ser Leu Glu
            180

<210> SEQ ID NO 97
<211> LENGTH: 308
<212> TYPE: PRT
<213> ORGANISM: Aeromonas hydrophila

<400> SEQUENCE: 97

Ile Val Met Phe Gly Asp Ser Leu Ser Asp Thr Gly Lys Met Tyr Ser
1               5                   10                  15

Lys Met Arg Gly Tyr Leu Pro Ser Ser Pro Pro Tyr Tyr Glu Gly Arg
            20                  25                  30

Phe Ser Asn Gly Pro Val Trp Leu Glu Gln Leu Thr Asn Glu Phe Pro
        35                  40                  45

Gly Leu Thr Ile Ala Asn Glu Ala Glu Gly Gly Pro Thr Ala Val Ala
    50                  55                  60
```

```
Tyr Asn Lys Ile Ser Trp Asn Pro Lys Tyr Gln Val Ile Asn Asn Leu
 65                  70                  75                  80

Asp Tyr Glu Val Thr Gln Phe Leu Gln Lys Asp Ser Phe Lys Pro Asp
                 85                  90                  95

Asp Leu Val Ile Leu Trp Val Gly Ala Asn Asp Tyr Leu Ala Tyr Gly
            100                 105                 110

Trp Asn Thr Glu Gln Asp Ala Lys Arg Val Arg Asp Ala Ile Ser Asp
        115                 120                 125

Ala Ala Asn Arg Met Val Leu Asn Gly Ala Lys Glu Ile Leu Leu Phe
130                 135                 140

Asn Leu Pro Asp Leu Gly Gln Asn Pro Ser Ala Arg Ser Gln Lys Val
145                 150                 155                 160

Val Glu Ala Ala Ser His Val Ser Ala Tyr His Asn Gln Leu Leu Leu
                165                 170                 175

Asn Leu Ala Arg Gln Leu Ala Pro Thr Gly Met Val Lys Leu Phe Glu
            180                 185                 190

Ile Asp Lys Gln Phe Ala Glu Met Leu Arg Asp Pro Gln Asn Phe Gly
        195                 200                 205

Leu Ser Asp Gln Arg Asn Ala Cys Tyr Gly Gly Ser Tyr Val Trp Lys
210                 215                 220

Pro Phe Ala Ser Arg Ser Ala Ser Thr Asp Ser Gln Leu Ser Ala Phe
225                 230                 235                 240

Asn Pro Gln Glu Arg Leu Ala Ile Ala Gly Asn Pro Leu Leu Ala Gln
                245                 250                 255

Ala Val Ala Ser Pro Met Ala Ala Arg Ser Ala Ser Thr Leu Asn Cys
            260                 265                 270

Glu Gly Lys Met Phe Trp Asp Gln Val His Pro Thr Thr Val Val His
        275                 280                 285

Ala Ala Leu Ser Glu Pro Ala Ala Thr Phe Ile Glu Ser Gln Tyr Glu
290                 295                 300

Phe Leu Ala His
305

<210> SEQ ID NO 98
<211> LENGTH: 167
<212> TYPE: PRT
<213> ORGANISM: Escherichia coli

<400> SEQUENCE: 98

Leu Leu Ile Leu Gly Asp Ser Leu Ser Ala Gly Tyr Arg Met Ser Ala
 1               5                  10                  15

Ser Ala Ala Trp Pro Ala Leu Leu Asn Asp Lys Trp Gln Ser Lys Thr
                20                  25                  30

Ser Val Val Asn Ala Ser Ile Ser Gly Asp Thr Ser Gln Gln Gly Leu
            35                  40                  45

Ala Arg Leu Pro Ala Leu Leu Lys Gln His Gln Pro Arg Trp Val Leu
        50                  55                  60

Val Glu Leu Gly Gly Asn Asp Gly Leu Arg Gly Phe Gln Pro Gln Gln
 65                  70                  75                  80

Thr Glu Gln Thr Leu Arg Gln Ile Leu Gln Asp Val Lys Ala Ala Asn
                 85                  90                  95

Ala Glu Pro Leu Leu Met Gln Ile Arg Leu Pro Ala Asn Tyr Gly Arg
            100                 105                 110

Arg Tyr Asn Glu Ala Phe Ser Ala Ile Tyr Pro Lys Leu Ala Lys Glu
```

```
                   115                 120                 125

Phe Asp Val Pro Leu Leu Pro Phe Phe Met Glu Glu Val Tyr Leu Lys
    130                 135                 140

Pro Gln Trp Met Gln Asp Asp Gly Ile His Pro Asn Arg Asp Ala Gln
145                 150                 155                 160

Pro Phe Ile Ala Asp Trp Met
                165

<210> SEQ ID NO 99
<211> LENGTH: 295
<212> TYPE: PRT
<213> ORGANISM: Aeromonas hydrophila

<400> SEQUENCE: 99

Ile Val Met Phe Gly Asp Ser Leu Ser Asp Thr Gly Lys Met Tyr Ser
1               5                   10                  15

Lys Met Arg Gly Tyr Leu Pro Ser Ser Pro Tyr Tyr Glu Gly Arg
                20                  25                  30

Phe Ser Asn Gly Pro Val Trp Leu Glu Gln Leu Thr Asn Glu Phe Pro
            35                  40                  45

Gly Leu Thr Ile Ala Asn Glu Ala Glu Gly Pro Thr Ala Val Ala
        50                  55                  60

Tyr Asn Lys Ile Ser Trp Asn Pro Lys Tyr Gln Val Ile Asn Asn Leu
65                  70                  75                  80

Asp Tyr Glu Val Thr Gln Phe Leu Gln Lys Asp Ser Phe Lys Pro Asp
                85                  90                  95

Asp Leu Val Ile Leu Trp Val Gly Ala Asn Asp Tyr Leu Ala Tyr Gly
            100                 105                 110

Trp Asn Thr Glu Gln Asp Ala Lys Arg Val Arg Asp Ala Ile Ser Asp
        115                 120                 125

Ala Ala Asn Arg Met Val Leu Asn Gly Ala Lys Glu Ile Leu Leu Phe
    130                 135                 140

Asn Leu Pro Asp Leu Gly Gln Asn Pro Ser Ala Arg Ser Gln Lys Val
145                 150                 155                 160

Val Glu Ala Ala Ser His Val Ser Ala Tyr His Asn Gln Leu Leu Leu
                165                 170                 175

Asn Leu Ala Arg Gln Leu Ala Pro Thr Gly Met Val Lys Leu Phe Glu
            180                 185                 190

Ile Asp Lys Gln Phe Ala Glu Met Leu Arg Asp Pro Gln Asn Phe Gly
        195                 200                 205

Leu Ser Asp Gln Arg Asn Ala Cys Tyr Gly Gly Ser Tyr Val Trp Lys
    210                 215                 220

Pro Phe Ala Ser Arg Ser Ala Ser Thr Asp Ser Gln Leu Ser Ala Phe
225                 230                 235                 240

Asn Pro Gln Glu Arg Leu Ala Ile Ala Gly Asn Pro Leu Leu Ala Gln
                245                 250                 255

Ala Val Ala Ser Pro Met Ala Ala Arg Ser Ala Ser Thr Leu Asn Cys
            260                 265                 270

Glu Gly Lys Met Phe Trp Asp Gln Val His Pro Thr Thr Val Val His
        275                 280                 285

Ala Ala Leu Ser Glu Pro Ala
    290                 295

<210> SEQ ID NO 100
<211> LENGTH: 335
```

```
<212> TYPE: PRT
<213> ORGANISM: Aeromonas hydrophila

<400> SEQUENCE: 100

Met Lys Lys Trp Phe Val Cys Leu Leu Gly Leu Val Ala Leu Thr Val
1               5                   10                  15

Gln Ala Ala Asp Ser Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
        35                  40                  45

Leu Pro Ser Ser Pro Pro Tyr Tyr Glu Gly Arg Phe Ser Asn Gly Pro
    50                  55                  60

Val Trp Leu Glu Gln Leu Thr Asn Glu Phe Pro Gly Leu Thr Ile Ala
65                  70                  75                  80

Asn Glu Ala Glu Gly Gly Pro Thr Ala Val Ala Tyr Asn Lys Ile Ser
                85                  90                  95

Trp Asn Pro Lys Tyr Gln Val Ile Asn Asn Leu Asp Tyr Glu Val Thr
            100                 105                 110

Gln Phe Leu Gln Lys Asp Ser Phe Lys Pro Asp Asp Leu Val Ile Leu
        115                 120                 125

Trp Val Gly Ala Asn Asp Tyr Leu Ala Tyr Gly Trp Asn Thr Glu Gln
    130                 135                 140

Asp Ala Lys Arg Val Arg Asp Ala Ile Ser Asp Ala Ala Asn Arg Met
145                 150                 155                 160

Val Leu Asn Gly Ala Lys Glu Ile Leu Leu Phe Asn Leu Pro Asp Leu
                165                 170                 175

Gly Gln Asn Pro Ser Ala Arg Ser Gln Lys Val Val Glu Ala Ala Ser
            180                 185                 190

His Val Ser Ala Tyr His Asn Gln Leu Leu Asn Leu Ala Arg Gln
        195                 200                 205

Leu Ala Pro Thr Gly Met Val Lys Leu Phe Glu Ile Asp Lys Gln Phe
    210                 215                 220

Ala Glu Met Leu Arg Asp Pro Gln Asn Phe Gly Leu Ser Asp Gln Arg
225                 230                 235                 240

Asn Ala Cys Tyr Gly Gly Ser Tyr Val Trp Lys Pro Phe Ala Ser Arg
                245                 250                 255

Ser Ala Ser Thr Asp Ser Gln Leu Ser Ala Phe Asn Pro Gln Glu Arg
            260                 265                 270

Leu Ala Ile Ala Gly Asn Pro Leu Leu Ala Gln Ala Val Ala Ser Pro
        275                 280                 285

Met Ala Ala Arg Ser Ala Ser Thr Leu Asn Cys Glu Gly Lys Met Phe
290                 295                 300

Trp Asp Gln Val His Pro Thr Thr Val Val His Ala Ala Leu Ser Glu
305                 310                 315                 320

Pro Ala Ala Thr Phe Ile Glu Ser Gln Tyr Glu Phe Leu Ala His
                325                 330                 335

<210> SEQ ID NO 101
<211> LENGTH: 318
<212> TYPE: PRT
<213> ORGANISM: Aeromonas salmonicida

<400> SEQUENCE: 101

Ala Asp Thr Arg Pro Ala Phe Ser Arg Ile Val Met Phe Gly Asp Ser
1               5                   10                  15
```

```
Leu Ser Asp Thr Gly Lys Met Tyr Ser Lys Met Arg Gly Tyr Leu Pro
            20                  25                  30

Ser Ser Pro Pro Tyr Tyr Glu Gly Arg Phe Ser Asn Gly Pro Val Trp
        35                  40                  45

Leu Glu Gln Leu Thr Lys Gln Phe Pro Gly Leu Thr Ile Ala Asn Glu
50                  55                  60

Ala Glu Gly Gly Ala Thr Ala Val Ala Tyr Asn Lys Ile Ser Trp Asn
65                  70                  75                  80

Pro Lys Tyr Gln Val Tyr Asn Asn Leu Asp Tyr Glu Val Thr Gln Phe
                85                  90                  95

Leu Gln Lys Asp Ser Phe Lys Pro Asp Asp Leu Val Ile Leu Trp Val
            100                 105                 110

Gly Ala Asn Asp Tyr Leu Ala Tyr Gly Trp Asn Thr Glu Gln Asp Ala
        115                 120                 125

Lys Arg Val Arg Asp Ala Ile Ser Asp Ala Ala Asn Arg Met Val Leu
130                 135                 140

Asn Gly Ala Lys Gln Ile Leu Leu Phe Asn Leu Pro Asp Leu Gly Gln
145                 150                 155                 160

Asn Pro Ser Ala Arg Ser Gln Lys Val Val Glu Ala Val Ser His Val
                165                 170                 175

Ser Ala Tyr His Asn Lys Leu Leu Leu Asn Leu Ala Arg Gln Leu Ala
            180                 185                 190

Pro Thr Gly Met Val Lys Leu Phe Glu Ile Asp Lys Gln Phe Ala Glu
        195                 200                 205

Met Leu Arg Asp Pro Gln Asn Phe Gly Leu Ser Asp Val Glu Asn Pro
210                 215                 220

Cys Tyr Asp Gly Gly Tyr Val Trp Lys Pro Phe Ala Thr Arg Ser Val
225                 230                 235                 240

Ser Thr Asp Arg Gln Leu Ser Ala Phe Ser Pro Gln Glu Arg Leu Ala
                245                 250                 255

Ile Ala Gly Asn Pro Leu Leu Ala Gln Ala Val Ala Ser Pro Met Ala
            260                 265                 270

Arg Arg Ser Ala Ser Pro Leu Asn Cys Glu Gly Lys Met Phe Trp Asp
        275                 280                 285

Gln Val His Pro Thr Thr Val Val His Ala Ala Leu Ser Glu Arg Ala
290                 295                 300

Ala Thr Phe Ile Glu Thr Gln Tyr Glu Phe Leu Ala His Gly
305                 310                 315

<210> SEQ ID NO 102
<211> LENGTH: 50
<212> TYPE: PRT
<213> ORGANISM: Artificial
<220> FEATURE:
<223> OTHER INFORMATION: Consensus sequence

<400> SEQUENCE: 102

Arg Pro Ala Phe Ser Arg Ile Val Met Phe Gly Asp Ser Leu Ser Asp
1               5                   10                  15

Thr Gly Lys Met Tyr Ser Lys Met Arg Gly Tyr Leu Pro Ser Ser Pro
            20                  25                  30

Pro Tyr Tyr Glu Gly Arg Phe Ser Asn Gly Pro Val Trp Leu Glu Gln
        35                  40                  45

Leu Thr
    50
```

<210> SEQ ID NO 103
<211> LENGTH: 13
<212> TYPE: PRT
<213> ORGANISM: Artificial
<220> FEATURE:
<223> OTHER INFORMATION: Consensus sequence

<400> SEQUENCE: 103

Phe Pro Gly Leu Thr Ile Ala Asn Glu Ala Glu Gly Gly
1               5                   10

<210> SEQ ID NO 104
<211> LENGTH: 79
<212> TYPE: PRT
<213> ORGANISM: Artificial
<220> FEATURE:
<223> OTHER INFORMATION: Consensus sequence

<400> SEQUENCE: 104

Thr Ala Val Ala Tyr Asn Lys Ile Ser Trp Asn Pro Lys Tyr Gln Val
1               5                   10                  15

Ile Asn Asn Leu Asp Tyr Glu Val Thr Gln Phe Leu Gln Lys Asp Ser
                20                  25                  30

Phe Lys Pro Asp Asp Leu Val Ile Leu Trp Val Gly Ala Asn Asp Tyr
            35                  40                  45

Leu Ala Tyr Gly Trp Asn Thr Glu Gln Asp Ala Lys Arg Val Arg Asp
        50                  55                  60

Ala Ile Ser Asp Ala Ala Asn Arg Met Val Leu Asn Gly Ala Lys
65                  70                  75

<210> SEQ ID NO 105
<211> LENGTH: 23
<212> TYPE: PRT
<213> ORGANISM: Artificial
<220> FEATURE:
<223> OTHER INFORMATION: Consensus sequence

<400> SEQUENCE: 105

Ile Leu Leu Phe Asn Leu Pro Asp Leu Gly Gln Asn Pro Ser Ala Arg
1               5                   10                  15

Ser Gln Lys Val Val Glu Ala
            20

<210> SEQ ID NO 106
<211> LENGTH: 8
<212> TYPE: PRT
<213> ORGANISM: Artificial
<220> FEATURE:
<223> OTHER INFORMATION: Consensus sequence

<400> SEQUENCE: 106

Ser His Val Ser Ala Tyr His Asn
1               5

<210> SEQ ID NO 107
<211> LENGTH: 38
<212> TYPE: PRT
<213> ORGANISM: Artificial
<220> FEATURE:
<223> OTHER INFORMATION: Consensus sequence

<400> SEQUENCE: 107

Leu Leu Leu Asn Leu Ala Arg Gln Leu Ala Pro Thr Gly Met Val Lys
1               5                   10                  15

-continued

Leu Phe Glu Ile Asp Lys Gln Phe Ala Glu Met Leu Arg Asp Pro Gln
            20                  25                  30

Asn Phe Gly Leu Ser Asp
        35

<210> SEQ ID NO 108
<211> LENGTH: 7
<212> TYPE: PRT
<213> ORGANISM: Artificial
<220> FEATURE:
<223> OTHER INFORMATION: Consensus sequence

<400> SEQUENCE: 108

Tyr Val Trp Lys Pro Phe Ala
1               5

<210> SEQ ID NO 109
<211> LENGTH: 5
<212> TYPE: PRT
<213> ORGANISM: Artificial
<220> FEATURE:
<223> OTHER INFORMATION: Consensus sequence

<400> SEQUENCE: 109

Gln Leu Ser Ala Phe
1               5

<210> SEQ ID NO 110
<211> LENGTH: 22
<212> TYPE: PRT
<213> ORGANISM: Artificial
<220> FEATURE:
<223> OTHER INFORMATION: Consensus sequence

<400> SEQUENCE: 110

Pro Gln Glu Arg Leu Ala Ile Ala Gly Asn Pro Leu Leu Ala Gln Ala
1               5                   10                  15

Val Ala Ser Pro Met Ala
            20

<210> SEQ ID NO 111
<211> LENGTH: 4
<212> TYPE: PRT
<213> ORGANISM: Artificial
<220> FEATURE:
<223> OTHER INFORMATION: Consensus sequence

<400> SEQUENCE: 111

Arg Ser Ala Ser
1

<210> SEQ ID NO 112
<211> LENGTH: 24
<212> TYPE: PRT
<213> ORGANISM: Artificial
<220> FEATURE:
<223> OTHER INFORMATION: Consensus sequence

<400> SEQUENCE: 112

Leu Asn Cys Glu Gly Lys Met Phe Trp Asp Gln Val His Pro Thr Thr
1               5                   10                  15

Val Val His Ala Ala Leu Ser Glu
            20

```
<210> SEQ ID NO 113
<211> LENGTH: 5
<212> TYPE: PRT
<213> ORGANISM: Artificial
<220> FEATURE:
<223> OTHER INFORMATION: Consensus sequence

<400> SEQUENCE: 113

Ala Ala Thr Phe Ile
1               5

<210> SEQ ID NO 114
<211> LENGTH: 7
<212> TYPE: PRT
<213> ORGANISM: Artificial
<220> FEATURE:
<223> OTHER INFORMATION: Consensus sequence

<400> SEQUENCE: 114

Gln Tyr Glu Phe Leu Ala His
1               5

<210> SEQ ID NO 115
<211> LENGTH: 1225
<212> TYPE: DNA
<213> ORGANISM: Artificial
<220> FEATURE:
<223> OTHER INFORMATION: XhoI insert containing the LAT-KLM3' precursor
      gene
<220> FEATURE:
<221> NAME/KEY: CDS
<222> LOCATION: (101)..(1144)

<400> SEQUENCE: 115
gcttttcttt tggaagaaaa tatagggaaa atggtacttg ttaaaaattc ggaatattta         60
tacaatatca tatgtttcac attgaaaggg gaggagaatc atg aaa caa caa aaa        115
                                              Met Lys Gln Gln Lys
                                                1               5 cgg ctt tac gcc cga ttg ctg acg ctg tta ttt gcg ctc atc ttc ttg        163
Arg Leu Tyr Ala Arg Leu Leu Thr Leu Leu Phe Ala Leu Ile Phe Leu
             10                  15                  20 ctg cct cat tct gca gct tca gca gca gat aca aga ccg gcg ttt agc        211
Leu Pro His Ser Ala Ala Ser Ala Ala Asp Thr Arg Pro Ala Phe Ser
         25                  30                  35 cgg atc gtc atg ttt gga gat agc ctg agc gat acg ggc aaa atg tat        259
Arg Ile Val Met Phe Gly Asp Ser Leu Ser Asp Thr Gly Lys Met Tyr
     40                  45                  50 agc aaa atg aga ggc tat ctt ccg tca agc ccg ccg tat tat gaa ggc        307
Ser Lys Met Arg Gly Tyr Leu Pro Ser Ser Pro Pro Tyr Tyr Glu Gly
 55                  60                  65 cgc ttt agc aat gga ccg gtc tgg ctg gaa caa ctg acg aaa caa ttt        355
Arg Phe Ser Asn Gly Pro Val Trp Leu Glu Gln Leu Thr Lys Gln Phe
 70                  75                  80                  85 ccg gga ctg acg atc gct aat gaa gca gaa gga gga gca aca gcg gtc        403
Pro Gly Leu Thr Ile Ala Asn Glu Ala Glu Gly Gly Ala Thr Ala Val
             90                  95                 100 gcc tat aac aaa atc agc tgg gac ccg aaa tat cag gtc atc aac aac        451
Ala Tyr Asn Lys Ile Ser Trp Asp Pro Lys Tyr Gln Val Ile Asn Asn
        105                 110                 115 ctg gac tat gaa gtc aca cag ttt ctt cag aaa gac agc ttt aaa ccg        499
Leu Asp Tyr Glu Val Thr Gln Phe Leu Gln Lys Asp Ser Phe Lys Pro
    120                 125                 130 gat gat ctg gtc atc ctt tgg gtc ggc gcc aat gat tat ctg gcg tat        547
Asp Asp Leu Val Ile Leu Trp Val Gly Ala Asn Asp Tyr Leu Ala Tyr
```

```
                 135                 140                 145
ggc tgg aac aca gaa caa gat gcc aaa aga gtc aga gat gcc atc agc        595
Gly Trp Asn Thr Glu Gln Asp Ala Lys Arg Val Arg Asp Ala Ile Ser
150                 155                 160                 165 gat gcc gct aat aga atg gtc ctg aac ggc gcc aaa caa atc ctg ctg        643
Asp Ala Ala Asn Arg Met Val Leu Asn Gly Ala Lys Gln Ile Leu Leu
                170                 175                 180 ttt aac ctg ccg gat ctg gga caa aat ccg agc gcc aga agc caa aaa        691
Phe Asn Leu Pro Asp Leu Gly Gln Asn Pro Ser Ala Arg Ser Gln Lys
            185                 190                 195 gtc gtc gaa gca gtc agc cat gtc agc gcc tat cat aac aaa ctg ctg        739
Val Val Glu Ala Val Ser His Val Ser Ala Tyr His Asn Lys Leu Leu
        200                 205                 210 ctg aac ctg gca aga caa ttg gca ccg acg gga atg gtt aaa ttg ttt        787
Leu Asn Leu Ala Arg Gln Leu Ala Pro Thr Gly Met Val Lys Leu Phe
    215                 220                 225 gaa att gac aaa cag ttt gcc gaa atg ctg aga gat ccg caa aat ttt        835
Glu Ile Asp Lys Gln Phe Ala Glu Met Leu Arg Asp Pro Gln Asn Phe
230                 235                 240                 245 ggc ctg agc gat gtc gaa aac ccg tgc tat gat ggc gga tat gtc tgg        883
Gly Leu Ser Asp Val Glu Asn Pro Cys Tyr Asp Gly Gly Tyr Val Trp
                250                 255                 260 aaa ccg ttt gcc aca aga agc gtc agc acg gat aga caa ctg tca gcg        931
Lys Pro Phe Ala Thr Arg Ser Val Ser Thr Asp Arg Gln Leu Ser Ala
            265                 270                 275 ttt agc ccg caa gaa aga ctg gca atc gcc gga aat ccg ctt ttg gca        979
Phe Ser Pro Gln Glu Arg Leu Ala Ile Ala Gly Asn Pro Leu Leu Ala
        280                 285                 290 caa gca gtt gct tca ccg atg gca aga aga tca gca agc ccg ctg aat       1027
Gln Ala Val Ala Ser Pro Met Ala Arg Arg Ser Ala Ser Pro Leu Asn
    295                 300                 305 tgc gaa ggc aaa atg ttt tgg gat cag gtc cat ccg aca aca gtt gtc       1075
Cys Glu Gly Lys Met Phe Trp Asp Gln Val His Pro Thr Thr Val Val
310                 315                 320                 325 cat gct gcc ctt tca gaa aga gcg gcg acg ttt atc gaa aca cag tat       1123
His Ala Ala Leu Ser Glu Arg Ala Ala Thr Phe Ile Glu Thr Gln Tyr
                330                 335                 340 gaa ttt ctg gcc cat ggc tga gttaacagag gacggatttc ctgaaggaaa          1174
Glu Phe Leu Ala His Gly
            345 tccgtttttt tattttaagc ttggagacaa ggtaaaggat aaaacctcga g              1225

<210> SEQ ID NO 116
<211> LENGTH: 347
<212> TYPE: PRT
<213> ORGANISM: Artificial
<220> FEATURE:
<223> OTHER INFORMATION: Synthetic Construct

<400> SEQUENCE: 116

Met Lys Gln Gln Lys Arg Leu Tyr Ala Arg Leu Leu Thr Leu Leu Phe
1               5                   10                  15

Ala Leu Ile Phe Leu Leu Pro His Ser Ala Ala Ser Ala Ala Asp Thr
            20                  25                  30

Arg Pro Ala Phe Ser Arg Ile Val Met Phe Gly Asp Ser Leu Ser Asp
        35                  40                  45

Thr Gly Lys Met Tyr Ser Lys Met Arg Gly Tyr Leu Pro Ser Ser Pro
    50                  55                  60

Pro Tyr Tyr Glu Gly Arg Phe Ser Asn Gly Pro Val Trp Leu Glu Gln
```

```
                65                  70                  75                  80
Leu Thr Lys Gln Phe Pro Gly Leu Thr Ile Ala Asn Glu Ala Glu Gly
                    85                  90                  95
Gly Ala Thr Ala Val Ala Tyr Asn Lys Ile Ser Trp Asp Pro Lys Tyr
                100                 105                 110
Gln Val Ile Asn Asn Leu Asp Tyr Glu Val Thr Gln Phe Leu Gln Lys
                115                 120                 125
Asp Ser Phe Lys Pro Asp Leu Val Ile Leu Trp Val Gly Ala Asn
130                 135                 140
Asp Tyr Leu Ala Tyr Gly Trp Asn Thr Glu Gln Asp Ala Lys Arg Val
145                 150                 155                 160
Arg Asp Ala Ile Ser Asp Ala Ala Asn Arg Met Val Leu Asn Gly Ala
                165                 170                 175
Lys Gln Ile Leu Leu Phe Asn Leu Pro Asp Leu Gly Gln Asn Pro Ser
                180                 185                 190
Ala Arg Ser Gln Lys Val Val Glu Ala Val Ser His Val Ser Ala Tyr
                195                 200                 205
His Asn Lys Leu Leu Leu Asn Leu Ala Arg Gln Leu Ala Pro Thr Gly
                210                 215                 220
Met Val Lys Leu Phe Glu Ile Asp Lys Gln Phe Ala Glu Met Leu Arg
225                 230                 235                 240
Asp Pro Gln Asn Phe Gly Leu Ser Asp Val Glu Asn Pro Cys Tyr Asp
                245                 250                 255
Gly Gly Tyr Val Trp Lys Pro Phe Ala Thr Arg Ser Val Ser Thr Asp
                260                 265                 270
Arg Gln Leu Ser Ala Phe Ser Pro Gln Glu Arg Leu Ala Ile Ala Gly
                275                 280                 285
Asn Pro Leu Leu Ala Gln Ala Val Ala Ser Pro Met Ala Arg Arg Ser
                290                 295                 300
Ala Ser Pro Leu Asn Cys Glu Gly Lys Met Phe Trp Asp Gln Val His
305                 310                 315                 320
Pro Thr Thr Val Val His Ala Ala Leu Ser Glu Arg Ala Ala Thr Phe
                325                 330                 335
Ile Glu Thr Gln Tyr Glu Phe Leu Ala His Gly
                340                 345

<210> SEQ ID NO 117
<211> LENGTH: 4
<212> TYPE: PRT
<213> ORGANISM: Artificial
<220> FEATURE:
<223> OTHER INFORMATION: Sequence motif
<220> FEATURE:
<221> NAME/KEY: VARIANT
<222> LOCATION: (4)..(4)
<223> OTHER INFORMATION: Xaa may be one or more of the following amino
      acid residues Leu, Ala, Val, Ile, Phe, Tyr, His, Gln, Thr, Asn,
      Met or Ser.

<400> SEQUENCE: 117

Gly Asp Ser Xaa
1

<210> SEQ ID NO 118
<211> LENGTH: 5
<212> TYPE: PRT
<213> ORGANISM: Artificial
<220> FEATURE:
<223> OTHER INFORMATION: Sequence motif
```

```
<220> FEATURE:
<221> NAME/KEY: VARIANT
<222> LOCATION: (2)..(2)
<223> OTHER INFORMATION: May be Gly
<220> FEATURE:
<221> NAME/KEY: VARIANT
<222> LOCATION: (5)..(5)
<223> OTHER INFORMATION: May be Ala or Leu

<400> SEQUENCE: 118

Gly Ala Asn Asp Tyr
1               5

<210> SEQ ID NO 119
<211> LENGTH: 56
<212> TYPE: DNA
<213> ORGANISM: Artificial Sequence
<220> FEATURE:
<223> OTHER INFORMATION: Terminator sequence

<400> SEQUENCE: 119
gctgacaaat aaaaagaagc aggtatggag gaacctgctt ctttttacta ttattg        56

<210> SEQ ID NO 120
<211> LENGTH: 232
<212> TYPE: PRT
<213> ORGANISM: Aspergillus aculeatus

<400> SEQUENCE: 120

Thr Thr Val Tyr Leu Ala Gly Asp Ser Thr Met Ala Lys Asn Gly Gly
1               5                   10                  15

Gly Ser Gly Thr Asn Gly Trp Gly Glu Tyr Leu Ala Ser Tyr Leu Ser
                20                  25                  30

Ala Thr Val Val Asn Asp Ala Val Ala Gly Arg Ser Ala Arg Ser Tyr
            35                  40                  45

Thr Arg Glu Gly Arg Phe Glu Asn Ile Ala Asp Val Val Thr Ala Gly
        50                  55                  60

Asp Tyr Val Ile Val Glu Phe Gly His Asn Asp Gly Gly Ser Leu Ser
65                  70                  75                  80

Thr Asp Asn Gly Arg Thr Asp Cys Ser Gly Thr Gly Ala Glu Val Cys
                85                  90                  95

Tyr Ser Val Tyr Asp Gly Val Asn Glu Thr Ile Leu Thr Phe Pro Ala
            100                 105                 110

Tyr Leu Glu Asn Ala Ala Lys Leu Phe Thr Ala Lys Gly Ala Lys Val
        115                 120                 125

Ile Leu Ser Ser Gln Thr Pro Asn Asn Pro Trp Glu Thr Gly Thr Phe
130                 135                 140

Val Asn Ser Pro Thr Arg Phe Val Glu Tyr Ala Glu Leu Ala Ala Glu
145                 150                 155                 160

Val Ala Gly Val Glu Tyr Val Asp His Trp Ser Tyr Val Asp Ser Ile
                165                 170                 175

Tyr Glu Thr Leu Gly Asn Ala Thr Val Asn Ser Tyr Phe Pro Ile Asp
            180                 185                 190

His Thr His Thr Ser Pro Ala Gly Ala Glu Val Val Ala Glu Ala Phe
        195                 200                 205

Leu Lys Ala Val Val Cys Thr Gly Thr Ser Leu Lys Ser Val Leu Thr
    210                 215                 220

Thr Thr Ser Phe Glu Gly Thr Cys
225                 230
```

```
<210> SEQ ID NO 121
<211> LENGTH: 184
<212> TYPE: PRT
<213> ORGANISM: Escherichia coli

<400> SEQUENCE: 121

Ala Asp Thr Leu Leu Ile Leu Gly Asp Ser Leu Ser Ala Gly Tyr Arg
 1               5                  10                  15

Met Ser Ala Ser Ala Ala Trp Pro Ala Leu Leu Asn Asp Lys Trp Gln
            20                  25                  30

Ser Lys Thr Ser Val Val Asn Ala Ser Ile Ser Gly Asp Thr Ser Gln
                35                  40                  45

Gln Gly Leu Ala Arg Leu Pro Ala Leu Leu Lys Gln His Gln Pro Arg
        50                  55                  60

Trp Val Leu Val Glu Leu Gly Gly Asn Asp Gly Leu Arg Gly Phe Gln
 65                  70                  75                  80

Pro Gln Gln Thr Glu Gln Thr Leu Arg Gln Ile Leu Gln Asp Val Lys
                85                  90                  95

Ala Ala Asn Ala Glu Pro Leu Leu Met Gln Ile Arg Leu Pro Ala Asn
            100                 105                 110

Tyr Gly Arg Arg Tyr Asn Glu Ala Phe Ser Ala Ile Tyr Pro Lys Leu
        115                 120                 125

Ala Lys Glu Phe Asp Val Pro Leu Leu Pro Phe Phe Met Glu Glu Val
    130                 135                 140

Tyr Leu Lys Pro Gln Trp Met Gln Asp Asp Gly Ile His Pro Asn Arg
145                 150                 155                 160

Asp Ala Gln Pro Phe Ile Ala Asp Trp Met Ala Lys Gln Leu Gln Pro
                165                 170                 175

Leu Val Asn His Asp Ser Leu Glu
            180
```

PROCESS OF WATER DEGUMMING AN EDIBLE OIL

CLAIM OF PRIORITY

This application claims priority under 35 USC 371 to International Application No. PCT/GB2008/004064, filed on Dec. 11, 2008, which claims priority to British Application Serial No. 0725035.0, filed on Dec. 21, 2008, British Application Serial No. 0809177.9, filed on May 20, 2008, and U.S. Provisional Application 61/058,378, filed on Jun. 3, 2008, each of which is incorporated by reference in its entirety.

REFERENCE TO RELATED APPLICATIONS

Reference is made to the following related applications: US 2002-0009518, US 2004-0091574, WO2004/064537, WO2004/064987, WO2005/066347, WO2005/066351, U.S. Application Ser. No. 60/764,430 filed on 2 Feb. 2006, WO2006/008508, International Patent Application Number PCT/IB2007/000558 and U.S. application Ser. No. 11/671, 953. Each of these applications and each of the documents cited in each of these applications ("application cited documents"), and each document referenced or cited in the application cited documents, either in the text or during the prosecution of those applications, as well as all arguments in support of patentability advanced during such prosecution, are hereby incorporated herein by reference. Various documents are also cited in this text ("herein cited documents"). Each of the herein cited documents, and each document cited or referenced in the herein cited documents, is hereby incorporated herein by reference.

SEQUENCE LISTING

The sequence listing submitted via EFS, in compliance with 37 C.F.R. §1.52(e), is incorporated herein by reference. The sequence listing text file submitted via EFS contains the text file created on May 24, 2013, which is 186 kilobytes in size.

FIELD OF THE PRESENT INVENTION

The present invention relates to a process for edible oil (preferably vegetable oil) refining using a lipid acyltransferase. The present invention further relates to a process for treating an edible oil (preferably a crude edible oil) (e.g. a vegetable oil) and/or a gum phase of an edible oil (preferably vegetable oil) using a lipid acyltransferase.

BACKGROUND OF THE PRESENT INVENTION

Lipid acyltransferases are known to be advantageous in food applications. Lipid acyltransferases have been found to have significant acyltransferase activity in foodstuffs. This activity has surprising beneficial applications in methods of preparing foodstuffs.

For instance, WO 2004/064537 discloses a method for the in situ production of an emulsifier by use of a lipid acyltransferase and the advantages associated therewith.

International Patent Application No. PCT/IB2001/000558 teaches the expression of lipid acyltransferases in (heterologous) host cell and is incorporated herein by reference.

The purpose of edible oil refining is to remove undesirable impurities that affect quality (taste, smell and appearance for example)) and storability.

Due to the wide variety of these impurities—free fatty acids, metal ions, colour compounds, odours, gums etc.—a series of processes of chemical and physical nature are conventionally employed for refining (see for example Bailey's Industrial Oil and Fat Products—2006 John Wiley & Sons—Sixth Edition).

Traditionally two processes have been used for degumming of oil which are the physical degumming and the chemical degumming processes.

In the so-called chemical refining, almost all free fatty acid content is removed by initial treatment with a large excess of NaOH. Also the phospholipids content is decreased to a phosphorus level typically below 10 ppm. The oil is subsequently bleached and deodorised.

The so-called physical refining generally consists of a water-degumming step followed by acid degumming, neutralisation, bleaching, steam stripping to remove free fatty acids and deodorisation.

Instead of using acid degumming during physical refinement developments were made to use enzymatic degumming.

The enzymatic degumming process was developed based on the use of pancreatic phospholipase. Because this enzyme was non-kosher the phospholipase was eventually substituted by a microbial phospholipase A1 (Lecitase Ultra™-Novozymes, Denmark) (Oil Mill Gazetteer, Vol 111 July 2005 pp 2-4).

The enzymatic process has several advantages over the chemical or the physical degumming processes including cost savings, higher yield and a more environmentally friendly process.

The enzymatic oil degumming process was based on the addition of a phospholipase to an oil which was already water degummed.

In WO2006/008508 lipid acyltransferases were taught for use in enzymatic degumming of edible oils. WO 2006/008508 teaches addition of a lipid acyltransferase to a water-degummed oil or the addition of a lipid acyltransferase to a crude oil without the need for the oil to undergo a water-degumming process.

"Water-degummed oil" may typically be obtained by a conventional "water degumming process" comprising mixing 1-2% w/w of hot soft water with warm (70-90° C.) crude oil (AOCS Introduction to the Processing of Fats and Oils—Table 8—Degumming Processes—http://www.aocs.org/meetings/education/mod3sample.pdf). A rule of thumb is that that amount of water added to crude oil is typically approximately equal to the amount of phospholipids in the crude oil. Usual treatment periods are 30-60 minutes. The water-degumming step removes the phosphatides and mucilaginous gums which become insoluble in the oil when hydrated. The hydrated phosphatides and gums can be separated from the oil by settling, filtration or centrifugation—centrifugation being the more prevalent practice. The essential object in said water-degumming process is to separate the hydrated phosphatides from the oil. The mixing of hot water into the oil, described above, should herein be understood broadly as mixing of an aqueous solution into the oil according to standard water-degumming procedures in the art.

In the conventional water degumming process the main part of the phosphatides are removed in a heavy gum phase. At the end of the water degumming process an oil phase is separated from a gum phase. Although the gum phase can be processed further into commercial products it is essentially viewed as a bi-product of oil refining. It is the oil phase which is commercially important. However, because the phosphatides can be good emulsifiers some oil is inevitably lost in the gum phase during water degumming. This leads to reduced yields of oil in the oil phase following water degumming.

With increases in oil prices and an increasing need for vegetable oil for biodiesel it is important to optimise the processing of edible oils for high oil yield.

SUMMARY ASPECTS OF THE PRESENT INVENTION

Aspects of the present invention are presented in the claims and in the following commentary.

It has surprisingly been found that by adding one or more lipid acyltransferases to a crude edible oil during or before carrying out a water degumming process the yield of oil in the oil phase can be significantly increased. In other words, losses of oil to the gum phase can be significantly reduced.

In addition, it has surprisingly been found that by adding one or more lipid acyltransferases to a crude edible oil during or before carrying out a water degumming process the gum phase obtained is much less viscous. This may allow for more favourable centrifugation parameters.

It has also surprisingly been found that by adding one or more lipid acyltransferases to a crude edible oil during or before carrying out a water degumming process, the gum phase obtained from this process can be incubated or stored and (due to residual active lipid acyltransferase) further hydrolysis of phospholipids in the gum phase can be observed. The inventors have then found that it is then possible to isolate an oily phase containing free fatty acids (the acid oil) and the remaining triglycerides in the gum phase. This acid oil can be sold with a higher value than the normal gum phase which is added to meal. In addition, it has surprisingly been found that the remaining solid phase (after separation of the acid oil) has higher a phosphor level than normal gum and thus can be used as a source of organic phosphor.

It has also been surprisingly found that the combination of one or more lipid acyltransferases and one or more phospholipase C (PLC) enzymes results in synergistic effects when used in the degumming of edible oils (e.g. vegetable oils).

DETAILED ASPECTS OF THE PRESENT INVENTION

According to a first aspect of the present invention there is provided a process of water degumming an edible oil (preferably a crude edible oil) comprising the steps of: a) admixing approximately 0.1-5% w/w water with an edible oil (preferably a crude edible oil) and a lipid acyltransferase, b) agitating the admixture for between about 10 minutes and 180 minutes at about 45° C. to about 90° C., and c) separating the oil phase and the gum phase.

According to a second aspect of the present invention there is provided a use of a lipid acyltransferase during water degumming of an edible oil (preferably during the water degumming of a crude edible oil) for increasing the yield of oil in the oil phase after completion of the water degumming process.

According to a third aspect of the present invention there is provided a use of a lipid acyltransferase during water degumming of an edible oil (preferably during the water degumming of a crude edible oil) for decreasing the viscosity of the gum phase after completion of the water degumming process.

The increase in yield and/or decrease in viscosity is when compared with the oil phase and/or gum phase of a comparable oil degummed (either water degummed or enzymatically water degummed) without the use of the lipid acyltransferase.

According to a fourth aspect the present invention provides a process of water degumming an edible oil (preferably a crude edible oil) comprising the steps of: a) admixing approximately 0.1-5% w/w water with an edible oil (preferably a crude edible oil) and a lipid acyltransferase, b) agitating the admixture for between about 10 minutes and 180 minutes at about 45° C. to about 90° C., c) separating the oil phase and the gum phase, d) incubating the gum phase comprising active lipid acyltransferase enzyme for between a minimum of about 2 hours and a maximum of 7 days (suitably up to about 1-2 days) and e) separating (e.g. by centrifugation) the oil from the gum phase.

The present invention further provides a method of treating a gum phase (preferably obtainable or obtained from degumming—such as water degumming or enzymatic degumming or a combination thereof—an edible oil) wherein the gum phase is incubated with one or more (active) lipid acyltransferase enzymes (alone or in combination with one or more phospholipase C enzyme) for between a minimum of about 2 hours and a maximum of 7 days (suitably up to about 1-2 days) and separating (e.g. by centrifugation) the oil from the gum phase.

The present invention yet further provides the use of a lipid acyltransferase (alone or in combination with a phospholipase C) in the incubation of a gum phase (obtainable or obtained from degumming—such as water degumming, enzymatic degumming or a combination thereof—an edible oil) for increasing the yield of oil and/or producing a solid phase (after separation of the acid oil) with an improved phosphor level than normal gum.

The use of the enzyme(s) increases the value of the acid oil compared with the gum because the acid oil can be used for fatty acid production. Fatty acid has a higher value than a gum which is otherwise added to meal.

The improvements and/or increases are when compared with a gum phase which has not been treated by a lipid acyltransferase (alone or in combination with a phospholipase C).

Suitably the one or more lipid acyltransferase enzymes in the gum phase may have residual active enzyme which may have been transferred to the gum phase after enzymatic degumming of the edible oil. Alternatively the lipid acyltransferase enzyme in the gum phase may be added lipid acyltransferase—which enzyme may be added at the beginning or during the incubation of the gum phase.

Notably the oil at the end of the process in the fourth aspect (and other treatments of the gum phase) is an "acid oil". This acid oil can be sold with a higher value than the normal gum phase which is added to meal. The remaining gum phase (after separation of the acid oil) is sometimes referred to as a solid phase. It has surprisingly been found that the remaining solid phase (after separation of the acid oil) has higher a phosphor level than normal gum and thus can be used as a source of organic phosphor.

Suitably the gum phase may be incubated with the lipid acyltransferase (either alone or with one or more phospholipase C enzymes) at about 30 to about 70° C., preferably at about 40 to about 60° C., preferably at about 40 to about 50° C., preferably at about 40 to about 45° C.

Preferably, the gum phase obtained from enzymatic water degumming of crude oil with lipid acyltransferase may be incubated at about 30 to about 70° C., preferably at about 40 to about 60° C., preferably at about 40 to about 50° C., preferably at about 40 to about 45° C.

Suitably the lipid acyltransferase is one classified under the Enzyme Nomenclature classification (E.C. 2.3.1.43).

In one embodiment preferably the lipid acyl transferase is used in combination with a phospholipase C (E.C. 3.1.4.3).

In one preferable embodiment a lipid acyltransferase (E.C. 2.3.1.43) is used in combination with a phospholipase C (E.C. 3.1.4.3).

Therefore according to one aspect of the present invention there is provided a process of water degumming an edible oil (preferably a crude edible oil) comprising the steps of: a) admixing approximately 0.1-5% w/w water with an edible oil (preferably a crude edible oil) and a combination of a lipid acyltransferase and a phospholipase C, b) agitating the admixture for between about 10 minutes and 180 minutes at about 45° C. to about 90° C., and c) separating the oil phase and the gum phase.

Without wishing to be bound by theory it has surprisingly been found that the lipid acyltransferase can use the diglyceride (produced by the reaction of the phospholipase C) as an acceptor molecule to produce triglyceride. Thus when a lipid acyltransferase is used in combination with a phospholipase C the interaction between these enzymes results in a synergistic increase in the amount of triglyceride in an oil comprising both enzymes compared with a comparable oil comprising either enzyme alone or a comparable oil comprising no enzyme. Advantageously when a lipid acyltransferase is used in combination with a phospholipase C the interaction between these enzymes results in a synergistic decrease in the amount of diglyceride in an oil comprising both enzymes compared with a comparable oil comprising either enzyme alone or a comparable oil comprising no enzyme. When a lipid acyltransferase is used in combination with a phospholipase C the interaction between these enzymes results in a synergistic increase oil yield in an oil comprising both enzymes compared with a comparable oil comprising either enzyme alone or a comparable oil comprising no enzyme.

The use of a combination of these enzymes has significant advantages over the use of a phospholipase C alone as the accumulation of diglycerides in an oil (which can occur when a phospholipase C is used alone) can be detrimental to the oil because it can have a negative impact on the "smoke point" of the oil and/or can have a negative impact on the crystallisation properties of more saturated fat sources.

Hence in the present invention another advantage of the use of lipid acyltransferases (particularly when in combination with a phospholipase C) is that the amount of diglyceride in the oil can be reduced compared with a comparable oil without the lipid acyltransferase and/or particularly compared with a comparable oil treated with phospholipase C alone.

In another aspect of the present invention there is provided a use of a lipid acyltransferase in combination with a phospholipase C during water degumming of an edible oil (preferably during the water degumming of a crude edible oil) for increasing the yield of oil and/or for increasing triglyceride levels in the oil phase after completion of the water degumming process and/or for reducing the diglyceride level in the oil phase after completion of the water degumming process.

According to yet another aspect of the present invention there is provided a use of a lipid acyltransferase in combination with a phospholipase C during water degumming of an edible oil (preferably during the water degumming of a crude edible oil) for decreasing the viscosity of the gum phase after completion of the water degumming process.

These increases and/or reductions are when compared with a comparable degummed edible oil which has not been treated with a lipid acyltransferase in combination with a phospholipase C.

Generally the increases and/or reductions discussed herein are when compared with a comparable process or a comparable oil which has not been treated with a lipid acyltransferase (either alone or in combination with a phospholipase C).

According to another aspect the present invention provides a process of water degumming an edible oil (preferably a crude edible oil) comprising the steps of: a) admixing approximately 0.1-5% w/w water with an edible oil (preferably a crude edible oil) and a lipid acyltransferase in combination with a phospholipase C, b) agitating the admixture for between about 10 minutes and 180 minutes at about 45° C. to about 90° C., c) separating the oil phase and the gum phase, d) incubating the gum phase comprising active lipid acyltransferase for between a minimum of about 2 hours and a maximum of 7 days (suitably for up to about 1-2 days) and e) separating (e.g. by centrifugation) oil from the gum phase.

When a phospholipid degrading enzyme (preferably a lipid acyltransferase) is used in combination with a phospholipase C the phospholipase C may be added before, at the same time or after the addition of the lipid acyltransferase enzyme.

In one embodiment preferably the phospholipase C is added before the lipid acyltransferase.

It has been surprisingly found that using a combination of a lipid acyltransferase and a phospholipase C significantly increases the yield of oil in the oil phase after completion of the water degumming process.

Without wishing to be bound by theory, it is envisaged that the phospholipase C hydrolyses the phospholipid (e.g. phosphatidylcholine) to a diglyceride (e.g. 1,2-diacylglycerol) and a phosphate moiety (e.g. choline phosphate) and the lipid acyltransferase then transfers a fatty acid onto the diglyceride formed by the phospholipase C—thus forming more triglyceride and increasing the oil yield. This effect leads to a synergistic (i.e. preferably more than additive) increase on oil yield.

In one embodiment, suitably the method of degumming an edible oil and/or use according to the present invention may be carried out at between about 45-90° C., preferably between about 45 to about 70° C.

In another embodiment, suitably the method of degumming an edible oil process and/or use according to the present invention may be carried out at above about 44° C., more preferably above about 45° C., more preferably above about 50° C.

In another embodiment, suitably the process and/or use according to the present invention may be carried out at below about 60° C., preferably below about 65° C., preferably below about 70° C.

In one embodiment, suitably the process and/or use according to the present invention may be carried out at between about 45-70° C., preferably between about 45-68° C., more preferably between about 50-65° C. degrees Celsius.

Suitably the temperature of the oil and/or water may be at the desired reaction temperature when the enzyme is admixed therewith.

The oil and/or water may be heated and/or cooled to the desired temperature before and/or during enzyme addition. Therefore in one embodiment it is envisaged that a further step of the process according to the present invention may be the cooling and/or heating of the oil and/or water.

Preferably the water content for the process according to the present invention may be between about 0.1-4% w/w, more preferably between about 0.1-3% w/w, more preferably between about 0.5-3% w/w.

In one embodiment the water content for the process according to the present invention may be between about 1-3% w/w.

In one embodiment the water content for the process according to the present invention may be less than about 3% w/w, suitably less than about 2%.

In one embodiment the water content for the process may be less than 1%. Reducing the amount of water to less than about 1% can result in a significant financial advantage in a water degumming process. Therefore being able to reduce the amount of water to less than about 1% can lead to significant cost reductions.

Suitably the reaction time (i.e. the time period in which the admixture is agitated) may be between about 10 minutes and about 180 minutes, preferably between about 15 minutes and about 180 minutes, more preferably between about 15 minutes and 60 minutes, even more preferably between about 15 minutes and about 35 minutes.

In one embodiment suitably the reaction time may be between about 30 minutes and about 180 minutes, preferably between about 30 minutes and about 60 minutes.

In one embodiment the process is preferably carried out at above about pH 4.5, above about pH 5 or above about pH 6.

Preferably the process is carried out between about pH 4.6 and about pH 10.0, more preferably between about pH 5.0 and about pH 10.0, more preferably between about pH 6.0 and about pH 10.0, more preferably between about pH 5.0 and about pH 7.0, more preferably between about pH 5.0 and about pH 6.5, and even more preferably between about pH 5.5 and pH 6.0.

In one embodiment the process may be carried out at a pH between about 5.3 to 8.3.

In one embodiment the process may be carried out at a pH between about 6-6.5, preferably about 6.3.

Suitably the pH may be neutral (about pH 5.0-about pH 7.0) in the methods and/or uses of the present invention.

Preferably the enzyme treatment occurs in the degumming process without pH adjustment of the oil and/or water. Therefore typically, the pH will be about 5.5-7.5.

This results in a significant advantage over prior art processes using phospholipase A enzymes which are typically only highly active in acid pH conditions, i.e. pH4-5. Therefore typically in prior art processes (for example using phospholipase A enzymes) the pH of the oil must be adjusted to more acidic conditions.

In addition, the use of a lipid acyltransferase with a phospholipase C enzyme has a significant advantage compared with the use of say a phospholipase A with a phospholipase C enzyme because the pH optima for lipid acyltransferases typically coincide much better with the pH optima for phospholipase C enzymes. Therefore, generally there is no "pH-conflict" when lipid acyltransferases are used in combination with phospholipase C enzymes. This contrasts sharply with the use of phospholipase A enzymes in combination with phospholipase C enzymes. Therefore, the use of lipid acyltransferases in combination with phospholipase C enzymes provides a significant improvement as both enzymes can work in their optimal pH range or simultaneously.

The separation of the oil phase and the gum phase may be carried out by any conventional separation method. Preferably the separation is carried out by centrifugation.

One significant advantage of the use of lipid acyltransferases (either alone or preferably in combination with a phospholipase C enzyme) is that the enzyme treatment makes it possible to adjust the centrifuge to control the amount of phosphor in the final oil. Without wishing to be bound by theory this is achievable because the viscosity of the oil is significantly reduced compared with an oil not treated with the lipid acyltransferase (either alone or preferably in combination with a phospholipase C enzyme). This is a significant advance over prior art processes. Typically, in conventional degumming processes the centrifugation results in a phosphor level in the oil of about 50 ppm. In fact the specification guide for the level of phosphor in an edible oil is that it should be less than 200 ppm. It is actually optimal to have oils with a phosphor level as close as possible to the 200 ppm level. The use of the lipid acyltransferase (either alone or preferably in combination with a phospholipase C enzyme) results in an oil which can be centrifuged to a phosphor level of between about 100-200 ppm, preferably about 170-190 ppm, more preferably about 180 ppm. Adjustment of the centrifuge to give these levels of phosphor had prior to the present invention been very difficult and provides a significant improvement in respect of the present invention.

Suitably the water may be admixed with the edible oil, prior to or at the same time as admixing with the enzyme. Alternatively, the edible oil and enzyme may be admixed before admixing with the water.

In one embodiment the oil, water and enzyme may be pumped in a stream simultaneously or substantially simultaneously through a mixer and into a holding tank.

Suitably the enzyme may be inactivated at during and/or at the end of the process.

The enzyme may be inactivated before or after separation of the oil phase and the gum phase.

Suitably the enzyme may be heat deactivated by heating for 10 mins at 75-85° C. or at above 92° C.

In one embodiment suitably the enzyme may be not deactivated in the gum phase. Thus when the gum phase is collected and incubated the enzyme may further degrade the phospholipids in the gum phase. After an extended incubation of the gum phase a further separation may be carried out (e.g. by centrifugation) in order to recover yet more oil from the gum phase. This may increase yet further the oil yield.

Without wishing to be bound by theory, the enzyme is thought to degrade the phospholipids to free fatty acids in the gum phase thus releasing triacylglyceride which had been previously emulsified with the phospholipids. This lowers the viscosity of the gum phase and allows the triacylglycerides and free fatty acids to be separated, for example by centrifugation.

In one embodiment suitably the process of the present invention may be carried out without the addition of an alkaline, such as NaOH for example.

In another embodiment suitably the process of the present invention may be carried out in the presence of an alkali, such as NaOH for example. When NaOH is added, preferably it is not added in an amount which exceeds about 0.2 ml (4% solution) NaOH per 100 g oil.

Enzymes suitable for use in the methods and/or uses of the invention may have lipid acyltransferase activity as determined using the "Transferase Assay (Cholesterol: Phospholipid) (TrU)" below.

Determination of Transferase activity "TRANSFERASE ASSAY (CHOLESTEROL:PHOSPHOLIPID)" (TrU)

Substrate: 50 mg Cholesterol (Sigma C8503) and 450 mg Soya phosphatidylcholine (PC), Avanti #441601 is dissolved in chloroform, and chloroform is evaporated at 40° C. under vacuum.

300 mg PC:cholesterol 9:1 is dispersed at 40° C. in 10 ml 50 mM HEPES buffer pH 7.

Enzymation:

250 µl substrate is added in a glass with lid at 40° C.

25 µl enzyme solution is added and incubated during agitation for 10 minutes at 40° C.

The enzyme added should esterify 2-5% of the cholesterol in the assay.

Also a blank with 25 µl water instead of enzyme solution is analysed.

After 10 minutes 5 ml Hexan:Isopropanol 3:2 is added.

The amount of cholesterol ester is analysed by HPTLC using Cholesteryl stearate (Sigma C3549) standard for calibration.

Transferase activity is calculated as the amount of cholesterol ester formation per minute under assay conditions.

One Transferase Unit (TrU) is defined as µmol cholesterol ester produced per minute at 40° C. and pH 7 in accordance with the transferase assay given above.

Preferably, the lipid acyltransferase used in the method and uses of the present invention will have a specific transferase unit (TrU) per mg enzyme of at least 25 TrU/mg enzyme protein.

Suitably the lipid acyltransferase for use in the present invention may be dosed in amount of 0.05 to 50 TrU per g oil, suitably in an amount of 0.5 to 5 TrU per g oil.

More preferably the enzymes suitable for use in the methods and/or uses of the present invention have lipid acyltransferase activity as defined by the protocol below:

Protocol for the Determination of % Acyltransferase Activity:

An edible oil to which a lipid acyltransferase according to the present invention has been added may be extracted following the enzymatic reaction with $CHCl_3:CH_3OH$ 2:1 and the organic phase containing the lipid material is isolated and analysed by GLC and HPLC according to the procedure detailed hereinbelow. From the GLC and HPLC analyses the amount of free fatty acids and one or more of sterol/stand esters; are determined. A control edible oil to which no enzyme according to the present invention has been added, is analysed in the same way.

Calculation:

From the results of the GLC and HPLC analyses the increase in free fatty acids and sterol/stanol esters can be calculated:

Δ% fatty acid=% Fatty acid(enzyme)−% fatty acid (control);

Mv fatty acid=average molecular weight of the fatty acids;

$A$=Δ% sterol ester/Mv sterol ester(where Δ% sterol ester=% sterol/stanol ester(enzyme)−% sterol/stanol ester(control) and Mv sterol ester=average molecular weight of the sterol/stanol esters);

The transferase activity is calculated as a percentage of the total enzymatic activity:

$$\% \text{ transferase activity} = \frac{A \times 100}{A + \Delta\% \text{ fatty acid}/(Mv \text{ fatty acid})}$$

If the free fatty acids are increased in the edible oil they are preferably not increased substantially, i.e. to a significant degree. By this we mean, that the increase in free fatty acid does not adversely affect the quality of the edible oil.

The edible oil used for the acyltransferase activity assay is preferably the soya bean oil supplemented with plant sterol (1%) and phosphatidylcholine (2%) oil using the method:

Plant sterol and phosphatidylcholine were dissolved in soya bean oil by heating to 95° C. during agitation. The oil was then cooled to 40° C. and the enzymes were added. Water was added to a total concentration of 5% of the oil phase. The sample was maintained at 40° C. with magnetic stirring and samples were taken out after 4 and 20 hours and analysed by TLC.

For the assay the enzyme dosage used is preferably 0.2 TIPU-K/g oil, more preferably 0.08 TIPU-K/g oil, preferably 0.01 TIPU-K/g oil. The level of phospholipid present in the oil and/or the % conversion of sterol is preferably determined after 0.5, 1, 2, 4 and 20 hours, more preferably after 20 hours.

When the enzyme used is a lipid acyltransferase enzyme preferably the incubation time is effective to ensure that there is at least 5% transferase activity, preferably at least 10% transferase activity, preferably at least 15%, 20%, 25% 26%, 28%, 30%, 40% 50%, 60% or 75% transferase activity.

The % transferase activity (i.e. the transferase activity as a percentage of the total enzymatic activity) may be determined by the protocol taught above.

In some aspects of the present invention, the term "without substantially increasing free fatty acids" as used herein means that the amount of free fatty acid in a edible oil treated with an lipid acyltransferase according to the present invention is less than the amount of free fatty acid produced in the edible oil when an enzyme other than a lipid acyltransferase according to the present invention had been used, such as for example as compared with the amount of free fatty acid produced when a conventional phospholipase enzyme, e.g. Lecitase Ultra™ (Novozymes A/S, Denmark), had been used.

In addition to, or instead of, assessing the % transferase activity in an oil (above), to identify the lipid acyl transferase enzymes most preferable for use in the methods of the invention the following assay entitled "Protocol for identifying lipid acyltransferases for use in the present invention" can be employed.

Protocol for Identifying Lipid Acyltransferases

A lipid acyltransferase in accordance with the present invention is one which results in:
  i) the removal of phospholipid present in a soya bean oil supplemented with plant sterol (1%) and phosphatidylcholine (2%) oil (using the method: Plant sterol and phosphatidylcholine were dissolved in soya bean oil by heating to 95° C. during agitation. The oil was then cooled to 40° C. and the enzymes were added. The sample was maintained at 40° C. with magnetic stirring and samples were taken out after 0.5, 1, 2, 4 and 20 hours and analysed by TLC); and/or
  ii) the conversion (% conversion) of the added sterol to sterol-ester (using the method taught in i) above). The GLC method for determining the level of sterol and sterol esters as taught in Example 2 may be used.

For the assay the enzyme dosage used may be 0.2 TIPU-K/g oil, preferably 0.08 TIPU-K/g oil, preferably 0.01 TIPU-K/g oil. The level of phospholipid present in the oil and/or the conversion (% conversion) of sterol is preferably determined after 0.5, 1, 2, 4 and 20 hours, more preferably after 20 hours.

In the protocol for identifying lipid acyl transferases, after enzymatic treatment, 5% water is preferably added and thoroughly mixed with the oil. The oil is then separated into an oil and water phase using centrifugation (see "Enzyme-catalyzed degumming of vegetable oils" by Buchold, H. and Laurgi A.-G., Fett Wissenschaft Technologie (1993), 95(8), 300-4, ISSN: 0931-5985), and the oil phase can then be analysed for phosphorus content using the following protocol ("Assay for Phosphorus Content"):

Assay for Phosphorus Content

The level of phospholipid present in an oil after water degumming is determined by first preparing the oil sample according to the sample preparation taught in the AOAC Official Method 999.10 (>Lead, Cadmium, Zinc, Copper, and Iron in Foods Atomic Absorption Spectrophotometry after Microwave Digestion, First Action 1999 NMKL-AOAC Method). The amount of phospholipids in the oil is then measured by analysing the phosphorus content in the oil sample after degumming according to the AOAC Official Method Ca 20-99: Analysis of Phosphorus in oil by inductively Coupled Plasma Optical Emission Spectroscopy.

The amount of phosphorus present in the oil phase after using the present invention is typically not significantly different from the phosphorus content in the oil phase after conventional water degumming (i.e. without enzyme).

The oil yield using the present invention in the oil phase using the present invention is substantially increased compared with oil phase after using a conventional water degumming process (i.e. without enzyme). Suitably the process and/or use according to the present invention improves yield by about 0.25 to 7%, such as by about 0.25 to 3%, or about 0.5 to 2%, or about 1 to 2% compared with the same oil which has undergone the same water degumming process without addition of the enzyme.

Surprisingly it was found that the addition of enzyme in the process according to the present invention provides significantly higher oil yield in the oil phase without necessarily significantly reducing the phosphorus content of the oil phase compared with a comparable oil phase obtained using a comparative water degumming process but without addition of enzyme.

Suitably the amount of phosphorus in the oil phase when the oil has been treated in accordance with a process or use of the present invention may be 0-80%, suitably 0-50%, suitably 0-10%, suitably 0-1% less than the phosphorus content of an oil phase obtained using a comparative water degumming process but without addition of enzyme.

Notably the oil phase obtained in the process according to the present invention may be further degummed to remove phosphatides and/or phospholipids. For example the oil phase may undergo either enzymatic degumming and/or acid degumming.

The % conversion of the sterol present in the oil is at least 1%, preferably at least 5%, preferably at least 10%, preferably at least 20%, preferably at least 30%, preferably at least 40%, preferably at least 50%, preferably at least 60%, preferably at least 70%, preferably at least 80%, preferably at least 90%, preferably at least 95%.

In one embodiment the % conversion of the sterol present in the oil is at least 5%, preferably at least 20%.

In some aspects, the lipid acyltransferase for use in any one of the methods and/or uses of the present invention may comprise a GDSx motif and/or a GANDY motif.

Preferably, the lipid acyltransferase enzyme is characterised as an enzyme which possesses acyltransferase activity and which comprises the amino acid sequence motif GDSX, wherein X is one or more of the following amino acid residues L, A, V, I, F, Y, H, Q, T, N, M or S.

Suitably, the nucleotide sequence encoding a lipid acyltransferase or lipid acyltransferase for use in any one of the methods and/or uses of the present invention may be obtainable, preferably obtained, from an organism from one or more of the following genera: *Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas* and *Candida*. Preferably, the lipid acyltransferase is obtainable, preferably obtained, from an organism from the genus *Aeromonas*.

In some aspects of the present invention, the nucleotide sequence encoding a lipid acyltransferase for use in any one of the methods and/or uses of the present invention encodes a lipid acyltransferase that comprises an aspartic acid residue at a position corresponding to N-80 in the amino acid sequence of the *Aeromonas salmonicida* lipid acyltransferase shown as SEQ ID No. 35.

In some aspects of the present invention, the lipid acyltransferase for use in any one of the methods and/or uses of the present invention is a lipid acyltransferase that comprises an aspartic acid residue at a position corresponding to N-80 in the amino acid sequence of the *Aeromonas salmonicida* lipid acyltransferase shown as SEQ ID No. 35.

In addition or in the alternative, the nucleotide sequence encoding a lipid acyltransferase for use in any one of the methods and/or uses of the present invention encodes a lipid acyltransferase that may comprise the amino acid sequence shown as SEQ ID No. 16, or an amino acid sequence which has 75% or more homology thereto. Suitably, the nucleotide sequence encoding a lipid acyltransferase encodes a lipid acyltransferase that may comprise the amino acid sequence shown as SEQ ID No. 16.

In addition or in the alternative, the nucleotide sequence encoding a lipid acyltransferase for use in any one of the methods and/or uses of the present invention encodes a lipid acyltransferase that may comprise the amino acid sequence shown as SEQ ID No. 68, or an amino acid sequence which has 75% or more homology thereto. Suitably, the nucleotide sequence encoding a lipid acyltransferase encodes a lipid acyltransferase that may comprise the amino acid sequence shown as SEQ ID No. 68.

In one embodiment the lipid acyltransferase for use in any one of the methods and/or uses of the present invention has an amino acid sequence shown in SEQ ID No. 16 or SEQ ID No. 68, or has an amino acid sequence which has at least 75% identity therewith, preferably at least 80%, preferably at least 85%, preferably at least 95%, preferably at least 98% identity therewith.

In one embodiment the lipid acyltransferase for use in any one of the methods and/or uses of the present invention is encoded by a nucleotide sequence shown in SEQ ID No. 49, or is encoded by a nucleotide sequence which has at least 75% identity therewith, preferably at least 80%, preferably at least 85%, preferably at least 95%, preferably at least 98% identity therewith.

In one embodiment preferably the lipid acyltransferase for use in any one of the methods and/or uses of the present invention is a lipid acyltransferase that is expressed in *Bacillus licheniformis* by transforming said *B. licheniformis* with a nucleotide sequence shown in SEQ ID No. 1 or a nucleotide sequence having at least 75% therewith (more preferably at least 80%, more preferably at least 85%, more preferably at least 95%, more preferably at least 98% identity therewith); culturing said *B. licheniformis* and isolating the lipid acyltransferase(s) produced therein.

The term "edible oil" as uses herein may encompass vegetable oils.

Preferably, the edible oil prior to treatment in accordance with the present invention is a crude edible oil comprising a non-hydratable phosphorus content of about 50-3000 ppm, more preferably in the range of about 50-1400 ppm, more preferably in the range of about 200-1400 ppm, and even more preferably in the range of about 400-1200 ppm.

In one aspect, the crude edible oil has, prior to carrying out the method of the invention, a phosphorous content above 350 ppm, more preferably above 400 ppm, even more preferably above 500 ppm, and most preferably above 600 ppm.

Preferably the edible oil is a vegetable oil.

Oils encompassed by the method according to the present invention may include, but are not limited to, one or more of soya bean oil, canola oil, corn oil, cottonseed oil, palm oil, coconut oil, rice bran oil, peanut oil, olive oil, safflower oil, palm kernel oil, rape seed oil and sunflower oil.

Preferably, the oil is one or more of soya bean oil, corn oil, sunflower oil and rape seed oil (sometimes referred to as canola oil).

More preferably, the oil is one or more of soya bean oil, sunflower oil or rape seed oil.

Most preferably, the oil is soya bean oil.

As used herein, "crude oil" (also referred to herein as a non-degummed oil) may be a pressed or extracted oil or a mixture thereof.

The phosphatide content in a crude oil may vary from 0.5-3% w/w corresponding to a phosphorus content in the range of 200-1200 ppm, more preferably in the range of 250-1200 ppm.

Apart from the phosphatides the crude oil may also contain small concentrations of carbohydrates, sugar compounds and metal/phosphatide acid complexes of Ca, Mg and Fe.

Advantageously, the method and uses of the present invention enable degumming of edible oils in a low water (<5%, preferably less than 2%, more preferably less than 1%) environments. Therefore water degumming can be performed with adding less water than when using a conventional water degumming process.

A further advantage of the present invention is the production of sterol esters in the oil phase.

Suitably the enzyme may be dosed in a range of about 0.01-10 TIPU-K/g oil, suitably the enzyme may be dosed in the range of about 0.05 to 1.5 TIPU-K/g oil, more preferably at 0.2-1 TIPU-K/g oil.

When the enzyme is a lipid acyltransferase suitably it may be dosed in the range of about 0.01 TIPU-K units/g oil to 5 TIPU-K units/g oil. In one embodiment the lipid acyltransferase may be dosed in the range of about 0.1 to about 1 TIPU-K units/g oil, more preferably the lipid acyltransferase may be dosed in the range of about 0.1 to about 0.5 TIPU-K units/g oil, more preferably the lipid acyltransferase may be dosed in the range of about 0.1 to about 0.3 TIPU-K units/g oil.

When the enzyme is a phospholipase suitably it may be dosed in the range of about 0.5-10 TIPU-K units/g oil. In one embodiment the phospholipase may be dosed in the range of about 0.5-5 TIPU-K units/g oil, preferably the phospholipase may be dosed in the range of about 0.5-1.5 TIPU-K units/g oil. Suitably the phospholipase may be dosed in the range of about 1.0-3 TIPU-K units/g oil.

Phospholipase Activity, TIPU-K:

Substrate: 1.75% L-Plant Phosphatidylcholin 95% (441601, Avanti Polar Lipids), 6.3% Triton X-100 (#T9284, Sigma) and 5 mM $CaCl_2$ dissolved in 50 mm Hepes pH 7.0. Assay procedure: Samples, calibration, and control were diluted in 10 mM HEPES pH 7.0, 0.1% Triton X-100 (#T9284, Sigma). Analysis was carried out using a Konelab Autoanalyzer (Thermo, Finland). The assay was run at 30 C. 34 μL substrate was thermostatted for 180 seconds, before 4 μL sample was added. Enzymation lasted 600 sec. The amount of free fatty acid liberated during enzymation was measured using the NEFA C kit (999-75406, WAKO, Germany). 56 μL NEFA A was added and the mixture was incubated for 300 sec. Afterwards, 113 μL NEFA B was added and the mixture was incubated for 300 sec. OD 520 nm was then measured. Enzyme activity (μmol FFA/minmL) was calculated based on a standard enzyme preparation.

Enzyme activity TIPU-K was calculated as micromole free fatty acid (FFA) produced per minute under assay conditions.

In the present invention the process is preferably not a caustic neutralisation process (i.e. is not an acid-water degumming process and/or is not a acid-caustic degumming process). In other words, the process preferably does not comprise the addition of acids (such as phosphoric, citric, ascorbic, sulphuric, fumaric, maleic, hydrochloric and/or acetic acids) or caustics (such as KOH and NaOH), or does not comprise the addition of substantial amounts of acids or caustics. In other words if acids and/or caustics are added in the process of the present invention they are added at less than 0.004%.

For the ease of reference, these and further aspects of the present invention are now discussed under appropriate section headings. However, the teachings under each section are not necessarily limited to each particular section.

Phospholipase C

As mentioned above, the phospholipid degrading enzyme (preferably a lipid acyltransferase) may be used in combination with a phospholipase C (E.C. 3.1.4.3).

The phospholipase C may be any available phospholipase C enzyme and may be selected from one or more of the following phospholipase C enzymes: Purifine® (available from Verenium, US); a phospholipase C from *Clostridium perfringens* (such as the phospholipase C available from Sigma, Ref P7633); a phospholipase C from *Bacillus cereus* (such as the phospholipase C available from Sigma, Ref P6621); a phospholipase C enzyme taught in WO2008/036863 (incorporated herein by reference).

Advantages

One advantage of the present invention is that an increased oil yield is obtained at the end of the water degumming process. The increase in oil yield is compared with a comparable water degumming process but without the addition of an enzyme in accordance with the present invention.

Without wishing to be bound by theory, the increased yield may be due to a decreased emulsifying effect caused by the removal of the phospholipids to the gum phase. Phospholipids are good emulsifiers and may be emulsified with triacylglyceride thus when the phospholipids are removed to the gum phase some oil in the form of triacylglyceride (oil) is also removed. A reduction in the viscosity of the gum phase due to the degradation of the phospholipids helps prevent the loss of oil to the gum phase (as separation is of the gum phase and the oil is much easier).

In addition or alternatively (without wishing to be bound by theory) when a lipid acyltransferase is used in accordance with the present invention sterol esters are formed by transferring a fatty acid moiety from a phospholipids to a sterol. This fatty acid moiety esterified to sterol by the lipid acyltransferase enzyme reaction is found in the oil phase and not in the gum phase. In conventional water degumming processes (without addition of lipid acyltransferase) these fatty acid moieties are lost to the gum phase.

A further advantage of the present invention is that when a lipid acyltransferase is used the pH in the water degumming process (about pH 5.0 or 5.5 to about pH 6.5 or 7) does not need to be adjusted. This pH results in a high reactivity of the lipid acyltransferase.

Another advantage of the present invention when using a lipid acyltransferase is the fatty acid from the phospholipids is transferred onto a sterol to form sterol esters. This on its own may contribute from between 0.1 to 0.15% increase in yield in the oil phase.

A further advantage of the present invention (particularly when using a lipid acyltransferase) is that the gum phase is less viscous compared with the gum phase from a comparable water degumming process but without the addition of an enzyme in accordance with the present invention. Lower viscosity in the gum phase results in it being easier to separate from the oil phase, i.e. by centrifugation.

In addition the gum phase may have a lower water content hence it may be easier to dry out.

A yet further advantage of the present invention is that there is a reduced triglyceride concentration in the gum phase.

The process of the present invention may result in a decreased fouling in the processing plant. This means that cleaning of the plant may be easier.

Without wishing to be bound by theory it has surprisingly been found that the lipid acyltransferase can use the diglyceride (produced by the reaction of the phospholipase C) as an acceptor molecule to produce triglyceride. Thus when a lipid acyltransferase is used in combination with a phospholipase C the interaction between these enzymes results in a synergistic increase in the amount of triglyceride in an oil comprising both enzymes compared with a comparable oil comprising either enzyme alone or a comparable oil comprising no enzyme. When a lipid acyltransferase is used in combination with a phospholipase C the interaction between these enzymes results in a synergistic increase oil yield in an oil comprising both enzymes compared with a comparable oil comprising either enzyme alone or a comparable oil comprising no enzyme.

The use of a combination of these enzymes has significant advantages over the use of a phospholipase C alone as the accumulation of diglycerides in an oil (which can occur when a phospholipase C is used alone) can be detrimental to the oil because it can have a negative impact on the "smoke point" of the oil and/or can have a negative impact on the crystallisation properties of more saturated fat sources.

Hence in the present invention another advantage of the use of lipid acyltransferases (particularly when in combination with a phospholipase C) is that the amount of diglyceride in the oil can be reduced compared with a comparable oil without the lipid acyltransferase and/or particularly compared with a comparable oil treated with phospholipase C alone.

Use of the enzyme(s) in accordance with the present invention can reducing the amount of water needed in the process to less than about 1%. This can result in a significant financial advantage in a water degumming process. Therefore being able to reduce the amount of water to less than about 1% can lead to significant cost reductions.

Preferably the enzyme treatment occurs in the degumming process without pH adjustment of the oil and/or water. This results in a significant advantage over prior art processes using phospholipase A enzymes which are typically only highly active in acid pH conditions. Typically in prior art processes (for example using phospholipase A enzymes) the pH of the oil must be adjusted before and/or during the degumming process. This is not necessary with the present invention.

In addition, the use of a lipid acyltransferase in combination with a phospholipase C enzyme has a significant advantage compared with the use of say a phospholipase A with a phospholipase C enzyme because the pH optima for lipid acyltransferases typically coincide much better with the pH optima for phospholipase C enzymes. Therefore, generally there is no "pH-conflict" when lipid acyltransferases are used in combination with phospholipase C enzymes. This contrasts sharply with the use of phospholipase A enzymes in combination with phospholipase C enzymes. Therefore, the use of lipid acyltransferases in combination with phospholipase C enzymes provides a significant improvement as both enzymes can work in their optimal pH range or simultaneously.

Notably in the method which comprises treatment of the gum phase with a lipid acyltransferase (either alone or in combination with a phospholipase C) the "acid oil" produced at the end of this process can be sold with a higher value than the normal gum phase which is added to meal. In addition the remaining gum phase (after separation of the acid oil) has surprisingly been found to have a higher phosphor level than normal gum and thus can be used as a source of organic phosphor.

Host Cell

The host organism can be a prokaryotic or a eukaryotic organism.

In one embodiment of the present invention the lipid acyl transferase according to the present invention in expressed in a host cell, for example a bacterial cells, such as a *Bacillus* spp, for example a *Bacillus licheniformis* host cell.

Alternative host cells may be fungi, yeasts or plants for example.

It has been found that the use of a *Bacillus licheniformis* host cell results in increased expression of a lipid acyltransferase when compared with other organisms, such as *Bacillus subtilis*.

A lipid acyltransferase from *Aeromonas salmonicida* has been inserted into a number of conventional expression vectors, designed to be optimal for the expression in *Bacillus subtilis*, *Hansenula polymorpha*, *Schizosaccharomyces pombe* and *Aspergillus tubigensis*, respectively. Only very low levels were, however, detected in *Hansenula polymorpha*, *Schizosaccharomyces pombe* and *Aspergillus tubigensis*. The expression levels were below 1 µg/ml, and it was not possible to select cells which yielded enough protein to initiate a commercial production (results not shown). In contrast, *Bacillus licheniformis* was able to produce protein levels, which are attractive for an economically feasible production.

In particular, it has been found that expression in *B. licheniformis* is approximately 100-times greater than expression in *B. subtilis* under the control of aprE promoter or is approximately 100-times greater than expression in *S. lividans* under the control of an A4 promoter and fused to cellulose (results not shown herein).

The host cell may be any *Bacillus* cell other than *B. subtilis*. Preferably, said *Bacillus* host cell being from one of the following species: *Bacillus licheniformis; B. alkalophilus; B. amyloliquefaciens; B. circulans; B. clausii; B. coagulans; B. firmus; B. lautus; B. lentus; B. megaterium; B. pumilus* or *B. stearothermophilus*.

The term "host cell"—in relation to the present invention includes any cell that comprises either a nucleotide sequence encoding a lipid acyltransferase as defined herein or an expression vector as defined herein and which is used in the recombinant production of a lipid acyltransferase having the specific properties as defined herein.

Suitably, the host cell may be a protease deficient or protease minus strain and/or an α-amylase deficient or α-amylase minus strain.

The term "heterologous" as used herein means a sequence derived from a separate genetic source or species. A heterologous sequence is a non-host sequence, a modified sequence, a sequence from a different host cell strain, or a homologous sequence from a different chromosomal location of the host cell.

A "homologous" sequence is a sequence that is found in the same genetic source or species i.e. it is naturally occurring in the relevant species of host cell.

The term "recombinant lipid acyltransferase" as used herein means that the lipid acyltransferase has been produced by means of genetic recombination. For instance, the nucleotide sequence encoding the lipid acyltransferase has been inserted into a cloning vector, resulting in a *B. licheniformis* cell characterised by the presence of the heterologous lipid acyltransferase.

Regulatory Sequences

In some applications, a lipid acyltransferase sequence for use in the methods and/or uses of the present invention may be obtained by operably linking a nucleotide sequence encoding same to a regulatory sequence which is capable of providing for the expression of the nucleotide sequence, such as by the chosen host cell (such as a *B. licheniformis* cell).

By way of example, a vector comprising the nucleotide sequence of the present invention operably linked to such a regulatory sequence, i.e. the vector is an expression vector, may be used.

The term "operably linked" refers to a juxtaposition wherein the components described are in a relationship permitting them to function in their intended manner. A regulatory sequence "operably linked" to a coding sequence is ligated in such a way that expression of the coding sequence is achieved under conditions compatible with the control sequences.

The term "regulatory sequences" includes promoters and enhancers and other expression regulation signals.

The term "promoter" is used in the normal sense of the art, e.g. an RNA polymerase binding site.

Enhanced expression of the nucleotide sequence encoding the enzyme having the specific properties as defined herein may also be achieved by the selection of regulatory regions, e.g. promoter, secretion leader and terminator regions that are not regulatory regions for the nucleotide sequence encoding the enzyme in nature.

Suitably, the nucleotide sequence of the present invention may be operably linked to at least a promoter.

Suitably, the nucleotide sequence encoding a lipid acyltransferase may be operably linked to at a nucleotide sequence encoding a terminator sequence. Examples of suitable terminator sequences for use in any one of the vectors, host cells, methods and/or uses of the present invention include: an α-amylase terminator sequence (for instance, CGGGACTTACCGAAAGAAACCATCAAT-GATGGTTTCTTTTTTGTTCATAAA—SEQ ID No. 64), an alkaline protease terminator sequence (for instance, CAA-GACTAAAGACCGTTCGCCCGTTTTTG-CAATAAGGGGGCGAATCTTACATAAAA ATA—SEQ ID No. 65), a glutamic-acid specific terminator sequence (for instance, ACGGCCGTTAGATGTGACAGCCCGTTC-CAAAAGGAAGCGGGCTGTCTTCGTGTAT TATTGT—SEQ ID No. 66), a levanase terminator sequence (for instance, TCTTTTAAAGGAAAGGCTGGAATGCCCG-GCATTCCAGCCACATGATCATCGTTT—SEQ ID No. 67) and a subtilisin E terminator sequence (for instance, GCT-GACAAATAAAAAGAAGCAGGTATGGAG-GAACCTGCTTCTTTTTACTATTATTG). Suitably, the nucleotide sequence encoding a lipid acyltransferase may be operably linked to an α-amylase terminator, such as a *B. licheniformis* α-amylase terminator.

Promoter

The promoter sequence to be used in accordance with the present invention may be heterologous or homologous to the sequence encoding a lipid acyltransferase.

The promoter sequence may be any promoter sequence capable of directing expression of a lipid acyltransferase in the host cell of choice.

Suitably, the promoter sequence may be homologous to a *Bacillus* species, for example *B. licheniformis*. Preferably, the promoter sequence is homologous to the host cell of choice.

Suitably the promoter sequence may be homologous to the host cell. "Homologous to the host cell" means originating within the host organism; i.e. a promoter sequence which is found naturally in the host organism.

Suitably, the promoter sequence may be selected from the group consisting of a nucleotide sequence encoding: an α-amylase promoter, a protease promoter, a subtilisin promoter, a glutamic acid-specific protease promoter and a levansucrase promoter.

Suitably the promoter sequence may be a nucleotide sequence encoding: the LAT (e.g. the alpha-amylase promoter from *B. licheniformis*, also known as AmyL), AprL (e.g. subtilisin Carlsberg promoter), EndoGluC (e.g. the glutamic-acid specific promoter from *B. licheniformis*), AmyQ (e.g. the alpha amylase promoter from *B. amyloliquefaciens* alpha-amylase promoter) and SacB (e.g. the *B. subtilis* levansucrase promoter).

Other examples of promoters suitable for directing the transcription of a nucleic acid sequence in the methods of the present invention include: the promoter of the *Bacillus lentus* alkaline protease gene (aprH); the promoter of the *Bacillus subtilis* alpha-amylase gene (amyE); the promoter of the *Bacillus stearothermophilus* maltogenic amylase gene (amyM); the promoter of the *Bacillus licheniformis* penicillinase gene (penP); the promoters of the *Bacillus subtilis* xylA and xylB genes; and/or the promoter of the *Bacillus thuringiensis* subsp. *tenebrionis* CryIIIA gene.

In a preferred embodiment, the promoter sequence is an α-amylase promoter (such as a *Bacillus licheniformis* α-amylase promoter). Preferably, the promoter sequence comprises the −35 to −10 sequence of the *B. licheniformis* α-amylase promoter—see FIGS. 53 and 55.

The "−35 to −10 sequence" describes the position relative to the transcription start site. Both the "−35" and the "−10" are boxes, i.e. a number of nucleotides, each comprising 6 nucleotides and these boxes are separated by 17 nucleotides. These 17 nucleotides are often referred to as a "spacer". This is illustrated in FIG. 55, where the −35 and the −10 boxes are underlined. For the avoidance of doubt, where "−35 to −10 sequence" is used herein it refers to a sequence from the start of the −35 box to the end of the −10 box i.e. including both the −35 box, the 17 nucleotide long spacer and the −10 box.

Signal Peptide

The lipid acyltransferase produced by a host cell by expression of the nucleotide sequence encoding the lipid acyltransferase may be secreted or may be contained intracellularly depending on the sequence and/or the vector used.

A signal sequence may be used to direct secretion of the coding sequences through a particular cell membrane. The signal sequences may be natural or foreign to the lipid acyltransferase coding sequence. For instance, the signal peptide coding sequence may be obtained form an amylase or protease gene from a *Bacillus* species, preferably from *Bacillus licheniformis*.

Suitable signal peptide coding sequences may be obtained from one or more of the following genes: maltogenic α-amylase gene, subtilisin gene, beta-lactamase gene, neutral protease gene, prsA gene, and/or acyltransferase gene.

Preferably, the signal peptide is a signal peptide of *B. licheniformis* α-amylase, *Aeromonas* acyltransferase (for instance, mkkwfvcllglialtvqa—SEQ ID No. 21), *B. subtilis* subtilisin (for instance, mrskklwisllfaltliftmafsnmsaqa—SEQ ID No. 22) or *B. licheniformis* subtilisin (for instance, mmrkksfwfgmltafmlvftmefsdsasa—SEQ ID No. 23). Suitably, the signal peptide may be the signal peptide of *B. licheniformis* α-amylase.

However, any signal peptide coding sequence capable of directing the expressed lipid acyltransferase into the secretory pathway of a *Bacillus* host cell (preferably a *B. licheniformis* host cell) of choice may be used.

In some embodiments of the present invention, a nucleotide sequence encoding a signal peptide may be operably linked to a nucleotide sequence encoding a lipid acyltransferase of choice.

The lipid acyltransferase of choice may be expressed in a host cell as defined herein as a fusion protein.

Expression Vector

The term "expression vector" means a construct capable of in vivo or in vitro expression.

Preferably, the expression vector is incorporated in the genome of the organism, such as a *B. licheniformis* host. The term "incorporated" preferably covers stable incorporation into the genome.

The nucleotide sequence encoding a lipid acyltransferase as defined herein may be present in a vector, in which the nucleotide sequence is operably linked to regulatory sequences such that the regulatory sequences are capable of providing the expression of the nucleotide sequence by a suitable host organism (such as *B. licheniformis*), i.e. the vector is an expression vector.

The vectors of the present invention may be transformed into a suitable host cell as described above to provide for expression of a polypeptide having lipid acyltransferase activity as defined herein.

The choice of vector, e.g. plasmid, cosmid, virus or phage vector, genomic insert, will often depend on the host cell into which it is to be introduced. The present invention may cover other forms of expression vectors which serve equivalent functions and which are, or become, known in the art.

Once transformed into the host cell of choice, the vector may replicate and function independently of the host cell's genome, or may integrate into the genome itself.

The vectors may contain one or more selectable marker genes—such as a gene which confers antibiotic resistance e.g. ampicillin, kanamycin, chloramphenicol or tetracyclin resistance. Alternatively, the selection may be accomplished by co-transformation (as described in WO91/17243).

Vectors may be used in vitro, for example for the production of RNA or used to transfect or transform a host cell.

The vector may further comprise a nucleotide sequence enabling the vector to replicate in the host cell in question. Examples of such sequences are the origins of replication of plasmids pUC19, pACYC177, pUB110, pE194, pAMB1 and pIJ702.

Lipid Acyl Transferase

The nucleotide sequence encoding a lipid acyl transferase for use in any one of the methods and/or uses of the present invention may encode a natural lipid acyl transferase or a variant lipid acyl transferase.

The lipid acyl transferase for use in any one of the methods and/or uses of the present invention may be a natural lipid acyl transferase or a variant lipid acyl transferase.

For instance, the nucleotide sequence encoding a lipid acyl transferase for use in the present invention may be one as described in WO2004/064537, WO2004/064987, WO2005/066347, or WO2006/008508. These documents are incorporated herein by reference.

The term "lipid acyl transferase" as used herein preferably means an enzyme that has acyltransferase activity (generally classified as E.C. 2.3.1.x, for example 2.3.1.43), whereby the enzyme is capable of transferring an acyl group from a lipid to one or more acceptor substrates, such as one or more of the following: a sterol; a stanol; a carbohydrate; a protein; a protein subunit; a sugar alcohol, such as ascorbic acid and/or glycerol—preferably glycerol and/or a sterol, such as cholesterol.

Preferably, the lipid acyl transferase for use in any one of the methods and/or uses of the present invention is a lipid acyltransferase that is capable of transferring an acyl group from a phospholipid (as defined herein) to a sugar alcohol, such as ascorbic acid and/or glycerol and/or a sterol, preferably glycerol or a sterol, most preferably a sterol (e.g. cholesterol).

For some aspects the "acyl acceptor" according to the present invention may be any compound comprising a hydroxy group (—OH), such as for example, polyvalent alcohols, including glycerol; sterols; stanols; carbohydrates; hydroxy acids including fruit acids, citric acid, tartaric acid, lactic acid and ascorbic acid; proteins or a sub-unit thereof, such as amino acids, protein hydrolysates and peptides (partly hydrolysed protein) for example; and mixtures and derivatives thereof. Preferably, the "acyl acceptor" according to the present invention is not water.

The acyl acceptor is preferably not a monoglyceride.

In one embodiment the acyl acceptor may be a diglyceride.

In one aspect, the lipid acyltransferase for use in the methods and/or uses of the present invention preferably is able to transfer an acyl group from a lipid to a sterol and/or a stanol.

In another aspect, the lipid acyltransferase for use in the methods and/or uses of the present invention may, as well as being able to transfer an acyl group from a lipid to a sterol and/or a stanol, additionally be able to transfer the acyl group from a lipid to one or more of the following: a carbohydrate, a protein, a protein subunit, glycerol, fatty alcohol.

Suitably, the acyl acceptor may be naturally found in the oil. Alternatively the acyl acceptor may be added to the oil (e.g. the acyl acceptor may be extraneous to the oil). For instance, in some embodiments a sterol and/or stanol may be added to the oil prior to or during the degumming process. This is particularly important if the amount of acyl acceptor is rate limiting on the acyltransferase reaction. Addition of an acyl acceptor may lead to reductions in free fatty acids and/or higher acyl acceptor ester formation compared to an oil where no additional acyl acceptor is added.

Preferably, the lipid substrate upon which the lipid acyl acts is one or more of the following lipids: a phospholipid, such as a lecithin, e.g. phosphatidylcholine and/or phosphatidylethanolamine.

This lipid substrate may be referred to herein as the "lipid acyl donor". The term lecithin as used herein encompasses phosphatidylcholine, phosphatidylethanolamine, phosphatidylinositol, phosphatidylserine and phosphatidylglycerol.

Preferred lipid acyltransferases for use in the present invention are identified as those which have a high activity such as high phospholipid hydrolytic activity or high phospholipid transferase activity on phospholipids in an oil environment, most preferably lipid acyl transferases for use in the present invention have a high phospholipid to sterol transferase activity.

As detailed above, other acyl-transferases suitable for use in the methods of the invention may be identified by identifying the presence of the GDSx, GANDY and HPT blocks either by alignment of the pFam00657 consensus sequence (SEQ ID No 1), and/or alignment to a GDSx acyltransferase, for example SEQ ID No 28. In order to assess their suitability for degumming, i.e. identify those enzymes which have a transferase activity of at least 5%, more preferably at least 10%, more preferably at least 20%, more preferably at least 30%, more preferably at least 40%, more preferably 50%, more preferably at least 60%, more preferably at least 70%, more preferably at least 80%, more preferably at least 90% and more preferably at least 98% of the total enzyme activity, such acyltransferases are tested using the "Protocol for the determination of % acyltransferase activity" assay detailed hereinabove.

For some aspects, preferably the lipid acyl transferase for use in any one of the methods and/or uses of the present invention is a lipid acyltransferase that is incapable, or substantially incapable, of acting on a triglyceride and/or a 1-monoglyceride and/or 2-monoglyceride.

For some aspects, preferably the lipid acyl transferase for use in any one of the methods and/or uses of the present invention is a lipid acyltransferase that does not exhibit triacylglycerol lipase activity (E.C. 3.1.1.3) or does not exhibit significant triacylglycerol lipase activity (E.C. 3.1.1.3).

The ability to hydrolyse triglyceride (E.C. 3.1.1.3 activity) may be determined by lipase activity is determined according to Food Chemical Codex (3rd Ed., 1981, pp 492-493) modified to sunflower oil and pH 5.5 instead of olive oil and pH 6.5. The lipase activity is measured as LUS (lipase units sunflower) where 1 LUS is defined as the quantity of enzyme which can release 1 [mu]mol of fatty acids per minute from sunflower oil under the above assay conditions. Alternatively the LUT assay as defined in WO9845453 may be used. This reference is incorporated herein by reference.

The lipid acyl transferase for use in any one of the methods and/or uses of the present invention may be a lipid acyltransferase which is substantially incapable of acting on a triglyceride may have a LUS/mg of less than 1000, for example less than 500, such as less than 300, preferably less than 200, more preferably less than 100, more preferably less than 50, more preferably less than 20, more preferably less than 10, such as less than 5, less than 2, more preferably less than 1 LUS/mg. Alternatively LUT/mg activity is less than 500, such as less than 300, preferably less than 200, more preferably less than 100, more preferably less than 50, more preferably less than 20, more preferably less than 10, such as less than 5, less than 2, more preferably less than 1 LUT/mg.

The lipid acyl transferase for use in any one of the methods and/or uses of the present invention may be a lipid acyltransferase which is substantially incapable of acting on a monoglyceride. This may be determined by using monooleate (M7765 1-Oleoyl-rac-glycerol 99%) in place of the sunflower oil in the LUS assay. 1 MGHU is defined as the quantity of enzyme which can release 1 [mu]mol of fatty acids per minute from monoglyceride under the assay conditions.

The lipid acyl transferase for use in any one of the methods and/or uses of the present invention is a lipid acyltransferase which is preferably substantially incapable of acting on a triglyceride may have a MGHU/mg of less than 5000, for example less than 1000, for example less than 500, such as less than 300, preferably less than 200, more preferably less than 100, more preferably less than 50, more preferably less than 20, more preferably less than 10, such as less than 5, less than 2, more preferably less than 1 MGHU/mg.

Suitably, the lipid acyltransferase for use in any one of the methods and/or uses of the present invention is a lipid acyltransferase which in addition to its lipid acyltransferase activity may also exhibit one or more of the following phospholipase activities: phospholipase A2 activity (E.C. 3.1.1.4) and/or phospholipase A1 activity (E.C. 3.1.1.32). The lipid acyl transferase may also have phospholipase B activity (E.C. 3.1.1.5).

Suitably, for some aspects the lipid acyltransferase may be capable of transferring an acyl group from a phospholipid to a stanol and/or sterol, preferably cholesterol.

For some aspects, preferably the lipid acyltransferase for use any one of the methods and/or uses of the present invention encodes a lipid acyltransferase that is capable of transferring an acyl group from a phospholipid to a sterol and/or a stanol to form at least a sterol ester and/or a stanol ester.

Thus, in one embodiment the "acyl acceptor" according to the present invention may be a plant sterol/stanol.

Preferably, the lipid acyltransferase enzyme may be characterised using the following criteria:
  the enzyme possesses acyl transferase activity which may be defined as ester transfer activity whereby the acyl part of an original ester bond of a lipid acyl donor is transferred to an acyl acceptor to form a new ester; and
  the enzyme comprises the amino acid sequence motif GDSX, wherein X is one or more of the following amino acid residues L, A, V, I, F, Y, H, Q, T, N, M or S.

Preferably, X of the GDSX motif is L or Y. More preferably, X of the GDSX motif is L. Thus, preferably the enzyme according to the present invention comprises the amino acid sequence motif GDSL.

The GDSX motif is comprised of four conserved amino acids. Preferably, the serine within the motif is a catalytic serine of the lipid acyl transferase enzyme. Suitably, the serine of the GDSX motif may be in a position corresponding to Ser-16 in *Aeromonas hydrophila* lipid acyltransferase enzyme taught in Brumlik & Buckley (Journal of Bacteriology April 1996, Vol. 178, No. 7, p 2060-2064).

To determine if a protein has the GDSX motif according to the present invention, the sequence is preferably compared with the hidden markov model profiles (HMM profiles) of the pfam database in accordance with the procedures taught in WO2004/064537 or WO2004/064987, incorporated herein by reference.

Preferably the lipid acyl transferase enzyme can be aligned using the Pfam00657 consensus sequence (for a full explanation see WO2004/064537 or WO2004/064987).

Preferably, a positive match with the hidden markov model profile (HMM profile) of the pfam00657 domain family indicates the presence of the GDSL or GDSX domain according to the present invention.

Preferably when aligned with the Pfam00657 consensus sequence the lipid acyltransferase for use in the methods or uses of the invention may have at least one, preferably more than one, preferably more than two, of the following, a GDSx block, a GANDY block, a HPT block. Suitably, the lipid acyltransferase may have a GDSx block and a GANDY block. Alternatively, the enzyme may have a GDSx block and a HPT block. Preferably the enzyme comprises at least a GDSx block. See WO2004/064537 or WO2004/064987 for further details.

Preferably, residues of the GANDY motif are selected from GANDY, GGNDA, GGNDL, most preferably GANDY.

Preferably, when aligned with the Pfam00657 consensus sequence the enzyme for use in the methods or uses of the invention have at least one, preferably more than one, preferably more than two, preferably more than three, preferably more than four, preferably more than five, preferably more than six, preferably more than seven, preferably more than eight, preferably more than nine, preferably more than ten, preferably more than eleven, preferably more than twelve, preferably more than thirteen, preferably more than fourteen, of the following amino acid residues when compared to the reference *A. hydrophilia* polypeptide sequence, namely SEQ ID No. 1: 28hid, 29hid, 30hid, 31hid, 32gly, 33Asp, 34Ser, 35hid, 130hid, 131Gly, 132Hid, 133Asn, 134Asp, 135hid, 309His.

The pfam00657 GDSX domain is a unique identifier which distinguishes proteins possessing this domain from other enzymes.

The pfam00657 consensus sequence is presented in FIG. 3 as SEQ ID No. 2. This is derived from the identification of the pfam family 00657, database version 6, which may also be referred to as pfam00657.6 herein.

The consensus sequence may be updated by using further releases of the pfam database (for example see WO2004/064537 or WO2004/064987).

In one embodiment, the lipid acyl transferase enzyme for use in any one of the methods and/or uses of the present invention is a lipid acyltransferase that may be characterised using the following criteria:
  (i) the enzyme possesses acyl transferase activity which may be defined as ester transfer activity whereby the acyl part of an original ester bond of a lipid acyl donor is transferred to acyl acceptor to form a new ester;
  (ii) the enzyme comprises the amino acid sequence motif GDSX, wherein X is one or more of the following amino acid residues L, A, V, I, F, Y, H, Q, T, N, M or S;
  (iii) the enzyme comprises His-309 or comprises a histidine residue at a position corresponding to His-309 in the *Aeromonas hydrophila* lipid acyltransferase enzyme shown in FIGS. 2 and 4 (SEQ ID No. 1 or SEQ ID No. 3).

Preferably, the amino acid residue of the GDSX motif is L.

In SEQ ID No. 3 or SEQ ID No. 1 the first 18 amino acid residues form a signal sequence. His-309 of the full length sequence, that is the protein including the signal sequence, equates to His-291 of the mature part of the protein, i.e. the sequence without the signal sequence.

In one embodiment, the lipid acyl transferase enzyme for use any one of the methods and uses of the present invention is a lipid acyltransferase that comprises the following catalytic triad: Ser-34, Asp-306 and His-309 or comprises a serine residue, an aspartic acid residue and a histidine residue, respectively, at positions corresponding to Ser-34, Asp-306 and His-309 in the *Aeromonas hydrophila* lipid acyl transferase enzyme shown in FIG. 4 (SEQ ID No. 3) or FIG. 2 (SEQ ID No. 1). As stated above, in the sequence shown in SEQ ID No. 3 or SEQ ID No. 1 the first 18 amino acid residues form a signal sequence. Ser-34, Asp-306 and His-309 of the full length sequence, that is the protein including the signal sequence, equate to Ser-16, Asp-288 and His-291 of the mature part of the protein, i.e. the sequence without the signal sequence. In the pfam00657 consensus sequence, as given in FIG. 3 (SEQ ID No. 2) the active site residues correspond to Ser-7, Asp-345 and His-348.

In one embodiment, the lipid acyl transferase enzyme for use any one of the methods and/or uses of the present invention is a lipid acyltransferase that may be characterised using the following criteria:
  the enzyme possesses acyl transferase activity which may be defined as ester transfer activity whereby the acyl part of an original ester bond of a first lipid acyl donor is transferred to an acyl acceptor to form a new ester; and
  the enzyme comprises at least Gly-32, Asp-33, Ser-34, Asp-134 and His-309 or comprises glycine, aspartic acid, serine, aspartic acid and histidine residues at positions corresponding to Gly-32, Asp-33, Ser-34, Asp-134 and His-309, respectively, in the *Aeromonas hydrophila* lipid acyltransferase enzyme shown in SEQ ID No. 3 or SEQ ID No. 1.

Suitably, the lipid acyltransferase enzyme for use in any one of the methods and/or uses of the present invention may be encoded by one of the following nucleotide sequences:
(a) the nucleotide sequence shown as SEQ ID No. 36 (see FIG. 29);
(b) the nucleotide sequence shown as SEQ ID No. 38 (see FIG. 31);
(c) the nucleotide sequence shown as SEQ ID No. 39 (see FIG. 32);
(d) the nucleotide sequence shown as SEQ ID No. 42 (see FIG. 35);
(e) the nucleotide sequence shown as SEQ ID No. 44 (see FIG. 37);
(f) the nucleotide sequence shown as SEQ ID No. 46 (see FIG. 39);
(g) the nucleotide sequence shown as SEQ ID No. 48 (see FIG. 41);
(h) the nucleotide sequence shown as SEQ ID No. 49 (see FIG. 57);
(i) the nucleotide sequence shown as SEQ ID No. 50 (see FIG. 58);
(j) the nucleotide sequence shown as SEQ ID No. 51 (see FIG. 59);
(k) the nucleotide sequence shown as SEQ ID No. 52 (see FIG. 60);
(l) the nucleotide sequence shown as SEQ ID No. 53 (see FIG. 61);
(m) the nucleotide sequence shown as SEQ ID No. 54 (see FIG. 62);
(n) the nucleotide sequence shown as SEQ ID No. 55 (see FIG. 63);
(o) the nucleotide sequence shown as SEQ ID No. 56 (see FIG. 64);
(p) the nucleotide sequence shown as SEQ ID No. 57 (see FIG. 65);
(q) the nucleotide sequence shown as SEQ ID No. 58 (see FIG. 66);
(r) the nucleotide sequence shown as SEQ ID No. 59 (see FIG. 67);
(s) the nucleotide sequence shown as SEQ ID No. 60 (see FIG. 68);
(t) the nucleotide sequence shown as SEQ ID No. 61 (see FIG. 69);
(u) the nucleotide sequence shown as SEQ ID No. 62 (see FIG. 70);
(v) the nucleotide sequence shown as SEQ ID No. 63 (see FIG. 71);
(w) or
a nucleotide sequence which has 70% or more, preferably 75% or more, identity with any one of the sequences shown as SEQ ID No. 36, SEQ ID No. 38, SEQ ID No. 39, SEQ ID No. 42, SEQ ID No. 44, SEQ ID No. 46, SEQ ID No. 48, SEQ ID No. 49, SEQ ID No. 50, SEQ ID No. 51, SEQ ID No. 52, SEQ ID No. 53, SEQ ID No. 54, SEQ ID No. 55, SEQ ID No. 56, SEQ ID No. 57, SEQ ID No. 58, SEQ ID No. 59, SEQ ID No. 60, SEQ ID No. 61, SEQ ID No. 62 or SEQ ID No. 63.

Suitably the nucleotide sequence may have 80% or more, preferably 85% or more, more preferably 90% or more and even more preferably 95% or more identity with any one of the sequences shown as SEQ ID No. 36, SEQ ID No. 38, SEQ ID No. 39, SEQ ID No. 42, SEQ ID No. 44, SEQ ID No. 46, SEQ ID No. 48, SEQ ID No. 49, SEQ ID No. 50, SEQ ID No. 51, SEQ ID No. 52, SEQ ID No. 53, SEQ ID No. 54, SEQ ID No. 55, SEQ ID No. 56, SEQ ID No. 57, SEQ ID No. 58, SEQ ID No. 59, SEQ ID No. 60, SEQ ID No. 61, SEQ ID No. 62 or SEQ ID No. 63.

In one embodiment, the nucleotide sequence encoding a lipid acyltransferase enzyme for use any one of the methods and uses of the present invention is a nucleotide sequence which has 70% or more, preferably 75% or more, identity with any one of the sequences shown as: SEQ ID No. 49, SEQ ID No. 50, SEQ ID No. 51, SEQ ID No. 62, and SEQ ID No. 63. Suitably the nucleotide sequence may have 80% or more, preferably 85% or more, more preferably 90% or more and even more preferably 95% or more identity with any one of the sequences shown as: SEQ ID No. 49, SEQ ID No. 50, SEQ ID No. 51, SEQ ID No. 62, and SEQ ID No. 63.

In one embodiment, the nucleotide sequence encoding a lipid acyltransferase enzyme for use in any one of the methods and uses of the present invention is a nucleotide sequence which has 70% or more, 75% or more, 80% or more, preferably 85% or more, more preferably 90% or more and even more preferably 95% or more identity the sequence shown as SEQ ID No. 49.

Suitably, the lipid acyl transferase enzyme for use any one of the methods and/or uses of the present invention may be a lipid acyltransferase that comprises one or more of the following amino acid sequences:
(i) the amino acid sequence shown as SEQ ID No. 68
(ii) the amino acid sequence shown as SEQ ID No. 3
(iii) the amino acid sequence shown as SEQ ID No. 4
(iv) the amino acid sequence shown as SEQ ID No. 5
(v) the amino acid sequence shown as SEQ ID No. 6
(vi) the amino acid sequence shown as SEQ ID No. 7
(vii) the amino acid sequence shown as SEQ ID No. 8
(viii) the amino acid sequence shown as SEQ ID No. 9
(ix) the amino acid sequence shown as SEQ ID No. 10
(x) the amino acid sequence shown as SEQ ID No. 11
(xi) the amino acid sequence shown as SEQ ID No. 12
(xii) the amino acid sequence shown as SEQ ID No. 13
(xiii) the amino acid sequence shown as SEQ ID No. 14
(xiv) the amino acid sequence shown as SEQ ID No. 1
(xv) the amino acid sequence shown as SEQ ID No. 15
(xvi) the amino acid sequence shown as SEQ ID No. 16
(xvii) the amino acid sequence shown as SEQ ID No. 17
(xviii) the amino acid sequence shown as SEQ ID No. 18
(xix) the amino acid sequence shown as SEQ ID No. 34
(xx) the amino acid sequence shown as SEQ ID No. 35 or
an amino acid sequence which has 75%, 80%, 85%, 90%, 95%, 98% or more identity with any one of the sequences shown as SEQ ID No. 68, SEQ ID No. 1, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14 or SEQ ID No. 15, SEQ ID No. 16, SEQ ID No. 17, SEQ ID No. 18, SEQ ID No. 34 or SEQ ID No. 35.

Suitably, the lipid acyl transferase enzyme for use any one of the methods and uses of the present invention may be a lipid acyltransferase that comprises either the amino acid sequence shown as SEQ ID No. 68, or as SEQ ID No. 3 or as SEQ ID No. 4 or SEQ ID No. 1 or SEQ ID No. 15 or SEQ ID No. 16, or SEQ ID No. 34 or SEQ ID No. 35 or comprises an amino acid sequence which has 75% or more, preferably 80% or more, preferably 85% or more, preferably 90% or more, preferably 95% or more, identity with the amino acid sequence shown as SEQ ID No. 68 or the amino acid sequence shown as SEQ ID No. 3 or the amino acid sequence shown as SEQ ID No. 4 or the amino acid sequence shown as SEQ ID No. 1 or the amino acid sequence shown as SEQ ID No. 15 or the amino acid sequence shown as SEQ ID No. 16 or the amino acid sequence shown as SEQ ID No. 34 or the amino acid sequence shown as SEQ ID No. 35.

Suitably the lipid acyl transferase enzyme for use any one of the methods and/or uses of the present invention may be a lipid acyltransferase that comprises an amino acid sequence which has 80% or more, preferably 85% or more, more preferably 90% or more and even more preferably 95% or more identity with any one of the sequences shown as SEQ ID No. 68, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 1, SEQ ID No. 15, SEQ ID No. 16, SEQ ID No. 17, SEQ ID No. 18, SEQ ID No. 34 or SEQ ID No. 35.

Suitably, the lipid acyltransferase enzyme for use any one of the methods and/or uses of the present invention may be a lipid acyltransferase that comprises one or more of the following amino acid sequences:
(a) an amino acid sequence shown as amino acid residues 1-100 of SEQ ID No. 3 or SEQ ID No. 1;
(b) an amino acid sequence shown as amino acids residues 101-200 of SEQ ID No. 3 or SEQ ID No. 1;
(c) an amino acid sequence shown as amino acid residues 201-300 of SEQ ID No. 3 or SEQ ID No. 1; or
(d) an amino acid sequence which has 75% or more, preferably 85% or more, more preferably 90% or more, even more preferably 95% or more identity to any one of the amino acid sequences defined in (a)-(c) above.

Suitably, the lipid acyl transferase enzyme for use in methods and uses of the present invention may comprise one or more of the following amino acid sequences:
(a) an amino acid sequence shown as amino acid residues 28-39 of SEQ ID No. 3 or SEQ ID No. 1;
(b) an amino acid sequence shown as amino acids residues 77-88 of SEQ ID No. 3 or SEQ ID No. 1;
(c) an amino acid sequence shown as amino acid residues 126-136 of SEQ ID No. 3 or SEQ ID No. 1;
(d) an amino acid sequence shown as amino acid residues 163-175 of SEQ ID No. 3 or SEQ ID No. 1;
(e) an amino acid sequence shown as amino acid residues 304-311 of SEQ ID No. 3 or SEQ ID No. 1; or
(f) an amino acid sequence which has 75% or more, preferably 85% or more, more preferably 90% or more, even more preferably 95% or more identity to any one of the amino acid sequences defined in (a)-(e) above.

In one aspect, the lipid acyl transferase enzyme for use any one of the methods and/or uses of the present invention is a lipid acyltransferase that may be the lipid acyl transferase from *Candida parapsilosis* as taught in EP 1 275 711. Thus in one aspect the lipid acyl transferase for use in the method and uses of the present invention may be a lipid acyl transferase comprising one of the amino acid sequences taught in SEQ ID No. 17 or SEQ ID No. 18.

Much by preference, the lipid acyl transferase enzyme for use in any one of the methods and uses of the present invention is a lipid acyltransferase that may be a lipid acyl transferase comprising the amino acid sequence shown as SEQ ID No. 16, or an amino acid sequence which has 75% or more, preferably 85% or more, more preferably 90% or more, even more preferably 95% or more, even preferably 98% or more, or even more preferably 99% or more identity to SEQ ID No. 16. This enzyme could be considered a variant enzyme.

In one aspect, the lipid acyltransferase enzyme for use any one of the methods and/or uses of the present invention is a lipid acyltransferase that may be a lecithin:cholesterol acyltransferase (LCAT) or variant thereof (for example a variant made by molecular evolution)

Suitable LCATs are known in the art and may be obtainable from one or more of the following organisms for example:

mammals, rat, mice, chickens, *Drosophila melanogaster*, plants, including *Arabidopsis* and *Oryza sativa*, nematodes, fungi and yeast.

In one embodiment the lipid acyltransferase enzyme for use any one of the methods and/or uses of the present invention is a lipid acyltransferase that may be the lipid acyltransferase obtainable, preferably obtained, from the *E. coli* strains TOP 10 harbouring pPet12aAhydro and pPet12aASalmo deposited by Danisco A/S of Langebrogade 1, DK-1001 Copenhagen K, Denmark under the Budapest Treaty on the International Recognition of the Deposit of Microorganisms for the purposes of Patent Procedure at the National Collection of Industrial, Marine and Food Bacteria (NCIMB) 23 St. Machar Street, Aberdeen Scotland, GB on 22 Dec. 2003 under accession numbers NCIMB 41204 and NCIMB 41205, respectively.

A lipid acyltransferase enzyme for use in any one of the methods and/or uses of the present invention may be a phospholipid glycerol acyl transferase. Phospholipid glycerol acyl transferases include those isolated from *Aeromonas* spp., preferably *Aeromonas hydrophila* or *A. salmonicida*, most preferably *A. salmonicida* or variants thereof.

Most preferred lipid acyl transferases for use in the present invention are encoded by SEQ ID No.s 1, 3, 4, 15, 16, 34 and 35. It will be recognised by the skilled person that it is preferable that the signal peptides of the acyl transferase has been cleaved during expression of the transferase. The signal peptide of SEQ ID No.s 1, 3, 4, 15 and 16 are amino acids 1-18. Therefore the most preferred regions are amino acids 19-335 for SEQ ID No. 1 and SEQ ID No. 3 (*A. hydrophilia*) and amino acids 19-336 for SEQ ID No. 4, SEQ ID No. 15 and SEQ ID No. 16. (*A. salmonicida*). When used to determine the homology of identity of the amino acid sequences, it is preferred that the alignments as herein described use the mature sequence.

In one embodiment, suitably the lipid acyl transferase for use in the present invention comprises (or consists of) the amino acid sequence shown in SEQ ID No. 16 or comprises (or consists of) an amino acid sequence which has at least 70%, at least 75%, at least 85%, at least 90%, at least 95%, at least 98% identity to SEQ ID No. 16.

In one embodiment, suitably the lipid acyl transferase for use in the present invention is encoded by a nucleotide sequence encoding the amino acid sequence comprising (or consisting of) the amino acid sequence shown in SEQ ID No. 68 or comprises (or consists of) an amino acid sequence which has at least 70%, at least 75%, at least 85%, at least 90%, at least 95%, at least 98% identity to SEQ ID No. 68.

Therefore the most preferred regions for determining homology (identity) are amino acids 19-335 for SEQ ID No. 1 and 3 (*A. hydrophilia*) and amino acids 19-336 for SEQ ID No.s 4, 15 and 16 (*A. salmonicida*). SEQ ID No.s 34 and 35 are mature protein sequences of a lipid acyl transferase from *A. hydrophilia* and *A. salmonicida* respectively which may or may not undergo further post-translational modification.

A lipid acyltransferase enzyme for use any one of the methods and uses of the present invention may be a lipid acyltransferase that may also be isolated from *Thermobifida*, preferably *T. fusca*, most preferably that encoded by SEQ ID No. 28.

Suitable lipid acyltransferases for use in accordance with the present invention and/or in the methods of the present invention may comprise any one of the following amino acid sequences and/or be encoded by the following nucleotide sequences:
a) a nucleic acid which encodes a polypeptide exhibiting lipid acyltransferase activity and is at least 70% identical (preferably at least 80%, more preferably at least 90% identical) with the polypeptide sequence shown in SEQ ID No. 16 or with the polypeptide shown in SEQ ID no. 68;
b) a (isolated) polypeptide comprising (or consisting of) an amino acid sequence as shown in SEQ ID No. 16 or SEQ ID No. 68 or an amino acid sequence which is at least 70% identical (preferably at least 80% identical, more preferably at least 90% identical) with SEQ ID No. 16 or SEQ ID No. 68;
c) a nucleic acid encoding a lipid acyltransferase, which nucleic acid comprises (or consists of) a nucleotide sequence shown as SEQ ID No. 49 or a nucleotide sequence which is at least 70% identical (preferably at least 80%, more preferably at least 90% identical) with the nucleotide sequence shown as SEQ ID No. 49;
d) a nucleic acid which hybridises under medium or high stringency conditions to a nucleic acid probe comprising the nucleotide sequence shown as SEQ ID No. 49 and encodes for a polypeptide exhibiting lipid acyltransferase activity;
e) a nucleic acid which is a fragment of the nucleic acid sequences specified in a), c) or d); or
f) a polypeptide which is a fragment of the polypeptide specified in b).

A lipid acyltransferase enzyme for use any one of the methods and uses of the present invention may be a lipid acyltransferase that may also be isolated from *Streptomyces*, preferable *S. avermitis*, most preferably that encoded by SEQ ID No. 32. Other possible enzymes for use in the present invention from *Streptomyces* include those encoded by SEQ ID No.s 5, 6, 9, 10, 11, 12, 13, 14, 31, and 33.

An enzyme for use in the invention may also be isolated from *Corynebacterium*, preferably *C. efficiens*, most preferably that encoded by SEQ ID No. 29.

Suitably, the lipid acyltransferase enzyme for use any one of the methods and/or uses of the present invention may be a lipid acyltransferase that comprises any one of the amino acid sequences shown as SEQ ID No.s 37, 38, 40, 41, 43, 45, or 47 or an amino acid sequence which has at least 70%, 75%, 80%, 85%, 90%, 95%, 96%, 97% or 98% identity therewith, or may be encoded by any one of the nucleotide sequences shown as SEQ ID No.s 36, 39, 42, 44, 46, or 48 or a nucleotide sequence which has at least 70%, 75%, 80%, 85%, 90%, 95%, 96%, 97% or 98% identity therewith.

In one embodiment, the nucleotide sequence encoding a lipid acyltransferase enzyme for use any one of the methods and/or uses of the present invention is selected from the group consisting of:
a) a nucleic acid comprising a nucleotide sequence shown in SEQ ID No. 36;
b) a nucleic acid which is related to the nucleotide sequence of SEQ ID No. by the degeneration of the genetic code; and
c) a nucleic acid comprising a nucleotide sequence which has at least 70% identity with the nucleotide sequence shown in SEQ ID No. 36.

In one embodiment, the lipid acyltransferase enzyme for use any one of the methods and/or uses of the present invention is a lipid acyltransferase that comprises an amino acid sequence as shown in SEQ ID No. 37 or an amino acid sequence which has at least 60% identity thereto.

In a further embodiment the lipid acyltransferase enzyme for use any one of the methods and/or uses of the present invention may be a lipid acyltransferase comprising any one of the amino acid sequences shown as SEQ ID No. 37, 38, 40, 41, 43, 45 or 47 or an amino acid sequence which has at least 70%, 75%, 80% or 85%, 90%, 95%, 96%, 97% or 98% identity therewith, or may be encoded by any one of the nucleotide sequences shown as SEQ ID No. 39, 42, 44, 46 or 48 or a nucleotide sequence which has at least 70%, 75%, 80%, 85%, 90%, 95%, 96%, 97% or 98% identity therewith.

In a further embodiment the lipid acyltransferase enzyme for use any one of the methods and/or uses of the present invention may be a lipid acyltransferase comprising any one of amino sequences shown as SEQ ID No. 38, 40, 41, 45 or 47 or an amino acid sequence which has at least 70%, 75%, 80%, 85%, 90%, 95%, 96%, 97% or 98% identity therewith for the uses described herein.

In a further embodiment the lipid acyltransferase for use in any one of the methods and/or uses of the present invention may be a lipid acyltransferase comprising any one of amino sequences shown as SEQ ID No. 38, 40, or 47 or an amino acid sequence which has at least 70%, 75%, 80%, 85%, 90%, 95%, 96%, 97% or 98% identity therewith for the uses described herein.

More preferably in one embodiment the lipid acyltransferase for use in any one of the methods and/or uses of the present invention may be a lipid acyltransferase comprising the amino acid sequence shown as SEQ ID No. 47 or an amino acid sequence which has at least 70%, 75%, 80%, 85%, 90%, 95%, 96%, 97% or 98% identity therewith.

In another embodiment the lipid acyltransferase for use in any one of the methods and uses of the present invention may be a lipid acyltransferase comprising the amino acid sequence shown as SEQ ID No. 43 or 44 or an amino acid sequence which has at least 80%, 85%, 90%, 95%, 96%, 97% or 98% identity therewith.

In another embodiment the lipid acyltransferase for use in any one of the methods and uses of the present invention may be a lipid acyltransferase comprising the amino acid sequence shown as SEQ ID No. 41 or an amino acid sequence which has at least 70%, 75%, 80%, 85%, 90%, 95%, 96%, 97% or 98% identity therewith.

In one embodiment the lipid acyltransferase for use in any one of the methods and uses of the present invention may be encoded by a nucleic acid selected from the group consisting of:
  a) a nucleic acid comprising a nucleotide sequence shown in SEQ ID No. 36;
  b) a nucleic acid which is related to the nucleotide sequence of SEQ ID No. 36 by the degeneration of the genetic code; and
  c) a nucleic acid comprising a nucleotide sequence which has at least 70% identity with the nucleotide sequence shown in SEQ ID No. 36.

In one embodiment the lipid acyltransferase according to the present invention may be a lipid acyltransferase obtainable, preferably obtained, from the *Streptomyces* strains L130 or L131 deposited by Danisco A/S of Langebrogade 1, DK-1001 Copenhagen K, Denmark under the Budapest Treaty on the International Recognition of the Deposit of Microorganisms for the purposes of Patent Procedure at the National Collection of Industrial, Marine and Food Bacteria (NCIMB) 23 St. Machar Street, Aberdeen Scotland, GB on 25 Jun. 2004 under accession numbers NCIMB 41226 and NCIMB 41227, respectively.

Suitable nucleotide sequences encoding a lipid acyltransferase for use in any one of the methods and/or uses of the present invention may encode a polynucleotide encoding a lipid acyltransferase (SEQ ID No. 16 or SEQ ID No. 68); or may encode an amino acid sequence of a lipid acyltransferase (SEQ ID No. 16 or SEQ ID No. 68).

A suitable lipid acyltransferases for use in any one of the methods and/or uses of the present invention may be an amino acid sequence which may be identified by alignment to the L131 (SEQ ID No. 37) sequence using Align X, the Clustal W pairwise alignment algorithm of VectorNTI using default settings.

An alignment of the L131 and homologues from *S. avermitilis* and *T. fusca* illustrates that the conservation of the GDSx motif (GDSY in L131 and *S. avermitilis* and *T. fusca*), the GANDY box, which is either GGNDA or GGNDL, and the HPT block (considered to be the conserved catalytic histidine). These three conserved blocks are highlighted in FIG. 42.

When aligned to either the pfam Pfam00657 consensus sequence (as described in WO04/064987) and/or the L131 sequence herein disclosed (SEQ ID No 37) it is possible to identify three conserved regions, the GDSx block, the GANDY block and the HTP block (see WO04/064987 for further details).

When aligned to either the pfam Pfam00657 consensus sequence (as described in WO04/064987) and/or the L131 sequence herein disclosed (SEQ ID No 37)
i) The lipid acyltransferase for use in any one of the methods and uses of the present invention may be a lipid acyltransferase that has a GDSx motif, more preferably a GDSx motif selected from GDSL or GDSY motif.
and/or
ii) The lipid acyltransferase for use in any one of the methods and uses of the present invention may be a lipid acyltransferase that, has a GANDY block, more preferably a GANDY block comprising amino GGNDx, more preferably GGNDA or GGNDL.
and/or
iii) The lipid acyltransferase for use in any one of the methods and uses of the present invention may be a lipid acyltransferase that has preferably an HTP block.
and preferably
iv) the lipid acyltransferase for use in any one of the methods and uses of the present invention may be a lipid acyltransferase that has preferably a GDSx or GDSY motif, and a GANDY block comprising amino GGNDx, preferably GGNDA or GGNDL, and a HIP block (conserved histidine).

In one embodiment the enzyme according to the present invention may be preferably not a phospholipase enzyme, such as a phospholipase A1 classified as E.C. 3.1.1.32 or a phospholipase A2 classified as E.C. 3.1.1.4.

Variant Lipid Acyl Transferase

In a preferred embodiment the nucleotide sequence encoding a lipid acyltransferase for use in any one of the methods and/or uses of the present invention may encode a lipid acyltransferase that is a variant lipid acyl transferase.

Variants which have an increased activity on phospholipids, such as increased hydrolytic activity and/or increased transferase activity, preferably increased transferase activity on phospholipids may be used.

Preferably the variant lipid acyltransferase is prepared by one or more amino acid modifications of the lipid acyl transferases as defined hereinabove.

Suitably, the lipid acyltransferase for use in any one of the methods and uses of the present invention may be a lipid acyltransferase that may be a variant lipid acyltransferase, in which case the enzyme may be characterised in that the enzyme comprises the amino acid sequence motif GDSX, wherein X is one or more of the following amino acid residues L, A, V, I, F, Y, H, Q, T, N, M or S, and wherein the variant enzyme comprises one or more amino acid modifications compared with a parent sequence at any one or more of the amino acid residues defined in set 2 or set 4 or set 6 or set 7 (as defined WO2005/066347 and hereinbelow).

For instance the variant lipid acyltransferase may be characterised in that the enzyme comprises the amino acid sequence motif GDSX, wherein X is one or more of the following amino acid residues L, A, V, I, F, Y, H, Q, T, N, M or S, and wherein the variant enzyme comprises one or more amino acid modifications compared with a parent sequence at any one or more of the amino acid residues detailed in set 2 or set 4 or set 6 or set 7 (as defined in WO2005/066347 and hereinbelow) identified by said parent sequence being structurally aligned with the structural model of P10480 defined herein, which is preferably obtained by structural alignment of P10480 crystal structure coordinates with 1IVN.PDB and/or 1DEO.PDB as defined WO2005/066347 and hereinbelow.

In a further embodiment a lipid acyltransferase for use in any one of the methods and/or uses of the present invention may be a variant lipid acyltransferase that may be characterised in that the enzyme comprises the amino acid sequence motif GDSX, wherein X is one or more of the following amino acid residues L, A, V, I, F, Y, H, Q, T, N, M or S, and wherein the variant enzyme comprises one or more amino acid modifications compared with a parent sequence at any one or more of the amino acid residues taught in set 2 identified when said parent sequence is aligned to the pfam consensus sequence (SEQ ID No. 2—FIG. 3) and modified according to a structural model of P10480 to ensure best fit overlap as defined WO2005/066347 and hereinbelow.

Suitably a lipid acyltransferase for use in any one of the methods and uses of the present invention may be a variant lipid acyltransferase enzyme that may comprise an amino acid sequence, which amino acid sequence is shown as SEQ ID No. 68, SEQ ID No. 16, SEQ ID No. 34, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 1, SEQ ID No. 15, SEQ ID No. 25, SEQ ID No. 26, SEQ ID No. 27, SEQ ID No. 28, SEQ ID No. 29, SEQ ID No. 30, SEQ ID No. 32, SEQ ID No. 33 or SEQ ID No. 35 except for one or more amino acid modifications at any one or more of the amino acid residues defined in set 2 or set 4 or set 6 or set 7 (as defined WO2005/066347 and hereinbelow) identified by sequence alignment with SEQ ID No. 34.

Alternatively the lipid acyltransferase may be a variant lipid acyltransferase enzyme comprising an amino acid sequence, which amino acid sequence is shown as SEQ ID No. 34, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 1, SEQ ID No. 15, SEQ ID No. 25, SEQ ID No. 26, SEQ ID No. 27, SEQ ID No. 28, SEQ ID No. 29, SEQ ID No. 30, SEQ ID No. 16, SEQ ID No. 68, SEQ ID No. 32, SEQ ID No. 33 or SEQ ID No. 35 except for one or more amino acid modifications at any one or more of the amino acid residues defined in set 2 or set 4 or set 6 or set 7 as defined WO2005/066347 and hereinbelow, identified by said parent sequence being structurally aligned with the structural model of P10480 defined herein, which is preferably obtained by structural alignment of P10480 crystal structure coordinates with 1IVN.PDB and/or 1DEO.PDB as taught within WO2005/066347 and hereinbelow.

Alternatively, the lipid acyltransferase may be a variant lipid acyltransferase enzyme comprising an amino acid sequence, which amino acid sequence is shown as SEQ ID No. 34, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 1, SEQ ID No. 15, SEQ ID No. 25, SEQ ID No. 26, SEQ ID No. 27, SEQ ID No. 28, SEQ ID No. 29, SEQ ID No. 30, SEQ ID No. 32, SEQ ID No. 33, SEQ ID No. 16, SEQ ID No. 68 or SEQ ID No. 35 except for one or more amino acid modifications at any one or more of the amino acid residues taught in set 2 identified when said parent sequence is aligned to the pfam consensus sequence (SEQ ID No. 2) and modified according to a structural model of P10480 to ensure best fit overlap as taught within WO2005/066347 and hereinbelow.

Preferably, the parent enzyme is an enzyme which comprises, or is homologous to, the amino acid sequence shown as SEQ ID No. 34 and/or SEQ ID No. 15 and/or SEQ ID No. 35.

Preferably, the lipid acyltransferase may be a variant enzyme which comprises an amino acid sequence, which amino acid sequence is shown as SEQ ID No. 34 or SEQ ID No. 35 except for one or more amino acid modifications at any one or more of the amino acid residues defined in set 2 or set 4 or set 6 or set 7 as defined in WO2005/066347 and hereinbelow.

DEFINITION OF SETS

Amino Acid Set 1:

Amino acid set 1 (note that these are amino acids in 1IVN—FIG. 53 and FIG. 54) Gly8, Asp9, Ser10, Leu11, Ser12, Tyr15, Gly44, Asp45, Thr46, Glu69, Leu70, Gly71, Gly72, Asn73, Asp74, Gly75, Leu76, Gln106, Ile107, Arg108, Leu109, Pro110, Tyr113, Phe121, Phe139, Phe140, Met141, Tyr145, Met151, Asp154, His157, Gly155, Ile156, Pro158

The highly conserved motifs, such as GDSx and catalytic residues, were deselected from set 1 (residues underlined). For the avoidance of doubt, set 1 defines the amino acid residues within 10 Å of the central carbon atom of a glycerol in the active site of the 1IVN model.

Amino Acid Set 2:

Amino acid set 2 (note that the numbering of the amino acids refers to the amino acids in the P10480 mature sequence)
Leu17, Lys22, Met23, Gly40, Asn80, Pro81, Lys82, Asn87, Asn88, Trp111, Val112, Ala114, Tyr117, Leu118, Pro156, Gly159, Gln160, Asn161; Pro162, Ser163, Ala164, Arg165, Ser166, Gln167, Lys168, Val169, Val170, Glu171, Ala172, Tyr179, His180, Asn181, Met209, Leu210, Arg211, Asn215, Lys284, Met285, Gln289 and Val290.

| Table of selected residues in Set 1 compared with Set 2: | | | |
|---|---|---|---|
| IVN model | | | P10480 |
| | A. hyd homologue | | Mature sequence Residue |
| IVN | PFAM | Structure | Number |
| Gly8 | Gly32 | | |
| Asp9 | Asp33 | | |
| Ser10 | Ser34 | | |
| Leu11 | Leu35 | | Leu17 |
| Ser12 | Ser36 | | Ser18 |
| | | | Lys22 |
| | | | Met23 |
| Tyr15 | Gly58 | | Gly40 |
| Gly44 | Asn98 | | Asn80 |
| Asp45 | Pro99 | | Pro81 |
| Thr46 | Lys100 | | Lys82 |
| | | | Asn87 |
| | | | Asn88 |
| Glu69 | Trp129 | | Trp111 |
| Leu70 | Val130 | | Val112 |

-continued

Table of selected residues in Set 1 compared with Set 2:

| IVN model | | | P10480 |
|---|---|---|---|
| | A. hyd homologue | | Mature sequence Residue |
| IVN | PFAM | Structure | Number |
| Gly71 | Gly131 | | |
| Gly72 | Ala132 | | Ala114 |
| Asn73 | Asn133 | | |
| Asp74 | Asp134 | | |
| Gly75 | Tyr135 | | Tyr117 |
| Leu76 | Leu136 | | Leu118 |
| Gln106 | | Pro174 | Pro156 |
| Ile107 | | Gly177 | Gly159 |
| Arg108 | | Gln178 | Gln160 |
| Leu109 | | Asn179 | Asn161 |
| Pro110 | | 180 to 190 | Pro162 |
| Tyr113 | | | Ser163 |
| | | | Ala164 |
| | | | Arg165 |
| | | | Ser166 |
| | | | Gln167 |
| | | | Lys168 |
| | | | Val169 |
| | | | Val170 |
| | | | Glu171 |
| | | | Ala172 |
| Phe121 | His198 | Tyr197 | Tyr179 |
| | | His198 | His180 |
| | | Asn199 | Asn181 |
| Phe139 | Met227 | | Met209 |
| Phe140 | Leu228 | | Leu210 |
| Met141 | Arg229 | | Arg211 |
| Tyr145 | Asn233 | | Asn215 |
| | | | Lys284 |
| Met151 | Met303 | | Met285 |
| Asp154 | Asp306 | | |
| Gly155 | Gln307 | | Gln289 |
| Ile156 | Val308 | | Val290 |
| His157 | His309 | | |
| Pro158 | Pro310 | | |

Amino Acid Set 3:

Amino acid set 3 is identical to set 2 but refers to the *Aeromonas salmonicida* (SEQ ID No. 4) coding sequence, i.e. the amino acid residue numbers are 18 higher in set 3 as this reflects the difference between the amino acid numbering in the mature protein (SEQ ID No. 34) compared with the protein including a signal sequence (SEQ ID No. 25).

The mature proteins of *Aeromonas salmonicida* GDSX (SEQ ID No. 4) and *Aeromonas hydrophila* GDSX (SEQ ID No. 34) differ in five amino acids. These are Thr3Ser, Gln182Lys, Glu309Ala, Ser310Asn, and Gly318-, where the *salmonicida* residue is listed first and the *hydrophila* residue is listed last. The *hydrophila* protein is only 317 amino acids long and lacks a residue in position 318. The *Aeromonas salmonicida* GDSX has considerably high activity on polar lipids such as galactolipid substrates than the *Aeromonas hydrophila* protein. Site scanning was performed on all five amino acid positions.

Amino Acid Set 4:
Amino acid set 4 is S3, Q182, E309, S310, and -318.

Amino Acid Set 5:
F13S, D15N, S18G, S18V, Y30F, D116N, D116E, D157 N, Y226F, D228N Y230F.

Amino Acid Set 6:
Amino acid set 6 is Ser3, Leu17, Lys22, Met23, Gly40, Asn80, Pro81, Lys82, Asn 87, Asn88, Trp111, Val112, Ala114, Tyr117, Leu118, Pro156, Gly159, Gln160, Asn161, Pro162, Ser163, Ala164, Arg165, Ser166, Gln167, Lys168, Val169, Val170, Glu171, Ala172, Tyr179, His180, Asn181, Gln182, Met209, Leu210, Arg211, Asn215, Lys284, Met285, Gln289, Val290, Glu309, Ser310, -318.

The numbering of the amino acids in set 6 refers to the amino acids residues in P10480 (SEQ ID No. 25)—corresponding amino acids in other sequence backbones can be determined by homology alignment and/or structural alignment to P10480 and/or 1IVN.

Amino Acid Set 7:
Amino acid set 7 is Ser3, Leu17, Lys22, Met23, Gly40, Asn80, Pro81, Lys82, Asn 87, Asn88, Trp111, Val112, Ala114, Tyr117, Leu118, Pro156, Gly159, Gln160, Asn161, Pro162, Ser163, Ala164, Arg165, Ser166, Gln167, Lys168, Val169, Val170, Glu171, Ala172, Tyr179, His180, Asn181, Gln182, Met209, Leu210, Arg211, Asn215, Lys284, Met285, Gln289, Val290, Glu309, Ser310, -318, Y30X (where X is selected from A, C, D, E, G, H, I, K, L, M, N, P, Q, R, S, T, V, or W), Y226X (where X is selected from A, C, D, E, G, H, I, K, L, M, N, P, Q, R, S, T, V, or W), Y230X (where X is selected from A, C, D, E, G, H, I, K, L, M, N, P, Q, R, S, T, V, or W), S18X (where X is selected from A, C, D, E, F, H, I, K, L, M, N, P, Q, R, T, W or Y), D157X (where X is selected from A, C, E, F, G, H, I, K, L, M, P, Q, R, S, T, V, W or Y).

The numbering of the amino acids in set 7 refers to the amino acids residues in P10480 (SEQ ID No. 25)—corresponding amino acids in other sequence backbones can be determined by homology alignment and/or structural alignment to P10480 and/or 1IVN).

Suitably, the variant enzyme comprises one or more of the following amino acid modifications compared with the parent enzyme:
S3E, A, G, K, M, Y, R, P, N, T or G
E309Q, R or A, preferably Q or R
-318Y, H, S or Y, preferably Y.

Preferably, X of the GDSX motif is L. Thus, preferably the parent enzyme comprises the amino acid motif GDSL.

Suitably, said first parent lipid acyltransferase may comprise any one of the following amino acid sequences: SEQ ID No. 34, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 1, SEQ ID No. 15, SEQ ID No. 25, SEQ ID No. 26, SEQ ID No. 27, SEQ ID No. 28, SEQ ID No. 29, SEQ ID No. 30, SEQ ID No. 32, SEQ ID No. 33 or SEQ ID No. 35.

Suitably, said second related lipid acyltransferase may comprise any one of the following amino acid sequences: SEQ ID No. 3, SEQ ID No. 34, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 1, SEQ ID No. 15, SEQ ID No. 25, SEQ ID No. 26, SEQ ID No. 27, SEQ ID No. 28, SEQ ID No. 29, SEQ ID No. 30, SEQ ID No. 32, SEQ ID No. 33 or SEQ ID No. 35.

The variant enzyme must comprise at least one amino acid modification compared with the parent enzyme. In some embodiments, the variant enzyme may comprise at least 2, preferably at least 3, preferably at least 4, preferably at least 5, preferably at least 6, preferably at least 7, preferably at least 8, preferably at least 9, preferably at least 10 amino acid modifications compared with the parent enzyme.

When referring to specific amino acid residues herein the numbering is that obtained from alignment of the variant sequence with the reference sequence shown as SEQ ID No. 34 or SEQ ID No. 35.

In one aspect preferably the variant enzyme comprises one or more of the following amino acid substitutions:
S3A, C, D, E, F, G, H, I, K, L, M, N, P, Q, R, T, V, W, or Y; and/or
L17A, C, D, E, F, G, H, I, K, M, N, P, Q, R, S, T, V, W, or Y; and/or
S18A, C, D, E, F, H, I, K, L, M, N, P, Q, R, T, W, or Y; and/or
K22A, C, D, E, F, G, H, I, L, M, N, P, Q, R, S, T, V, W, or Y; and/or
M23A, C, D, E, F, G, H, I, K, L, N, P, Q, R, S, T, V, W, or Y; and/or
Y30A, C, D, E, G, H, I, K, L, M, N, P, Q, R, S, T, V, or W; and/or
G40A, C, D, E, F, H, I, K, L, M, N, P, Q, R, S, T, V, W, or Y; and/or
N80A, C, D, E, F, G, H, I, K, L, M, P, Q, R, S, T, V, W, or Y; and/or
P81A, C, D, E, F, G, H, I, K, L, M, N, P, Q, R, S, T, V, W, or Y; and/or
K82A, C, D, E, F, G, H, I, L, M, N, P, Q, R, S, T, V, W, or Y; and/or
N87A, C, D, E, F, G, H, I, K, L, M, P, Q, R, S, T, V, W, or Y; and/or
N88A, C, D, E, F, G, H, I, K, L, M, P, Q, R, S, T, V, W, or Y; and/or
W111A, C, D, E, F, G, H, I, K, L, M, N, P, Q, R, S, T, V, W or Y; and/or
V112A, C, D, E, F, G, H, I, K, L, M, N, P, Q, R, S, T, W, or Y; and/or
A114C, D, E, F, G, H, I, K, L, M, N, P, Q, R, S, T, V, W, or Y; and/or
Y117A, C, D, E, F, G, H, I, K, L, M, N, P, Q, R, S, T, V, or W; and/or
L118A, C, D, E, F, G, H, I, K, M, N, P, Q, R, S, T, V, W, or Y; and/or
P156A, C, D, E, F, G, H, I, K, L, M, N, P, Q, R, S, T, V, W, or Y; and/or
D157A, C, E, F, G, H, I, K, L, M, P, Q, R, S, T, V, W, or Y; and/or
G159A, C, D, E, F, H, I, K, L, M, N, P, Q, R, S, T, V, W, or Y; and/or
Q160A, C, D, E, F, G, H, I, K, L, M, N, P, R, S, T, V, W, or Y; and/or
N161A, C, D, E, F, G, H, I, K, L, M P, Q, R, S, T, V, W, or Y; and/or
P162A, C, D, E, F, G, H, I, K, L, M, N, Q, R, S, T, V, W, or Y; and/or
S163A, C, D, E, F, G, H, I, K, L, M, N, P, Q, R, T, V, W, or Y; and/or
A164C, D, E, F, G, H, I, K, L, M, N, P, Q, R, S, T, V, W, or Y; and/or
R165A, C, D, E, F, G, H, I, K, L, M, N, P, Q, S, T, V, W, or Y; and/or
S166A, C, D, E, F, G, H, I, K, L, M, N, P, Q, R, T, V, W, or Y; and/or
Q167A, C, D, E, F, G, H, I, K, L, M, N, P, R, S, T, V, W, or Y; and/or
K168A, C, D, E, F, G, H, I, L, M, N, P, Q, R, S, T, V, W, or Y; and/or
V169A, C, D, E, F, G, H, I, K, L, M, N, P, Q, R, S, T, W, or Y; and/or
V170A, C, D, E, F, G, H, I, K, L, M, N, P, Q, R, S, T, W, or Y; and/or
E171A, C, D, F, G, H, I, K, L, M, N, P, Q, R, S, T, V, W, or Y; and/or
A172C, D, E, F, G, H, I, K, L, M, N, P, Q, R, S, T, V, W, or Y; and/or
Y179A, C, D, E, F, G, H, I, K, L, M, N, P, Q, R, S, T, V, or W; and/or
H180A, C, D, E, F, G, I, K, L, M, P, Q, R, S, T, V, W, or Y; and/or
N181A, C, D, E, F, G, H, I, K, L, M, P, Q, R, S, T, V, W, or Y; and/or
Q182A, C, D, E, F, G, H, I, K, L, M, N, P, R, S, T, V, W, or Y, preferably K; and/or
M209A, C, D, E, F, G, H, I, K, L, N, P, Q, R, S, T, V, W, or Y; and/or
L210A, C, D, E, F, G, H, I, K, M, N, P, Q, R, S, T, V, W, or Y; and/or
R211A, C, D, E, F, G, H, I, K, L, M, N, P, Q, R, S, T, V, W, or Y; and/or
N215A, C, D, E, F, G, H, I, K, L, M, N, P, Q, R, S, T, V, W, or Y; and/or
Y226A, C, D, E, G, H, I, K, L, M, N, P, Q, R, S, T, V, or W; and/or
Y230A, C, D, E, G, H, I, K, L, M, N, P, Q, R, S, T, V or W; and/or
K284A, C, D, E, F, G, H, I, L, M, N, P, Q, R, S, T, V, W, or Y; and/or
M285A, C, D, E, F, G, H, I, K, L, N, P, Q, R, S, T, V, W, or Y; and/or
Q289A, C, D, E, F, G, H, I, K, L, M, N, P, R, S, T, V, W, or Y; and/or
V290A, C, D, E, F, G, H, I, K, L, M, N, P, Q, R, S, T, W, or Y; and/or
E309A, C, D, F, G, H, I, K, L, M, N, P, Q, R, S, T, V, W, or Y; and/or
S310A, C, D, E, F, G, H, I, K, L, M, N, P, Q, R, T, V, W, or Y.

In addition or alternatively thereto there may be one or more C-terminal extensions. Preferably the additional C-terminal extension is comprised of one or more aliphatic amino acids, preferably a non-polar amino acid, more preferably of I, L, V or G. Thus, the present invention further provides for a variant enzyme comprising one or more of the following C-terminal extensions: 318I, 318L, 318V, 318G.

Preferred variant enzymes may have a decreased hydrolytic activity against a phospholipid, such as phosphatidylcholine (PC), may also have an increased transferase activity from a phospholipid.

Preferred variant enzymes may have an increased transferase activity from a phospholipid, such as phosphatidylcholine (PC), these may also have an increased hydrolytic activity against a phospholipid.

Modification of one or more of the following residues may result in a variant enzyme having an increased absolute transferase activity against phospholipid:
S3, D157, S310, E309, Y179, N215, K22, Q289, M23, H180, M209, L210, R211, P81, V112, N80, L82, N88; N87

Specific preferred modifications which may provide a variant enzyme having an improved transferase activity from a phospholipid may be selected from one or more of the following:
S3A, C, D, E, F, G, H, I, K, L, M, N, P, Q, R, T, V, W or Y; preferably N, E, K, R, A, P or M, most preferably S3A
D157A, C, E, F, G, H, I, K, L, M, N, P, Q, R, S, T, V, W or Y; preferably D157S, R, E, N, G, T, V, Q, K or C
S310A, C, D, E, F, G, H, I, K, L, M, N, P, Q, R, T, V, W or Y; preferably S310T –318 E
E309A, C, D, E, F, G, H, I, K, L, M, N, P, Q, R, T, V, W or Y; preferably E309 R, E, L, R or A
Y179A, C, D, E, F, G, H, I, K, L, M, N, P, Q, R, S, T, V or W; preferably Y179 D, T, E, R, N, V, K, Q or S, more preferably E, R, N, V, K or Q N215A, C, D, E, F, G, H, I, K, L, M, P, Q, R, S, T, V, W or Y; preferably N215 S, L, R or Y
K22A, C, D, E, F, G, H, I, L, M, N, P, Q, R, S, T, V, W or Y; preferably K22 E, R, C or A
Q289A, C, D, E, F, G, H, I, K, L, M, N, P, R, S, T, V, W or Y; preferably Q289 R, E, G, P or N
M23A, C, D, E, F, G, H, I, K, L N, P, Q, R, S, T, V, W or Y; preferably M23 K, Q, L, G, T or S
H180A, C, D, E, F, G, I, K, L, M, P, Q, R, S, T, V, W or Y; preferably H180 Q, R or K
M209A, C, D, E, F, G, H, I, K, L, N, P, Q, R, S, T, V, W or Y; preferably M209 Q, S, R, A, N, Y, E, V or L
L210A, C, D, E, F, G, H, I, K, M, N, P, Q, R, S, T, V, W or Y; preferably L210 R, A, V, S, T, I, W or M
R211A, C, D, E, F, G, H, I, K, L, M, N, P, Q, S, T, V, W or Y; preferably R211T
P81A, C, D, E, F, G, H, I, K, L, M, N, Q, R, S, T, V, W or Y; preferably P81G
V112A, C, D, E, F, G, H, I, K, L, M, N, P, Q, R, S, T, W or Y; preferably V112C
N80A, C, D, E, F, G, H, I, K, L, M, P, Q, R, S, T, V, W or Y; preferably N80 R, G, N, D, P, T, E, V, A or G
L82A, C, D, E, F, G, H, I, M, N, P, Q, R, S, T, V, W or Y; preferably L82N, S or E
N88A, C, D, E, F, G, H, I, K, L, M, P, Q, R, S, T, V, W or Y; preferably N88C
N87A, C, D, E, F, G, H, I, K, L, M, P, Q, R, S, T, V, W or Y; preferably N87M or G Preferred modification of one or more of the following residues results in a variant enzyme having an increased absolute transferase activity against phospholipid:

S3 N, R, A, G
M23 K, Q, L, G, T, S
H180 R
L82 G
Y179 E, R, N, V, K or Q
E309 R, S, L or A

One preferred modification is N80D. This is particularly the case when using the reference sequence SEQ ID No. 35 as the backbone. Thus, the reference sequence may be SEQ ID No. 16. This modification may be in combination with one or more further modifications. Therefore in a preferred embodiment of the present invention the nucleotide sequence encoding a lipid acyltransferase for use in any one of the methods and uses of the present invention may encode a lipid acyltransferase that comprises SEQ ID No. 35 or an amino acid sequence which has 75% or more, preferably 85% or more, more preferably 90% or more, even more preferably 95% or more, even more preferably 98% or more, or even more preferably 99% or more identity to SEQ ID No. 35.

As noted above, when referring to specific amino acid residues herein the numbering is that obtained from alignment of the variant sequence with the reference sequence shown as SEQ ID No. 34 or SEQ ID No. 35

Much by preference, the nucleotide sequence encoding a lipid acyltransferase for use in any one of the methods and uses of the present invention may encode a lipid comprising the amino acid sequence shown as SEQ ID No. 16 or the amino acid sequence shown as SEQ ID No. 68, or an amino acid sequence which has 70% or more, preferably 75% or more, preferably 85% or more, more preferably 90% or more, even more preferably 95% or more, even more preferably 98% or more, or even more preferably 99% or more identity to SEQ ID No. 16 or SEQ ID No. 68. This enzyme may be considered a variant enzyme.

For the purposes of the present invention, the degree of identity is based on the number of sequence elements which are the same. The degree of identity in accordance with the present invention for amino acid sequences may be suitably determined by means of computer programs known in the art, such as Vector NTI 10 (Invitrogen Corp.). For pairwise alignment the score used is preferably BLOSUM62 with Gap opening penalty of 10.0 and Gap extension penalty of 0.1.

Suitably, the degree of identity with regard to an amino acid sequence is determined over at least 20 contiguous amino acids, preferably over at least 30 contiguous amino acids, preferably over at least 40 contiguous amino acids, preferably over at least 50 contiguous amino acids, preferably over at least 60 contiguous amino acids.

Suitably, the degree of identity with regard to an amino acid sequence may be determined over the whole sequence.

Suitably, the nucleotide sequence encoding a lipid acyltransferase or the lipid acyl transferase enzyme for use in the present invention may be obtainable, preferably obtained, from organisms from one or more of the following genera: *Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas, Candida, Thermobifida* and *Corynebacterium*.

Suitably, the nucleotide sequence encoding a lipid acyltransferase or the lipid acyl transferase enzyme for use in the present invention may be obtainable, preferably obtained, from one or more of the following organisms: *Aeromonas hydrophila, Aeromonas salmonicida, Streptomyces coelicolor, Streptomyces rimosus, Mycobacterium, Streptococcus pyogenes, Lactococcus lactis, Streptococcus pyogenes, Streptococcus thermophilus, Streptomyces thermosacchari, Streptomyces avermitilis Lactobacillus helveticus, Desulfitobacterium dehalogenans, Bacillus* sp, *Campylobacter jejuni, Vibrionaceae, Xylella fastidiosa, Sulfolobus solfataricus, Saccharomyces cerevisiae, Aspergillus terreus, Schizosaccharomyces pombe, Listeria innocua, Listeria monocytogenes, Neisseria meningitidis, Mesorhizobium loti, Ralstonia solanacearum, Xanthomonas campestris, Xanthomonas axonopodis, Candida parapsilosis, Thermobifida fusca* and *Corynebacterium efficiens*.

In one aspect, preferably the nucleotide sequence encoding a lipid acyltransferase for use in any one of the methods and/or uses of the present invention encodes a lipid acyl transferase enzyme according to the present invention is obtainable, preferably obtained or derived, from one or more of *Aeromonas* spp., *Aeromonas hydrophila* or *Aeromonas salmonicida*.

In one aspect, preferably the lipid acyltransferase for use in any one of the methods and/or uses of the present invention is a lipid acyl transferase enzyme obtainable, preferably obtained or derived, from one or more of *Aeromonas* spp., *Aeromonas hydrophila* or *Aeromonas salmonicida*.

The term "transferase" as used herein is interchangeable with the term "lipid acyltransferase".

Suitably, the lipid acyltransferase as defined herein catalyses one or more of the following reactions: interesterification, transesterification, alcoholysis, hydrolysis.

The term "interesterification" refers to the enzymatic catalysed transfer of acyl groups between a lipid donor and lipid acceptor, wherein the lipid donor is not a free acyl group.

The term "transesterification" as used herein means the enzymatic catalysed transfer of an acyl group from a lipid donor (other than a free fatty acid) to an acyl acceptor (other than water).

As used herein, the term "alcoholysis" refers to the enzymatic cleavage of a covalent bond of an acid derivative by reaction with an alcohol ROH so that one of the products combines with the H of the alcohol and the other product combines with the OR group of the alcohol.

As used herein, the term "alcohol" refers to an alkyl compound containing a hydroxyl group.

As used herein, the term "hydrolysis" refers to the enzymatic catalysed transfer of an acyl group from a lipid to the OH group of a water molecule.

The term "without increasing or without substantially increasing the free fatty acids" as used herein means that preferably the lipid acyl transferase according to the present invention has 100% transferase activity (i.e. transfers 100% of the acyl groups from an acyl donor onto the acyl acceptor, with no hydrolytic activity); however, the enzyme may transfer less than 100% of the acyl groups present in the lipid acyl donor to the acyl acceptor. In which case, preferably the acyltransferase activity accounts for at least 5%, more preferably at least 10%, more preferably at least 20%, more preferably at least 30%, more preferably at least 40%, more preferably 50%, more preferably at least 60%, more preferably at least 70%, more preferably at least 80%, more preferably at least 90% and more preferably at least 98% of the total enzyme activity. The % transferase activity (i.e. the transferase activity as a percentage of the total enzymatic activity) may be determined by the following the "Assay for Transferase Activity" given above.

In some aspects of the present invention, the term "without substantially increasing free fatty acids" as used herein means that the amount of free fatty acid in a edible oil treated with an lipid acyltransferase according to the present invention is less than the amount of free fatty acid produced in the edible oil when an enzyme other than a lipid acyltransferase according to the present invention had been used, such as for example as compared with the amount of free fatty acid produced when a conventional phospholipase enzyme, e.g. Lecitase Ultra™ (Novozymes A/S, Denmark), had been used.

The term 'essentially consists' as used herein, when referring to a product or composition, preferably means that the product or composition, may consist of other products or compositions but only to a maximum concentration of, preferably 10%, such as 5%, such as 3%, such as 2% or 1%, or 0.5% or 0.1%.

In one preferred embodiment the lipid acyltransferase is used in combination with a lipase having one or more of the following enzyme activities: glycolipase activity (E.C. 3.1.1.26, phospholipase A2 activity (E.C. 3.1.1.4) or phospholipase A1 activity (E.C. 3.1.1.32). Suitably, lipase enzymes are well known within the art and include by way of example the following lipases: a phospholipase A1 LECITASE® ULTRA (Novozymes A/S, Denmark), phospholipase A2 (e.g. phospholipase A2 from LIPOMOD™ 22L from Biocatalysts, LIPOMAX™ and LysoMax PLA2™ from Genecor), LIPOLASE® (Novozymes A/S, Denmark).

In some embodiments it may be beneficial to combine the use of lipid acyltransferase with a phospholipase, such as phospholipase A1, phospholipase A2, phospholipase B, Phospholipase C and/or phospholipase D.

The combined use may be performed sequentially or concurrently, e.g. the lipid acyl transferase treatment may occur prior to or during the further enzyme treatment. Alternatively, the further enzyme treatment may occur prior to or during the lipid acyl transferase treatment.

In the case of sequential enzyme treatments, in some embodiments it may be advantageous to remove the first enzyme used, e.g. by heat deactivation or by use of an immobilised enzyme, prior to treatment with the second (and/or third etc.) enzyme.

Post-Transcription and Post-Translational Modifications

Suitably the lipid acyltransferase in accordance with the present invention may be encoded by any one of the nucleotide sequences taught herein.

Depending upon the host cell used post-transcriptional and/or post-translational modifications may be made. It is envisaged that the lipid acyltransferase for use in the present methods and/or uses encompasses lipid acyltransferases which have undergone post-transcriptional and/or post-translational modification.

By way of example only, the expression of the nucleotide sequence shown herein as SEQ ID No. 49 (see FIG. 57) in a host cell (such as Bacillus licheniformis for example) results in post-transcriptional and/or post-translational modifications which leads to the amino acid sequence shown herein as SEQ ID No. 68 (see FIG. 73).

SEQ ID No. 68 is the same as SEQ ID No. 16 (shown herein in FIG. 1) except that SEQ ID No. 68 has undergone post-translational and/or post-transcriptional modification to remove 38 amino acids.

Isolated

In one aspect, the lipid acyltransferase is a recovered/isolated lipid acyltransferase. Thus, the lipid acyltransferase produced may be in an isolated form.

In another aspect, the nucleotide sequence encoding a lipid acyltransferase for use in the present invention may be in an isolated form.

The term "isolated" means that the sequence or protein is at least substantially free from at least one other component with which the sequence or protein is naturally associated in nature and as found in nature.

Purified

In one aspect, the lipid acyltransferase may be in a purified form.

In another aspect, the nucleotide sequence encoding a lipid acyltransferase for use in the present invention may be in a purified form.

The term "purified" means that the sequence is in a relatively pure state—e.g. at least about 51% pure, or at least about 75%, or at least about 80%, or at least about 90% pure, or at least about 95% pure or at least about 98% pure.

Cloning a Nucleotide Sequence Encoding a Polypeptide According to the Present Invention A nucleotide sequence encoding either a polypeptide which has the specific properties as defined herein or a polypeptide which is suitable for modification may be isolated from any cell or organism producing said polypeptide. Various methods are well known within the art for the isolation of nucleotide sequences.

For example, a genomic DNA and/or cDNA library may be constructed using chromosomal DNA or messenger RNA from the organism producing the polypeptide. If the amino acid sequence of the polypeptide is known, labeled oligonucleotide probes may be synthesised and used to identify polypeptide-encoding clones from the genomic library prepared from the organism. Alternatively, a labelled oligonucleotide probe containing sequences homologous to another known polypeptide gene could be used to identify polypeptide-encoding clones. In the latter case, hybridisation and washing conditions of lower stringency are used.

Alternatively, polypeptide-encoding clones could be identified by inserting fragments of genomic DNA into an expression vector, such as a plasmid, transforming enzyme-negative bacteria with the resulting genomic DNA library, and then plating the transformed bacteria onto agar containing an enzyme inhibited by the polypeptide, thereby allowing clones expressing the polypeptide to be identified.

In a yet further alternative, the nucleotide sequence encoding the polypeptide may be prepared synthetically by established standard methods, e.g. the phosphoroamidite method described by Beucage S. L. et al (1981) Tetrahedron Letters 22, p 1859-1869, or the method described by Matthes et al (1984) EMBO J. 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al (Science (1988) 239, pp 487-491).

Nucleotide Sequences

The present invention also encompasses nucleotide sequences encoding polypeptides having the specific properties as defined herein. The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or antisense strand.

The term "nucleotide sequence" in relation to the present invention includes genomic DNA, cDNA, synthetic DNA, and RNA. Preferably it means DNA, more preferably cDNA for the coding sequence.

In a preferred embodiment, the nucleotide sequence per se encoding a polypeptide having the specific properties as defined herein does not cover the native nucleotide sequence in its natural environment when it is linked to its naturally associated sequence(s) that is/are also in its/their natural environment. For ease of reference, we shall call this preferred embodiment the "non-native nucleotide sequence". In this regard, the term "native nucleotide sequence" means an entire nucleotide sequence that is in its native environment and when operatively linked to an entire promoter with which it is naturally associated, which promoter is also in its native environment. Thus, the polypeptide of the present invention can be expressed by a nucleotide sequence in its native organism but wherein the nucleotide sequence is not under the control of the promoter with which it is naturally associated within that organism.

Preferably the polypeptide is not a native polypeptide. In this regard, the term "native polypeptide" means an entire polypeptide that is in its native environment and when it has been expressed by its native nucleotide sequence.

Typically, the nucleotide sequence encoding polypeptides having the specific properties as defined herein is prepared using recombinant DNA techniques (i.e. recombinant DNA). However, in an alternative embodiment of the invention, the nucleotide sequence could be synthesised, in whole or in part, using chemical methods well known in the art (see Caruthers M H et al (1980) Nuc Acids Res Symp Ser 215-23 and Horn T at al (1980) Nuc Acids Res Symp Ser 225-232).

Molecular Evolution

Once an enzyme-encoding nucleotide sequence has been isolated, or a putative enzyme-encoding nucleotide sequence has been identified, it may be desirable to modify the selected nucleotide sequence, for example it may be desirable to mutate the sequence in order to prepare an enzyme in accordance with the present invention.

Mutations may be introduced using synthetic oligonucleotides. These oligonucleotides contain nucleotide sequences flanking the desired mutation sites.

A suitable method is disclosed in Morinaga et al (Biotechnology (1984) 2, p 646-649). Another method of introducing mutations into enzyme-encoding nucleotide sequences is described in Nelson and Long (Analytical Biochemistry (1989), 180, p 147-151).

Instead of site directed mutagenesis, such as described above, one can introduce mutations randomly for instance using a commercial kit such as the GeneMorph PCR mutagenesis kit from Stratagene, or the Diversify PCR random mutagenesis kit from Clontech. EP 0 583 265 refers to methods of optimising PCR based mutagenesis, which can also be combined with the use of mutagenic DNA analogues such as those described in EP 0 866 796. Error prone PCR technologies are suitable for the production of variants of lipid acyl transferases with preferred characteristics. WO0206457 refers to molecular evolution of lipases.

A third method to obtain novel sequences is to fragment non-identical nucleotide sequences, either by using any number of restriction enzymes or an enzyme such as Dnase I, and reassembling full nucleotide sequences coding for functional proteins. Alternatively one can use one or multiple non-identical nucleotide sequences and introduce mutations during the reassembly of the full nucleotide sequence. DNA shuffling and family shuffling technologies are suitable for the production of variants of lipid acyl transferases with preferred characteristics. Suitable methods for performing 'shuffling' can be found in EP0 752 008, EP1 138 763, EP1 103 606. Shuffling can also be combined with other forms of DNA mutagenesis as described in U.S. Pat. No. 6,180,406 and WO 01/34835.

Thus, it is possible to produce numerous site directed or random mutations into a nucleotide sequence, either in vivo or in vitro, and to subsequently screen for improved functionality of the encoded polypeptide by various means. Using in silico and exo mediated recombination methods (see WO 00/58517, U.S. Pat. No. 6,344,328, U.S. Pat. No. 6,361,974), for example, molecular evolution can be performed where the variant produced retains very low homology to known enzymes or proteins. Such variants thereby obtained may have significant structural analogy to known transferase enzymes, but have very low amino acid sequence homology.

As a non-limiting example, In addition, mutations or natural variants of a polynucleotide sequence can be recombined with either the wild type or other mutations or natural variants to produce new variants. Such new variants can also be screened for improved functionality of the encoded polypeptide.

The application of the above-mentioned and similar molecular evolution methods allows the identification and selection of variants of the enzymes of the present invention which have preferred characteristics without any prior knowledge of protein structure or function, and allows the production of non-predictable but beneficial mutations or variants. There are numerous examples of the application of molecular evolution in the art for the optimisation or alteration of enzyme activity, such examples include, but are not limited to one or more of the following: optimised expression and/or activity in a host cell or in vitro, increased enzymatic activity, altered substrate and/or product specificity, increased or decreased enzymatic or structural stability, altered enzymatic activity/specificity in preferred environmental conditions, e.g. temperature, pH, substrate As will be apparent to a person skilled in the art, using molecular evolution tools an enzyme may be altered to improve the functionality of the enzyme.

Suitably, the nucleotide sequence encoding a lipid acyltransferase used in the invention may encode a variant lipid acyltransferase, i.e. the lipid acyltransferase may contain at least one amino acid substitution, deletion or addition, when compared to a parental enzyme. Variant enzymes retain at least 1%, 2%, 3%, 5%, 10%, 15%, 20%, 30%, 40%, 50%, 60%, 70%, 80%, 90%, 95%, 97%, 99% homology with the parent enzyme. Suitable parent enzymes may include any enzyme with esterase or lipase activity. Preferably, the parent enzyme aligns to the pfam00657 consensus sequence.

In a preferable embodiment a variant lipid acyltransferase enzyme retains or incorporates at least one or more of the pfam00657 consensus sequence amino acid residues found in the GDSx, GANDY and HPT blocks.

Enzymes, such as lipases with no or low lipid acyltransferase activity in an aqueous environment may be mutated using molecular evolution tools to introduce or enhance the transferase activity, thereby producing a lipid acyltransferase enzyme with significant transferase activity suitable for use in the compositions and methods of the present invention.

Suitably, the nucleotide sequence encoding a lipid acyltransferase for use in any one of the methods and/or uses of the present invention may encode a lipid acyltransferase that may be a variant with enhanced enzyme activity on polar lipids, preferably phospholipids and/or glycolipids when compared to the parent enzyme. Preferably, such variants also have low or no activity on lyso polar lipids. The enhanced activity on polar lipids, phospholipids and/or glycolipids may be the result of hydrolysis and/or transferase activity or a combination of both.

Variant lipid acyltransferases may have decreased activity on triglycerides, and/or monoglycerides and/or diglycerides compared with the parent enzyme.

Suitably the variant enzyme may have no activity on triglycerides and/or monoglycerides and/or diglycerides.

Alternatively, the variant enzyme may have increased thermostability.

The variant enzyme may have increased activity on one or more of the following, polar lipids, phospholipids, lecithin, phosphatidylcholine, glycolipids, digalactosyl monoglyceride, monogalactosyl monoglyceride.

Variants of lipid acyltransferases are known, and one or more of such variants may be suitable for use in the methods and uses according to the present invention and/or in the enzyme compositions according to the present invention. By way of example only, variants of lipid acyltransferases are described in the following references may be used in accordance with the present invention: Hilton & Buckley J. Biol. Chem. 1991 Jan. 15: 266 (2): 997-1000; Robertson at al J. Biol. Chem. 1994 Jan. 21; 269(3):2146-50; Brumlik at al J. Bacteriol 1996 April; 178 (7): 2060-4; Peelman et al Protein Sci. 1998 March; 7(3):587-99.

Amino Acid Sequences

The present invention also encompasses the use of amino acid sequences encoded by a nucleotide sequence which encodes a lipid acyltransferase for use in any one of the methods and/or uses of the present invention.

As used herein, the term "amino acid sequence" is synonymous with the term "polypeptide" and/or the term "protein". In some instances, the term "amino acid sequence" is synonymous with the term "peptide".

The amino acid sequence may be prepared/isolated from a suitable source, or it may be made synthetically or it may be prepared by use of recombinant DNA techniques.

Suitably, the amino acid sequences may be obtained from the isolated polypeptides taught herein by standard techniques.

One suitable method for determining amino acid sequences from isolated polypeptides is as follows:

Purified polypeptide may be freeze-dried and 100 µg of the freeze-dried material may be dissolved in 50 µl of a mixture of 8 M urea and 0.4 M ammonium hydrogen carbonate, pH 8.4. The dissolved protein may be denatured and reduced for 15 minutes at 50° C. following overlay with nitrogen and addition of 5 µl of 45 mM dithiothreitol. After cooling to room temperature, 5 µl of 100 mM iodoacetamide may be added for the cysteine residues to be derivatized for 15 minutes at room temperature in the dark under nitrogen.

135 µl of water and 5 µg of endoproteinase Lys-C in 5 µl of water may be added to the above reaction mixture and the digestion may be carried out at 37° C. under nitrogen for 24 hours.

The resulting peptides may be separated by reverse phase HPLC on a VYDAC C18 column (0.46×15 cm; 10 µm; The Separation Group, California, USA) using solvent A: 0.1% TFA in water and solvent B: 0.1% TFA in acetonitrile. Selected peptides may be re-chromatographed on a Develosil C18 column using the same solvent system, prior to N-terminal sequencing. Sequencing may be done using an Applied Biosystems 476A sequencer using pulsed liquid fast cycles according to the manufacturer's instructions (Applied Biosystems, California, USA).

Sequence Identity or Sequence Homology

Here, the term "homologue" means an entity having a certain homology with the subject amino acid sequences and the subject nucleotide sequences. Here, the term "homology" can be equated with "identity".

The homologous amino acid sequence and/or nucleotide sequence should provide and/or encode a polypeptide which retains the functional activity and/or enhances the activity of the enzyme.

In the present context, a homologous sequence is taken to include an amino acid sequence which may be at least 75, 85 or 90% identical, preferably at least 95 or 98% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence which may be at least 75, 85 or 90% identical, preferably at least 95 or 98% identical to a nucleotide sequence encoding a polypeptide of the present invention (the subject sequence). Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped"

alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons.

Calculation of maximum % homology therefore firstly requires the production of an optimal alignment, taking into consideration gap penalties. A suitable computer program for carrying out such an alignment is the Vector NTI (Invitrogen Corp.). Examples of other software that can perform sequence comparisons include, but are not limited to, the BLAST package (see Ausubel et al 1999 Short Protocols in Molecular Biology, 4$^{th}$ Ed—Chapter 18), and FASTA (Altschul et al 1990 J. Mol. Biol. 403-410). Both BLAST and FASTA are available for offline and online searching (see Ausubel et al 1999, pages 7-58 to 7-60). However, for some applications, it is preferred to use the Vector NTI program. A new tool, called BLAST 2 Sequences is also available for comparing protein and nucleotide sequence (see FEMS Microbiol Lett 1999 174(2): 247-50; FEMS Microbiol Lett 1999 177(1): 187-8 and tatiana@ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom symbol comparison table if supplied (see user manual for further details). For some applications, it is preferred to use the default values for the Vector NTI package.

Alternatively, percentage homologies may be calculated using the multiple alignment feature in Vector NTI (Invitrogen Corp.), based on an algorithm, analogous to CLUSTAL (Higgins D G & Sharp P M (1988), Gene 73(1), 237-244).

Once the software has produced an optimal alignment, it is possible to calculate % homology, preferably % sequence identity. The software typically does this as part of the sequence comparison and generates a numerical result.

Should Gap Penalties be used when determining sequence identity, then preferably the following parameters are used for pairwise alignment:

| FOR BLAST | |
|---|---|
| GAP OPEN | 0 |
| GAP EXTENSION | 0 |

| FOR CLUSTAL | DNA | PROTEIN | |
|---|---|---|---|
| WORD SIZE | 2 | 1 | K triple |
| GAP PENALTY | 15 | 10 | |
| GAP EXTENSION | 6.66 | 0.1 | |

In one embodiment, preferably the sequence identity for the nucleotide sequences is determined using CLUSTAL with the gap penalty and gap extension set as defined above.

Suitably, the degree of identity with regard to a nucleotide sequence is determined over at least 20 contiguous nucleotides, preferably over at least 30 contiguous nucleotides, preferably over at least 40 contiguous nucleotides, preferably over at least 50 contiguous nucleotides, preferably over at least 60 contiguous nucleotides, preferably over at least 100 contiguous nucleotides.

Suitably, the degree of identity with regard to a nucleotide sequence may be determined over the whole sequence.

In one embodiment the degree of amino acid sequence identity in accordance with the present invention may be suitably determined by means of computer programs known in the art, such as Vector NTI 10 (Invitrogen Corp.). For pairwise alignment the matrix used is preferably BLOSUM62 with Gap opening penalty of 10.0 and Gap extension penalty of 0.1.

Suitably, the degree of identity with regard to an amino acid sequence is determined over at least 20 contiguous amino acids, preferably over at least 30 contiguous amino acids, preferably over at least 40 contiguous amino acids, preferably over at least 50 contiguous amino acids, preferably over at least 60 contiguous amino acids.

Suitably, the degree of identity with regard to an amino acid sequence may be determined over the whole sequence.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
|---|---|---|
| | | I L V |
| | Polar-uncharged | C S T M |
| | | N Q |
| | Polar-charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

Nucleotide sequences for use in the present invention or encoding a polypeptide having the specific properties defined herein may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences.

The present invention also encompasses the use of nucleotide sequences that are complementary to the sequences discussed herein, or any derivative, fragment or derivative thereof. If the sequence is complementary to a fragment thereof then that sequence can be used as a probe to identify similar coding sequences in other organisms etc.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction polypeptide recognition sites, or to alter the property or function of the polypeptides encoded by the polynucleotides.

Polynucleotides (nucleotide sequences) of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15 to 30 nucleotides) flanking a region of the lipid targeting sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Hybridisation

The present invention also encompasses the use of sequences that are complementary to the sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies.

The present invention also encompasses the use of nucleotide sequences that are capable of hybridising to the sequences that are complementary to the subject sequences discussed herein, or any derivative, fragment or derivative thereof.

The present invention also encompasses sequences that are complementary to sequences that are capable of hybridising to the nucleotide sequences discussed herein.

Hybridisation conditions are based on the melting temperature (Tm) of the nucleotide binding complex, as taught in Berger and Kimmel (1987, Guide to Molecular Cloning Techniques, Methods in Enzymology, Vol. 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridisation can be used to identify or detect identical nucleotide sequences while an intermediate (or low) stringency hybridisation can be used to identify or detect similar or related polynucleotide sequences.

Preferably, the present invention encompasses the use of sequences that are complementary to sequences that are capable of hybridising under high stringency conditions or intermediate stringency conditions to nucleotide sequences encoding polypeptides having the specific properties as defined herein.

More preferably, the present invention encompasses the use of sequences that are complementary to sequences that are capable of hybridising under high stringency conditions (e.g. 65° C. and 0.1×SSC {1×SSC=0.15 M NaCl, 0.015 M Na-citrate pH 7.0}) to nucleotide sequences encoding polypeptides having the specific properties as defined herein.

The present invention also relates to the use of nucleotide sequences that can hybridise to the nucleotide sequences discussed herein (including complementary sequences of those discussed herein).

The present invention also relates to the use of nucleotide sequences that are complementary to sequences that can hybridise to the nucleotide sequences discussed herein (including complementary sequences of those discussed herein).

Also included within the scope of the present invention are the use of polynucleotide sequences that are capable of hybridising to the nucleotide sequences discussed herein under conditions of intermediate to maximal stringency.

In a preferred aspect, the present invention covers the use of nucleotide sequences that can hybridise to the nucleotide sequences discussed herein, or the complement thereof, under stringent conditions (e.g. 50° C. and 0.2×SSC).

In a more preferred aspect, the present invention covers the use of nucleotide sequences that can hybridise to the nucleotide sequences discussed herein, or the complement thereof, under high stringency conditions (e.g. 65° C. and 0.1×SSC).

Expression of Polypeptides

A nucleotide sequence for use in the present invention or for encoding a polypeptide having the specific properties as defined herein can be incorporated into a recombinant replicable vector. The vector may be used to replicate and express the nucleotide sequence, in polypeptide form, in and/or from a compatible host cell. Expression may be controlled using control sequences which include promoters/enhancers and other expression regulation signals. Prokaryotic promoters and promoters functional in eukaryotic cells may be used. Tissue specific or stimuli specific promoters may be used. Chimeric promoters may also be used comprising sequence elements from two or more different promoters described above.

The polypeptide produced by a host recombinant cell by expression of the nucleotide sequence may be secreted or may be contained intracellularly depending on the sequence and/or the vector used. The coding sequences can be designed with signal sequences which direct secretion of the substance coding sequences through a particular prokaryotic or eukaryotic cell membrane.

Constructs

The term "construct"—which is synonymous with terms such as "conjugate", "cassette" and "hybrid"—includes a nucleotide sequence encoding a polypeptide having the specific properties as defined herein for use according to the present invention directly or indirectly attached to a promoter. An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker which allows for the selection of the genetic construct.

For some applications, preferably the construct comprises at least a nucleotide sequence of the present invention or a nucleotide sequence encoding a polypeptide having the specific properties as defined herein operably linked to a promoter.

Organism

The term "organism" in relation to the present invention includes any organism that could comprise a nucleotide sequence according to the present invention or a nucleotide sequence encoding for a polypeptide having the specific properties as defined herein and/or products obtained therefrom.

The term "transgenic organism" in relation to the present invention includes any organism that comprises a nucleotide sequence coding for a polypeptide having the specific properties as defined herein and/or the products obtained therefrom, and/or wherein a promoter can allow expression of the nucleotide sequence coding for a polypeptide having the specific properties as defined herein within the organism. Preferably the nucleotide sequence is incorporated in the genome of the organism.

The term "transgenic organism" does not cover native nucleotide coding sequences in their natural environment when they are under the control of their native promoter which is also in its natural environment.

Therefore, the transgenic organism of the present invention includes an organism comprising any one of, or combinations of, a nucleotide sequence coding for a polypeptide having the specific properties as defined herein, constructs as defined herein, vectors as defined herein, plasmids as defined herein, cells as defined herein, or the products thereof. For example the transgenic organism can also comprise a nucleotide sequence coding for a polypeptide having the specific properties as defined herein under the control of a promoter not associated with a sequence encoding a lipid acyltransferase in nature.

Transformation of Host Cells/Organism

The host organism can be a prokaryotic or a eukaryotic organism.

Examples of suitable prokaryotic hosts include bacteria such as *E. coli* and *Bacillus licheniformis*, preferably *B. licheniformis*.

Teachings on the transformation of prokaryotic hosts is well documented in the art, for example see Sambrook et al (Molecular Cloning: A Laboratory Manual, 2nd edition, 1989, Cold Spring Harbor Laboratory Press). If a prokaryotic host is used then the nucleotide sequence may need to be suitably modified before transformation—such as by removal of introns.

In another embodiment the transgenic organism can be a yeast.

Filamentous fungi cells may be transformed using various methods known in the art—such as a process involving protoplast formation and transformation of the protoplasts followed by regeneration of the cell wall in a manner known. The use of *Aspergillus* as a host microorganism is described in EP 0 238 023.

Another host organism can be a plant. A review of the general techniques used for transforming plants may be found in articles by Potrykus (*Annu Rev Plant Physiol Plant Mol Biol* [1991] 42:205-225) and Christou (Agro-Food-Industry Hi-Tech March/April 1994 17-27). Further teachings on plant transformation may be found in EP-A-0449375.

General teachings on the transformation of fungi, yeasts and plants are presented in following sections.

Transformed Fungus

A host organism may be a fungus—such as a filamentous fungus. Examples of suitable such hosts include any member belonging to the genera *Thermomyces, Acremonium, Aspergillus, Penicillium, Mucor, Neurospora, Trichoderma* and the like.

Teachings on transforming filamentous fungi are reviewed in U.S. Pat. No. 5,741,665 which states that standard techniques for transformation of filamentous fungi and culturing the fungi are well known in the art. An extensive review of techniques as applied to *N. crassa* is found, for example in Davis and de Serres, *Methods Enzymol* (1971) 17A: 79-143.

Further teachings on transforming filamentous fungi are reviewed in U.S. Pat. No. 5,674,707.

In one aspect, the host organism can be of the genus *Aspergillus*, such as *Aspergillus niger*.

A transgenic *Aspergillus* according to the present invention can also be prepared by following, for example, the teachings of Turner G. 1994 (Vectors for genetic manipulation. In: Martinelli S. D., Kinghorn J. R. (Editors) *Aspergillus:* 50 years on. Progress in industrial microbiology vol 29. Elsevier Amsterdam 1994. pp. 641-666).

Gene expression in filamentous fungi has been reviewed in Punt et al. (2002) Trends Biotechnol 2002 May; 20(5):200-6, Archer & Peberdy Crit Rev Biotechnol (1997) 17(4):273-306.

Transformed Yeast

In another embodiment, the transgenic organism can be a yeast.

A review of the principles of heterologous gene expression in yeast are provided in, for example, *Methods Mol Biol* (1995), 49:341-54, and *Curr Opin Biotechnol* (1997) October; 8(5):554-60

In this regard, yeast—such as the species *Saccharomyces cerevisi* or *Pichia pastoris* (see FEMS Microbiol Rev (2000 24(1):45-66), may be used as a vehicle for heterologous gene expression.

A review of the principles of heterologous gene expression in *Saccharomyces cerevisiae* and secretion of gene products is given by E Hinchcliffe E Kenny (1993, "Yeast as a vehicle for the expression of heterologous genes", Yeasts, Vol 5, Anthony H Rose and J Stuart Harrison, eds, 2nd edition, Academic Press Ltd.).

For the transformation of yeast, several transformation protocols have been developed. For example, a transgenic *Saccharomyces* according to the present invention can be prepared by following the teachings of Hinnen et al., (1978, *Proceedings of the National Academy of Sciences of the USA* 75, 1929); Beggs, J D (1978, *Nature*, London, 275, 104); and Ito, H et al (1983, J Bacteriology 153, 163-168).

The transformed yeast cells may be selected using various selective markers—such as auxotrophic markers dominant antibiotic resistance markers.

A suitable yeast host organism can be selected from the biotechnologically relevant yeasts species such as, but not limited to, yeast species selected from *Pichia* spp., *Hansenula* spp., *Kluyveromyces, Yarrowinia* spp., *Saccharomyces* spp., including *S. cerevisiae*, or *Schizosaccharomyce* spp. including *Schizosaccharomyce pombe*.

A strain of the methylotrophic yeast species *Pichia pastoris* may be used as the host organism.

In one embodiment, the host organism may be a *Hansenula* species, such as *H. polymorpha* (as described in WO01/39544).

Transformed Plants/Plant Cells

A host organism suitable for the present invention may be a plant. A review of the general techniques may be found in articles by Potrykus (*Annu Rev Plant Physiol Plant Mol Biol* [1991]42:205-225) and Christou (Agro-Food-Industry Hi-Tech March/April 1994 17-27), or in WO01/16308. The transgenic plant may produce enhanced levels of phytosterol esters and phytostanol esters, for example.

Therefore the present invention also relates to a method for the production of a transgenic plant with enhanced levels of phytosterol esters and phytostanol esters, comprising the steps of transforming a plant cell with a lipid acyltransferase as defined herein (in particular with an expression vector or construct comprising a lipid acyltransferase as defined herein), and growing a plant from the transformed plant cell.

Secretion

Often, it is desirable for the polypeptide to be secreted from the expression host into the culture medium from where the enzyme may be more easily recovered. According to the present invention, the secretion leader sequence may be selected on the basis of the desired expression host. Hybrid signal sequences may also be used with the context of the present invention.

Typical examples of secretion leader sequences not associated with a nucleotide sequence encoding a lipid acyltransferase in nature are those originating from the fungal amyloglucosidase (AG) gene (glaA—both 18 and 24 amino acid versions e.g. from *Aspergillus*), the a-factor gene (yeasts e.g. *Saccharomyces, Kluyveromyces* and *Hansenula*) or the α-amylase gene (*Bacillus*).

Detection

A variety of protocols for detecting and measuring the expression of the amino acid sequence are known in the art. Examples include enzyme-linked immunosorbent assay (ELISA), radioimmunoassay (RIA) and fluorescent activated cell sorting (FACS).

A wide variety of labels and conjugation techniques are known by those skilled in the art and can be used in various nucleic and amino acid assays.

A number of companies such as Pharmacia Biotech (Piscataway, N.J.), Promega (Madison, Wis.), and US Biochemical Corp (Cleveland, Ohio) supply commercial kits and protocols for these procedures.

Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. No. 3,817,837; U.S. Pat. No. 3,850,752; U.S. Pat. No. 3,939,350; U.S. Pat. No. 3,996,345; U.S. Pat. No. 4,277,437; U.S. Pat. No. 4,275,149 and U.S. Pat. No. 4,366,241.

Also, recombinant immunoglobulins may be produced as shown in U.S. Pat. No. 4,816,567.

Fusion Proteins

The lipid acyltransferase for use in the present invention may be produced as a fusion protein, for example to aid in extraction and purification thereof. Examples of fusion protein partners include glutathione-S-transferase (GST), 6×His, GAL4 (DNA binding and/or transcriptional activation domains) and β-galactosidase. It may also be convenient to include a proteolytic cleavage site between the fusion protein partner and the protein sequence of interest to allow removal of fusion protein sequences. Preferably the fusion protein will not hinder the activity of the protein sequence.

Gene fusion expression systems in *E. coli* have been reviewed in Curr. Opin. Biotechnol. (1995) 6(5):501-6.

The amino acid sequence of a polypeptide having the specific properties as defined herein may be ligated to a non-native sequence to encode a fusion protein. For example, for screening of peptide libraries for agents capable of affecting the substance activity, it may be useful to encode a chimeric substance expressing a non-native epitope that is recognised by a commercially available antibody.

The invention will now be described, by way of example only, with reference to the following Figures and Examples.

FIG. 1 shows the amino acid sequence of a mutant *Aeromonas salmonicida* mature lipid acyltransferase (GOAT) with a mutation of Asn80Asp (notably, amino acid 80 is in the mature sequence) (SEQ ID 16);

FIG. 2 shows an amino acid sequence (SEQ ID No. 1) a lipid acyl transferase from *Aeromonas hydrophila* (ATCC #7965);

FIG. 3 shows a pfam00657 consensus sequence from database version 6 (SEQ ID No. 2);

FIG. 4 shows an amino acid sequence (SEQ ID No. 3) obtained from the organism *Aeromonas hydrophila* (P10480; GI:121051);

FIG. 5 shows an amino acid sequence (SEQ ID No. 4) obtained from the organism *Aeromonas salmonicida* (AAG098404; GI:9964017);

FIG. 6 shows an amino acid sequence (SEQ ID No. 5) obtained from the organism *Streptomyces coelicolor* A3(2) (Genbank accession number NP_631558);

FIG. 7 shows an amino acid sequence (SEQ ID No. 6) obtained from the organism *Streptomyces coelicolor* A3(2) (Genbank accession number: CAC42140);

FIG. 8 shows an amino acid sequence (SEQ ID No. 7) obtained from the organism *Saccharomyces cerevisiae* (Genbank accession number P41734);

FIG. 9 shows an amino acid sequence (SEQ ID No. 8) obtained from the organism *Ralstonia* (Genbank accession number: AL646052);

FIG. 10 shows SEQ ID No. 9. Scoe1 NCBI protein accession code CAB39707.1 GI:4539178 conserved hypothetical protein [*Streptomyces coelicolor* A3(2)];

FIG. 11 shows an amino acid shown as SEQ ID No. 10. Scoe2 NCBI protein accession code CAC01477.1 GI:9716139 conserved hypothetical protein [*Streptomyces coelicolor* A3(2)];

FIG. 12 shows an amino acid sequence (SEQ ID No. 11) Scoe3 NCBI protein accession code CAB88833.1 GI:7635996 putative secreted protein. [*Streptomyces coelicolor* A3(2)];

FIG. 13 shows an amino acid sequence (SEQ ID No. 12) Scoe4 NCBI protein accession code CAB89450.1 GI:7672261 putative secreted protein. [*Streptomyces coelicolor* A3(2)];

FIG. 14 shows an amino acid sequence (SEQ ID No. 13) Scoe5 NCBI protein accession code CAB62724.1 GI:6562793 putative lipoprotein [*Streptomyces coelicolor* A3(2)];

FIG. 15 shows an amino acid sequence (SEQ ID No. 14) Srim1 NCBI protein accession code AAK84028.1 GI:15082088 GDSL-lipase [*Streptomyces rimosus*];

FIG. 16 shows an amino acid sequence (SEQ ID No. 15) of a lipid acyltransferase from *Aeromonas salmonicida* subsp. *Salmonicida* (ATCC#14174);

FIG. 17 shows SEQ ID No. 19. Scoe1 NCBI protein accession code CAB39707.1 GI:4539178 conserved hypothetical protein [*Streptomyces coelicolor* A3(2)];

FIG. 18 shows an amino acid sequence (SEQ ID No. 25) of the fusion construct used for mutagenesis of the *Aeromonas hydrophile* lipid acyltransferase gene. The underlined amino acids is a xylanase signal peptide;

FIG. 19 shows a polypeptide sequence of a lipid acyltransferase enzyme from *Streptomyces* (SEQ ID No. 26);

FIG. 20 shows a polypeptide sequence of a lipid acyltransferase enzyme from *Thermobifida* (SEQ ID No. 27);

FIG. 21 shows a polypeptide sequence of a lipid acyltransferase enzyme from *Thermobifida* (SEQ ID No. 28);

FIG. 22 shows a polypeptide of a lipid acyltransferase enzyme from *Corynebacterium efficiens* GDSx 300 amino acid (SEQ ID No. 29);

FIG. 23 shows a polypeptide of a lipid acyltransferase enzyme from *Novosphingobium aromaticivorans* GDSx 284 amino acid (SEQ ID No. 30);

FIG. 24 shows a polypeptide of a lipid acyltransferase enzyme from *Streptomyces coelicolor* GDSx 269 aa (SEQ ID No. 31);

FIG. 25 shows a polypeptide of a lipid acyltransferase enzyme from *Streptomyces avermitilis*\GDSx 269 amino acid (SEQ ID No. 32);

FIG. 26 shows a polypeptide of a lipid acyltransferase enzyme from *Streptomyces* (SEQ ID No. 33);

FIG. 27 shows an amino acid sequence (SEQ ID No. 34) obtained from the organism *Aeromonas hydrophila* (P10480; GI:121051) (notably, this is the mature sequence);

FIG. 28 shows the amino acid sequence (SEQ ID No. 35) of a mutant *Aeromonas salmonicida* mature lipid acyltransferase (GOAT) (notably, this is the mature sequence);

FIG. 29 shows a nucleotide sequence (SEQ ID No. 36) from *Streptomyces thermosacchari*;

FIG. 30 shows an amino acid sequence (SEQ ID No. 37) from *Streptomyces thermosacchari*;

FIG. 31 shows an amino acid sequence (SEQ ID No. 38) from *Thermobifida fusca*/GDSx 548 amino acid;

FIG. 32 shows a nucleotide sequence (SEQ ID No. 39) from *Thermobifida fusca*;

FIG. 33 shows an amino acid sequence (SEQ ID No. 40) from *Thermobifida fusca*/GDSx;

FIG. 34 shows an amino acid sequence (SEQ ID No. 41) from *Corynebacterium efficiens*/GDSx 300 amino acid;

FIG. 35 shows a nucleotide sequence (SEQ ID No. 42) from *Corynebacterium efficiens;*

FIG. 36 shows an amino acid sequence (SEQ ID No. 43) from *S. coelicolor*/GDSx 268 amino acid;

FIG. 37 shows a nucleotide sequence (SEQ ID No. 44) from *S. coelicolor;*

FIG. 38 shows an amino acid sequence (SEQ ID No. 45) from *S. avermitilis;*

FIG. 39 shows a nucleotide sequence (SEQ ID No. 46) from *S. avermitilis;*

FIG. 40 shows an amino acid sequence (SEQ ID No. 47) from *Thermobifida fusca*/GDSx;

FIG. 41 shows a nucleotide sequence (SEQ ID No. 48) from *Thermobifida fusca*/GDSx;

FIG. 42 shows an alignment of the L131 and homologues from *S. avermitilis* and *T. fusca* illustrates that the conservation of the GDSx motif (GDSY in L131 and *S. avermitilis* and *T. fusca*), the GANDY box, which is either GGNDA or GGNDL, and the HPT block (considered to be the conserved catalytic histidine). These three conserved blocks are highlighted;

FIG. 43 shows SEQ ID No 17 which is the amino acid sequence of a lipid acyltransferase from *Candida parapsilosis;*

FIG. 44 shows SEQ ID No 18 which is the amino acid sequence of a lipid acyltransferase from *Candida parapsilosis;*

Figure 48:
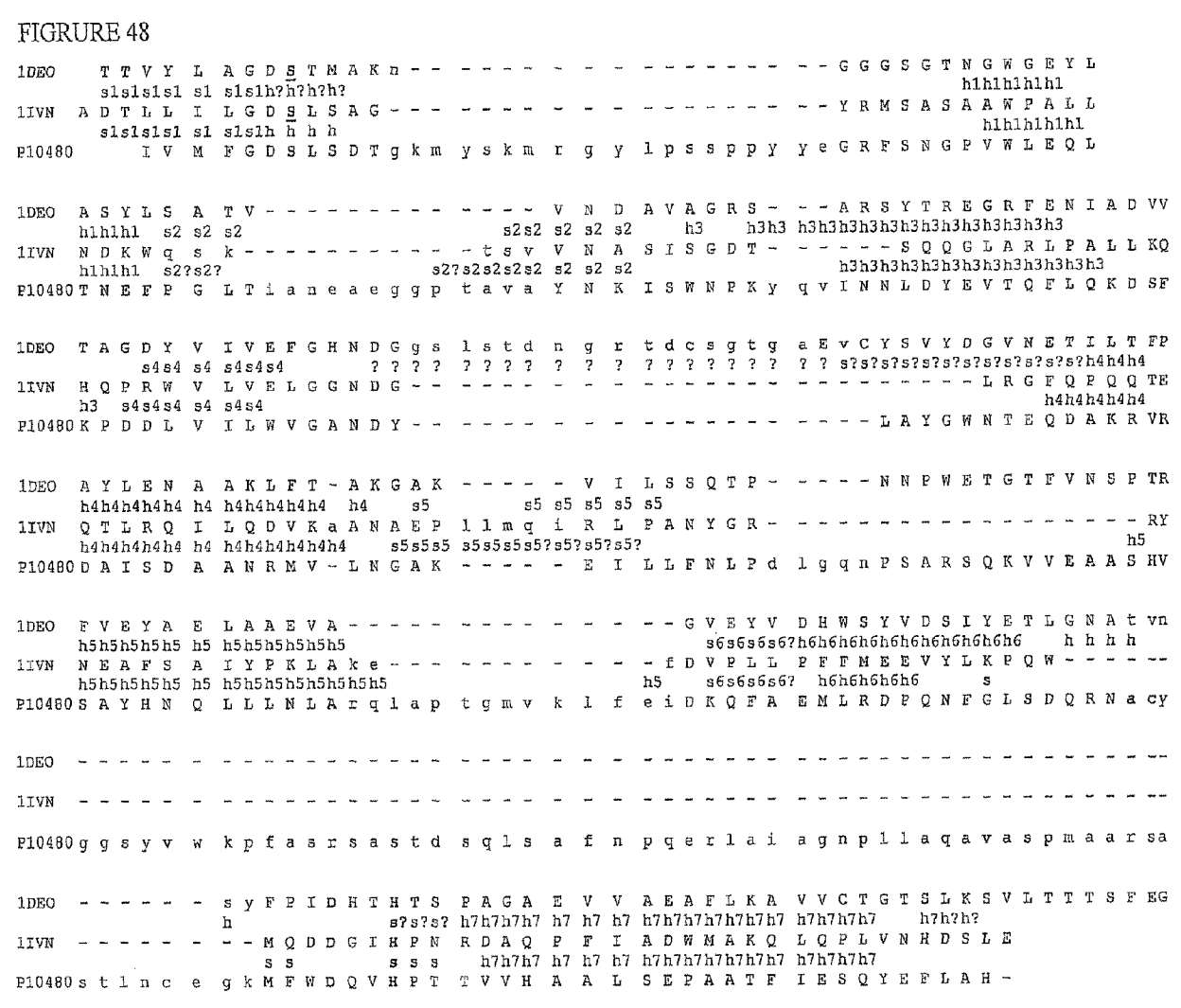

FIG. 48 shows alignment 1 of 1DEO (SEQ ID No. 120), 1IVN (SEQ ID No. 121), and P10480 (SEQ ID No. 34);

FIG. 49 shows alignment 2 of 1DEO (SEQ ID No. 120), 1IVN (SEQ ID No. 121), and P10480 (SEQ ID No. 34);

Figure 50:
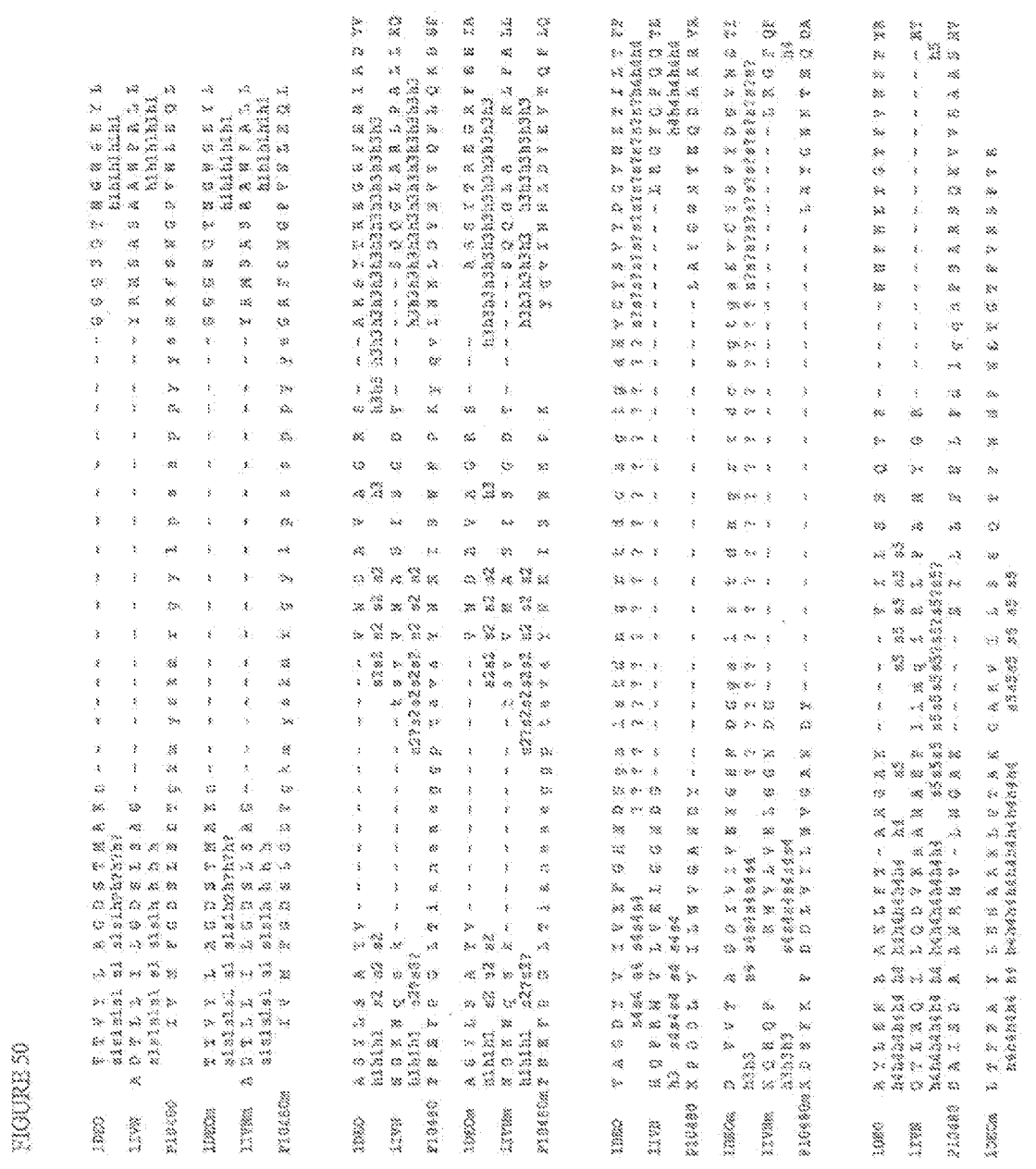

FIGS. 50 and 51 show an alignment of 1IVN (SEQ ID No. 121) to P10480 (SEQ ID No. 34) (P10480 is the database sequence for *A. hydrophila* enzyme), this alignment was obtained from the PFAM database and used in the model building process;

Figure 45:
FIG. 45 shows a ribbon representation of the 1IVN.PDB crystal structure which has glycerol in the active site. The Figure was made using the Deep View Swiss-PDB viewer.
Figure 46:
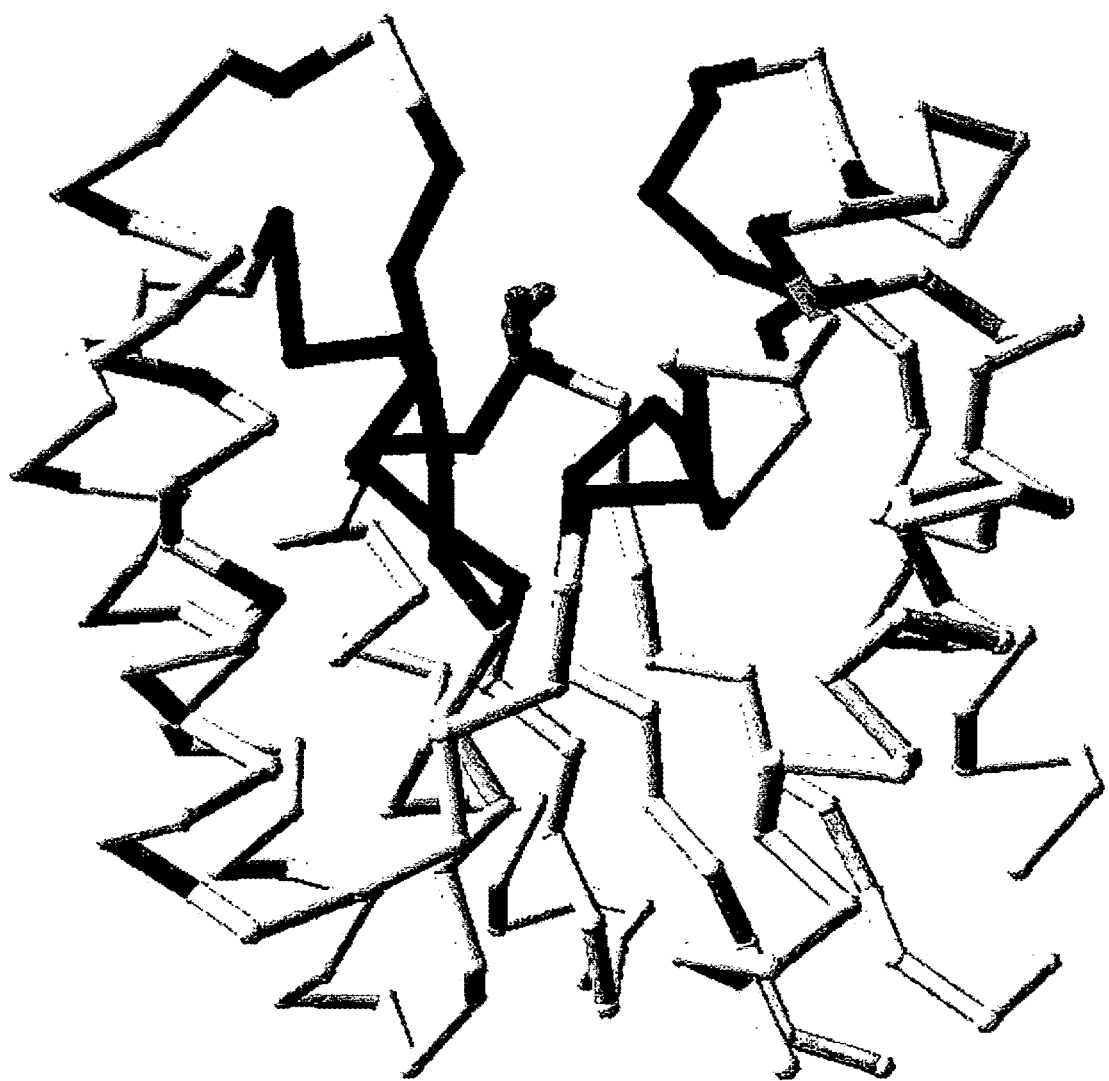
FIG. 46 shows 1IVN.PDB Crystal Structure—Side View using Deep View Swiss-PDB viewer, with glycerol in active site-residues within 10 Å of active site glycerol are coloured black.
Figure 47:
FIG. 47 shows 1IVN.PDB Crystal Structure—Top View using Deep View Swiss-PDB viewer, with glycerol in active site—residues within 10 Å of active site glycerol are coloured black.
Figure 54:
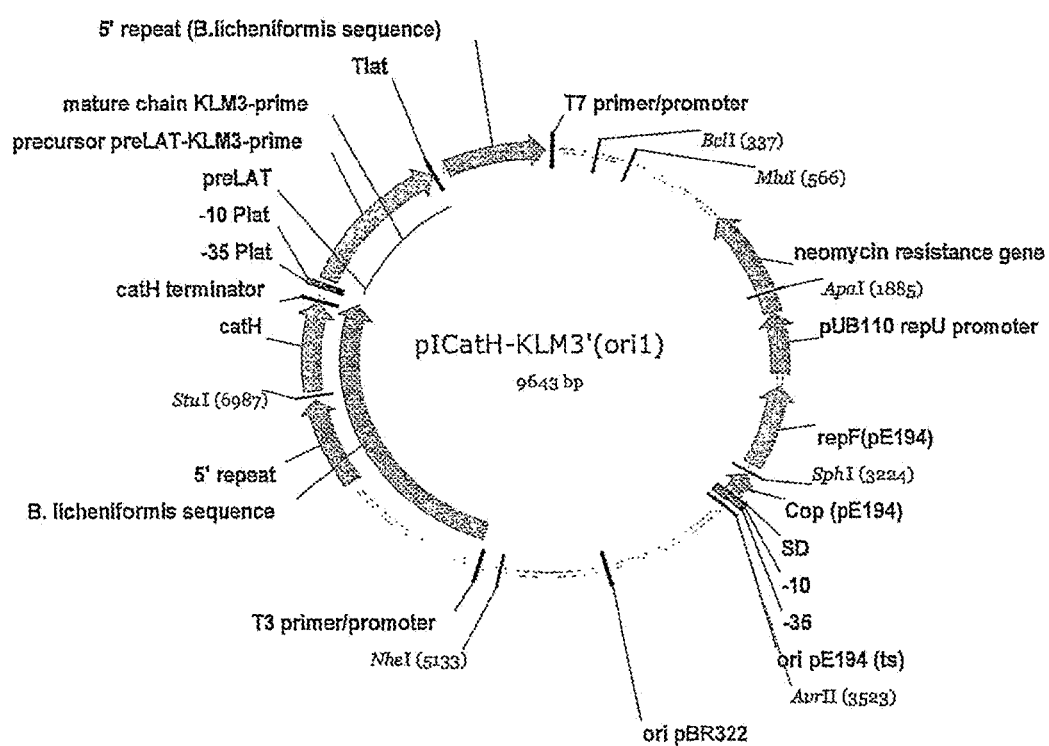
Figure 56:
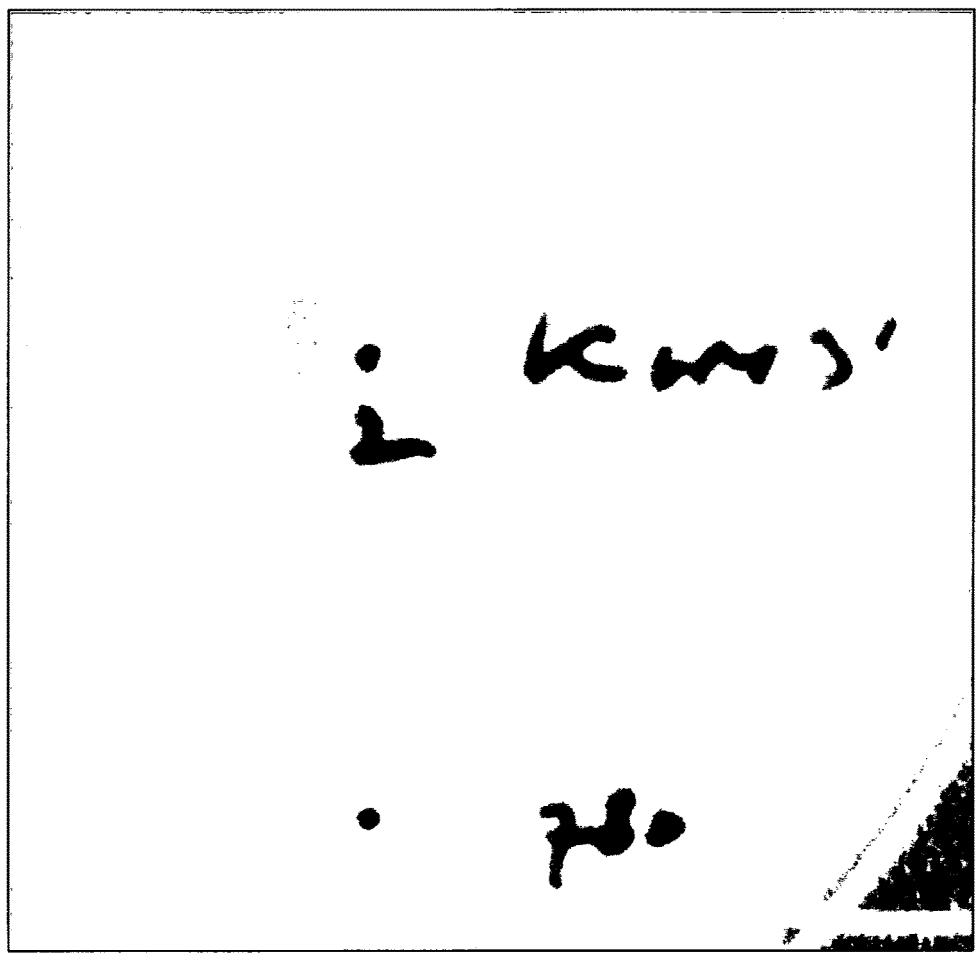

FIG. 52 shows an alignment where P10480 is the database sequence for *Aeromonas hydrophila*. This sequence is used for the model construction and the site selection. Note that the full protein (SEQ ID No. 25) is depicted, the mature protein (equivalent to SEQ ID No. 34) starts at residue 19. A. sal is *Aeromonas salmonicida* (SEQ ID No. 4) GDSX lipase, A. hyd is *Aeromonas hydrophila* (SEQ ID No. 34) GDSX lipase. The consensus sequence contains a * at the position of a difference between the listed sequences;

FIG. 53 shows a gene construct used in Example 1;

FIG. 54 shows a codon optimised gene construct (no. 052907) used in Example 1; and FIG. 55 shows the sequence of the XhoI insert containing the LAT-KLM3' precursor gene (SEQ ID No. 115), the −35 and −10 boxes are underlined;

FIG. 56 shows BML780-KLM3'CAP50 (comprising SEQ ID No. 16—upper colony) and BML780 (the empty host strain—lower colony) after 48 h growth at 37° C. on 1% tributyrin agar;

FIG. 57 shows a nucleotide sequence from *Aeromonas salmonicida* (SEQ ID No. 49) including the signal sequence (preLAT—positions 1 to 87);

FIG. 58 shows a nucleotide sequence (SEQ ID No. 50) encoding a lipid acyl transferase according to the present invention obtained from the organism *Aeromonas hydrophila;*

FIG. 59 shows a nucleotide sequence (SEQ ID No. 51) encoding a lipid acyl transferase according to the present invention obtained from the organism *Aeromonas salmonicida;*

FIG. 60 shows a nucleotide sequence (SEQ ID No. 52) encoding a lipid acyl transferase according to the present invention obtained from the organism *Streptomyces coelicolor* A3(2) (Genbank accession number NC_003888.1: 8327480 . . . 8328367);

FIG. 61 shows a nucleotide sequence (SEQ ID No. 53) encoding a lipid acyl transferase according to the present invention obtained from the organism *Streptomyces coelicolor* A3(2) (Genbank accession number AL939131.1: 265480 . . . 266367);

FIG. 62 shows a nucleotide sequence (SEQ ID No. 54) encoding a lipid acyl transferase according to the present invention obtained from the organism *Saccharomyces cerevisiae* (Genbank accession number Z75034);

FIG. 63 shows a nucleotide sequence (SEQ ID No. 55) encoding a lipid acyl transferase according to the present invention obtained from the organism *Ralstonia;*

FIG. 64 shows a nucleotide sequence shown as SEQ ID No. 56 encoding NCBI protein accession code CAB39707.1 GI:4539178 conserved hypothetical protein [*Streptomyces coelicolor* A3(2)];

FIG. 65 shows a nucleotide sequence shown as SEQ ID No. 57 encoding Scoe2 NCBI protein accession code CAC01477.1 GI:9716139 conserved hypothetical protein [*Streptomyces coelicolor* A3(2)];

FIG. 66 shows a nucleotide sequence shown as SEQ ID No. 58 encoding Scoe3 NCBI protein accession code CAB88833.1 GI:7635996 putative secreted protein. [*Streptomyces coelicolor* A3 (2)];

FIG. 67 shows a nucleotide sequence shown as SEQ ID No. 59 encoding Scoe4 NCBI protein accession code CAB89450.1 GI:7672261 putative secreted protein. [*Streptomyces coelicolor* A3(2)];

FIG. 68 shows a nucleotide sequence shown as SEQ ID No. 60, encoding Scoe5 NCBI protein accession code CAB62724.1 GI:6562793 putative lipoprotein [*Streptomyces coelicolor* A3(2)];

FIG. 69 shows a nucleotide sequence shown as SEQ ID No. 61 encoding Srim1 NCBI protein accession code AAK84028.1 GI:15082088 GDSL-lipase [*Streptomyces rimosus];*

Figure 74A:
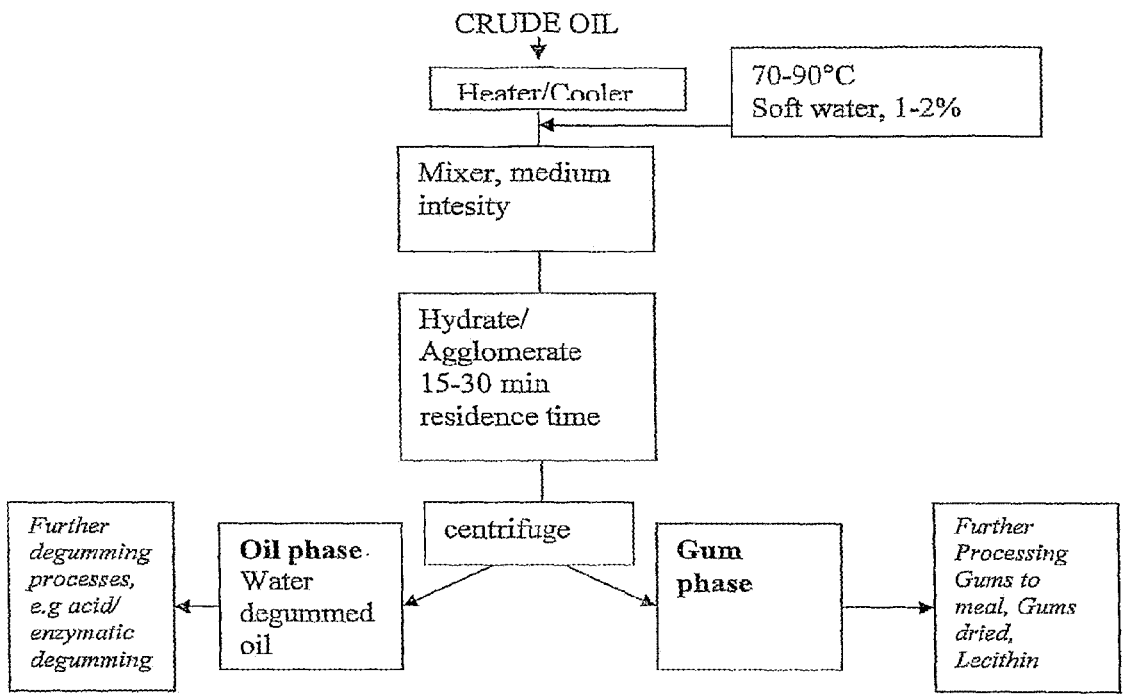
Figure 74B:
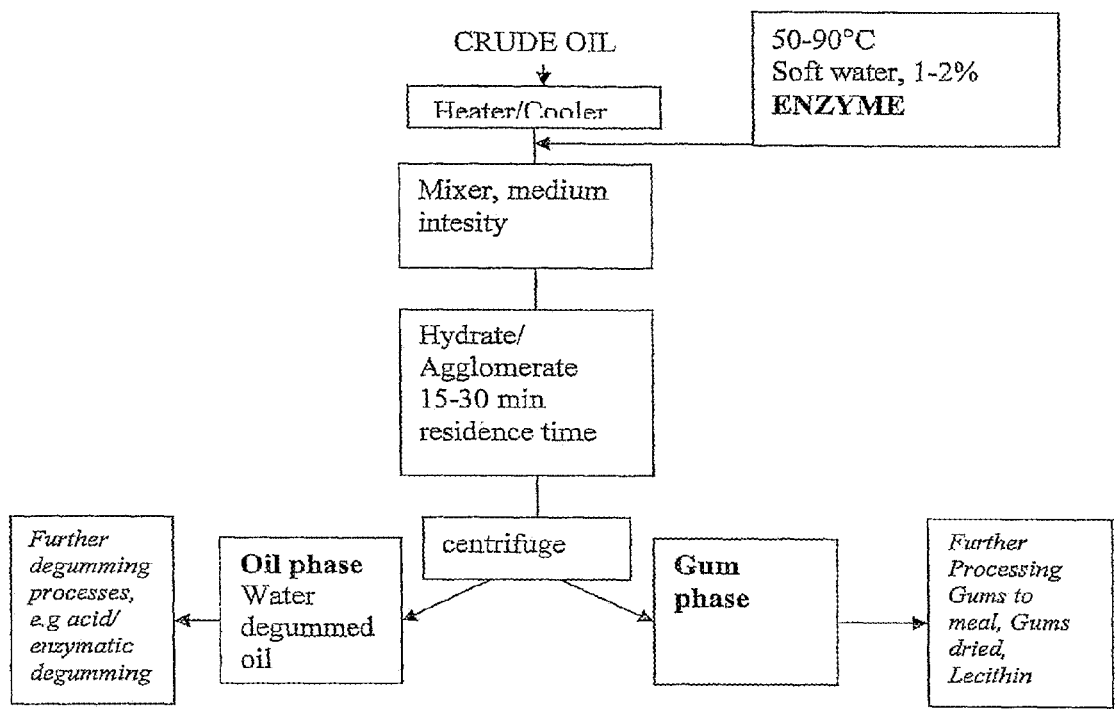
Figure 75:
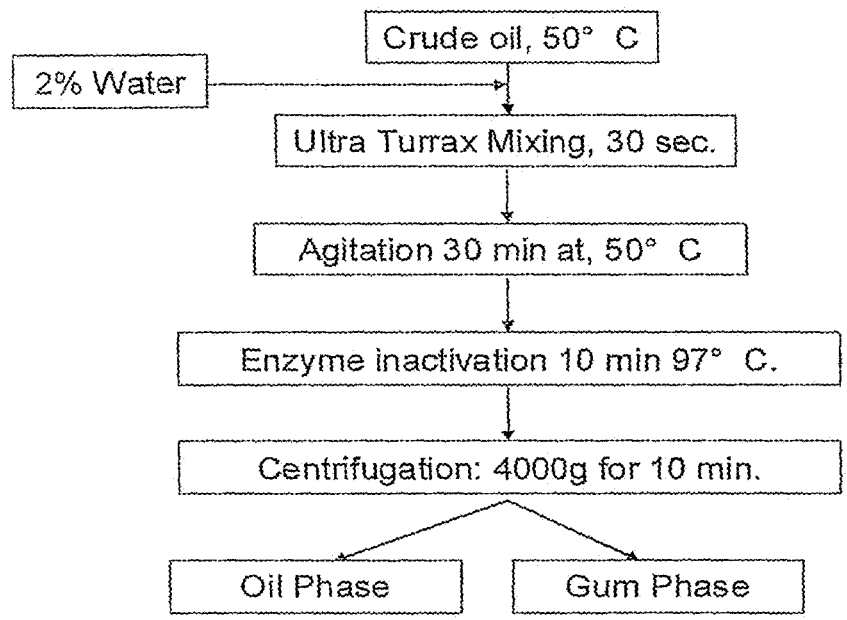
Figure 76:
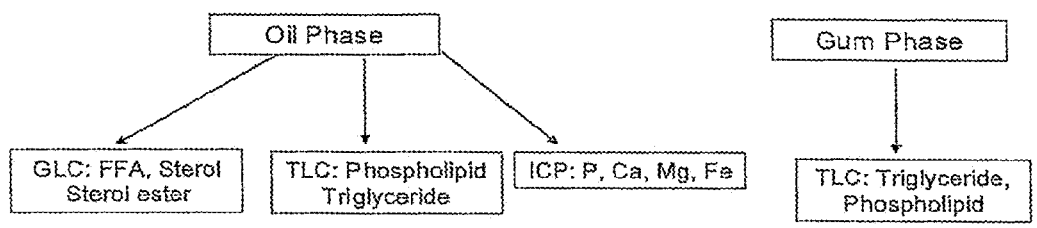
Figure 77:
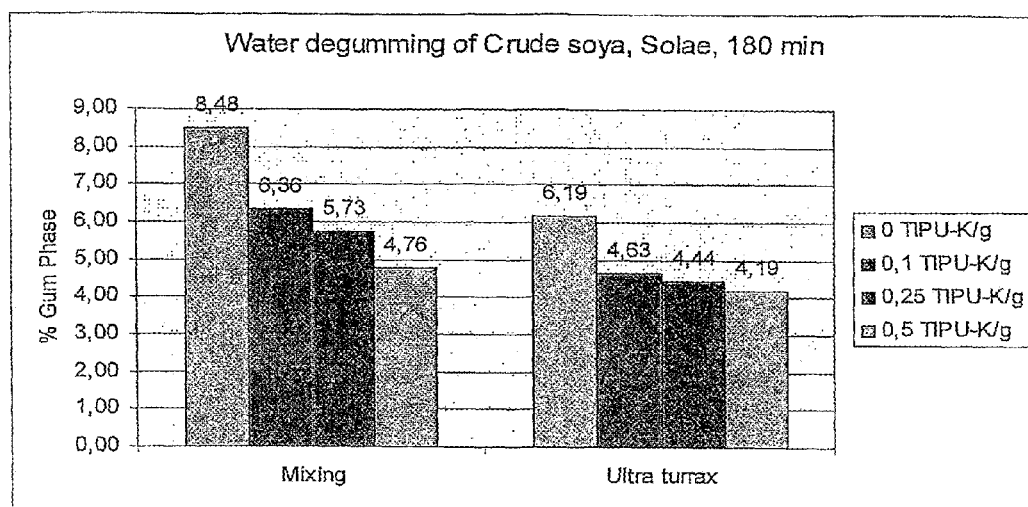
Figure 78:
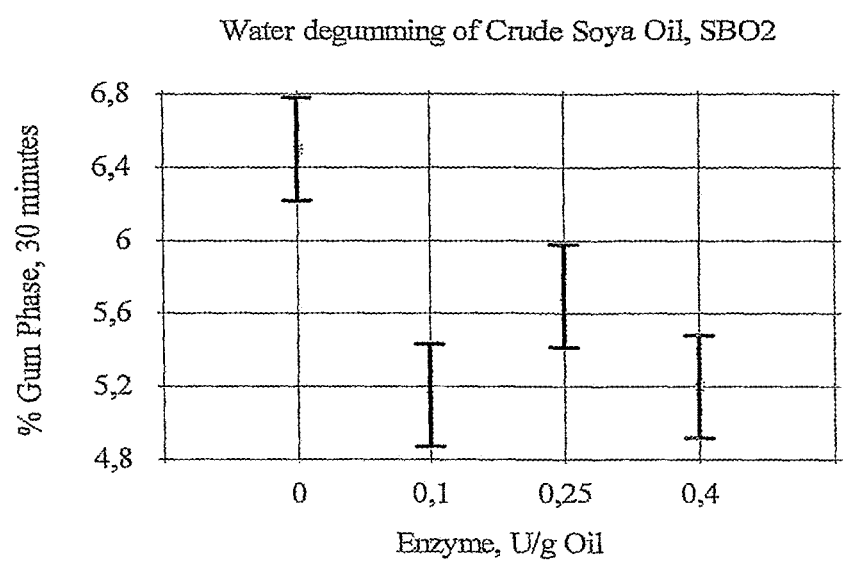
Figure 79:
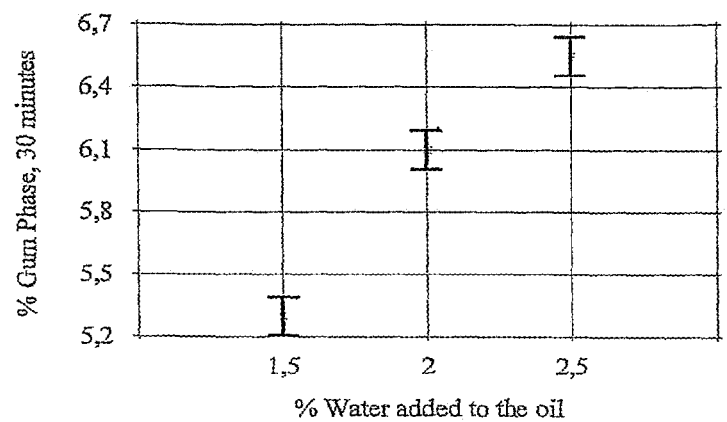
Figure 80:
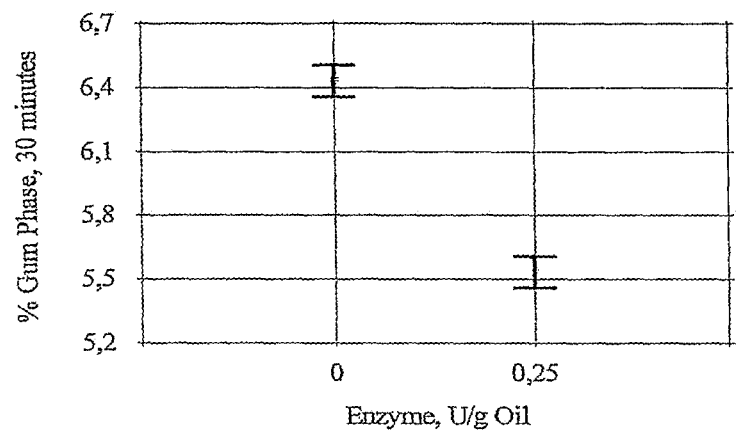
Figure 81:
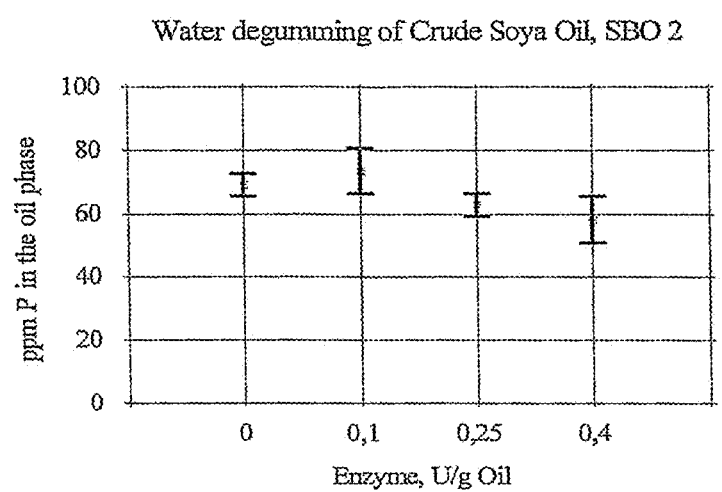
Figure 82:
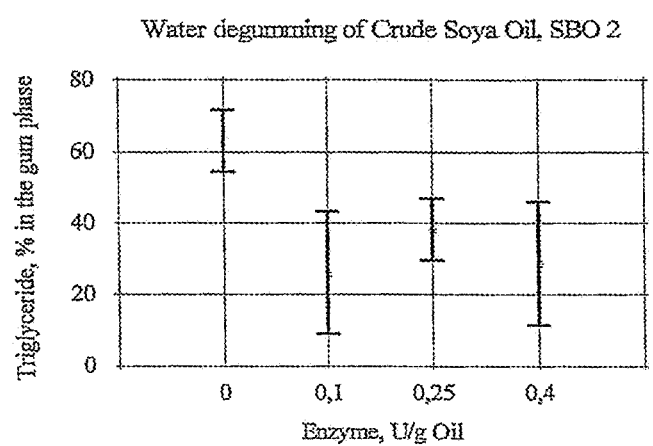
Figure 83:
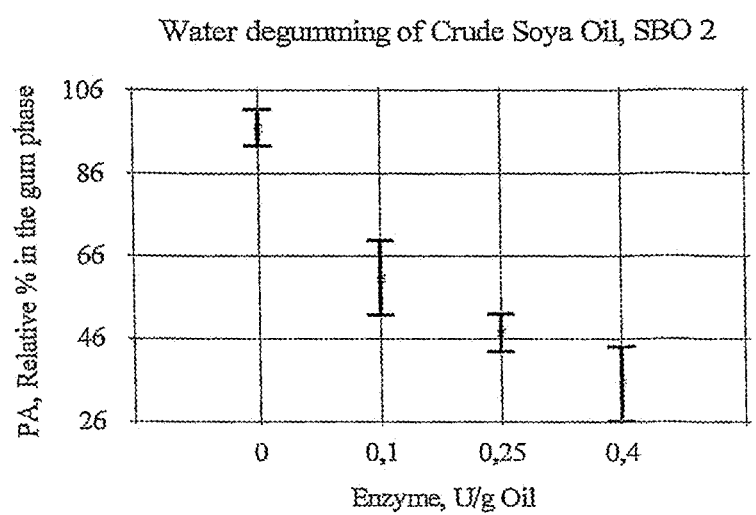
Figure 84:
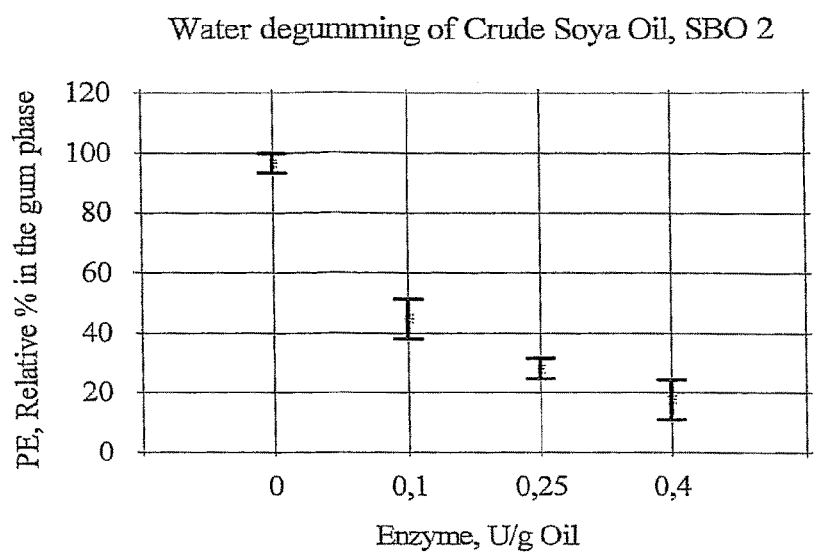
Figure 85:
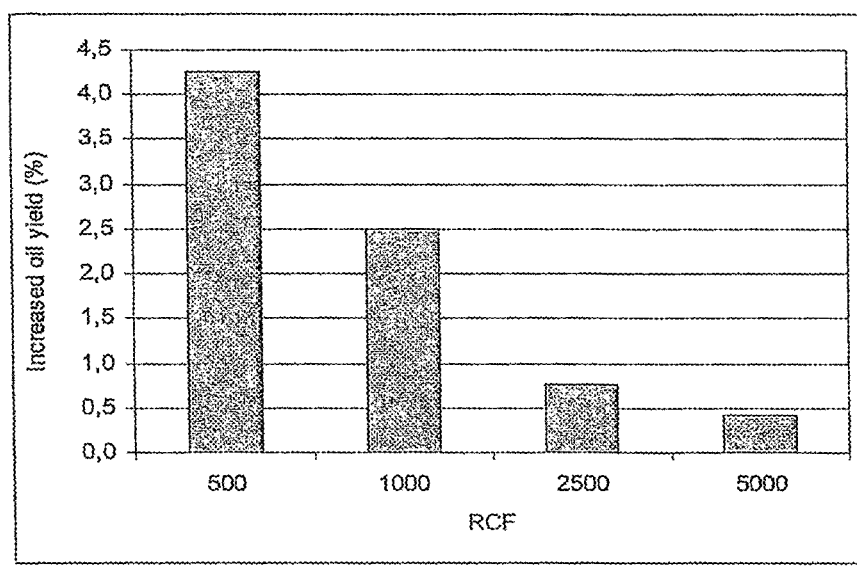
Figure 86:
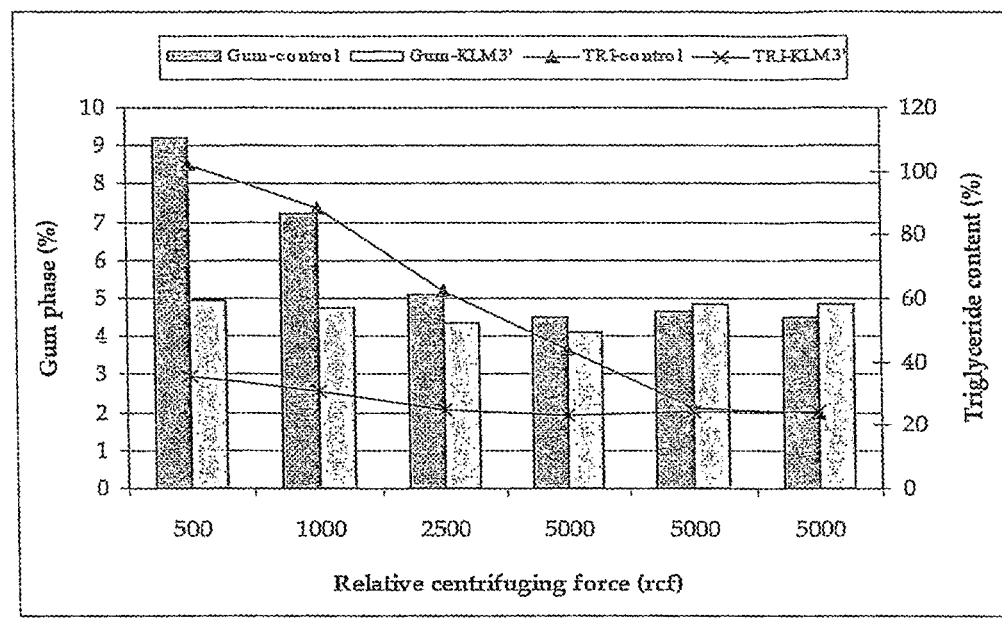
Figure 87:
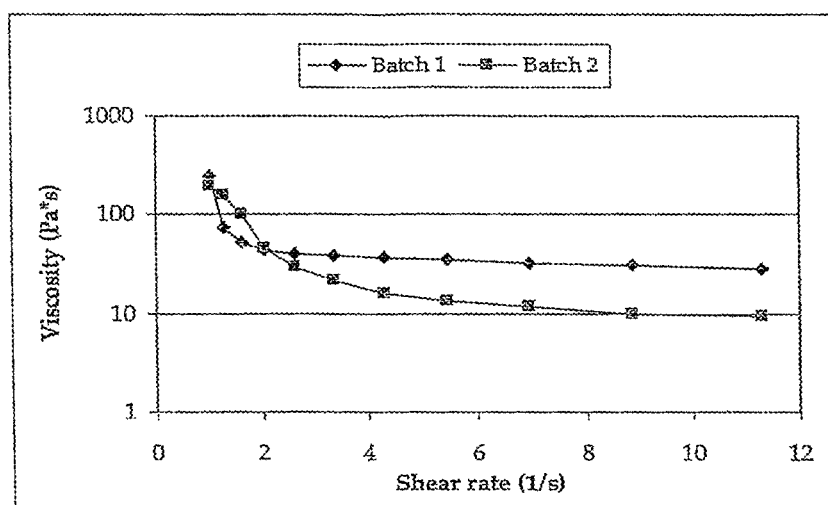
Figure 88:
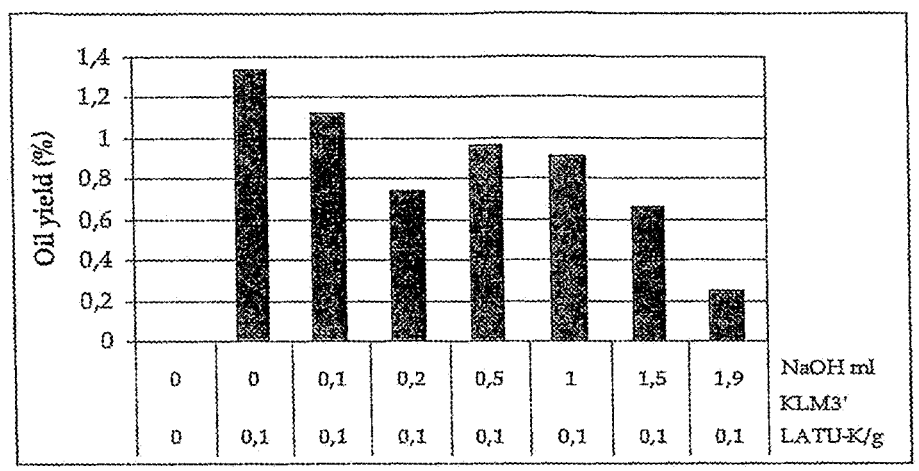
Figure 89:
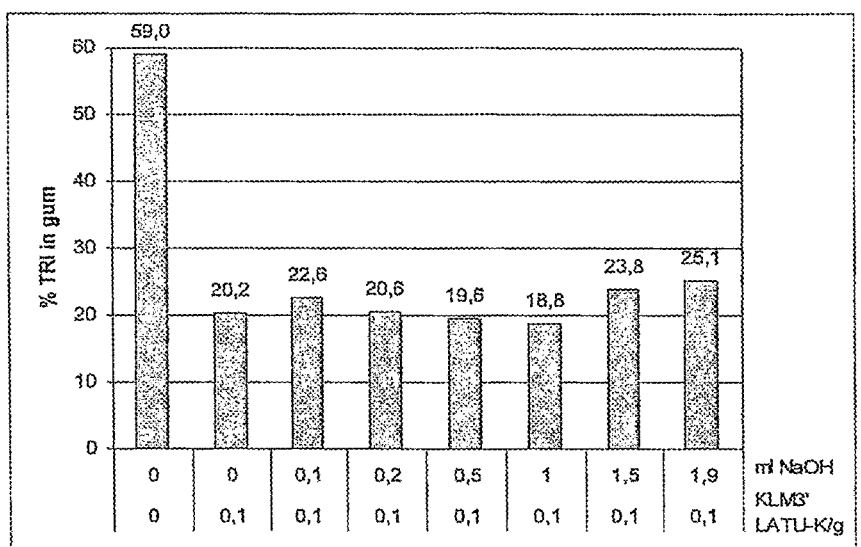
Figure 90:
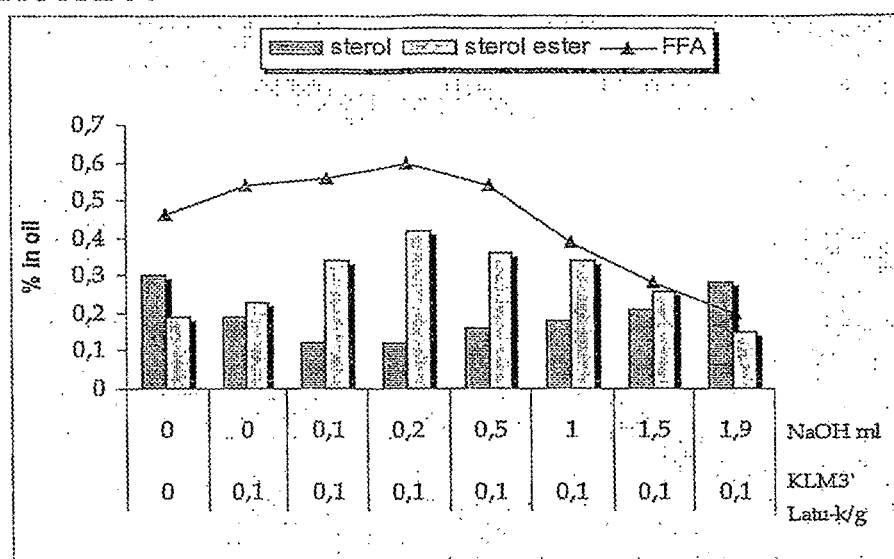
Figure 91:
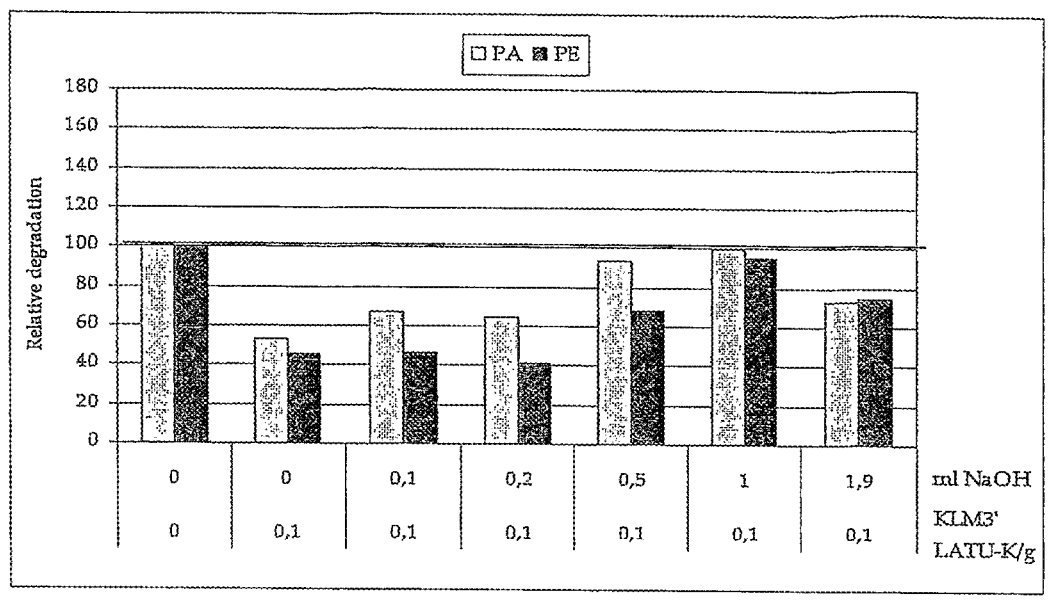
Figure 92:
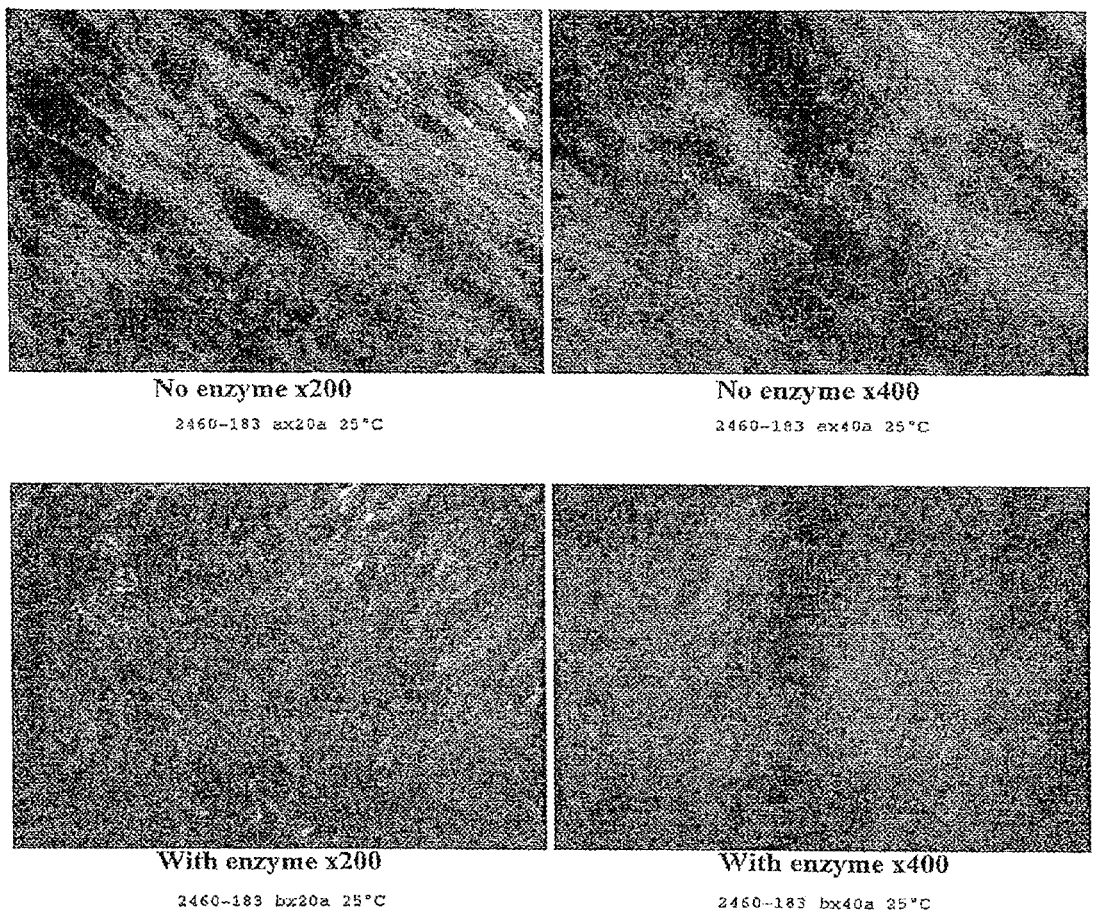
Figure 94:
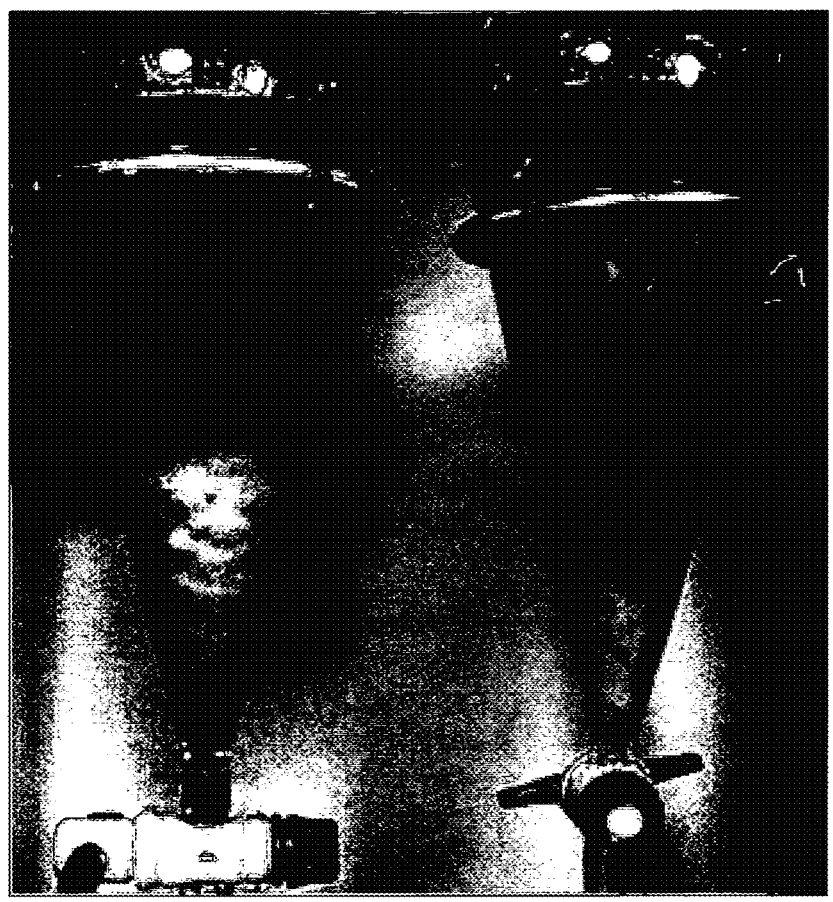
Figure 96:
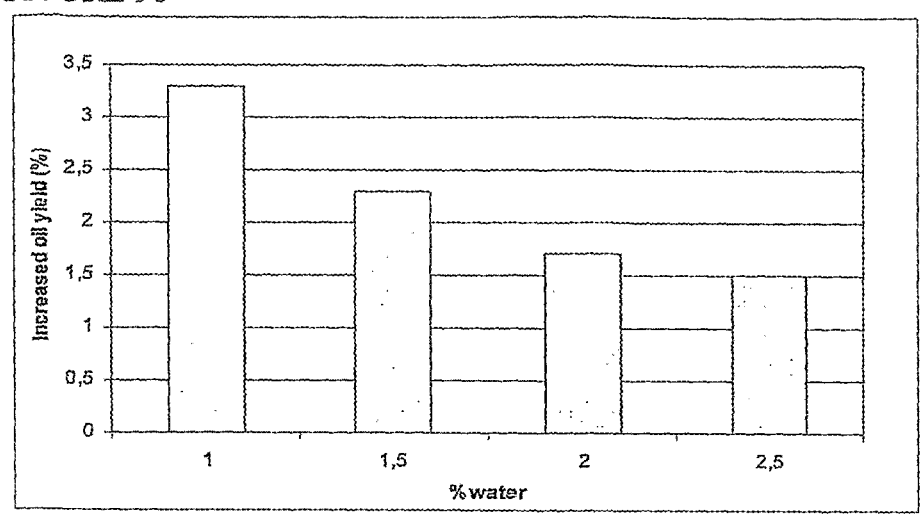
Figure 97:
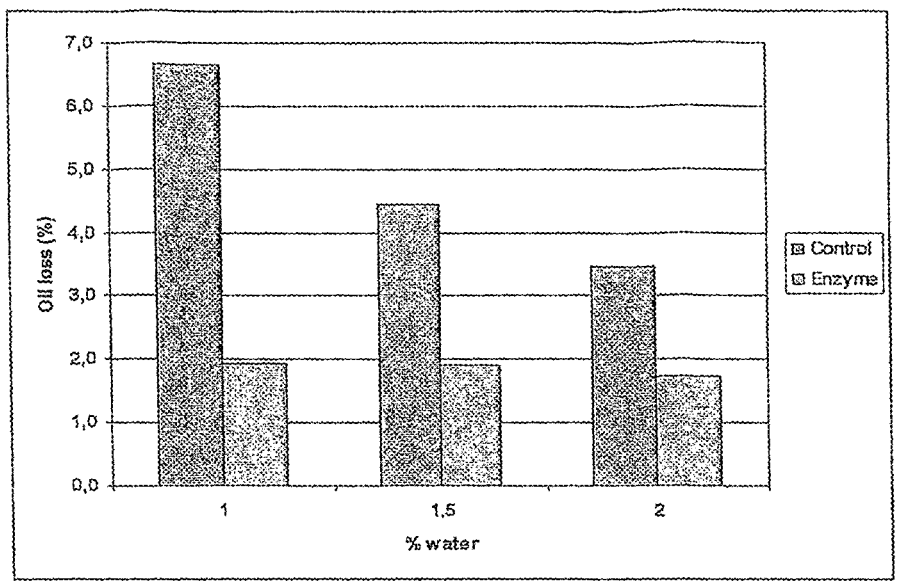
Figure 98:
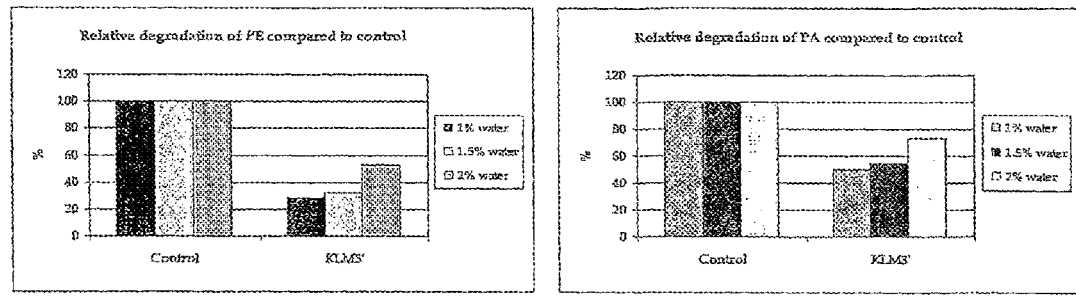
Figure 99:
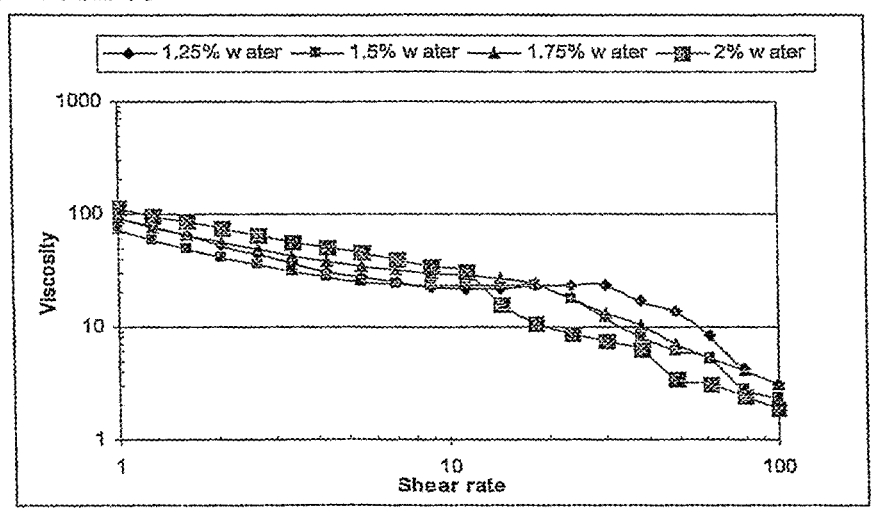
Figure 100:
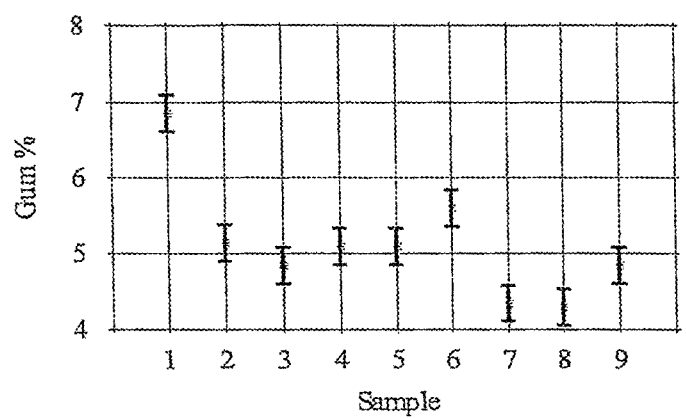
Figure 101:
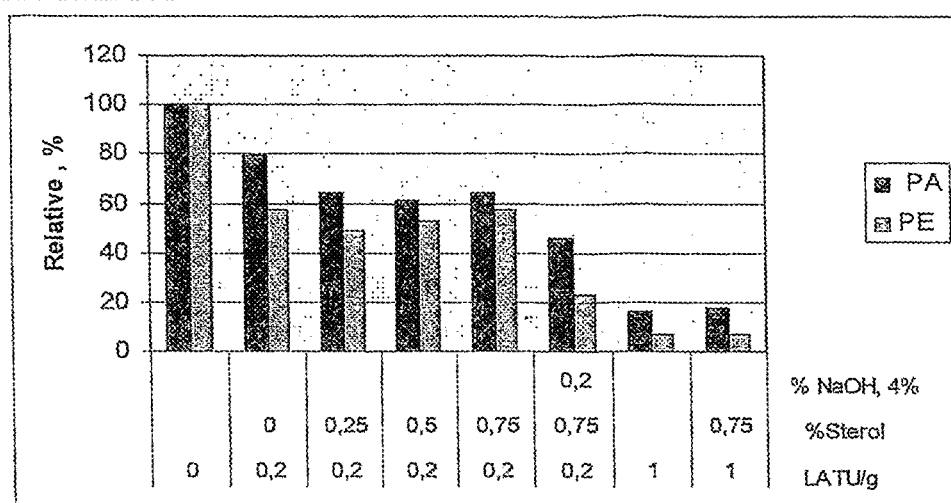
Figure 102:
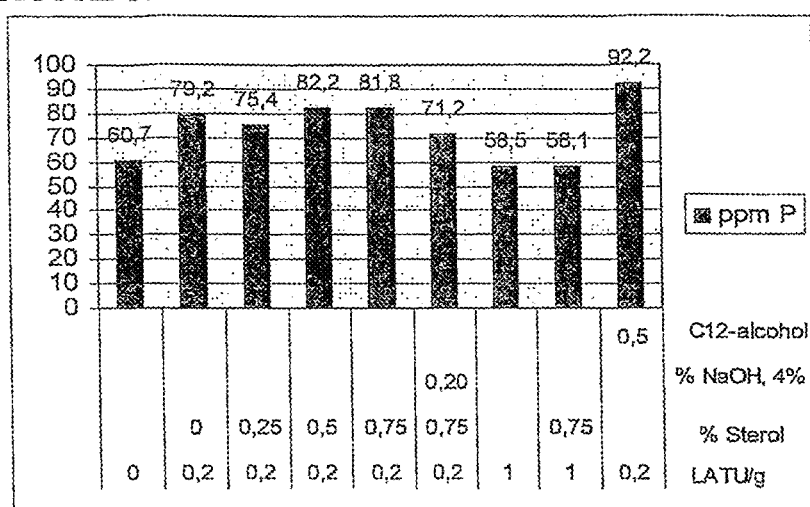
Figure 103:
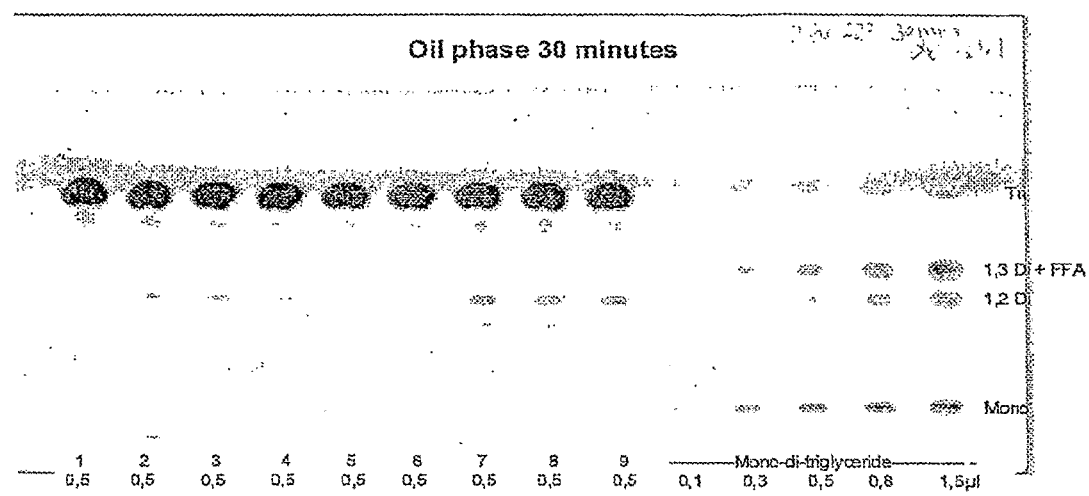
Figure 104:
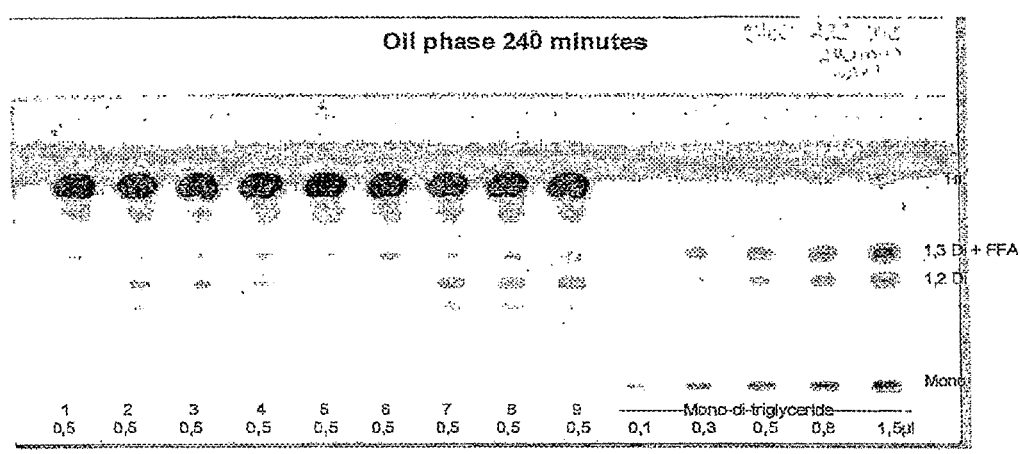
Figure 105:
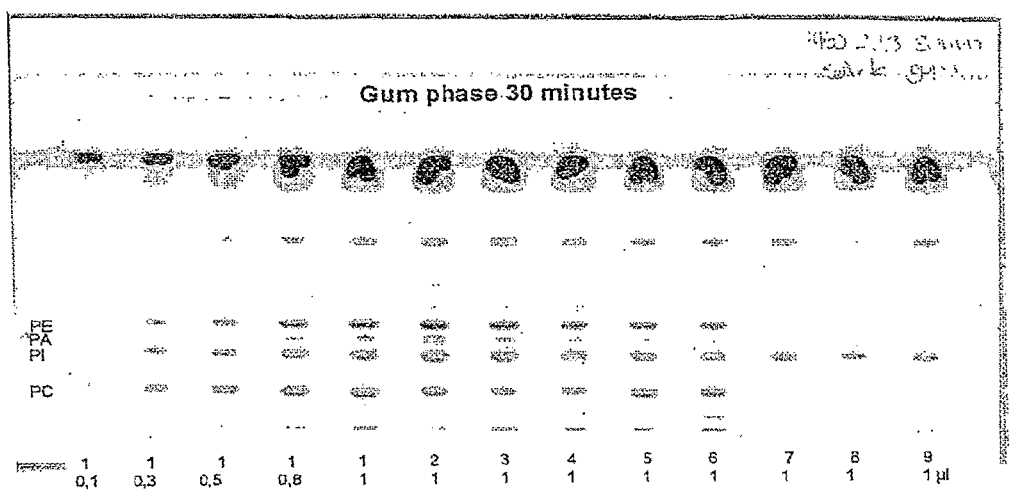
Figure 106:
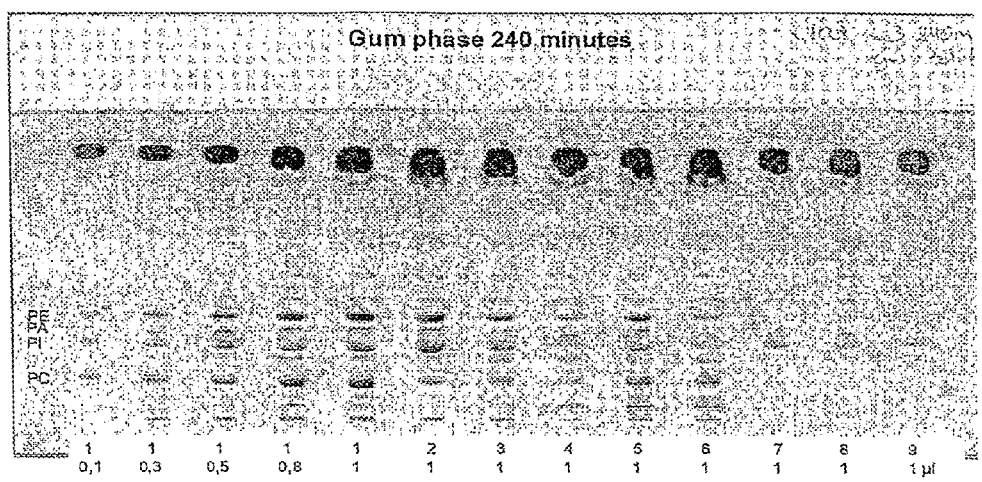
Figure 107:
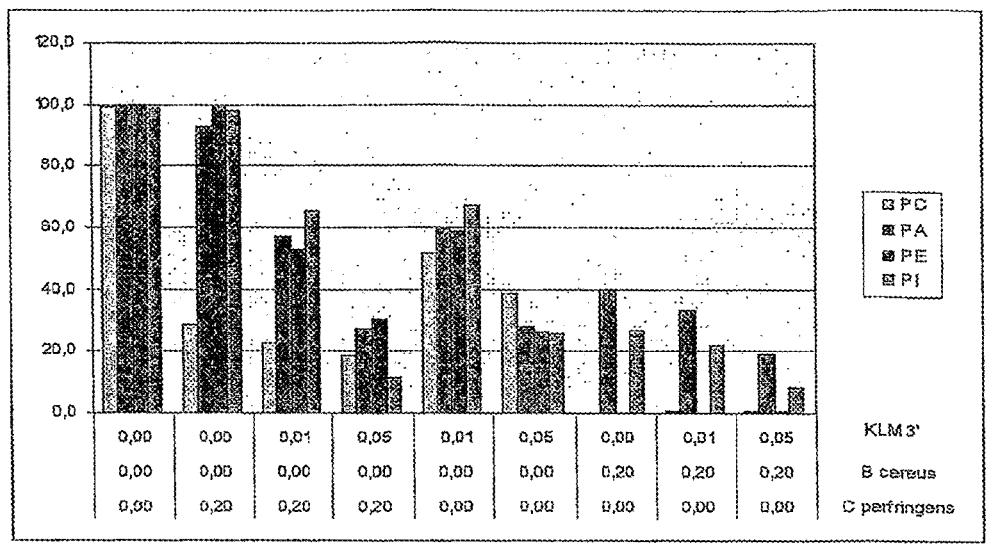
Figure 108:
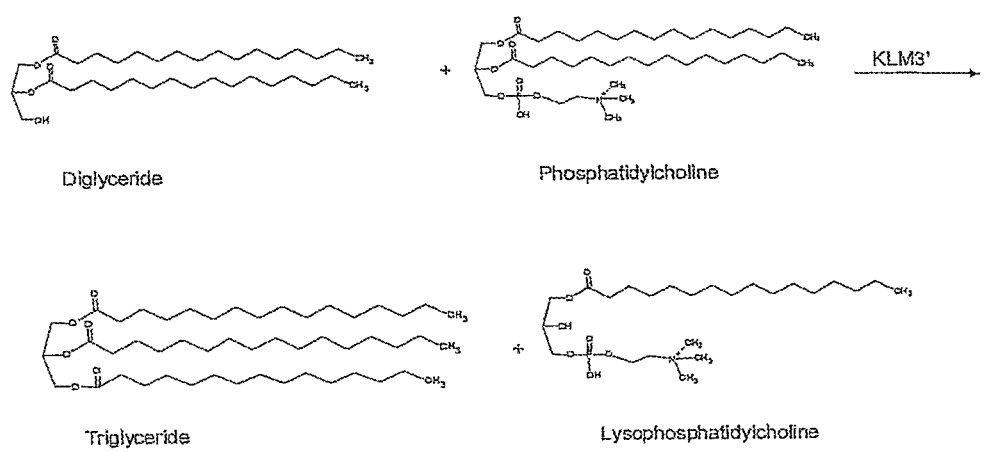
Figure 109:
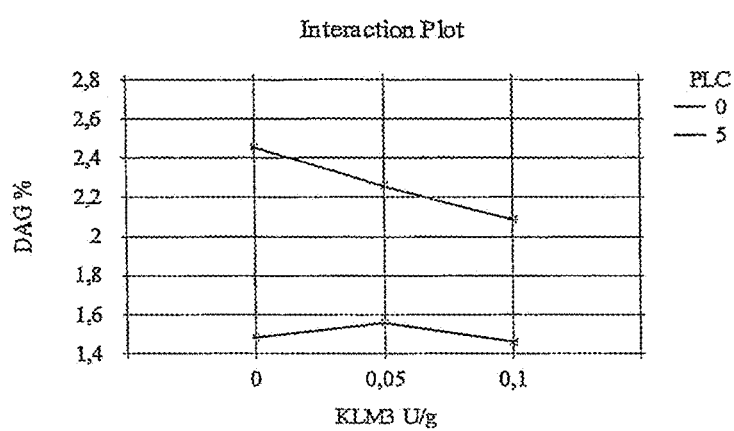
Figure 110:
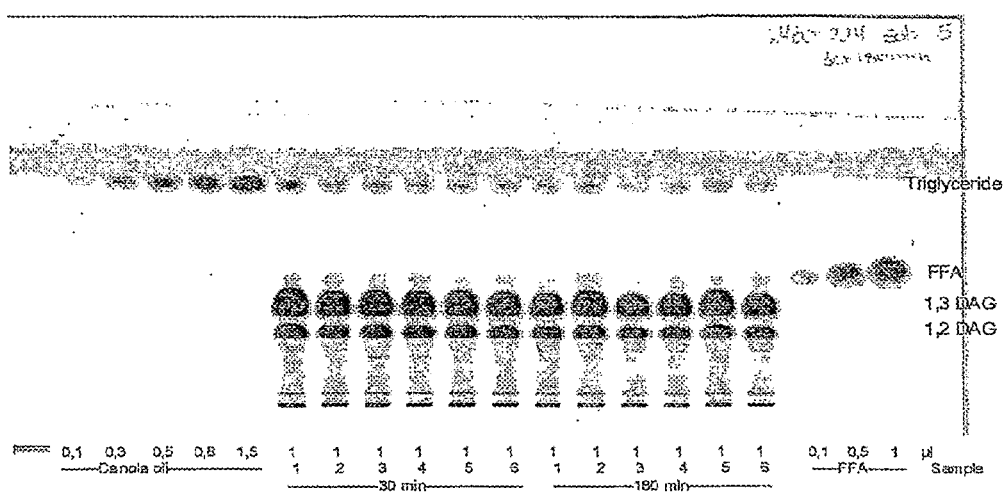
Figure 111:
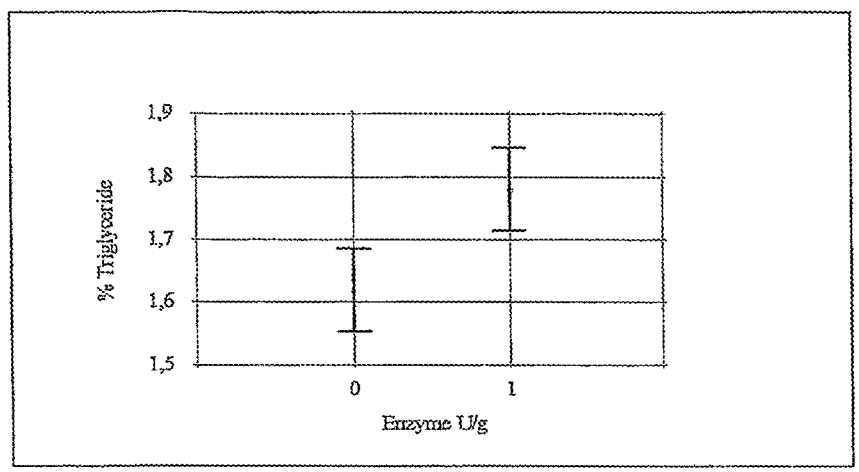
Figure 112:
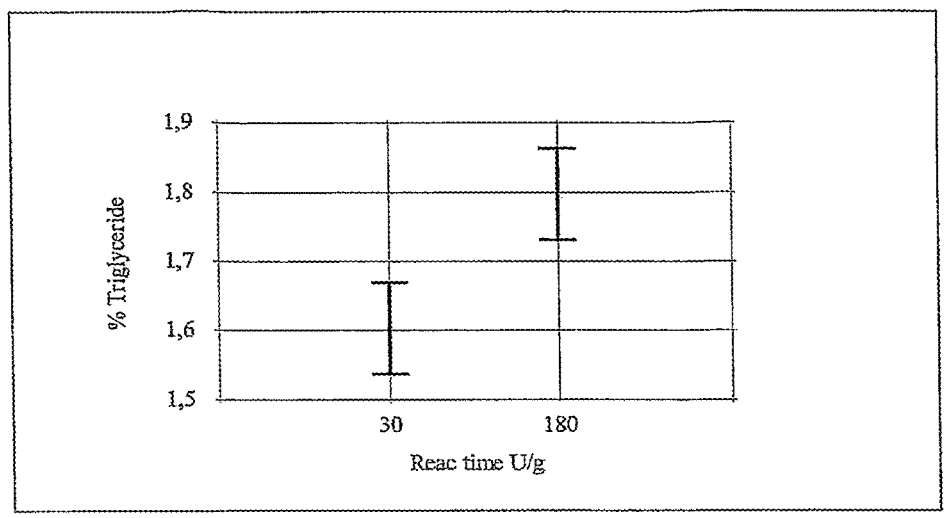
Figure 113:
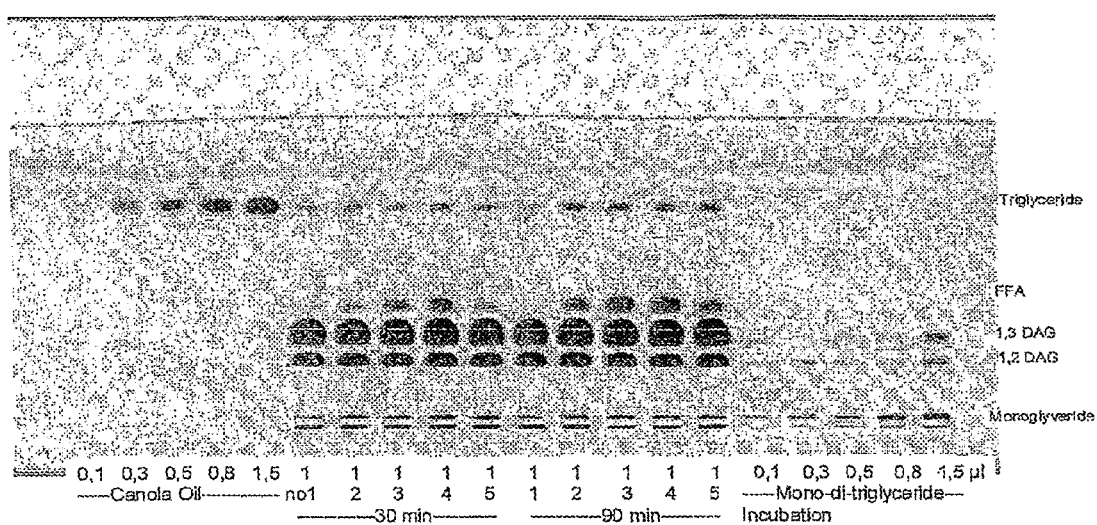
Figure 114:
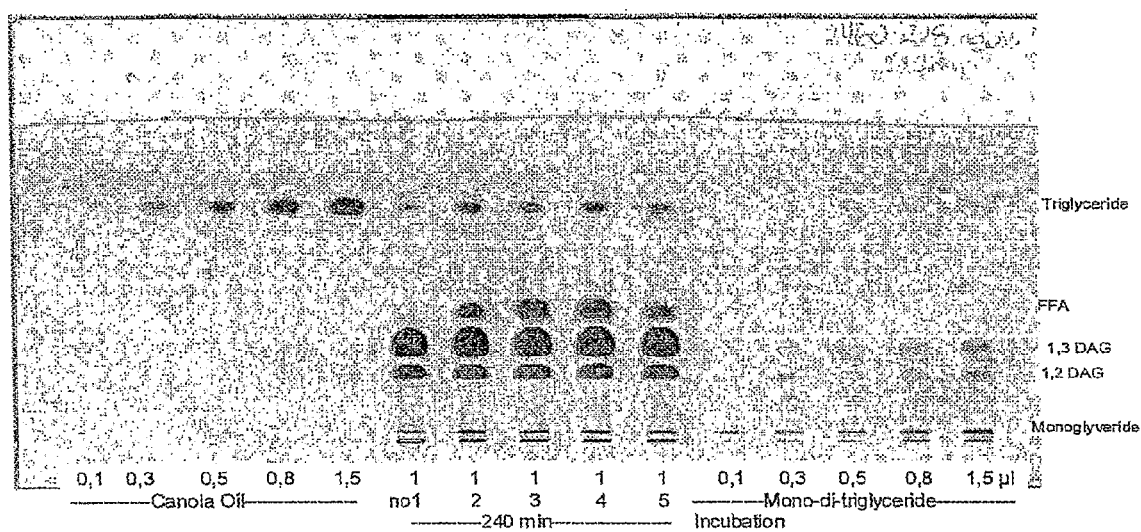
Figure 115:
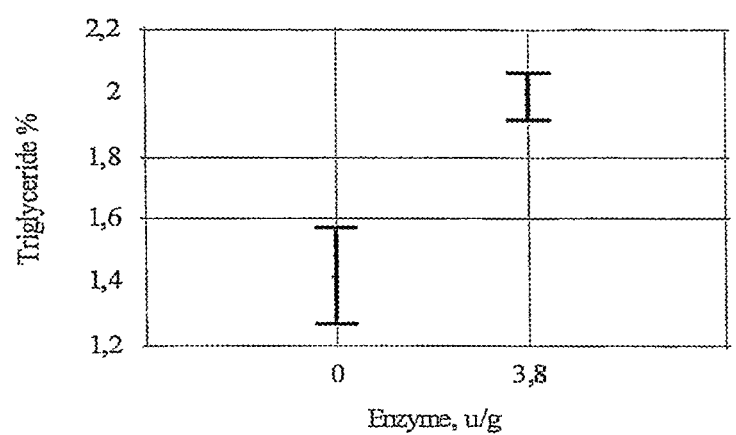
Figure 116:
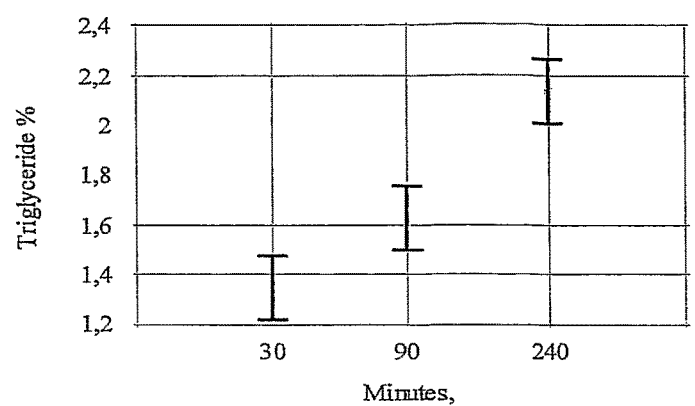
Figure 117:
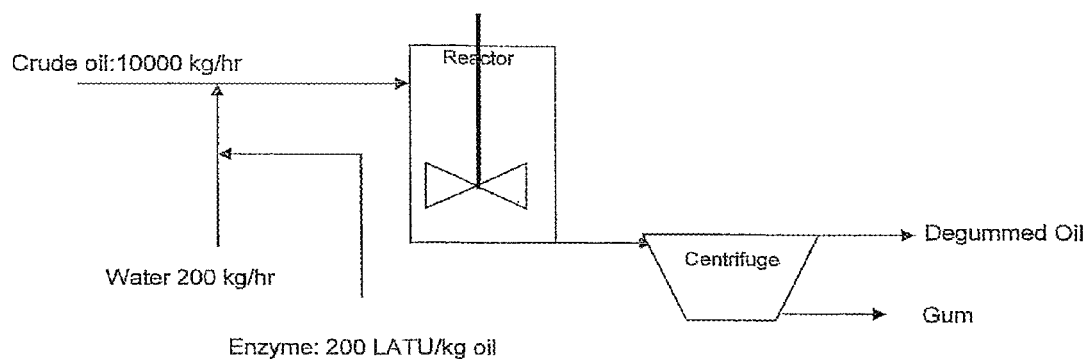
Figure 118:
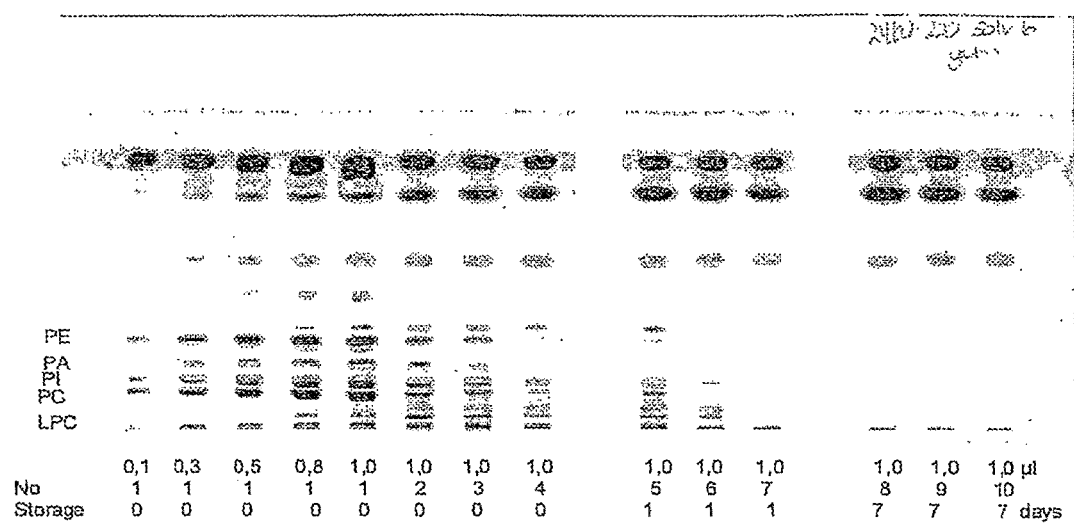
Figure 119:
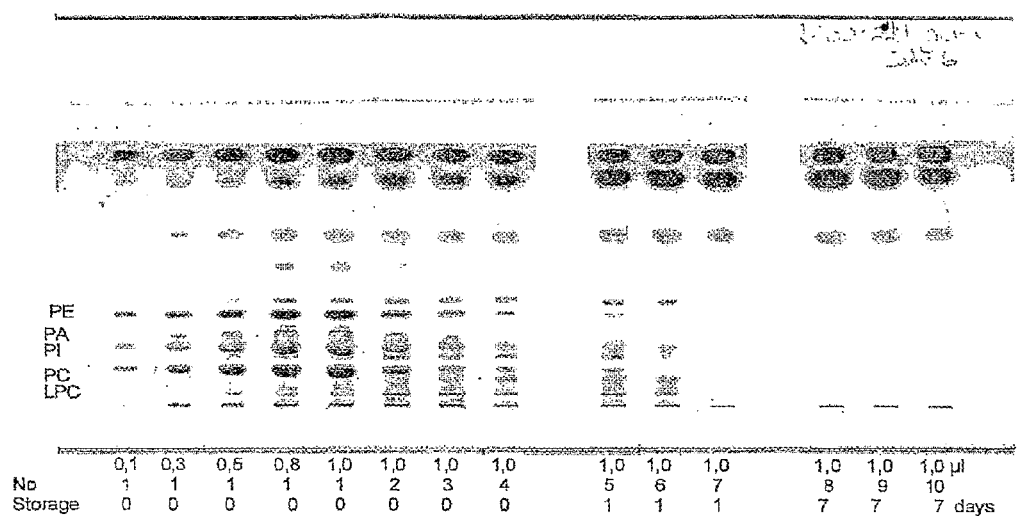

FIG. 70 shows a nucleotide sequence (SEQ ID No. 62) encoding a lipid acyltransferase from *Aeromonas hydrophila* (ATCC #7965);

FIG. 71 shows a nucleotide sequence (SEQ ID No 63) encoding a lipid acyltransferase from *Aeromonas salmonicida* subsp. *Salmonicida* (ATCC#14174);

FIG. 72 shows a nucleotide sequence (SEQ ID No. 24) encoding an enzyme from *Aeromonas hydrophila* including a xylanase signal peptide;

FIG. 73 shows the amino acid sequence of a mutant *Aeromonas salmonicida* mature lipid acyltransferase (GCAT) with a mutation of Asn80Asp (notably, amino acid 80 is in the mature sequence)—shown herein as SEQ ID No. 16—and after undergoing post-translational modification as SEQ ID No. 68—amino acid residues 235 and 236 of SEQ ID No. 68 are not covalently linked following post-translational modification. The two peptides formed are held together by one or more S—S bridges. Amino acid 236 in SEQ ID No. 68 corresponds with the amino acid residue number 274 in SEQ ID No. 16 shown herein;

FIG. 74a shows a conventional process for water degumming/refining crude edible oil. At the end of the water degumming the oil phase and the gum phase are separated. After this the oil phase and gum phase may be further processed by conventional/known methods;

FIG. 74b shows the process according to the present invention for water degumming/refining crude edible oil with an enzyme. The oil phase obtained when the oil and gum phase are separated has a much higher yield compared with the oil phase of a comparative process (i.e. one shown in FIG. 74a—i.e. water degumming without the addition of an enzyme). The oil phase and/or gum phase may optionally undergo further processing, such as further conventional processing FIG. 75 shows a flow diagram of a lab scale water degumming process according to the present invention;

FIG. 76 shows a diagram for analysis of the gum phase and the oil phase following water degumming (i.e. Step 1 of FIG. 74a or b);

FIG. 77 shows the gum phase after 3 hours following water degumming of crude soyabean oil in accordance with the present invention;

FIG. 78 shows the % age gum after 30 minutes water degumming with and without enzyme of crude soya oil;

FIG. 79 shows the effect of the amount of water (1.5, 2 or 2.5%) on the amount of gum following water degumming of crude soya oil;

FIG. 80 shows the effect with and without enzyme by degumming with different amounts of water (1.5, 2 or 2.5%) on the amount of gum following water degumming of crude soya oil with and without enzyme;

FIG. 81 shows the ppm of phosphorus in the oil phase following water degumming of crude soya oil with different dosages of enzyme. Column 1 is the control without enzyme;

FIG. 82 shows the % triglyceride in the gum phase following water degumming of crude soya oil at different enzyme dosages. Column 1 is the control without enzyme;

FIG. 83 shows the relative % PA in the gum phase following water degumming of crude soya oil at different enzyme dosages. Column 1 is the control without enzyme;

FIG. 84 shows the relative % PE in the gum phase following water degumming of crude soya oil at different enzyme dosages. Column 1 is the control without enzyme;

FIG. 85 Increased oil yield (%) obtained in enzymatic degumming compared to control. Oils are centrifuged at different relative centrifuging force for 3 min;

FIG. 86 shows the content (%) of gum and amount of triglyceride in gum, obtained from oils centrifuged at different times (minutes shown in bars) and different relative centrifuging forces are shown. Batch 3: control, 55° C., 4: with enzyme (KLM3'), 55° C.;

FIG. 87 shows viscosity as a function of shear rate. Measurements are based on gum from batch 1: control, 70° C. and batch 2: with enzyme, 70° C.;

FIG. 88 shows oil yield (%) calculated from the amount of gum (control) subtracted amount of gum (enzymatic sample);

FIG. 89 shows results from TLC analysis of the gum phase. Triglyceride content (%) in gums obtained from degumming with increasing amount (0, 0.1, 0.2, 0.5, 1, 1.5 and 1.9 ml 4%-solution) of NaOH;

FIG. 90 shows GC-results. Contents (%) of FFA's, phytosterols and phytosterol esters in oils, degummed with increasing ml of NaOH—Sample 1: control (without enzyme and NaOH); Samples 2-8: enzymatic samples with KLM3' (0.1 TIPU-k/g) and increasing amounts (0, 0.1, 0.2, 0.5, 1, 1.5 and 1.9 ml 4%-solution) of NaOH;

FIG. 91 shows results from TLC analysis of the gum phase. Relative degradation of phospholipids (PA, PE, PC and PI) in gums. Sample 1: control (without enzyme and NaOH), sample 2-7: enzymatic samples with KLM3' (0.1 TIPU-K/g) and increasing ml of NaOH;

FIG. 92 shows microscopy analysis of gums from conventional water degumming and enzymatic water degumming in accordance with the present invention (pictures 200 and 400 magnifications at 25° C.);

FIG. 93 shows X-ray analysis on gum phases from conventional and enzymatic degumming;

FIG. 94 shows sedimentation funnels (day 3). Left: control, right: enzyme treated oil;

FIG. 95 shows microscopy analysis on gums from conventional and enzymatic water degumming;

FIG. 96 shows increased oil yield obtained in enzymatic degumming compared to the control;

FIG. 97 shows oil loss in the control and an enzymatic water degummed sample (in accordance with the present invention) carried out with 1, 1.5 and 2% water. Calculation oil loss: (% gum/% triglyceride in gum)×100%;

FIG. 98 shows the relative degradation of phosphatidic acid and phosphatidylethanolamine in enzymatic (KLM3') gum samples compared to the control (no enzyme);

FIG. 99 shows viscosity measurements of enzymatic gum phases, obtained from degumming with varying amount of water (1.25, 1.5, 1.75 and 2%);

FIG. 100 shows Gum Phase from water degumming of crude soya with KLM3', and with addition of acceptor as shown in Table 1 of Example 9;

FIG. 101 shows the relative amount of phospholipid in gum phase analysed by HPTLC;

FIG. 102 shows ICP analysis of phosphor in oil from water degumming of crude soya oil (table 1 of Example 9);

FIG. 103: Example 13 TLC (running buffer 1) of sample 1 to 9 after 30 minutes incubation;

FIG. 104: Example 13 TLC (running buffer 1) of sample 1 to 9 after 240 minutes incubation;

FIG. 105: Example 13 TLC (running buffer 6) of sample 1 to 9 after 30 minutes incubation. PE=phosphatidylethanolamine, PA=phosphatidic acid, PI=phosphatidylinositol and PC=phosphatidylcholine;

FIG. 106: Example 13 TLC (running buffer 6) of sample 1 to 9 after 240 minutes incubation. PE=phosphatidylethanolamine, PA=phosphatidic acid, PI=phosphatidylinositol and PC=phosphatidylcholine;

FIG. 107: Example 13 Relative degradation of phospholipids by enzymatic treatment of crude oil with lipid acyltransferase (KLM3') and phospholipase C (PLC). 240 minutes reaction time;

FIG. 108: Example 13 Phospholipid diglyceride acyltransferase reaction;
FIG. 109: Example 13 Interaction of Phospholipase C and KLM3' on diglyceride (DAG) level in degumming of crude soya oil;
FIG. 110: Example 13 TLC analysis;
FIG. 111 shows the effect of enzyme addition on triglyceride;
FIG. 112 shows the effect of reaction time on triglyceride;
FIG. 113 shows TLC analysis of diglyceride/PC substrate incubated with acyltransferase for 30 and 90 minutes as detailed in Example 13;
FIG. 114 shows TLC analysis of diglyceride/PC substrate incubated with acyltransferase for 30 and 90 minutes as detailed in Example 13;
FIG. 115 shows the effect of acyltransferase enzyme on triglyceride formation in a substrate of diglyceride/PC 80/20;
FIG. 116 shows the effect of incubation time on triglyceride formation in a substrate of diglyceride/PC 80/20;
FIG. 117 shows a flow diagram for enzymatic water degumming;
FIG. 118 shows TLC analysis of the gum phase samples following water degumming at 55° C. and incubation for 0 d, 1 d or 7 d as detailed in Example 15; and
FIG. 119 shows TLC analysis of the gum phase samples following water degumming at 45° C. and incubation for 0 d, 1 d or 7 d as detailed in Example 15.

EXAMPLE 1

Expression of KLM3' in *Bacillus licheniformis*

A nucleotide sequence (SEQ ID No. 49) encoding a lipid acyltransferase (SEQ. ID No. 16, hereinafter KLM3') was expressed in *Bacillus licheniformis* as a fusion protein with the signal peptide of *B. licheniformis* [alpha]-amylase (LAT) (see FIGS. 53 and 54). For optimal expression in *Bacillus*, a codon optimized gene construct (no. 052907) was ordered at Geneart (Geneart AG, Regensburg, Germany).

Construct no. 052907 contains an incomplete LAT promoter (only the −10 sequence) in front of the LAT-KLM3' precursor gene and the LAT transcription (Tlat) downstream of the LAT-KLM3' precursor gene (see FIGS. 53 and 55). To create a XhoI fragment that contains the LAT-KLM3' precursor gene flanked by the complete LAT promoter at the 5' end and the LAT terminator at the 3' end, a PCR (polymerase chain reaction) amplification was performed with the primers Plat5XhoI_FW and EBS2XhoI_RV and gene construct 052907 as template.

```
Plat5XhoI_FW:
ccccgctcgaggcttttcttttggaagaaaatatagggaaaatggtact tgttaaaaattcggaatatttatacaatatcatatgtttcacattgaaa gggg EBS2XhoI_RV:
tggaatctcgaggttttatcctttaccttgtctcc
```

PCR was performed on a thermocycler with Phusion High Fidelity DNA polymerase (Finnzymes OY, Espoo, Finland) according to the instructions of the manufacturer (annealing temperature of 55 [deg.] C.).

The resulting PCR fragment was digested with restriction enzyme XhoI and ligated with T4 DNA ligase into XhoI digested plCatH according to the instructions of the supplier (Invitrogen, Carlsbad, Calif. USA).

The ligation mixture was transformed into *B. subtilis* strain SC6.1 as described in U.S. Patent Application US20020182734 (International Publication WO 02/14490). The sequence of the XhoI insert containing the LAT-KLM3' precursor gene was confirmed by DNA sequencing (Base-Clear, Leiden, The Netherlands) and one of the correct plasmid clones was designated plCatH-KLM3'(ori1) (FIG. 53). plCatH-KLM3'(ori1) was transformed into *B. licheniformis* strain BML780 (a derivative of BRA7 and BML612, see WO2005111203) at the permissive temperature (37 [deg.] C.).

One neomycin resistant (neoR) and chloramphenicol resistant (CmR) transformant was selected and designated BML780(plCatH-KLM3'(ori1)). The plasmid in BML780 (plCatH-KLM3'(ori1)) was integrated into the catH region on the *B. licheniformis* genome by growing the strain at a non-permissive temperature (50 [deg.] C) in medium with 5 [mu] g/ml chloramphenicol. One CmR resistant clone was selected and designated BML780-plCatH-KLM3'(ori1). BML780-plCatH-KLM3'(ori1) was grown again at the permissive temperature for several generations without antibiotics to loop-out vector sequences and then one neomycin sensitive (neoS), CmR clone was selected. In this clone, vector sequences of plCatH on the chromosome are excised (including the neomycin resistance gene) and only the catH-LATKLM3' cassette is left. Next, the catH-LATKLM3' cassette on the chromosome was amplified by growing the strain in/on media with increasing concentrations of chloramphenicol. After various rounds of amplification, one clone (resistant against 50 [mu]g/ml chloramphenicol) was selected and designated BML780-KLM3'CAP50. To verify KLM3' expression, BML780-KLM3'CAP50 and BML780 (the empty host strain) were grown for 48 h at 37 [deg.] C on a Heart Infusion (Bacto) agar plate with 1% tributyrin. A clearing zone, indicative for lipid acyltransferase activity, was clearly visible around the colony of BML780-KLM3'CAP50 but not around the host strain BML780 (see FIG. 56). This result shows that a substantial amount of KLM3' is expressed in *B. licheniformis* strain BML780-KLM3'CAP50 and that these KLM3' molecules are functional.

COMPARATIVE EXAMPLE 1

Vector Construct

The plasmid construct is pCS32new N80D, which is a pCCmini derivative carrying the sequence encoding the mature form of the native *Aeromonas salmonicida* Glycerophospholipid-cholesterol acyltransferase with a Asn to Asp substitution at position 80 (KLM3'), under control of the p32 promoter and with a CGTase signal sequence.

The host strain used for the expression, is in the *bacillus subtilis* OS21ΔAprE strain The expression level is measured as transferase activity, expressed as % cholesterol esterified, calculated from the difference in free cholesterol in the reference sample and free cholesterol in the enzyme sample in reactions with PC ($T_{PC}$) as donor and cholesterol as acceptor molecule.

Culture Conditions 5 ml of LB broth (Casein enzymatic digest, 10 g/l; low-sodium Yeast extract, 5 g/l; Sodium Chloride, 5 g/l; Inert tableting aids, 2 g/l) supplemented with 50 mg/l kanamycin, was inoculated with a single colony and incubated at 30° C. for 6 hours at 205 rpm. 0.7 ml of this culture was used to inoculate 50 ml of SAS media ($K_2HPO_4$, 10 g/l; MOPS (3-morpholinopropane sulfonic acid), 40 g/l; Sodium Chloride, 5 WI; Antifoam (Sin 260), 5 drops/I; Soy flour degreased, 20 g/l; Biospringer 106 (100% dw YE), 20 g/l) supplemented with 50 mg/l kanamycin and a solution of high maltose starch hydrolysates (60 g/l). Incubation was continued for 40 hours at 30° C. and 180 rpm before the culture supernatant was separated by centrifugation at 19000 rpm for 30 min. The supernatant was transferred into a clean tube and directly used for transferase activity measurement.

Preparation of Substrates and Enzymatic Reaction

PC (Avanti Polar Lipids #441601) and cholesterol (Sigma C8503) was scaled in the ratio 9:1, dissolved in chloroform, and evaporated to dryness.

The substrate was prepared by dispersion of 3% PC:Cholesterol 9:1 in 50 mM Hepes buffer pH 7.

0.250 ml substrate solution was transferred into a 3 ml glass tube with screw lid. 0.025 ml culture supernatant was added and the mixture was incubated at 40° C. for 2 hours. A reference sample with water instead of enzyme was also prepared. Heating the reaction mixture in a boiling water bath for 10 minutes stopped the enzyme reaction. 2 ml of 99% ethanol was added to the reaction mixture before submitted to cholesterol assay analysis.

Cholesterol Assay

100 μl substrate containing 1.4 U/ml Cholesterol oxidase (SERVA Electrophoresis GmbH cat. No 17109), 0.4 mg/ml ABTS (Sigma A-1888), 6 U/ml Peroxidase (Sigma 6782) in 0.1 M Tris-HCl, pH 6.6 and 0.5% Triton X-100 (Sigma X-100) was incubated at 37° C. for 5 minutes before 5 μl enzyme reaction sample was added and mixed. The reaction mixture was incubated for further 5 minutes and $OD_{405}$ was measured. The content of cholesterol was calculated from the analyses of standard solutions of cholesterol containing 0.4 mg/ml, 0.3 mg/ml, 0.20 mg/ml, 0.1 mg/ml, 0.05 mg/ml, and 0 mg/ml cholesterol in 99% EtOH.

Results

The table shows the average of 8 separate expression cultures

| Strain | $T_{PC}$[a] |
|---|---|
| OS21ΔAprE[pCS32new] | 74.2 ± 10.1[b] |

[a]$T_{PC}$ is the transferase activity, expressed as % cholesterol esterified, calculated from the difference in free cholesterol in the reference sample and free cholesterol in the enzyme sample in reactions with PC as donor molecule and cholesterol as acceptor molecule.
[b]Average of 8 separate expression cultures

EXAMPLE 2

Use of a Lipid Acyltransferase in Water Degumming

Materials and Methods
Enzyme:
  KLM3': a lipid acyltransferase taught in Example 1 having SEQ ID No. 68 (Also referred to herein as "K932")-1128 TIPU/ml
Oil:
  SBO 1: Crude soya bean oil from Solae, Aarhus, DK. 27.09.2007 Delite (Based on beans from Canada)
  SBO 2: Crude Soya Oil from Brazil
  RSO 3: Crude extracted Rapeseed Oil from Aarhus Karlshamn
  RSO 4: Crude pressed Rapeseed Oil from Scanola, Aarhus, DK
  Soy Lecithin Mix Standard (ST16) from Spectra Lipid, Germany
Methods:
HPTLC:
  Applicator: Automatic TLC Sampler 4, CAMAG
  HPTLC plate: 20×10 cm, Merck no. 1.05641. Activated 10 minutes at 160° C. before use.
Application:
  Oil phase: 5 μl of a 8% solution of oil in Chloroform:Methanol 2:1 was applied to the HPTLC plate using Automatic TLC Sampler.
  Gum phase: Gum phase from 10 gram oil was dissolved in 7.5 ml chloroform:methanol 2:1.
  1 μl of the sample was applied to the HPTLC plate.
  TLC applicator.
  Running buffer 6: Chloroform:1-propanol:Methylacetate:Methanol: 0.25% KCl in water 25:25:25:10:9
  Running buffer 5: P-ether:MTBE 30:70
  Elution: The plate was eluted 7 cm using an Automatic Developing Chamber ADC2 from Camag.
Development:
  The plate was dried in an oven for 10 minutes at 160° C., cooled, and dipped into 6% cupri acetate in 16% $H_3PO_4$. Dried additionally 10 minutes at 160° C. and evaluated directly.
  After development the plates were scanned on a Camag Scanner and the area of each component (spot) on the TLC plate was calculated.
Calculation
Oil Phase:
  The amount of phospholipid in the oil phase was calculated by analysing a Standard lecithin with known concentrations of phospholipids (PE, PA, PI, PC, PS) at different concentrations on the same TLC plate as the oil samples. Based on the standard mixture a calibration curve for each phospholipid was produced and used for calculation of the phospholipid concentration of each phospholipid in the oil sample. Based on the mol weight of the concentration of phospholipids were converted to ppm P (phosphorus).
Gum Phase:
  The content of triglyceride in the gum phase was calculated based on analysing a standard refined vegetable oil on the same plate as the gum phase. Based on the analysis of the vegetable oil a calibration curve was produced and used for calculation of the triglyceride in the gum phase.

The analysis of the phospholipids in the gum phase was based on applying different volumes of the gum phase from the control (without enzyme added) on the same plate as the other gum phases. Based on the analysis of phospholipids (PE and PA) in the control gum phase a calibration curve was produced and used for calculation of the amount of phospholipids in the enzyme treated samples relative to the amount of phospholipid in the control which was defined as 100%.

pH Measurement:

The pH of samples from oil degumming was analysed by a fluorescence method described in http://www.3i-usa.com/downloads/hydrop_man.pdf, i.e. The pH measurement was conducted by using a HydroPlate® HP96C from Presens, Josef Engert Str. 11, D-93053 Regensburg, Germany.

The HydroPlate® is a sterile, polystyrene microtiter plate in the common 96-well format with 96 integrated sensors. A sensor is immobilised on the bottom of each well. The sensor can be read out from the bottom side. This can be done by almost any commercially available fluorescence plate reader. The assay is bases on 2 different, fluorescent dyes: A pH-sensitive indicator and an inert reference dye. This combination ensures a precise, internally referenced signal for achieving the most exact results of the experiments.

pH can alternatively be measured by using a pH electrode according Bo Yang et al JAOCS, Vol. 83, No. 7 (2006) pp 653-658.

Determination of Water in Oil

Residual water in the oil is determined by AOCS method Ca 2c-25 or equivalent.

GLC Analysis

Perkin Elmer Autosystem 9000 Capillary Gas Chromatograph equipped with WCOT fused silica column 12.5 m x 0.25 mm ID x 0.1 µ film thickness 5% phenyl-methyl-silicone (CP Sil 8 CB from Chrompack).

Carrier gas: Helium.
Injector. PSSI cold split injection (initial temp 50° C. heated to 385° C.), volume 1.0 µl
Detector FID: 395° C.

| Oven program (used since 30 Oct. 2003): | 1 | 2 | 3 |
|---|---|---|---|
| Oven temperature, ° C. | 90 | 280 | 350 |
| Isothermal, time, min. | 1 | 0 | 10 |
| Temperature rate, ° C./min. |  | 15 | 4 |

Sample preparation: 50 mg sample was dissolved in 12 ml Pyridin, containing internal standard heptadecane, 0.5 mg/ml. 500 µl sample solution was then transferred to a crimp vial, 100 µl MSTFA:TMCS—99:1 (N-Methyl-N-trimethyl-silyl-trifluoraceamid) was added and reacted for 20 minutes at 60° C.

Calculation: Response factors for sterol, sterol palmitate and sterol stearate were determined from pure reference material (weighing pure material 8-10 mg in 12 ml Pyridin, containing internal standard heptadecane, 0.5 mg/ml.).

Enzyme Assay, TIPU

Substrate:

0.6% L-α Phosphatidylcholine 95% Plant (Avanti #441601), 0.4% Triton-X 100 (Sigma X-100), and 5 mM $CaCl_2$ were dissolved in 0.05M HEPES buffer pH 7.

Assay Procedure:

34 µl substrate was added to a cuvette, using a KoneLab automatic analyzer. At time T=0 min, 4 µl enzyme solution was added. Also a blank with water instead of enzyme was analyzed. The sample was mixed and incubated at 30° C. for 10 minutes.

The free fatty acid content of sample was analyzed by using the NEFA C kit from WAKO GmbH.

Enzyme activity TIPU pH 7 was calculated as micromole fatty acid produced per minute under assay conditions.

Degumming Procedure Lab Scale.

100 g crude soya oil was scaled into a 250 ml Blue Cap flask with lid and heated to 50° C. or 55° C. or 60° C. or 65° C. or 70° C.

Water was then added to the oil followed by enzyme addition. The oil was homogenised with an Ultra Turrax mixer for 30 seconds, and then agitated for 30 minutes with magnetic stirring at 450 rpm.

After 30, 120 or 180 minutes, 10 ml oil was transferred to a 12 ml centrifuge tube (previously scaled). The oil was heated to 97° C. in a boiling water bath for 10 minutes, and then immediately centrifuged at 5000 g for 5 minutes.

Oil was decanted from the gum phase and the tubes were drained for 30 minutes and the weight of both phases measured. (See FIG. 75).

The oil phase was analysed for free sterols, sterol esters and free fatty acids by GLC, and the oil phase was also analysed by TLC. (See FIG. 76).

Results

EXAMPLE 2a

In this experiment KLM3' was tested in the water degumming process of crude SBO 1.

Different dosages of KLM3' from 0.1 to 0.5 TIPU/g oil were tested and also the impact of Ultra Turrax mixing was tested.

The Table below together with FIG. 77 show a clear reduction of the gum phase and improved oil yield (in the oil phase) in the samples treated with KLM3'.

An increase of about 2% oil was seen and there was a tendency that an increased yield was obtained by increasing the enzyme dosage.

The mixing also had an impact on the gum phase. It was seen that Ultra Turrax treatment of the oil for 30 sec just after enzyme addition gave a smaller gum phase, but the effect of the enzyme addition was almost the same with or without Ultra Turrax mixing. In the industry it is normal to pump the oil through a static mixer or a dynamic mixer after water addition, and in order to imitate this at laboratory scale it was decided to use Ultra Turrax mixing.

| 2460-150 (Example 2a) | | 1* | 2 | 3 | 4 | 5* | 6 | 7 | 8 |
|---|---|---|---|---|---|---|---|---|---|
| Crude Soya oil Solae d. 27 Sept. 2007 | g | 100 | 100 | 100 | 100 | 100 | 100 | 100 | 100 |
| KLM3' 100 TIPU/ml | ml | 0 | 0.1 | 0.25 | 0.5 | 0 | 0.1 | 0.25 | 0.5 |
| Extra Water | ml | 2.00 | 1.90 | 1.75 | 1.50 | 2.00 | 1.90 | 1.75 | 1.50 |
| TIPU/g oil | | 0.00 | 0.10 | 0.25 | 0.50 | 0.00 | 0.10 | 0.25 | 0.50 |
| % water | | 2 | 2 | 2 | 2 | 2 | 2 | 2 | 2 |
| Ultra Turrax | | − | − | − | − | + | + | + | + |
| pH | | 5.39 | 5.7 | 5.91 | 5.72 | 5.55 | 5.99 | 5.72 | 5.49 |
| Gum Phase, % | | 8.48 | 6.36 | 5.73 | 4.76 | 6.19 | 4.63 | 4.44 | 4.19 |
| Oil Phase % | | 91.5 | 93.6 | 94.3 | 95.2 | 93.8 | 95.4 | 95.6 | 95.8 |

*control without enzyme addition

EXAMPLE 2b

Two different crude SBOs were tested in water degumming according to standard procedure with or without the addition of the KLM3' enzyme. The enzyme dosage was 0.25 TIPU/g.

Recipe

| 2460-151 (Example 2b) | | 1 | 2 | 3 | 4 |
|---|---|---|---|---|---|
| SBO 1 | g | 100 | 100 | | |
| SBO 2 | g | | | 100 | 100 |
| KLM3' 100 TIPU/ml | ml | 0 | 0.25 | 0 | 0.25 |
| Extra Water | ml | 2.00 | 1.75 | 2.00 | 1.75 |
| TIPU/g oil | | 0.00 | 0.25 | 0.00 | 0.25 |
| % water | | 2 | 2 | 2 | 2 |
| pH | | 5.78 | 5.75 | 5.73 | 5.68 |

The results shown in the table below indicate a clear reduction of the gum phase both after 30 minutes and 120 minutes reaction time, which corresponds to a higher oil yield. Analysis of sterol and sterol ester in the oil phase showed a high conversion of sterol to sterol ester in the enzyme treated samples. It is also observed that the amount of free fatty acid (FFA) increased, because a hydrolytic activity also had taken place.

Results

| 2460-151 | SBO 1 | SBO 1 | SBO 2 | SBO 2 |
|---|---|---|---|---|
| KLM3', U/g oil | 0 | 0.25 | 0 | 0.25 |
| % Gum, 30 min | 6.20 | 5.21 | 5.66 | 4.80 |
| % Gum, 120 min | 5.59 | 4.86 | 5.24 | 3.90 |
| % Oil, 30 min | 93.8 | 94.79 | 94.34 | 95.2 |
| % Oil, 120 min | 94.41 | 95.14 | 94.76 | 96.1 |
| Oil Phase | | | | |
| FFA total | 0.37 | 0.53 | 0.64 | 0.85 |
| Sterols | 0.31 | 0.09 | 0.27 | 0.07 |
| Sterol ester | 0.14 | 0.47 | 0.12 | 0.50 |

EXAMPLE 2c

In this experiment different dosages of KLM3' were tested in water degumming of SBO 2 at 50° C. Different levels of water, namely 1.5%, 2% and 2.5%, were also tested in the process with and without addition of enzyme.

Recipe

| 2460-152 (Example 2c) | | 1 | 2 | 3 | 4 | 5 | 6 | 7 | 8 |
|---|---|---|---|---|---|---|---|---|---|
| SBO 2 | g | 100 | 100 | 100 | 100 | 100 | 100 | 100 | 100 |
| KLM3' 100 TIPU/ml | ml | 0 | 0.1 | 0.25 | 0.4 | 0 | 0.25 | 0 | 0.25 |
| Extra Water | ml | 2.00 | 1.90 | 1.75 | 1.60 | 1.50 | 1.25 | 2.50 | 2.25 |
| TIPU/g oil | | 0.00 | 0.10 | 0.25 | 0.40 | 0.00 | 0.25 | 0.00 | 0.25 |
| % water | | 2 | 2 | 2 | 2 | 1.5 | 1.5 | 2.5 | 2.5 |
| pH | | 5.32 | 5.92 | 5.72 | 5.59 | 5.58 | 5.73 | 5.30 | 5.81 |

The results shown in the tables and also in FIG. 78, FIG. 79, FIG. 80, FIG. 81, FIG. 82, FIG. 83 and FIG. 84 below clearly indicate a reduced amount of gum phase and because the sum of gum phase and oil phase is 100% it is concluded that the acyltransferase (KLM3') contributes to improvement in oil yield in the oil phase.

It was also observed that the content of phospholipid in the gum phase was reduced in the enzyme treated samples. Both the phosphatidylethanolamine (PE) and phosphatidic acid (PA) were reduced in the gum phase relative to the amount of these phospholipids in the gum phase without enzyme treatment. The amount of triglyceride in the gum phase was also smaller in the enzyme treated gum phases, which also confirms that the increase in oil yield (in the oil phase) in the enzyme treated samples.

The amount of water added to the crude soya oil also showed as expected an impact on the amount of gum phase, but the results also confirmed the effect of acyltransferese on yield at different water addition relative to the control without enzyme addition (see FIG. 80).

In the water degumming experiments the pH was in the range of 5.5 to 6 which explains high enzyme activity at low dosage and a high conversion of sterol to sterol esters.

Results

| 2460-152 | | 1 | 2 | 3 | 4 | 5 | 6 | 7 | 8 |
|---|---|---|---|---|---|---|---|---|---|
| Gum phase | | | | | | | | | |
| Gum, 30 min | % | 6.48 | 5.14 | 5.68 | 5.19 | 5.73 | 4.85 | 7.06 | 6.03 |
| Gum, 120 min | % | 5.79 | 5.88 | 4.86 | 4.94 | 5.65 | 5.07 | 6.12 | 5.96 |
| TLC analysis | | | | | | | | | |
| Phosphor | ppm | 66 | 73 | 64 | 58 | 76 | 62 | 65 | 62 |
| PA, | % rel. | 100 | 61 | 45 | 35 | 86 | 47 | 105 | 50 |
| PE | % rel. | 100 | 45 | 24 | 18 | 88 | 26 | 102 | 34 |
| Triglyceride | % | 65 | 26 | 37 | 29 | 62 | 41 | 62 | 38 |
| GLC analysis | | | | | | | | | |
| FFA, | % | 0.63 | 0.71 | 0.78 | 0.87 | 0.57 | 0.79 | 0.57 | 0.73 |
| Free Sterols | | 0.27 | 0.12 | 0.06 | 0.05 | 0.27 | 0.06 | 0.26 | 0.11 |
| Sterol Esters | | 0.18 | 0.41 | 0.47 | 0.51 | 0.12 | 0.53 | 0.13 | 0.40 |

The analyses were made in duplicate and the results were used for Statistical evaluation of results using StatGraphic S Plus software.

EXAMPLE 2d

In order to investigate the effect of KLM3' on oil yield at different temperature the enzyme was tested in water degumming of SBO2 at 55, 60, 65 and 70° C.

Recipe

| 2460-154, 155, 156 and 157 | | 1 | 2 | 3 | 4 |
|---|---|---|---|---|---|
| SBO 2 | g | 100 | 100 | 100 | 100 |
| KLM3' 100 TIPU/ml | ml | 0 | 0.10 | 0.20 | 0.30 |
| Extra Water | ml | 2.00 | 1.90 | 1.80 | 1.70 |
| TIPU/g oil | | 0.00 | 0.10 | 0.20 | 0.30 |
| % water | | 2 | 2 | 2 | 2 |

The results shown in the Table below clearly illustrate the effect of KLM3' on the amount of gum phase. A dosage of 0.1 TIPU/g oil at all temperatures gave a significant reduction in the amount of gum. Increasing the amount of enzyme to 0.2 and 0.3 further decreased the gum phase a little.

Results

% Gum phase by water degumming of SBO 2 at different temperature, reaction times and enzyme dosages.

| Temperature ° C. | Reaction time minutes | Enzyme 0 TIPU/g | Enzyme 0.1 TIPU/g | Enzyme 0.2 TIPU/g | Enzyme 0.3 TIPU/g |
|---|---|---|---|---|---|
| 55 | 30 | 6.53 | 4.77 | 5.12 | 5.54 |
| 60 | 30 | 6.64 | 4.83 | 4.73 | 4.55 |
| 65 | 30 | 6.79 | 5.63 | 5.05 | 4.94 |
| 70 | 30 | 6.49 | 4.58 | 4.36 | 4.23 |
| 55 | 120 | 6.29 | 4.94 | 4.72 | 4.80 |
| 60 | 120 | 5.79 | 4.76 | 4.47 | 4.05 |
| 65 | 120 | 6.70 | 5.37 | 4.84 | 5.39 |
| 70 | 120 | 5.05 | 4.41 | 3.39 | 3.00 |

EXAMPLE 3

Enzymatic Water Degumming in Pilot Plant

Recipe

Ingredients applied in pilot water degumming trials.
Batch 1: control, 70° C.,
Batch 2: with enzyme (namely the lipid acyltransferase K932—sometimes referred to herein as KLM3'—which has the amino acid sequence shown herein as SEQ ID No. 68), 70° C.,
Batch 3: control, 55° C. and
Batch 4: with enzyme (namely the lipid acyltransferase K932—sometimes referred to herein as KLM3'—which has the amino acid sequence shown herein as SEQ ID No. 68), 55° C.

| | | Batch | | | |
|---|---|---|---|---|---|
| | | 1 | 2 | 3 | 4 |
| | | Journal no. | | | |
| | Amount | 2460-158 | | 2460-160 | |
| Crude Soya Oil | kg | 20 | 20 | 20 | 20 |
| K932, 1128 TIPU/ml | Ml | 0 | 3.55 | 0 | 3.55 |
| Extra Water | Ml | 400.30 | 396.10 | 400.1 | 396.47 |
| TIPU-K/g oil | | 0.00 | 0.2 | 0.00 | 0.2 |
| Water | % | 2 | 2 | 2 | 2 |

Water Degumming Pilot Plant Procedure

The oil was initially heated under $N_2$ coverage and agitation in a 50-liter tank. Afterwards, water (and enzyme) was added to the oil. In the initial experiments (batches 1 and 2), the oil was re-circulated after addition of the water and enzyme, using a homogenizer (Silverson, Chesham Sweden). In batches 3 and 4 only a re-circulation pump was used to lower the agitation in the tank.

Oil samples were collected (batches 1-4) for laboratory analysis after 30 minutes of enzyme activity and placed in a boiling water bath (10 minutes) in order to inactivate the enzyme. Inactivation of the remaining oil in the tank was done by heating the oil to 75° C. (under agitation). Subsequently, centrifuging was carried out in a preheated (hot water) centrifuge (Alfa Laval) and the oil phase was tapped in buckets and weighed. Different centrifuge capacity adjustments were tested, it was not possible to monitor the separated gum phase, as the volume of the centrifuge was too large compared to the amount of oil. The gum phase was, thus, collected from the lid of the centrifuge, where it had accumulated.

Laboratory Water Degumming and Centrifuging 100 g crude soya oil was scaled into a 250 ml blue cap flask with lid and heated to 55° C. Water was added to the oil followed by enzyme addition. The oil was homogenised using an Ultra Turrax mixer for 30 seconds, and then agitated for 30 minutes with magnetic stirring at 450 rpm. After 30 minutes, 10 ml oil was transferred to a 12 ml centrifuge tube (previously scaled). The oil was heated to 97° C. in a boiling water bath for 10 minutes, and then immediately centrifuged at different relative centrifuging forces (500, 1000, 2500 and 5000) for varying times (3, 6 and 10 minutes).

Oil was decanted from the gum phase, and the tubes were drained for 15 minutes, and the weights of both phases were measured. The oil phase was analysed for free phytosterols, sterol esters and free fatty acids by GLC, and the oil phase was analysed by HPTLC.

Results and Discussion

Oil Yield

FIG. 85 shows the increased oil yield obtained from enzymatic degumming of crude soybean oil in accordance with the present invention compared to the control. The oil, is centrifuged at increasing relative centrifuging force (rcf) (500, 1000, 2500 and 5000) for 3 minutes and oil yield is calculated from amount (%) of gum in the control subtracted amount of gum in enzymatic samples.

Clearly it is seen that the oil yield increases in enzymatic degumming compared to the control and that the oil yield increases with decreasing rcf.

Effect of Centrifugation

The amount of triglycerides in gums and amount of gum, obtained from oil samples centrifuged at different times (minutes in bars) are shown for batches 3 and 4 in FIG. 86.

The results illustrate that rcf affects the amount (%) of gum obtained from conventional degumming (blue bars). Initially, at low rcf (500-1000), the amount of gum is high (high triglyceride content) compared to the amount obtained at relative centrifuging forces of 2500 to 5000. Centrifuging time (3, 6 and 10 minutes) does not seem to affect the amount of gum, at least not when centrifuged at 5000 rd.

Inspecting the gum obtained from enzymatic degumming according to the present invention, the amount does not seem to be affected by rcf and time. Without wishing to be bound by theory this may be explained by differences in viscosity between gums obtained from conventional and enzymatic degumming according to the present invention. In FIG. 87, measurements of the viscosity, based on gum phases, are shown. The viscosity decreases with increasing shear rate for both types of gum, however, the viscosity decreases to a higher extent in gums obtained from enzymatic degumming in accordance with the present invention.

Besides, increased oil yield, the decreased viscosity achieved with the present invention may have other benefits for an industrial water degumming processing. It is likely that production capacity may be increased.

EXAMPLE 4

Evaluation of NaOH in Water Degumming of Crude Soy Bean Oil

Recipe

Water Degumming Lab Procedure 100 g crude soya oil was scaled into a 250 ml blue cap flask with lid and heated to 55° C. Water and NaOH was added to the oil followed by enzyme addition. The oil was homogenised using an Ultra Turrax mixer for 30 seconds and agitated for 30 minutes with magnetic stirring at 450 rpm. After 30 minutes, approximately 10 ml oil was transferred to a 12 ml centrifuge tube (previously scaled). The oil was heated to 97° C. in a boiling water bath for 10 minutes.

Results and Discussion

Analysis of Oil Yield

FIG. 88 shows the increased oil yield, obtained from enzymatic degumming with KLM3' (namely the lipid acyltransferase K932—sometimes referred to herein as KLM3'—which has the amino acid sequence shown herein as SEQ ID No. 68) (0.1 TIPU-K/g) and increasing amount of NaOH (0, 0.1, 0.2, 0.5, 1, 1.5 and 1.9 ml 4%-solution). Calculations are based on the amount of gum in the control subtracted the amount of gum in enzymatic samples.

Highest oil yield increase is achieved by enzymatic degumming without NaOH and generally increased oil yield (%) decreases with increasing amount of NaOH. This most likely may be explained from the increased saponification of triglycerides with increasing amount of NaOH. However, inspecting the triglycerides in the control and enzymatic gum samples (FIG. 89), the content is not markedly higher in NaOH-treated gums than usually observed without NaOH. The level of triglyceride in enzymatic samples without NaOH likewise is comparable to previous observations.

Analysis of Fatty Acids, Phytosterols and Phytosterol Ester in Oil

The content of phytosterols, phytosterol esters and free fatty acids in the control and enzymatic degummed oils is depicted in FIG. 90. The content of phytosterol esters increases from 0.19% (control) to 0.42% (0.2 ml NaOH), where it reaches a maximum. After this point the phytosterol esters decrease to 0.15%. Accordingly, an initial decrease of phytosterols from 0.3-0.12%, followed by an increase from 0.12-0.28%, is observed.

The FFA's similarly increase to the point of pH 6.3 (0.2 ml NaOH), most likely because of increased saponification.

The results clearly illustrate that running the water degumming at higher pH increases the transferase activity of the lipid acyltransferase KLM3'. Even a slight increase in pH (e.g. 0.1 ml NaOH) increases the formation of phytosterol esters with approximately 50%, almost without affecting the formation of FFA's in the oil (increases 0.02%). The increase in FFA's is important to consider, as the FFA's evaporate during the deodorization step and thus are regarded as oil loss.

Analysis of Phospholipid Content in Oil

Table 2 shows the content (ppm) of phospholipids (phosphatidyl-ethanolamine and phosphatidic acid) in oils (control and enzymatic samples) degummed with increasing amount (0, 0.1, 0.2, 0.5, 1 and 1.9 ml) of NaOH.

TABLE 1

Samples for water degumming trials

| Journal 2460-181 | | 1 | 2 | 3 | 4 | 5 | 6 | 7 | 8 |
|---|---|---|---|---|---|---|---|---|---|
| Crude soya bean oil | g | 100 | 100 | 100 | 100 | 100 | 100 | 100 | 100 |
| K932 100 TIPU/ml | ml | 0 | 0.1 | 0.1 | 0.1 | 0.1 | 0.1 | 0.1 | 0.1 |
| 4% NaOH-solution | ml | 0 | 0 | 0.1 | 0.2 | 0.5 | 1 | 1.5 | 1.9 |
| Extra Water | ml | 2.00 | 1.90 | 1.80 | 1.70 | 1.40 | 0.90 | 0.40 | 0.00 |
| TIPU-K/g oil | | 0.00 | 0.10 | 0.10 | 0.10 | 0.10 | 0.10 | 0.10 | 0.10 |
| % water | | 2 | 2 | 2 | 2 | 2 | 2 | 2 | 2 |

TABLE 2

Content (ppm) phosphor from PA, PE, PC and total phosphor in oils, degummed with increasing amount (0, 0.1, 0.2, 0.5, 1, 1.5 and 1.9 ml) of 4%-NaOH-solution.

| | Sample | | | | | | | |
|---|---|---|---|---|---|---|---|---|
| pH | 5.3 | 5.9 | 6.3 | 6.6 | 7.4 | 7.8 | 8.2 | 8.3 |
| KLM3' (TIPU-K/g) | 0 | 0.1 | 0.1 | 0.1 | 0.1 | 0.1 | 0.1 | 0.1 |
| NaOH (ml) | 0 | 0 | 0.1 | 0.2 | 0.5 | 1 | 1.5 | 1.9 |
| PA | 34.0 | 33.8 | 35.3 | 38.4 | 36.8 | 36.7 | 34.8 | 38.8 |
| PE | 6.8 | 5.9 | 5.0 | 5.6 | 4.9 | 4.0 | 5.0 | 4.6 |
| PC | 1.9 | 0.8 | 0 | 0 | 0 | 0.7 | 2.8 | 0.9 |
| Total phosphor content | 42.8 | 40.6 | 40.2 | 44.1 | 41.8 | 41.5 | 42.6 | 44.3 |

Highest reduction (40.2 ppm) of phosphor is observed in oils, degummed with 0.1 ml NaOH (pH 6.3), however, a comparable content is obtained under normal degumming conditions (0 ml NaOH). Hence, it appears that increasing the pH 1.0 unit does affect the hydrolytic activity of KLM3'. At pH higher than 6.3 (>0.2 ml NaOH), a reduced phospholipid degradation is observed compared to "normal" enzymatic conditions.

Analysis of Phospholipid Content in Gum

FIG. 91 shows the relative degradation of phosphatidic acid (PA), phosphatidyl-ethanolamine (PE), phosphatidyl-choline and phosphatidylinositol (PI) in enzymatic gum samples compared to the control. The degradation of phospholipids in the control is set to 100% and the content in enzymatic samples is calculated relatively to the control.

The degradation of phospholipid in enzymatic samples with 0, 0.1 and 0.2 ml NaOH is analogous. Hence, applying NaOH in amounts less than 0.2 ml does not impair the degradation of phospholipids compared to enzymatic degumming with KLM3' only. On the contrary, reduced degradation is observed in oils with NaOH applied in higher amounts (0.5, 1 and 1.9 ml).

Conclusion

Increasing the pH with NaOH in water degumming of crude soy bean oil turned out, as expected, to increase the activity of KLM3'. Formation of phytosterol esters increased concurrent with increasing amount of NaOH. Maximum phytosterol ester level (0.42%) was obtained at pH 6.3 (0.2 ml NaOH), where after a continuous decrease followed. A similar pattern was observed for the FFA's in the oil, which increased from 0.46% in the control to 0.60% in oils, degummed with 0.2 ml NaOH, where after it decreased.

Small amounts of NaOH did not affect the hydrolytic activity of KLM3', as observed from comparable levels of phospholipids in oils, degummed with 0 and 0.1 ml NaOH. Degradation of phospholipids in the gum phase was reduced compared to normal enzymatic degumming (KLM3' only) at pH above 7.5 (>0.5 ml NaOH).

Highest oil yield increase was achieved by enzymatic degumming without NaOH and generally the % increased oil yield decreased with increasing amount of NaOH.

The conclusion of the present experiment is that small amounts of NaOH may be advantageous for the formation of phytosterol esters in water degumming, however, NaOH does not add positively to the oil yield and phospholipid degradation.

EXAMPLE 5

Analysis of Gum Phase from Enzymatic Water Degumming

Microscopy and X-Ray Analysis

Recipe

| | | 1 | 2 |
|---|---|---|---|
| Crude Soya oil Solae | g | 100 | 100 |
| K932 100 TIPU-K/ml | ml | 0 | 0.20 |
| Extra Water | ml | 2.00 | 1.80 |
| TIPU-K/g oil | | 0.00 | 0.20 |
| % water | | 2 | 2 |

Water Degumming Laboratory Procedure 100 g crude soya oil was scaled into a 250 ml blue cap flask with lid and heated to 55° C. Water was added to the oil followed by enzyme addition. The oil was homogenised using an Ultra Turrax mixer for 30 seconds and agitated for 30 minutes with magnetic stirring at 450 rpm. After 30 minutes, the oil was centrifuged (2000 rcf for 3 minutes). The gum phase was taken for microscopy- and x-ray analysis.

Results and Discussion

Microscopy/X-Ray Analysis

Gums from control and enzymatic water degumming trials (the latter in accordance with the present invention) were collected for microscopy and x-ray analysis. The gum phases were studied in the microscope (plane polarised light) at different temperatures (25, 35, 45, 55 and 65° C.). At all temperatures the gum was in a lamellar phase (lipid bi-layers separated by water layers), as seen for the control and enzymatic sample (25° C.) in FIG. 92.

Some differences appear between the control and enzymatic sample. The control gum appears coarser than the enzymatically gummed sample in accordance with the present invention. Differences between the control and enzymatic sample also can be observed from x-ray analysis, as seen in FIG. 93.

The larger spacing of approximately 20 Å in the control compared to the enzyme treated sample corresponds to the length of a fatty acid chain (C18). The spacing expresses the water and phospholipid layer, hence, the larger spacing in the control could explain that the control contains an extra monolayer of fatty acids or that more water is absorbed in the gum phase.

EXAMPLE 6

Sedimentation Study

Recipe

| | | 1 | 2 |
|---|---|---|---|
| Crude Soya oil Solae | g | 200 | 200 |
| K932 100 TIPU-K/ml | ml | 0 | 0.4 |
| Extra Water | ml | 4.00 | 3.60 |
| TIPU-K/g oil | | 0.00 | 0.20 |
| % water | | 2 | 2 |

Procedure 200 g crude soya oil was scaled into a 250 ml blue cap flask with lid and heated to 55° C. Water was added to the oil followed by enzyme addition. The oil was homogenised using an Ultra Turrax mixer for 30 seconds and agitated for 30 minutes with magnetic stirring at 450 rpm. After 30 minutes, the samples were placed in separation funnels. Pictures of the gum phase were taken after 1, 3 and 6 days. After day six, the gums were taken for microscopy analysis.

Results

Pictures of Gum Phases/Microscopy

In FIG. 94 the oil and gum phase can be seen for the control and enzymatic sample. Sedimentation by gravity has been carried out for 3 days. Clear differences exist between the control and enzymatic sample, as seen from both the oil and gum phase.

The oil phase of enzymatic treated oil (i.e. treated in accordance with the present invention) is clearer than the control and a decreased amount of gum is observed compared to the control. The results may be explained from microscopy analysis (FIG. 95). The enzymatic treated gum is observed as an emulsion, while the control gum is lamellar phase.

EXAMPLE 7

Evaluation of Varying Amount of Water in Enzymatic Degumming of Crude Soybean Oil Recipes

| Journal 2460-165 | | 1 | 2 | 3 | 4 | 5 | 6 | 7 | 8 |
|---|---|---|---|---|---|---|---|---|---|
| Crude Soya oil Solae | G | 100 | 100 | 100 | 100 | 100 | 100 | 100 | 100 |
| K932 100 TIPU-K/ml | Ml | 0 | 0.2 | 0 | 0.2 | 0 | 0.2 | 0 | 0.2 |
| Extra Water | Ml | 1.00 | 0.800 | 1.50 | 1.30 | 2.00 | 1.80 | 2.50 | 2.30 |
| KLM3' activity (TIPU-K/g oil) | | 0.00 | 0.20 | 0.00 | 0.20 | 0.00 | 0.20 | 0.00 | 0.20 |
| % water | | 1 | 1 | 1.5 | 1.5 | 2 | 2 | 2.5 | 2.5 |

| Journal 2460-169 | | 1 | 2 | 3 | 4 | 5 | 6 |
|---|---|---|---|---|---|---|---|
| Crude Soya oil Solae | g | 100 | 100 | 100 | 100 | 100 | 100 |
| K932 100 TIPU-K/ml | ml | | | | 0.2 | 0.2 | 0.2 |
| Extra Water | ml | 1.00 | 1.50 | 2.00 | 0.80 | 1.30 | 1.80 |
| KLM3' activity (TIPU-K/g oil) | | | | | 0.20 | 0.20 | 0.20 |
| % water | | 1 | 1.5 | 2 | 1 | 1.5 | 2 |

| Journal 2460-170 | | 1 | 2 | 3 | 4 | 5 | 6 | 7 | 8 | 9 | 10 |
|---|---|---|---|---|---|---|---|---|---|---|---|
| Crude Soya oil Solae | g | 100 | 100 | 100 | 100 | 100 | 100 | 100 | 100 | 100 | 100 |
| K932 100 TIPU-K/ml | ml | 0 | 0 | 0 | 0 | 0 | 0.2 | 0.2 | 0.2 | 0.2 | 0.2 |
| Extra Water | ml | 1.00 | 1.25 | 1.50 | 1.75 | 2.00 | 0.80 | 1.05 | 1.30 | 1.55 | 1.80 |
| KLM3' activity (TIPU-K/g oil) | | 0.00 | 0.00 | 0.00 | 0.00 | 0 | 0.20 | 0.20 | 0.20 | 0.20 | 0.20 |
| % water | | 1.00 | 1.25 | 1.50 | 1.75 | 2.00 | 1.00 | 1.25 | 1.50 | 1.75 | 2.00 |

Water Degumming Laboratory Procedure 100 g crude soya oil was scaled into a 250 ml blue cap flask with lid and heated to 55° C. Water was added to the oil followed by enzyme addition. The oil was homogenised using an Ultra Turrax mixer for 30 seconds and agitated for 30 minutes with magnetic stirring at 450 rpm. After 30 minutes, approximately 10 ml oil was transferred to a 12 ml centrifuge tube (previously scaled). The oil was heated to 97° C. in a boiling water bath for 10 minutes. The tubes were centrifuges at 300 rcf for 3 minutes. Oil was decanted from the gum phase and drained for 15 minutes by turning the tube upside down. Based on the weight of the gum phase the oil yield was calculated.

Results and Discussion

Oil Yield

FIG. 96 shows the increased oil yield obtained from enzymatic water degumming of crude soybean oil with varying amounts of water. Increased oil yield is calculated from the amount of gum in the control subtracted amount of gum in enzymatic samples.

Enzymatic degumming attributes to an increased oil yield compared to the control and it appears that the oil yield increases with decreasing amount of water. The oil yield approximately increases 50% in enzymatic degumming compared to the control, when water is reduced from 2 to 1%.

These calculations are based on amount of gum and hence also include the triglyceride content in the gum phase. Inspecting the actual oil loss (based on amount of gum and triglyceride content in gum) (FIG. 97), the oil loss decreases in the control with increasing water content. However, in enzymatic degumming, the oil loss is somewhat unaffected by amount of water. Approximately 2% oil is lost in enzymatic degumming compared to 3.5-6.5% in the control.

The decreased amount of water in enzymatic water degumming may be a financial advantage for the industry (less process water) and most likely also with regard to energy savings during the drying of the gum phase.

Phospholipid Degradation in Gum Phase

The relative degradation (%) of phosphatidic acid (PA) and phosphatidylethanolamine (PE) in the enzymatic gum phases relative to the control is shown in FIG. 98.

Phospholipid degradation with KLM3' appears to be more pronounced at lower water concentrations. In overall enzymatic degumming with KLM3' and 1% water appears to be an advantage in respect to phospholipid degradation compared to degumming with 2% water.

Viscosity Measurements of the Gum Phase

The viscosity of enzymatic (KLM3' 0.2 TIPU-K/g) gum phases, from degumming with different amounts of water is shown in FIG. 99. The viscosity is not markedly affected by the different water content. At lower shear rate (up to approximately 10) the viscosity is somewhat similar for all samples, however, after this point the viscosity of samples with lowest amount (1.25%) of water increases, while gum samples highest amount (2%) of water increases.

EXAMPLE 8

Water Degumming of Crude Corn Oil

Abstract

Lipid acyltransferase, KLM3' (sometimes referred to as K932 and having the amino acid sequence shown herein as SEQ ID No. 68 was tested in a crude corn oil with the aim to study effects on oil yield in water degumming of this oil.
Materials and Methods
Enzyme:
  KLM3' K932. 1128 TIPU/g
Oil:
  Crude corn oil from Cargill, May 2008
Degumming Procedure:
  100 g crude corn oil was scaled into a 250 ml Blue Cap flask with lid and heated to 55° C.
  Water and enzyme was added and the oil was homogenised with an Ultra Turrax mixer for 30 seconds, and then agitated for 30 minutes with magnetic stirring at 450 rpm.
  After 30 minutes, 10 ml oil was transferred to a 12 ml tarred centrifuge tube and the oil weight noticed. The oil was heated to 97° C. in a boiling water bath for 10 minutes, and then immediately centrifuged at 3000 rcf for 3 minutes.
  Oil was decanted from the gum phase and drained for 15 minutes by turning the tube upside down. Based on the weight of the gum phase the oil yield was calculated relative to an oil not treated with enzyme.
  The gum phase was then analysed by HPTLC, and the degradation of the phospholipids in the gum phase was calculated.
Results
  The oil degumming process was conducted with different concentrations of KLM3'

TABLE 1

Recipe for degumming of Crude Corn Oil

| 2460-182 | | 1 | 2 | 3 | 4 | 5 |
|---|---|---|---|---|---|---|
| Crude Corn oil | g | 100 | 100 | 100 | 100 | 100 |
| K932 100 TIPU-K/ml | ml | 0 | 0.050 | 0.10 | 0.20 | 0.50 |
| Extra Water | ml | 2.00 | 1.95 | 1.90 | 1.80 | 1.50 |
| TIPU/g oil | | 0.00 | 0.05 | 0.10 | 0.20 | 0.50 |
| % water | | 2 | 2 | 2 | 2 | 2 |

The samples were treated as described in 'degumming procedure' and the amount of wet gum was determined in duplicate with results shown below.

TABLE 2

Gum Phase, % from water degumming of crude corn oil

| Sample | Enzyme, Units/g | Gum Phase | Yield increase |
|---|---|---|---|
| 1 | 0 | 6.0 | 0.00 |
| 2 | 0.05 | 5.7 | 0.28 |

TABLE 2-continued

Gum Phase, % from water degumming of crude corn oil

| Sample | Enzyme, Units/g | Gum Phase | Yield increase |
|---|---|---|---|
| 3 | 0.1 | 5.5 | 0.44 |
| 4 | 0.2 | 5.6 | 0.36 |
| 5 | 0.5 | 5.6 | 0.38 |

From the result in table 2 it is seen that KLM3' contribute to a decrease in the amount of gum phase by water degumming of crude corn oil. The reduced amount of gum phase corresponds to an increase in the oil phase of 0.28 to 0.44%.

The gum phase isolated from water degumming of crude corn oil was analysed by TLC and the reduction of phosphatidylethanolamine and phosphatidic acid was calculated relative to the amount in the gum without enzyme treatment. (Table 3)

TABLE 3

TLC analysis of Gum phase.

| Enzyme dosage TIPU/g oil | PA Relative % | PE Relative % |
|---|---|---|
| 0 | 100 | 100 |
| 0.05 | 88 | 85 |
| 0.1 | 73 | 68 |
| 0.2 | 75 | 72 |
| 0.5 | 72 | 64 |

PE = phosphatidylethanolamine
PA = Phosphatidic acid

The results from table 3 indicate the activity of KLM3' on phospholipids in crude corn oil. An increased enzyme activity is seen up to a dosage of 0.1 TIPU/g oil. At higher enzyme dosage the activity on the phospholipids levels off.

EXAMPLE 9

Water Degumming of Crude Soya Oil, and Addition of Acceptors

Lipid acyltransferase, KLM3', was tested in an crude soya bean oil from Solae with the aim to study effects of adding acceptor substrate for the enzyme KLM3'.

In this study a phytosterol product Generol 122 from Henkel, Germany, and a fatty alcohol, laurylalcohol was tested.

Addition of phytosterol to the oil produced more sterol ester concomitant with a reduction of free fatty acid formation. It is concluded that a higher degree of phospholipid conversion can be achieved without increased fatty acid production when more acceptor substrate is available.
Materials and Methods
Enzyme:
  KLM3' K932 (having amino acid sequence shown as SEQ ID No. 68-1128 TIPU/g
Phytosterol from soya: Generol 122 N, from Grünau, Illertissen, Germany.
Laurylalcohol: Sigma L-5375
Oil:
  Crude Soya Bean oil from Solae, January 2008
  Soy Lecithin Mix Standard (ST16) from Spectra Lipid, Germany.
Degumming Procedure:
  100 g crude soya oil, phytosterol and layrylalcohol was scaled into a 250 ml Blue Cap flask with lid and heated to 55° C. The phytosterol was completely dissolved in the oil before further processing.

Water and enzyme was added and the oil was homogenised with an Ultra Turrax mixer for 30 seconds, and then agitated for 30 minutes with magnetic stirring at 450 rpm.

After 30 minutes, 10 ml oil was transferred to a 12 ml tarred centrifuge tube and the oil weight noticed. The oil was heated to 97° C. in a boiling water bath for 10 minutes, and then immediately centrifuged at 3000 rcf for 3 minutes.

Oil was decanted from the gum phase and drained for 15 minutes by turning the tube upside down. Based on the weight of the gum phase the oil yield was calculated.

The oil phase and the gum phase was then analysed by HPTLC, and the amount of triglyceride in the gum phase and the degradation of the phospholipids in the oil phase was calculated Results The oil degumming process was conducted with different concentrations of KLM3, phytosterol and fatty alcohol as shown table 1.

TABLE 1

Recipe for degumming of Crude Soya Oil

| 2460-182 | | 1 | 2 | 3 | 4 | 5 | 6 | 7 | 8 | 9 |
|---|---|---|---|---|---|---|---|---|---|---|
| Crude Soya oil, Solae d. 16 Jan. 2008 | g | 100 | 100 | 100 | 100 | 100 | 100 | 100 | 100 | 100 |
| K932 100 TIPU-K/ml | ml | 0 | 0.20 | 0.20 | 0.20 | 0.2 | 0.2 | 1 | 1 | 0.2 |
| General 122 N | g | | 0 | 0.25 | 0.50 | 0.75 | 0.75 | | 0.75 | |
| 4% NaOH | ml | | | | | | 0.2 | | | |
| Lauryl alcohol | g | | | | | | | | | 0.5 |
| Extra Water | ml | 2.00 | 1.80 | 1.80 | 1.80 | 1.80 | 1.80 | 1.00 | 1.00 | 1.80 |
| pH | | 4.90 | 5.65 | 5.55 | 5.48 | 5.41 | 6.18 | 5.29 | 5.27 | 5.57 |
| TIPU/g oil | | 0.00 | 0.20 | 0.20 | 0.20 | 0.20 | 0.20 | 1.00 | 1.00 | 0.20 |
| % water | | 2 | 2 | 2 | 2 | 2 | 2 | 2 | 2 | 2 |

The samples were treated as described in 'degumming procedure' and the amount of wet gum was determined in duplicate with results shown in FIG. 100.

Addition of increasing amount of phytosterol did not contribute to any decrease in % gum, and pH adjustment (trial 6) did not have any significant effect on the amount of gum although there is a tendency to more gum in this trial. Addition of 0.2 TIPU/g of KLM3' had a significant effect on the gum content, and it was shown that an increase to 1 TIPU/g further decreased the amount of gum. Lauryl alcohol did not have any effect on the amount of gum.

The oil phase separated from the gum was analysed for free fatty acids, sterols and sterol esters by GLC.

The results in table 2 indicate an increase of 0.09% free fatty acid by enzymatic treatment with 0.2 TIPU/g (sample 2), but it is observed that sample 3 to 5 with increased level of phytosterols contains less free fatty acids. Also in sample 7 and 8 treated with 1 TIPU/g a reduction in free fatty acids is observed when more sterol is added to the oil. These results indicate that the hydrolytic reaction decreases with increased mount of sterols in the oil.

It should then be expected that the amount of sterol ester increase with increase sterol in the oil. This is also seen for sample 3, but with increased amount of sterols (sample 4 and 5), the amount of sterol esters does not change. Even a tendency to decreased amount of sterol ester in sample 5 is observed, but this is within the experimental error. Adjusting the pH by addition of NaOH however has a strong effect on sterol ester formation as seen before. Increased amount of enzyme (sample 7 and 8) also contribute to increase in sterol ester formation.

TABLE 2

GLC analyses of oil phase form water degumming of samples (see table 1)

| Sample | Free fatty acids, % | Sterols % | Sterol ester, % |
|---|---|---|---|
| 1 | 0.46 | 0.30 | 0.20 |
| 2 | 0.55 | 0.15 | 0.40 |
| 3 | 0.54 | 0.36 | 0.45 |
| 4 | 0.52 | 0.60 | 0.40 |
| 5 | 0.50 | 0.83 | 0.38 |
| 6 | 0.55 | 0.69 | 0.63 |
| 7 | 0.86 | 0.12 | 0.47 |
| 8 | 0.80 | 0.65 | 0.64 |
| 9 | 0.53 | 0.20 | 0.39 |

The gum phase isolated by water degumming of samples (table 1) were analysed by HPTLC and the degradation of certain phospholipids phosphatidylethanolamine (PE) and phosphatic acid (PA) were quantified relative to the control sample no 1. (FIG. 101)

The results in FIG. 101 indicate an increased degradation of PA and PE when 0.25% sterol is added, But increased dosage (0.5 and 0.75% sterol) does not contribute to further phospholipid degradation. This is in agreement with the observation about the effect on sterol ester formation (see table 2). pH adjustment with NaOH also has a strong effect on phospholipid degradation, but this is related to more enzyme activity with increased pH.

It is also seen that increase in enzyme dosage to 1 TIPU/g further degrades the phospholipids.

The oil phase isolated form the water degumming was analysed by ICP with the aim to analyse the amount of residual phosphor in the oil.

The results in FIG. 102 indicate that the level of phosphor in the oil is not very much dependent of the amount of sterol in the oil, but the results indicate that increased enzyme dosage (1 TIPU/g) has an effect on the phosphor level. Addition of laurylalcohol (C12-alcohol) has a negative effect on the level of phosphor in the oil phase.

Conclusion.

Addition of lipid acyltransferase KLM3' to crude oil catalyses the transfer of fatty acid moiety from phospholipid to sterol, during formation of sterol esters. On a molecular level the amount of sterol is less than ⅓ of the amount of phospholipids in crude soya oil. Because the acyl acceptor sterol is the limiting factor for KLM3' in crude soya oil, the hydrolysis reaction might occur depending on enzyme dosage and reaction time.

In this study it was found that the addition of more sterol to the crude oil will produces more sterol ester, when the oil is treated with lipid acyltransferase KLM3', and the amount of free fatty acids formed is reduced compared with an oil where no sterol was added.

Addition of extra sterol does not have much impact in the level of phosphor in the oil phase after water degumming, but it is observed that increased dosage of KLM3' reduces the level of phosphor in the oil phase. Addition of 0.5% laurylalcohol did not have much effect on the level of free fatty acid and no laurylalcohol ester was seen by GLC analysis.

EXAMPLE 10

Combination of a Lipid Acyltransferase and a Phospholipase C

Materials and Methods
Enzyme:
  Lipid Acyltransferase KLM3' K932. 1128 LATU/g (having the amino acid sequence shown herein as SEQ ID No. 68)
  Phospholipase C, Sigma P7633 15 Units/mg
Oil:
  Crude Soya Bean oil from Solae, Aarhus, DK
Degumming Procedure
  100 g crude soya oil is scaled into a 250 ml Blue Cap flask with lid and heated to 55° C. 0.14 ml 50% citric acid monohydrate is added. The oil is homogenised with an Ultra Turrax mixer for 30 seconds, and then agitated for 15 minutes with magnetic stirring at 450 rpm. 0.367 ml 1N NaOH is added followed by 2.5% water and 5 Units/g oil of Phospholipase C. The oil is again homogenised with an Ultra Turrax mixer for 30 seconds and agitated at 450 rpm with magnetic stirrer. After 2 hours reaction time 0.2 LATU/g oil of enzyme Lipid acyltransferase KLM3' is added and the reaction is continued for one hour more with stirring.

The oil is heated to 97° C. in a boiling water bath for 10 minutes, and then immediately centrifuged at 3000 rcf for 3 minutes.

Oil phase is decanted from the gum phase. The weight of the gum phase the oil phase is measured.

The oil phase is analysed for residual phospholipids by TLC, and ppm phosphor is analysed by ICP. Free sterol, sterol ester, free fatty acid and diglyceride are analysed by GLC.

The gum phase is analysed for triglyceride, diglyceride, residual phospholipids and free fatty acid.

The degradation of phospholipids in the gum phase is analysed by TLC

Results

The degumming process with a combination of lipid acyltransferase and phospholipase C is expected to increase the oil yield by more than 2% compared with an oil without enzyme treatment. Initial studies suggest that diglyceride has been produced in the oil phase in the enzyme treated sample.

In the oil phase after centrifugation a main part of the sterols will be esterified.

Preliminary investigations show that the phosphor level is below 5 ppm in the oil phase and a strong degradation of phospholipids in the gum phase. (i.e. Phosphatidylcholine (PC) and phosphatidylethanolamine (PE) almost completely disappearing and a strong degradation of phosphatidylinositol (PI) and phosphatidic acid (PA)).

EXAMPLE 11

Lipid Acyltransferase in Combination with Phospholipase C

Materials and Methods
Enzyme:
  Lipid Acyltransferase KLM3' K932. 1128 LATU/g
  Phospholipase C Sigma P7633 15 Units/mg
Oil:
  Crude Soya Bean oil from Solae, Aarhus, DK
Degumming Procedure
  100 g crude soya oil is scaled into a 250 ml Blue Cap flask with lid and heated to 55° C.
  3% water is added followed by 0.1 Units/g oil of Acyltransferase KLM3' and 5 Units Phospholipase C. The oil is homogenised with an Ultra Turrax mixer for 30 seconds, and then agitated for 30 minutes with magnetic stirring at 450 rpm.

After 30 minutes, 10 ml oil is transferred to a 12 ml tarred centrifuge tube and the oil weight noticed. The oil is heated to 97° C. in a boiling water bath for 10 minutes, and then immediately centrifuged at 3000 rcf for 3 minutes.

Oil phase is decanted from the gum phase and drained for 15 minutes by turning the tube upside down. Based on the weight of the gum phase the oil yield is calculated. The oil phase is analysed for residual phospholipids by TLC and ICP. Free sterol, sterol ester, free fatty acid and diglyceride are analysed by GLC.

The gum phase is analysed for triglyceride residual phospholipids and free fatty acid.

Results

Preliminary investigations suggest that the water degumming process with a combination of Lipid acyltransferase and phospholipase C results in a significant increase in the oil yield with more than 2% compared with an oil without enzyme treatment. Initial studies show that diglyceride is produced in the oil phase and a main part of the sterols in the oil phase is esterified.

EXAMPLE 12

Enzymatic Degumming with Lipid Acyltransferase KLM3 and Phospholipase C (PLC)

Materials and Methods
Enzyme:
  Lipid Acyltransferase KLM3' K932. 1128 LATU/g
  Phospholipase C Sigma P7633 15 Units/mg
Oil:
  Crude Soya Bean oil from Solae, Aarhus, DK
Degumming Procedure
  100 g crude soya oil is scaled into a 250 ml Blue Cap flask with lid and heated to 55° C.
  3% water is added followed by 5 Units/g oil of Phospholipase C. pH is adjusted to 5.5 with NaOH. The oil is homogenised with an Ultra Turrax mixer for 30 seconds, and then agitated for 15 minutes with magnetic stirring at 450 rpm. After 15 minutes a sample is taken out and 0.1 Units/g oil of Acyltransferase is added. The oil is agitated for a further 15 minutes at 55° C.

After 2×15 minutes reaction time, 10 ml oil is transferred to a 12 ml tarred centrifuge tube and the oil weight noticed. The oil is heated to 97° C. in a boiling water bath for 10 minutes, and then immediately centrifuged at 3000 rcf for 3 minutes.

Oil is decanted from the gum phase and drained for 15 minutes by turning the tube upside down. Based on the weight of the gum phase the oil yield is calculated.

The oil phase is analysed for residual phospholipids by TLC and ICP. Free sterol, sterol ester, free fatty acid and diglyceride are analysed by GLC.

The gum phase is analysed for triglyceride residual phospholipids and free fatty acid.

Results

Initial studies suggest that the water degumming process using a combination of Lipid acyltransferase and phospholipase C increases the oil yield by more than 2.5% compared with an oil without enzyme treatment. Preliminary investigations suggest that diglyceride has been produced after 15 minutes in the oil phase.

A main part of the sterols in the oil phase will be esterified. Preliminary investigations show that after 15 minutes a main part of the phosphatidylethanolamine (PE) and phosphatidylcholine (PC) has disappeared but less activity may be seen on phosphatidylinositol (PI) and phosphatidic acid (PA). In the sample after 30 minutes and centrifugation also a main part of the PI and PA will have disappeared.

EXAMPLE 13

Enzymatic Degumming with Lipid Acyltransferase KLM3 and Phospholipase C (PLC)

Lipid Acyltransferase KLM3' and Phospholipase C (PLC) from Sigma were tested alone and in combinations in water degumming of crude soya oil. Phospholipase C in oil degumming produced diglyceride from phospholipids in the oil. It was surprisingly shown that KLM3' can use the diglyceride as an acceptor molecule during production of triglyceride. Model experiments with substrate containing diglyceride and phosphatidylcholine confirmed that lipid acyltransferase (KLM3') catalyzes a transfer reaction of fatty acid moiety from phospholipid to diglyceride during production of triglyceride.

Commercial Relevance of the Results

This study was initiated with the aim to show that the combination of KLM3' and Phospholipase C (PLC) is highly advantageous when degumming of crude vegetable oils.

A phospholipase C from Verenium, U.S. (namely Purifine®) has been introduced for use in oil degumming (WO 2008/036863).

This enzyme is active on phospholipids (such as phosphatidylcholine and phosphatidylethanolamine) in crude oil forming diglyceride (diacylglycerol) and phosphor-choline, -ethanolamine, -inositol or -acid. Diglyceride produced during this process will form part of the oil during the oil degumming process and thus contribute to improved oil yield.

The inventors have shown that lipid acyltransferases (such as KLM3') can contribute to improved yield in oil degumming by modification of the phospholipids concomitant with sterol ester formation.

Lipid acyltransferases (such as KLM3') can use sterols as an acyl acceptor as well as other acceptors like alcohols including fatty alcohols.

The aim of the current study was to investigate any synergistic effect when a lipid acyltransferase (e.g. KLM3') was used in combination a phospholipase C.

Material and Methods:
  KLM3':Glycerophospholipid cholesterol acyltransferase (FoodPro LysoMax Oil) (K932) (SEQ ID No. 68) Lot no 102629600. Activity 1128 LATU/g
  Phospholipase C P7633 Sigma, from *Clostridium perfringens*, 135.3 mg solid: 3.8 unit/mg solid, 13.2 unit/mg protein
  Phospholipase C P6621 Sigma, from *Bacillus cereus*, 250 Units
  Diglyceride. Destilled diglyceride from sunflower oil, Jour 2641/064
  Phosphatidylcholine, Avanti #441601
  Mono-di-triglyceride: GRINDSTED® MONO-DI R 50/D
  Crude soya oil no 18: from, Argentina HPTLC Analysis The degradation of phospholipids in the gum phase from enzyme treated samples was analysed by HPTLC.

Applicator: Automatic TLC Sampler 4, CAMAG
HPTLC plate: 20×10 cm, Merck no. 1.05641. Activated 10 minutes at 160° C. before use.
Application:
  Gum phase from 10 gram oil was dissolved in 7.5 ml Hexan:Isopropanol 3:2.
  1 µl of the sample was applied to the HPTLC plate.
  A phospholipid standard (0.5% phospholipid (Spectra Lipid, Germany) was applied (0.1, 0.3, 0.5, 0.8 and 1.5 µl) and used for the calculation of the individual phospholipids in the gum.
  In some applications the phospholipid content was calculated relative to a control gum not treated with enzyme. This control sample was applied 0.1-0.3-0.5-0.8-1 µl and used for making calibrations curves.
  Oil phase. Approximately 90 mg was scaled and dissolved in 1 ml Hexan:Isopropanol 3:2.
  5 µl of the sample was applied to the HPTLC plate. Monodiglyceride 5 mg/ml of known concentration was applied at 0.1-0.3-0.5-0.8-1.5 µl and used for calculation of individual glyceride components
TLC Applicator.
Running buffer no. 1: P-ether:Methyl Tert Butyl Ketone: Acetic acid 50:50:1
Running buffer no 6: Chloroform:1-propanol:Methylacetate: Methanol: 0.25% KCl in water 25:25:25:10:9
Elution: The plate was eluted 7 cm using an Automatic Developing Chamber ADC2 from Camag.
Development:
  The plate was dried on a Camag TLC Plate Heater III for 6 minutes at 160° C., cooled, and dipped into 6% cupri acetate in 16% $H_3PO_4$. Additionally dried 10 minutes at 160° C. and evaluated directly.
  The density of the components on the TLC plate was analysed by a Camag TLC Scanner 3.
Gas Chromatography
  Free fatty acid in the gum phase was analysed by GLC.
  Mono-di-triglyceride, sterol and sterol ester of the oil phase was also analysed by GLC
Apparatus:

Perkin Elmer Autosystem 9000 Capillary Gas Chromatograph equipped with WCOT fused silica column 12.5 m × 0.25 mm ID × 0.1µ film thickness 5% phenyl-methyl-silicone (CP Sil 8 CB from Chrompack).
Carrier gas: Helium.
Injector: PSSI cold split injection (initial temp 50° C. heated to 385° C.), volume 1.0 µl
Detector FID: 395° C.

| Oven program (used since 30 Oct. 2003): | 1 | 2 | 3 |
|---|---|---|---|
| Oven temperature, ° C. | 90 | 280 | 350 |
| Isothermal, time, min. | 1 | 0 | 10 |
| Temperature rate, ° C./min. | 15 | 4 | |

Sample Preparation:
  The sample was dissolved in 12 ml Heptane:Pyridin, 2:1 containing internal standard heptadecane, 0.5 mg/ml. 500 µl sample solution was transferred to a crimp vial, 100 µl MSTFA (N-Methyl-N-trimethylsilyl-trifluoraceamid) was added and reacted for 15 minutes at 60° C.
Calculation:
  Response factors for sterol, sterol ester, free fatty acids, mono- di- and tri-glyceride were determined based on pure reference material.
Experimental:
  Acyltransferase KLM3' and PLC was tested in a water degumming process using crude soya oil with the recipes shown in Table 1

TABLE 1

|  |  | 1 | 2 | 3 | 4 | 5 | 6 | 7 | 8 | 9 |
|---|---|---|---|---|---|---|---|---|---|---|
| Crude soya oil from Argentina n | g | 10 | 10 | 10 | 10 | 10 | 10 | 10 | 10 | 10 |
| Phospholipase C P7633 | ml |  | 0.2 | 0.2 | 0.2 |  |  |  |  |  |
| Phospholipase C P6621 |  |  |  |  |  |  |  | 0.2 | 0.2 | 0.2 |
| K932 10 U/ml | ml |  |  | 0.01 | 0.05 | 0.01 | 0.05 |  | 0.01 | 0.05 |
| Water | ml | 0.250 | 0.050 | 0.040 | 0.000 | 0.240 | 0.200 | 0.050 | 0.040 | 0.000 |
| % water |  |  | 2.50 | 2.50 | 2.50 | 2.50 | 2.50 | 2.50 | 2.50 | 2.50 |

Phospholipase C P7633 Sigma, From *C. perfringens*, 135.3 mg solid:3.8 unit/mg solid, 32.9 mg enzyme in 0.5 ml water Phospholipase C P6621 Sigma, From *Bacillus cereus*, 250 Units dissolved in 1 ml water Acyltransferase KLM3' (K932) diluted to 10 LATU/ml The crude soya was heated to 45° C. in a 20 ml Wheaton glass. Water and enzyme was added.

The sample was homogenized by high shear mixing for 30 seconds.

The samples were placed on a heating block at 45° C. with magnetic agitation.

Samples of 1 ml were taken out after 30 and 240 minutes in an Eppendorf tube and the enzymes inactivated for 10 minutes at 97° C. Notably although deactivation of the enzyme is carried out in the experiments—this is not generally done in practice in industry. The deactivation is only carried out in the experiments herein so that an accurate analysis of the enzyme degradation.

The samples were centrifuged at 3000 rcf for 3 minutes. The oil phase was separated from the gum phase, and both phases were analysed by TLC and GLC.

Results
TLC Analysis

Samples taken out after 30 minutes and 240 minutes were analysed by TLC with results shown in FIGS. 103 to 106.

The TLC plates (FIG. 103 and FIG. 104) were scanned and used for quantitative determination of 1,2 diglyceride (DAG sn1,2) with results shown in Table 2 and 3 below.

The relative degradation of the phospholipids are shown in FIG. 107.

TABLE 2

TLC analysis of oil phase after 30 minutes reaction time.

| Test no. | Phospholipase C P7633 U/g | Phospholipase C P6621 U/g | K932 10 U/ml LATU/g | DAG sn_1,2 % |
|---|---|---|---|---|
| 1 | 0 | 0 | 0 | 0.33 |
| 2 | 5 | 0 | 0 | 0.72 |
| 3 | 5 | 0 | 0.01 | 0.67 |
| 4 | 5 | 0 | 0.05 | 0.60 |
| 5 | 0 | 0 | 0.01 | 0.37 |
| 6 | 0 | 0 | 0.05 | 0.29 |
| 7 | 0 | 5 | 0 | 1.28 |
| 8 | 0 | 5 | 0.01 | 1.22 |
| 9 | 0 | 5 | 0.05 | 1.19 |

TABLE 3

TLC analysis of oil phase after 240 minutes reaction time.

| Test no. | Phospholipase C P7633 U/g | Phospholipase C P6621 U/g | K932 LATU/g | DAG sn_1,2 % |
|---|---|---|---|---|
| 1 | 0 | 0 | 0 | 0.27 |
| 2 | 5 | 0 | 0 | 0.64 |
| 3 | 5 | 0 | 0.01 | 0.60 |
| 4 | 5 | 0 | 0.05 | 0.50 |
| 5 | 0 | 0 | 0.01 | 0.34 |
| 6 | 0 | 0 | 0.05 | 0.27 |
| 7 | 0 | 5 | 0 | 1.06 |
| 8 | 0 | 5 | 0.01 | 1.04 |
| 9 | 0 | 5 | 0.05 | 1.01 |

The results from Tables 2 and 3 above clearly indicate the formation of diglyceride caused by the PLC degradation of phospholipids. It is observed that with the dosage of PLC used the formation of sn 1,2 diglyceride has already reached its maximum after 30 minutes reaction time. It is also observed that the amount of sn 1,2 diglyceride decreases with increased dosage of KLM3' when used in combination with PLC.

This effect was observed for both phospholipase C enzymes but the effect was most pronounced when KLM3' was combined with Phospholipase C P7633 Sigma, from *C. perfringens*. This is most probably explained by the fact that PLC from *C. perfringens* only degraded a small part of the phospholipids, so more substrate was available for KLM3'.

The results in FIG. 107 also clearly show that Phospholipase C P7633 Sigma, from *C. perfringens* is mainly active on phosphatidylcholine (PC), and Phospholipase C P6621 Sigma, from *Bacillus cereus* has main activity on phosphatidylcholine (PC) and phosphatidylethanolamine (PE) and less activity on phosphatidic acid (PA) and phosphatidylinositol (PI). The results also proof that KLM3' can use all four types of phospholipids.

It is therefore concluded that acyltransferase KLM3' can use sn 1,2 diglyceride as an acceptor molecule and catalyses the reaction in FIG. 108.

GLC Analysis

The samples no 1 to 6 of oil phase from the experiment in Table 1 were also analysed by GLC.

The GLC analysis of total diglyceride (DAG), sterol sterol ester and FFA are listed in Table 4 below.

TABLE 4

GLC analysis of oil phase after 30 minutes and 240 minutes incubation.

| sample no | PLC U/g | KLM3 U/g | Reaction Time minutes | DAG % | Sterol % | Sterol ester % | FFA % |
|---|---|---|---|---|---|---|---|
| 1 | 0 | 0 | 30 | 1.34 | 0.25 | 0.12 | 0.22 |
| 2 | 5 | 0 | 30 | 2.58 | 0.26 | 0.13 | 0.21 |
| 3 | 5 | 0.05 | 30 | 2.39 | 0.18 | 0.26 | 0.22 |
| 4 | 5 | 0.1 | 30 | 2.10 | 0.09 | 0.42 | 0.28 |
| 5 | 0 | 0.05 | 30 | 1.43 | 0.15 | 0.33 | 0.22 |
| 6 | 0 | 0.1 | 30 | 1.24 | 0.06 | 0.49 | 0.33 |

TABLE 4-continued

GLC analysis of oil phase after 30 minutes and 240 minutes incubation.

| sample no | PLC U/g | KLM3 U/g | Reaction Time minutes | DAG % | Sterol % | Sterol ester % | FFA % |
|---|---|---|---|---|---|---|---|
| 1 | 0 | 0 | 240 | 1.63 | 0.22 | 0.13 | 0.20 |
| 2 | 5 | 0 | 240 | 2.33 | 0.25 | 0.13 | 0.20 |
| 3 | 5 | 0.05 | 240 | 2.13 | 0.08 | 0.45 | 0.29 |
| 4 | 5 | 0.1 | 240 | 2.08 | 0.04 | 0.48 | 0.43 |
| 5 | 0 | 0.05 | 240 | 1.69 | 0.04 | 0.49 | 0.32 |
| 6 | 0 | 0.1 | 240 | 1.68 | 0.04 | 0.50 | 0.56 |

The GLC analysis of samples taken out after 30 and 240 minutes reaction time confirmed what was already observed by TLC analysis, that Phospholipase C P7633 Sigma, from *C. perfringens* produced diglyceride from the phospholipids in the oil. The results also confirm the synergistic effect by reduced amount of diglyceride when Phospholipase C is combined with KLM3'. A statistical evaluation by ANOVA using Statgraphic software of the effect of PLC and KLM3' on the amount of diglyceride clearly indicates the interaction effect between these two enzymes, see FIG. 109.

PLC had no significant effect on the sterols in the oil but KLM3' converts free sterols to sterols esters. Sterols are a better acceptor molecule than DAG for KLM3' and therefore only 10-15% of the DAG in the reaction mixture were converted to triglyceride.

PLC does not have much impact on the level of free fatty acids (FFA) but it is observed that KLM3' in the high dosage and at extended reaction time contribute to increased level of FFA.

Jour. 2460-224:

Without wishing to be bound by theory the decrease in diglyceride by combining acyltransferase (KLM3') and phospholipase C (PLC) may be caused by substrate (phospholipid) competition when the two enzymes are used together.

In order to prove that KLM3' is able to use diglyceride as acceptor and catalyse the reaction mentioned in FIG. 108 a model experiment with the recipe shown in Table 5 below was conducted.

TABLE 5

Recipe for investigation of acyltransferase effect of KLM3' on diglyceride/phosphatidylcholine substrate.

| | | 1 | 2 | 3 | 4 | 5 | 6 |
|---|---|---|---|---|---|---|---|
| Diglyceride/PC 80/20 | g | 3 | 3 | 3 | 3 | 3 | 3 |
| Acyltransferase KLM3': 300 LATU/g | ml | 0 | 0.01 | | 0.01 | | 0.01 |
| Buffer | ml | 0.03 | 0.03 | 0.03 | 0.03 | 0.03 | 0.03 |
| Water 3% salt | | 0.01 | | 0.01 | | 0.01 | |
| Buffer: 1 100 mM Acetate pH 5.5 | | X | X | | | | |
| Buffer 2: 100 mM HEPES pH 7 | | | | X | X | | |
| Buffer 3. 100 mM MES pH 6 | | | | | | X | X |

Distilled diglyceride based on sunflower oil and phosphatidylcholine (PC) was mixed during heating and agitation to 80° C. until PC dissolved in the diglyceride.

The substrate was scaled in a 7 ml Dram Glass with screw lid and heated to 55° C. Enzyme, buffer and water was added, and the sample was agitated with magnetic stirring at 450 rpm.

After 30 and 180 minutes a sample was taken and analysed by TLC (FIG. 110).

The TLC plate was scanned and the triglyceride content in the samples was quantified from a standard curve made form the analysis of Canola oil with results shown in Table 6 below.

TABLE 6

| Buffer pH | Enzyme U/g | Reaction time minutes | Triglyceride % |
|---|---|---|---|
| 5.5 | 0 | 30 | 1.42 |
| 5.5 | 1 | 30 | 1.74 |
| 6 | 0 | 30 | 1.63 |
| 6 | 1 | 30 | 1.79 |
| 7 | 0 | 30 | 1.49 |
| 7 | 1 | 30 | 1.55 |
| 5.5 | 0 | 180 | 1.75 |
| 5.5 | 1 | 180 | 1.79 |
| 6 | 0 | 180 | 1.76 |
| 6 | 1 | 180 | 1.80 |
| 7 | 0 | 180 | 1.67 |
| 7 | 1 | 180 | 2.01 |

The results shown in Table 6 were analysed statistically by ANOVA using Statgraphic software with results shown in FIGS. 111 and 112.

The statistical evaluation of the triglyceride results from Table 6 confirm a significant increase in amount of triglyceride by addition of acyltransferase KLM3' to a substrate containing diglyceride and phosphatidylcholine.

Jour 2460-228

The experiment mentioned above in Table 5 was studied in further detail to investigate the effect of higher level of water on the transfer reaction of fatty acid moiety from phospholipid to diglyceride during formation of triglyceride. The experimental set up is listed in Table 7 below.

TABLE 7

Recipe for investigation of acyltransferase effect of KLM3' on diglyceride/phosphatidylcholine substrate.

| | | 1 | 2 | 3 | 4 | 5 |
|---|---|---|---|---|---|---|
| Diglyceride/Phosphatidylcholine 80/20 | g | 3 | 3 | 3 | 3 | 3 |
| Acyltransferase KLM3': 1128 LATU/ml | ml | 0 | 0.01 | 0.01 | 0.01 | 0.01 |
| Buffer: 1 100 mM Acetate pH 5.5 | ml | 0.05 | 0.05 | 0.05 | 0.05 | |
| Water | ml | 0.01 | | 0.09 | 0.165 | 0.14 |
| % water | | 2.00 | 2.00 | 5.00 | 7.50 | 5.00 |
| LATU/g substrate | | 0.0 | 3.8 | 3.8 | 3.8 | 3.8 |

Distilled diglyceride based on sunflower oil and phosphatidylcholine (PC) was mixed during heating and agitation to 80° C. until PC dissolved in the diglyceride.

The substrate was scaled in a 7 ml Dram Glass with screw lid and heated to 55° C. Enzyme, buffer and water was added, and the sample was agitated with magnetic stirring at 450 rpm After 30, 90 and 240 minutes a sample was taken and analysed by TLC TLC chromatograms are shown in FIG. 113 and FIG. 114.

The TLC plates were scanned and the content of triglyceride in the samples calculated based on a calibration curve made from triglyceride (Canola Oil). The results of triglyceride determination is shown in Table 8.

TABLE 8

Triglyceride analysis in diglyceride/PC substrate incubated with acyltransferase KLM3'

| Test no | Triglyceride, % 30 minutes | Triglyceride, % 90 minutes | Triglyceride, % 240 minutes |
|---|---|---|---|
| 1 | 1.33 | 1.36 | 1.58 |
| 2 | 1.55 | 1.91 | 2.56 |
| 3 | 1.59 | 2.02 | 2.65 |
| 4 | 1.57 | 1.81 | 2.29 |
| 5 | 1.56 | 1.91 | 2.46 |

The results in Table 8 were analysed statistically by ANOVA using Statgraphic software with results shown in FIG. 115 and FIG. 116.

The results from Table 8 and FIG. 115 and FIG. 116 clearly demonstrate the ability of acyltransferase KLM3' to produce triglyceride from a substrate of diglyceride and phosphatidylcholine.

Conclusion

Lipid acyltransferase KLM3' as well as phospholipase C (PLC) are known to contribute to increased oil yield in degumming of vegetable oil.

The effect of lipid acyltransferase KLM3' in oil degumming is based on a transfer reaction of fatty acid moiety from phospholipids to sterol during production lysophospholipids and sterol esters.

The effect of phospholipase C (PLC) relies on the conversion of phospholipids into diglyceride and water soluble phosphor-derivatives. The diglyceride produced in this reaction will accumulate in the oil phase by the degumming process, but it is not always preferable to have high diglyceride in the oil because it will have an impact on the smoke point of the oil and will also have an impact in the crystallisation properties of more saturated fat sources.

In the current study lipid acyltransferase KLM3' and Phospholipase C (PLC) were tested alone and in combination in a water degumming process. The experiments showed that PLC in the water degumming of soya oil produces diglyceride which forms part of the oil phase. When PLC was used in combination with KLM3' it was surprisingly shown that the amount of diglyceride produced by PLC was reduced and the sterol was converted to sterol esters indicating a synergistic effect between these two enzymes because KLM3' catalyses the transfer reaction of fatty acid moiety from phospholipid to diglyceride during formation of triglyceride.

The transfer reaction catalyzed by KLM3' of fatty acid moiety from phospholipid to diglyceride during formation of triglyceride was confirmed in a model system composed of diglyceride and phospholipid.

The results also showed that the two phospholipids tested do not have the same activity on all types of phospholipids, but KLM3 has almost the same activity on all four types of phospholipids found in crude soya oil. This also opens the possibility to use Phospholipase C in combination with KLM3' in order to get a further conversion of phospholipids.

EXAMPLE 14

Use of KLM3' in Water Degumming of Crude Soya Oil

Vegetable oil including soya bean oil contains 1 to 3% phospholipids, which are removed by an oil degumming process. The oil degumming process is normally divided into a water degumming process and a neutralisation process. Crude Soya bean oil with 1-3% phospholipids can not be shipped for export without water degumming aimed at reducing the phosphor level down to 200 ppm Phosphor or below to meet the specification for water degummed crude oil.

If the phosphor level is much lower than 200 ppm then this can be disadvantageous. Typically conventional degumming results in a phosphor level post-centrifugation of about 50 ppm. This is because it is not possible to control the centrifuge to give levels of phosphor which are less than 200 ppm but as close as possible to this level.

In contrast in the present case the use of the lipid acyltransferase the water degummed oil might preferably be adjusted to about 180 ppm phosphor.

Adjustment of the phosphor level in the enzymatic water degumming process of the present invention can preferably be done by adjusting the interphase between gum and oil in the centrifuge to get a little more phospholipid into the oil phase. In a conventional water degumming process the gum phase is however very thick and viscous, and it is therefore not easy to adjust the interphase in the centrifuge.

The present inventors have surprisingly found that when lipid acyltransferase (e.g. KLM3') is used in the water degumming process the interphase could be adjusted without problems in the centrifuge and could produce a degummed oil which was closer to the specification of a maximum of 200 ppm phosphor.

Experimental

The lipid acyltransferase KLM3' (SEQ ID No. 68) was used in water degumming of crude soya oil in the process outlined in FIG. 117.

The crude soya oil containing 1100 ppm phosphor was exposed to the water degumming process shown in FIG. 117. In the first experiment the degumming process was run without addition of the enzyme. In the second experiment the enzyme KLM3' was added, and after analysing the phosphor content of the water degummed oil the interphase between gum and oil in the centrifuge was adjusted towards the centre of the centrifuge. When the process was in balance again the phosphor was analysed again.

The result from the trials are shown in Table 1 below:

TABLE 1

| Water degumming | 1 | 2 | 3 |
|---|---|---|---|
| Enzyme KLM3', LATU/kg | 0 | 200 | 200 |
| Centrifuge fine Tuner setting | 185 | 185 | 195 |
| Phosphor in oil after centrifuge, ppm | 44* | 35* | 185 |

*not significant

Conclusion

In the experiment with enzymatic water degumming using KLM3' it was shown that the interphase between oil and gum in the centrifuge could easily be adjusted or controlled to produce water degummed oil with a phosphor level closer to specification (i.e. closer to but less than 200 ppm).

Under conventional water degumming conditions it is not always easy to adjust the interphase because of the consistency (high viscosity) of the gum phase does not allow such adjustment.

EXAMPLE 15

Enzymatic Reaction in the "Gum Phase" after Enzymatic Water Degumming of Vegetable Oils Lipid acyltransferase, LysoMax Oil (KLM3') was tested in water degumming of crude soya oil. Notably, the enzyme was not inactivated at the end of the enzymatic water degumming process—as would be routine in practice in industry. Therefore the enzymatic water degumming process was carried out in accordance with the Experimental protocol shown below. Notably enzyme was not inactivated after degumming.

The isolated gum phase from this process was incubated at 40° C., and the further degradation of phospholipid in the gum phase was analysed. The results surprisingly showed that the enzyme further hydrolysed phospholipid into lysophospholipids and free fatty acid. This is explained by the fact that the enzyme associates with the gum phase when the gum phase is separated from the oil phase by centrifugation.

Also the lyso-phospholipids were hydrolysed during storage, and after 7 days storage almost all phospholipids had disappeared from the gum phase.

Commercial Relevance of the Results

Enzymatic oil degumming of crude soya oil with KLM3' has shown that it is possible to improve the oil yield from 0.5 to 1.5%. The gum phase isolated from this process typically still contains some oil and phospholipids (EP1 624 047). It is known that by hydrolysis of the gum phase an oil phase can separate form the gum, which can be isolated by centrifugation or other means of separation. This oil phase containing high levels of free fatty acid can be sold as acid oil with higher value than the normal gum phase which is added to the meal.

A further aspect is that the remaining solid phase after separation of acid oil has higher phosphor level then normal gum and can be used as a source or organic phosphor.

Introduction

The inventors have surprisingly shown that the lipid acyltransferase LysoMax Oil (KLM3') is active in the gum phase isolated from enzymatic water degumming of crude soya oil. It was therefore speculated whether the enzyme could further degrade the phospholipids into free fatty acids which, by centrifugation, could be isolated as an acid oil together with the remaining triglyceride in the gum phase.

In this study the effect of different enzyme dosages and water degumming temperatures on the phospholipid degradation in the gum phase was examined.

Material and Methods:

KLM3':Glycerophospholipid cholesterol acyltransferase (FoodPro LysoMax Oil) (K932)

Lot no 102629600. 1 Activity 1128 LATU/g

Crude soya oil no 18: from, Argentina

HPTLC Analysis

The degradation of phospholipids in the gum phase from enzyme treated samples was analysed HPTLC.

Applicator: Automatic TLC Sampler 4, CAMAG
HPTLC plate: 20×10 cm, Merck no. 1.05641. Activated 10 minutes at 160° C. before use.
Application:
Gum phase from 10 gram oil was dissolved in 7.5 ml Hexan:Isopropanol 3:2.
1 µl of the sample was applied to the HPTLC plate.
A phospholipid standard (0.5% phospholipid (Spectra Lipid, Germany) was applied (0.1, 0.3, 0.5, 0.8 and 1.5 µl) and used for the calculation of the individual phospholipids in the gum.

In some applications the phospholipid content was calculated relative to a control gum n0ot treated with enzyme. This control sample was applied 0.1-0.3-0.5-0.8-1 µl and used for making calibrations curves.

Oil phase. Approximate 90 mg was scaled and dissolved in 1 ml Hexan:Isopropanol 3:2.

5 µl of the sample was applied to the HPTLC plate. Mono-diglyceride 5 mg/ml of known concentration was applied at 0.1-0.3-0.5-0.8-1.5 µl and used for calculation of individual glyceride components TLC Applicator.
Running buffer no. 1: P-ether:Methyl Tert Butyl Ketone: Acetic acid 50:50:1
Running buffer 6: Chloroform:1-propanol:Methylacetate: Methanol: 0.25% KCl in water 25:25:25:10:9
Elution: The plate was eluted 7 cm using an Automatic Developing Chamber ADC2 from Camag.
Development:
The plate was dried on a Camag TLC Plate Heater III for 10 minutes at 160° C., cooled, and dipped into 6% cupri acetate in 16% $H_3PO_4$. Additionally dried 10 minutes at 160° C. and evaluated directly.

The density of the components on the TLC plate was analysed by a Camag TLC Scanner 3.

Gas Chromatography

Free fatty acid in the gum phase was analysed by GLC.

Sterol, sterol ester and Mono-di-triglyceride of the oil phase was also analysed by GLC Apparatus Perkin Elmer Autosystem 9000 Capillary Gas Chromatograph equipped with WCOT fused silica column 12.5 m × 0.25 mm ID × 0.1µ film thickness 5% phenyl-methyl-silicone (CP Sil 8 CB from Chrompack).
Carrier gas: Helium.
Injector: PSSI cold split injection (initial temp 50° C. heated to 385° C.), volume 1.0 µl
Detector FID: 395° C.

| Oven program (used since 30 Oct. 2003): | 1 | 2 | 3 |
|---|---|---|---|
| Oven temperature, ° C. | 90 | 280 | 350 |
| Isothermal, time, min. | 1 | 0 | 10 |
| Temperature rate, ° C./min. | 15 | 4 | |

Sample Preparation

The sample was dissolved in 12 ml Heptane:Pyridin, 2:1 containing internal standard heptadecane, 0.5 mg/ml. 500 µl sample solution was transferred to a crimp vial, 100 µl MSTFA (N-Methyl-N-trimethylsilyl-trifluoraceamid) was added and reacted for 15 minutes at 60° C.

Calculation

Response factors for free fatty acids, mono- di- and triglyceride were determined based on pure reference material.

Experimental:

Lipid acyltransferase KLM3' was tested in crude soya oil in the recipes shown in table 1 below.

The degumming experiments in Table 1 were conducted at both 45 and 55° C.

| Jour. 2460-220 | | 1 | 2 | 3 | 4 | 5 | 6 | 7 | 8 | 9 | 10 |
|---|---|---|---|---|---|---|---|---|---|---|---|
| Crude soya oil | g | 10 | 10 | 10 | 10 | 10 | 10 | 10 | 10 | 10 | 10 |
| K932: 100 LATU-K/ml | ml | 0 | 0.01 | 0.02 | 0.05 | 0.01 | 0.02 | 0.05 | 0.01 | 0.02 | 0.05 |
| Extra Water | ml | 0.10 | 0.09 | 0.08 | 0.05 | 0.09 | 0.08 | 0.05 | 0.09 | 0.08 | 0.05 |
| LATU-K/g oil | | 0.00 | 0.10 | 0.20 | 0.50 | 0.10 | 0.20 | 0.50 | 0.10 | 0.20 | 0.50 |
| % water | | 1.00 | 1.00 | 1.00 | 1.00 | 1.00 | 1.00 | 1.00 | 1.00 | 1.00 | 1.00 |

The crude soya was heated to 55° C. (or 45° C.) in a 20 ml Wheaton glass. Water and enzyme was added. The sample was homogenized by high shear mixing for 30 seconds. The samples were placed on a heating block at 55° C. (or 45° C.) with magnetic agitation (450 rpm). After 30 minutes incubation the samples were centrifuged at 3000 rcf for 3 minutes.

The oil phase was separated form the gum phase by turning the tubes up side down for 15 minutes, which left the gum in the tubes.

The gum phase from each of samples 1 to 4 was then immediately frozen.

The gum phase from each of samples 5 to 8 were incubated at 40° C. for 1 day and then frozen.

The gum phase from each of samples 9-12 were incubated 7 days at 40° C.

All samples were analysed at the same time by TLC and GLC.

Results:

TLC analysis of gum phase samples from degumming at 55° C. are shown in FIG. 118 and the samples from degumming at 45° C. are shown in FIG. 119

Based on the scanning of the TLC chromatogram the relative content of phospholipid in the enzyme treated gum phase compared with the gum phase without enzyme treatment, was calculated (see Tables 2 and 3 below).

TABLE 2

Relative phospholipid in gum phase from water degumming at 45° C.

| sample no | Enzyme LATU/g | Time days | PC Rel. % | PA Rel. % | PE Rel. % | PI Rel. % |
|---|---|---|---|---|---|---|
| 1 | 0 | 0 | 100.0 | 100.0 | 100.0 | 100.0 |
| 2 | 0.1 | 0 | 40.5 | 48.6 | 38.5 | 43.0 |
| 3 | 0.2 | 0 | 21.5 | 33.7 | 22.4 | 26.9 |
| 4 | 0.5 | 0 | 7.4 | 23.1 | 9.0 | 15.6 |
| 5 | 0.1 | 1 | 6.4 | 41.9 | 6.0 | 17.2 |
| 6 | 0.2 | 1 | 2.3 | 25.7 | 1.9 | 12.5 |
| 7 | 0.5 | 1 | 1.3 | 10.7 | 0.0 | 4.2 |
| 8 | 0.1 | 7 | 0.0 | 17.1 | 0.0 | 8.1 |
| 9 | 0.2 | 7 | 2.5 | 9.4 | 0.0 | 4.8 |
| 10 | 0.5 | 7 | 0.0 | 0.0 | 0.0 | 3.7 |

The gum phase samples from 0 days were taken out just after the degumming reaction and centrifugation. At this point already a main part of the phospholipid is degraded and it is seen that the amount of lyso-phospholipid increases (Table 2). During incubation of the gum phase further hydrolysis of the phospholipids occurs, but also the lyso-phospholipids are hydrolysed.

The gum phases were analysed by GLC for free fatty acids (FFA) and triglyceride (see Table 3 below).

A fraction of the gum phase was extracted twice with Hexan Isopropanol 2:1 and the insoluble part was dried and quantified gravimetrically.

TABLE 3

GLC analysis of FFA and triglyceride in the gum phase and insoluble material

| Sample No | Incubation Days | Enzyme LATU/g | Dry basis % FFA | Dry basis % Triglyceride | Dry basis % FFA + Triglyceride | Hexan:IPA insoluble, %. |
|---|---|---|---|---|---|---|
| 1 | 0 | 0 | 1.9 | 64.0 | 66.0 | 2.7 |
| 2 | 0 | 0.1 | 7.0 | 41.5 | 48.6 | 3.6 |
| 3 | 0 | 0.2 | 8.2 | 42.5 | 50.7 | 6.0 |
| 4 | 0 | 0.5 | 7.4 | 43.1 | 50.5 | 26.9 |
| 5 | 1 | 0.1 | 16.3 | 36.4 | 52.7 | 15.7 |
| 6 | 1 | 0.2 | 16.6 | 39.8 | 56.4 | nd. |
| 7 | 1 | 0.5 | 12.6 | 40.3 | 53.0 | 41.1 |
| 8 | 7 | 0.1 | 21.2 | 37.3 | 58.5 | 35.6 |
| 9 | 7 | 0.2 | 19.2 | 37.1 | 56.4 | 33.3 |
| 10 | 7 | 0.5 | 14.6 | 42.1 | 56.7 | 38.7 |

TABLE 2

Relative phospholipid in gum phase from water degumming at 55° C.

| sample no | Enzyme LATU/g | Time days | LPC Rel. % | PC Rel. % | PA Rel. % | PE Rel. % | PI Rel. % |
|---|---|---|---|---|---|---|---|
| 1 | 0 | 0 | 100.0 | 100 | 100 | 100 | 100 |
| 2 | 0.1 | 0 | 571.2 | 31.2 | 35.8 | 26.1 | 55.0 |
| 3 | 0.2 | 0 | 144.5 | 18.0 | 24.1 | 13.1 | 39.6 |
| 4 | 0.5 | 0 | 45.6 | 3.3 | 17.1 | 3.0 | 16.3 |
| 5 | 0.1 | 1 | 452.5 | 4.6 | 17.6 | 3.0 | 24.6 |
| 6 | 0.2 | 1 | 26.7 | 1.0 | 15.5 | 0.4 | 9.5 |
| 7 | 0.5 | 1 | 2.0 | 0.0 | 6.2 | 0.0 | 2.5 |
| 8 | 0.1 | 7 | 3.0 | 0.0 | 8.0 | 0.0 | 3.2 |
| 9 | 0.2 | 7 | 1.0 | 0.0 | 4.0 | 0.0 | 2.1 |
| 10 | 0.5 | 7 | 0.2 | 0.0 | 0.0 | 0.0 | 2.6 |

The results shown in Table 3 clearly confirm that the enzymatic hydrolysis continues during storage of the gum phase at 40° C. up to 7 days.

The content of the gum phase which is not extractable with organic solvent (Hexan Isopropanol 2:1) is a measure for the amount of solid in the gum phase. When the phospholipids in the gum phase are hydrolyzed into FFA and phosphatidylglycerol the amount of material which is not soluble in Hexan:isopropanol increases. After 7 days incubation, more then 90% of the gum phase is composed of FFA, triglyceride and phosphatidylglycerol and no phospholipids are left in the gum phase. The composition of the gum phase after incubation makes it more easy to separate into an oily phase and a solid/water soluble phase, because no emulsifiers (phospholipids and lysophospholipids) are left in the gum.

Conclusion

During enzymatic degumming with a lipid acyltransferase (e.g. KLM3') a gum phase is isolated which contains active enzyme. Incubation of the gum phase at 40° C. further hydrolyses the phospholipids in the gum phase. Depending on the enzyme dosage all the phospholipids as well as the lyso-phospholipids are hydrolysed into fatty acids and phosphatidylglycerol. The elimination of the phospholipids in the gum phase makes it possible to isolate an oily phase containing free fatty acids and the remaining triglyceride in the gum phase.

In the degumming experiment conducted at 55° C., higher levels of phospholipid degradation were observed than running the experiment at 45° C. in both experiments the enzyme was active in the gum phase after separation and there was a tendency to an overall higher degree of hydrolysis during storage at 40° C. when the water degumming was conduced at 55° C.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

Danisco A/S
Langebrogade 1
DK-1001 Copenhagen
Denmark

RECEIPT IN THE CASE OF AN ORIGINAL DEPOSIT
issued pursuant to Rule 7.1 by the
INTERNATIONAL DEPOSITARY AUTHORITY
identified at the bottom of this page

NAME AND ADDRESS OF DEPOSITOR

| I. IDENTIFICATION OF THE MICROORGANISM | |
|---|---|
| Identification reference given by the DEPOSITOR: | Accession number given by the INTERNATIONAL DEPOSITARY AUTHORITY: |
| *Escherichia coli* TOP10pPet12aAhydro | NCIMB 41204 |

| II. SCIENTIFIC DESCRIPTION AND/OR PROPOSED TAXONOMIC DESIGNATION |
|---|
| The microorganism identified under I above was accompanied by: |
| ☐ a scientific description |
| ☒ a proposed taxonomic designation |
| (Mark with a cross where applicable) |

| III. RECEIPT AND ACCEPTANCE |
|---|
| This International Depositary Authority accepts the microorganism identified under I above, which was received by it on 22 December 2003 (date of the original deposit)¹ |

| IV. RECEIPT OF REQUEST FOR CONVERSION |
|---|
| The microorganism identified under I above was received by this International Depositary Authority on (date of the original deposit) and a request to convert the original deposit to a deposit under the Budapest Treaty was received by it on (date of receipt of request for conversion) |

| V. INTERNATIONAL DEPOSITARY AUTHORITY | |
|---|---|
| Name: NCIMB Ltd., | Signature(s) of person(s) having the power to represent the International Depositary Authority or of authorised official(s): |
| Address: 23 St Machar Drive Aberdeen AB24 3RY Scotland, UK. | Date: 9 January 2004 |

¹ Where Rule 6/4(d) applies, such date is the date on which the status of International Depositary Authority was acquired.

BUDAPEST TREATY ON THE INTERNATIONAL RECOGNITION OF THE DEPOSIT OF MICROORGANISMS FOR THE PURPOSES OF PATENT PROCEDURE

INTERNATIONAL FORM

Danisco A/S
Langebrogade 1
DK-1001 Copenhagen
Denmark

VIABILITY STATEMENT
issued pursuant to Rule 10.2 by the
INTERNATIONAL DEPOSITARY AUTHORITY
identified on the following page

NAME AND ADDRESS OF THE PARTY
TO WHOM THE VIABILITY STATEMENT
IS ISSUED

| I. DEPOSITOR | II. IDENTIFICATION OF THE MICROORGANISM |
|---|---|
| Name: AS ABOVE<br>Address: | Accession number given by the<br>INTERNATIONAL DEPOSITARY AUTHORITY:<br>NCIMB 41204<br>Date of the deposit or of the transfer[1]:<br>22 December 2003 |

III.- VIABILITY STATEMENT

The viability of the microorganism identified under II above was tested on 22 December 2003 [2]. On that date, the said microorganism was:

[X] viable

[ ] no longer viable

---

[1] Indicate the date of the original deposit or, where a new deposit or a transfer has been made, the most recent relevant date (date of the new deposit or date of the transfer).

[2] In the cases referred to in Rule 10.2(a)(ii) and (iii), refer to the most recent viability test.

[3] Mark with a cross the applicable box.

Form BP/9 (first page)

| IV. | CONDITIONS UNDER WHICH THE VIABILITY TEST HAS BEEN PERFORMED[4] |
|---|---|

| V. | INTERNATIONAL DEPOSITARY AUTHORITY |
|---|---|
| Name: NCIMB Ltd., <br> Address: 23 St Machar Drive <br> Aberdeen <br> AB24 3RY <br> Scotland | Signature(s) of person(s) having the power to represent the International Depositary Authority or of authorised official(s): <br><br> Date: 9 January 2004 |

[4] Fill in if the information has been requested and if the results of the test were negative.

Form BP/9 (second and last page)

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

Danisco A/S
Langebrogade 1
DK-1001 Copenhagen
Denmark

RECEIPT IN THE CASE OF AN ORIGINAL DEPOSIT
issued pursuant to Rule 7.1 by the
INTERNATIONAL DEPOSITARY AUTHORITY
identified at the bottom of this page

NAME AND ADDRESS OF DEPOSITOR

I. IDENTIFICATION OF THE MICROORGANISM

| Identification reference given by the DEPOSITOR: | Accession number given by the INTERNATIONAL DEPOSITARY AUTHORITY: |
|---|---|
| *Escherichia coli* TOP10pPet12aAsalmo | NCIMB 41205 |

II. SCIENTIFIC DESCRIPTION AND/OR PROPOSED TAXONOMIC DESIGNATION

The microorganism identified under I above was accompanied by:

[ ] a scientific description

[X] a proposed taxonomic designation (Mark with a cross where applicable)

III. RECEIPT AND ACCEPTANCE

This International Depositary Authority accepts the microorganism identified under I above, which was received by it on 22 December 2003 (date of the original deposit)[1]

IV. RECEIPT OF REQUEST FOR CONVERSION

The microorganism identified under I above was received by this International Depositary Authority on
(date of the original deposit) and a request to convert the original deposit to a deposit under the Budapest Treaty was received by it on
(date of receipt of request for conversion)

V. INTERNATIONAL DEPOSITARY AUTHORITY

Name: NCIMB Ltd.,

Address: 23 St Machar Drive
Aberdeen
AB24 3RY
Scotland, UK.

Signature(s) of person(s) having the power to represent the International Depositary Authority or of authorised official(s):

Date: 9 January 2004

[1] Where Rule 6/4(d) applies, such date is the date on which the status of International Depositary Authority was acquired.
Form BP/4 (sole page)

BUDAPEST TREATY ON THE INTERNATIONAL RECOGNITION OF THE DEPOSIT OF MICROORGANISMS FOR THE PURPOSES OF PATENT PROCEDURE

INTERNATIONAL FORM

Danisco A/S
Langebrogade 1
DK-1001 Copenhagen
Denmark

VIABILITY STATEMENT
issued pursuant to Rule 10.2 by the
INTERNATIONAL DEPOSITARY AUTHORITY
identified on the following page

NAME AND ADDRESS OF THE PARTY
TO WHOM THE VIABILITY STATEMENT
IS ISSUED

| I. DEPOSITOR | II. IDENTIFICATION OF THE MICROORGANISM |
|---|---|
| Name: AS ABOVE<br>Address: | Accession number given by the<br>INTERNATIONAL DEPOSITARY AUTHORITY:<br>NCIMB 41205<br>Date of the deposit or of the transfer[1]:<br><br>22 December 2003 |

III. VIABILITY STATEMENT

The viability of the microorganism identified under II above was tested on 22 December 2003 [2]. On that date, the said microorganism was:

[X] viable [3]

[ ] no longer viable [3]

[1] Indicate the date of the original deposit or, where a new deposit or a transfer has been made, the most recent relevant date (date of the new deposit or date of the transfer).

[2] In the cases referred to in Rule 10.2(a)(ii) and (iii), refer to the most recent viability test.

[3] Mark with a cross the applicable box.

Form BP/9 (first page)

| IV. | CONDITIONS UNDER WHICH THE VIABILITY TEST HAS BEEN PERFORMED[4] |
|---|---|

| V. | INTERNATIONAL DEPOSITARY AUTHORITY | |
|---|---|---|
| Name: NCIMB Ltd., <br> Address: 23 St Machar Drive <br> Aberdeen <br> AB24 3RY <br> Scotland | Signature(s) of person(s) having the power to represent the International Depositary Authority or of authorised official(s): 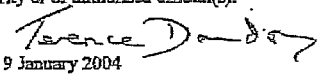 <br> Date: 9 January 2004 | |

[4] Fill in if the information has been requested and if the results of the test were negative.

Form BP/9 (second and last page)

BUDAPEST TREATY ON THE INTERNATIONAL RECOGNITION OF THE DEPOSIT OF MICROORGANISMS FOR THE PURPOSES OF PATENT PROCEDURE

Danisco Intellectual Assets
Danisco A/S
Langebrogade 1
DK-1001 Copenhagen
Denmark

INTERNATIONAL FORM

VIABILITY STATEMENT
issued pursuant to Rule 10.2 by the
INTERNATIONAL DEPOSITARY AUTHORITY
identified on the following page

NAME AND ADDRESS OF THE PARTY
TO WHOM THE VIABILITY STATEMENT
IS ISSUED

| DEPOSITOR | II. IDENTIFICATION OF THE MICROORGANISM |
|---|---|
| Name: AS ABOVE<br>Address: | Accession number given by the INTERNATIONAL DEPOSITARY AUTHORITY:<br>NCIMB 41226<br>Date of the deposit or of the transfer[1]:<br>23 June 2004 |

III. VIABILITY STATEMENT

The viability of the microorganism identified under II above was tested on 25 June 2004 [2]. On that date, the said microorganism was:

[X] viable

[ ] no longer viable

---

[1] Indicate the date of the original deposit or, where a new deposit or a transfer has been made, the most recent relevant date (date of the new deposit or date of the transfer).

[2] In the cases referred to in Rule 10.2(a)(ii) and (iii), refer to the most recent viability test.

[3] Mark with a cross the applicable box.

Form BP/9 (first page)

|  |
|---|
| '. CONDITIONS UNDER WHICH THE VIABILITY TEST HAS BEEN PERFORMED⁴. |
| |
| r. INTERNATIONAL DEPOSITARY AUTHORITY |
| Name: NCIMB Ltd.,      Signature(s) of person(s) having the power to represent the International Depositary Authority or of authorised official(s): 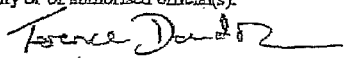<br>Address: 23 St Machar Drive<br>Aberdeen<br>AB24 3RY<br>Scotland      Date: 28 June 2004 |

⁴ Fill in if the information has been requested and if the results of the test were negative.

Form BP/9 (second and last page)

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

| Danisco Intellectual Assets<br>Danisco A/S<br>Langebrogade 1<br>DK-1001 Copenhagen<br>Denmark | RECEIPT IN THE CASE OF AN ORIGINAL DEPOSIT<br>issued pursuant to Rule 7.1 by the<br>INTERNATIONAL DEPOSITARY AUTHORITY<br>identified at the bottom of this page |
|---|---|

NAME AND ADDRESS OF DEPOSITOR

I. IDENTIFICATION OF THE MICROORGANISM

| Identification reference given by the DEPOSITOR: | Accession number given by the INTERNATIONAL DEPOSITARY AUTHORITY: |
|---|---|
| *Streptomyces* sp.<br>L131 | NCIMB 41227 |

II. SCIENTIFIC DESCRIPTION AND/OR PROPOSED TAXONOMIC DESIGNATION

The microorganism identified under I above was accompanied by:

[ ] a scientific description

[X] a proposed taxonomic designation (Mark with a cross where applicable)

III. RECEIPT AND ACCEPTANCE

This International Depositary Authority accepts the microorganism identified under I above, which was received by it on 23 June 2004 (date of the original deposit)

IV. RECEIPT OF REQUEST FOR CONVERSION

The microorganism identified under I above was received by this International Depositary Authority on
(date of the original deposit) and a request to convert the original deposit to a deposit under the Budapest Treaty was received by it on
           (date of receipt of request for conversion)

V. INTERNATIONAL DEPOSITARY AUTHORITY

| Name: NCIMB Ltd. | Signature(s) of person(s) having the power to represent the International Depositary Authority or of authorised official(s): |
|---|---|
| Address: 23 St Machar Drive<br>Aberdeen<br>AB24 3RY<br>Scotland, UK. | Date: 28 June 2004 |

Where Rule 6/4(d) applies, such date is the date on which the status of International Depositary Authority was acquired.

Form BP/4 (sole page)

BUDAPEST TREATY ON THE INTERNATIONAL
RECOGNITION OF THE DEPOSIT OF MICROORGANISMS
FOR THE PURPOSES OF PATENT PROCEDURE

Danisco Intellectual Assets
Danisco A/S
Langebrogade 1
DK-1001 Copenhagen
Denmark

INTERNATIONAL FORM

VIABILITY STATEMENT
issued pursuant to Rule 10.2 by the
INTERNATIONAL DEPOSITARY AUTHORITY
identified on the following page

NAME AND ADDRESS OF THE PARTY
TO WHOM THE VIABILITY STATEMENT
IS ISSUED

| I. DEPOSITOR | II. IDENTIFICATION OF THE MICROORGANISM |
|---|---|
| Name: AS ABOVE<br>Address: | Accession number given by the<br>INTERNATIONAL DEPOSITARY AUTHORITY:<br>NCIMB 41227<br>Date of the deposit or of the transfer[1]:<br><br>23 June 2003 |

III. VIABILITY STATEMENT

The viability of the microorganism identified under II above was tested on 25 June 2004 [2]. On that date, the said microorganism was:

[X] viable [3]

[ ] no longer viable [3]

[1] Indicate the date of the original deposit or, where a new deposit or a transfer has been made, the most recent relevant date (date of the new deposit or date of the transfer).

[2] In the cases referred to in Rule 10.2(a)(ii) and (iii), refer to the most recent viability test.

[3] Mark with a cross the applicable box.

Form BP/9 (first page)

| CONDITIONS UNDER WHICH THE VIABILITY TEST HAS BEEN PERFORMED[4] |
|---|
| |

| INTERNATIONAL DEPOSITARY AUTHORITY | |
|---|---|
| Name: NCIMB Ltd., <br><br> Address: 23 St Machar Drive <br> Aberdeen <br> AB24 3RY <br> Scotland | Signature(s) of person(s) having the power to represent the International Depositary Authority or of authorised official(s): <br><br> Date: 28 June 2004 |

[4] Fill in if the information has been requested and if the results of the test were negative.

Form BP/9 (second and last page)

The invention claimed is:

1. A method of water degumming a crude edible oil comprising the steps of: a) admixing approximately 0.1-5% w/w water with a crude edible oil and a lipid acyltransferase including a GDSx motif, a GANDY block and an HPT block, wherein a phospholipase C (E.C.3.1.4.3) is additionally admixed with the oil or water or lipid acyltransferase or a combination thereof wherein the lipid acyltransferase is not $PLA_1$ (E.C.3.1.1.32) or $PLA_2$ (E.C.3.1.1.4), b) agitating the admixture for between about 10 minutes and 180 minutes at about 45 to about 90° C., and c) separating the oil phase and the gum phase, wherein the lipid acyltransferase used has a transferase activity (TrU) per mg enzyme of at least 25 TrU/mg enzyme protein as determined using the following assay:
   a) 50 mg cholesterol and 450 mg Soya phosphatidylcholine is dissolved in chloroform and chloroform is evaporated at 40° C. under vacuum; 300 mg PC:cholesterol 9:1 is dispersed at 40° C. in 10 ml 50 mM HEPES buffer pH 7 to form the substrate;
   b) 250 µl substrate is added in a glass with lid at 40° C., 25 µl enzyme solution is added and incubated during agitation for 10 minutes at 40° C.;
   c) after 10 minutes 5 ml Hexan:Isopropanol 3:2 is added;
   d) the amount of cholesterol ester is analyzed by High Performance Thin Layer Chromatography (HPTLC) using Cholesteryl stearate standard for calibration; and
   e) transferase activity is calculated as the amount of cholesterol ester formation per minute.

2. A method according to claim 1 where the method further comprises d) incubating the gum phase comprising active lipid acyltransferase enzyme for between a minimum of about 2 hours and a maximum of 7 days and e) separating the oil from the gum phase.

3. A method according to claim 1 wherein the pH of the process is between about pH 5.0 to about pH 10.0.

4. A method according to claim 1 wherein the lipid acyltransferase comprises a GDSx motif or a GANDY motif.

5. A method according to claim 1 wherein the lipid acyltransferase enzyme is characterised as an enzyme which possesses acyltransferase activity and which comprises the amino acid sequence motif GDSX, wherein X is one or more of the following amino acid residues L, A, V, I, F, Y, H, Q, T, N, M or S.

6. A method according to claim 1 wherein the lipid acyltransferase for use in any one of the methods or uses or the combination thereof of the present invention may be obtainable, preferably obtained, from an organism from one or more of the following genera: *Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Raistonia, Xanthomonas* and *Candida*.

7. A method according to claim 6 wherein lipid acyltransferase is obtainable, preferably obtained, from an organism from the genus *Aeromonas*.

8. A method according to claim 1 wherein the lipid acyltransferase is a polypeptide having lipid acyltransferase activity which polypeptide is obtained by expression of the nucleotide sequence SEQ ID No. 49 or a nucleotide sequence which has 75% or more identity therewith.

9. A method according to claim 1 wherein the lipid acyltransferase is a polypeptide having lipid acyltransferase activity which polypeptide is obtained by expression of:
   a) the nucleotide sequence SEQ ID No. 49 or a nucleotide sequence which as has 75% or more identity therewith;
   b) a nucleic acid which encodes said polypeptide wherein said polypeptide is at least 70% identical with the polypeptide sequence SEQ ID No. 16 or with the polypeptide sequence SEQ ID No. 68;
   c) or a nucleic acid which hybridises under stringent conditions (50° C. and 0.2×SSC {1×SSC=0.15M NaCl, 0.015M Na-citrate pH 7.0)) to a nucleic probe comprising the nucleotide sequence SEQ ID No. 49.

10. A method according to claim 9 wherein the lipid acyltransferase is a polypeptide obtained by expression of the nucleotide sequences in *Bacillus licheniformis*.

11. A method according to claim 1 wherein the lipid acyltransferase is a polypeptide having lipid acyltransferase activity which polypeptide comprises any one of the amino acid sequences SEQ ID No. 68, SEQ ID No. 16, or an amino acid sequence which has 75% or more identity therewith.

12. A method according to claim 1 wherein the lipid acyltransferase is a polypeptide having lipid acyltransferase activity which polypeptide comprises the amino acid sequence shown as SEQ ID No. 68 or an amino acid sequence which as has 75% or more identity therewith.

* * * * *